US010624948B2

(12) United States Patent
Combette et al.

(10) Patent No.: US 10,624,948 B2
(45) Date of Patent: Apr. 21, 2020

(54) USE OF CELL-PERMEABLE PEPTIDE INHIBITORS OF THE JNK SIGNAL TRANSDUCTION PATHWAY FOR THE TREATMENT OF VARIOUS DISEASES

(71) Applicant: Xigen Inflammation Ltd., Limassol (CY)

(72) Inventors: Jean-Marc Combette, Saint Cergues (FR); Catherine Deloche, Geneva (CH)

(73) Assignee: XIGEN INFLAMMATION LTD., Limassol (CY)

( * ) Notice: Subject to any disclaimer, the term of this patent is extended or adjusted under 35 U.S.C. 154(b) by 0 days.

(21) Appl. No.: 14/891,067

(22) PCT Filed: Jun. 26, 2014

(86) PCT No.: PCT/EP2014/001736
§ 371 (c)(1),
(2) Date: Nov. 13, 2015

(87) PCT Pub. No.: WO2014/206563
PCT Pub. Date: Dec. 31, 2014

(65) Prior Publication Data
US 2016/0199444 A1 Jul. 14, 2016

(30) Foreign Application Priority Data

Jun. 26, 2013 (WO) .................. PCTEP2013/001881
Jun. 27, 2013 (WO) .................. PCT/EP2013/001896

(51) Int. Cl.
*A61K 38/17* (2006.01)
*C07K 14/47* (2006.01)
*A61K 38/55* (2006.01)

(52) U.S. Cl.
CPC .......... *A61K 38/1709* (2013.01); *A61K 38/55* (2013.01); *C07K 14/4703* (2013.01); *Y02A 50/414* (2018.01)

(58) Field of Classification Search
None
See application file for complete search history.

(56) References Cited

U.S. PATENT DOCUMENTS

| | | | |
|---|---|---|---|
| 4,631,211 A | 12/1986 | Houghten |
| 4,698,327 A | 10/1987 | Nagarajan et al. |
| 4,732,890 A | 3/1988 | Bonelli et al. |
| 5,169,933 A | 12/1992 | Anderson et al. |
| 5,595,756 A | 1/1997 | Bally et al. |
| 5,597,895 A | 1/1997 | Gaynor et al. |
| 5,670,617 A | 9/1997 | Frankel et al. |
| 5,672,479 A | 9/1997 | Johnson et al. |
| 5,674,980 A | 10/1997 | Frankel et al. |
| 5,686,264 A | 11/1997 | Gaynor et al. |
| 5,747,641 A | 5/1998 | Frankel et al. |
| 5,756,684 A | 5/1998 | Johnson et al. |
| 5,804,604 A | 9/1998 | Frankel et al. |
| 5,840,313 A | 11/1998 | Vahlne et al. |
| 5,880,261 A | 3/1999 | Waeber et al. |
| 5,989,814 A | 11/1999 | Frankel et al. |
| 5,994,108 A | 11/1999 | Gaynor et al. |
| 5,994,109 A | 11/1999 | Woo et al. |
| 6,043,083 A | 3/2000 | Davis et al. |
| 6,117,632 A | 9/2000 | O'Mahony |
| 6,265,386 B1 | 7/2001 | Campbell |
| 6,284,456 B1 | 9/2001 | Jones et al. |
| 6,300,317 B1 | 10/2001 | Szoka et al. |
| 6,316,003 B1 | 11/2001 | Frankel et al. |
| 6,348,185 B1 | 2/2002 | Piwnica-Worms |
| 6,420,031 B1 | 7/2002 | Parthasarathy et al. |
| 6,448,283 B1 | 9/2002 | Ylikoski et al. |
| 6,495,663 B1 | 12/2002 | Rothbard et al. |
| 6,586,403 B1 | 7/2003 | Mathison et al. |
| 6,610,820 B1 | 8/2003 | Bonny |
| 6,620,914 B1 | 9/2003 | Waeber et al. |
| 6,630,351 B1 | 10/2003 | Monahan et al. |
| 6,653,443 B2 | 11/2003 | Zhang et al. |
| 6,673,908 B1 | 1/2004 | Stanton, Jr. |
| 6,740,524 B1 | 5/2004 | Akuta et al. |
| 6,780,970 B2 | 8/2004 | Bonny |
| 6,881,825 B1 | 4/2005 | Robbins et al. |
| 6,960,648 B2 | 11/2005 | Bonny |
| 7,033,597 B2 | 4/2006 | Bonny |

(Continued)

FOREIGN PATENT DOCUMENTS

CA 2738951 A1 7/2010
CN 101263157 A 9/2008

(Continued)

OTHER PUBLICATIONS

Chung et al.,"Endogenous NGF Regulates Collagen Expression and Bladder Hypertrophy Through AKT and MAPK Pathways During Cystitis", JBC, 2010; 4206-4212.*

Dugan et al. ("Role of c-Jun N-terminal Kinase (JNK) activation in micturition reflexes in cyclophosphamide (CYP)-induced cystitis in female rats", Society for Neuroscience Abstract Viewer and Itinerary Planner, 41st Annual Meeting of the Society-for-Neuroscience, Washington, DC, Nov. 12-16, 2011 (Year: 2011).*

Chung et al., "Endogenous Nerve Growth Factor Regulates Collagen Expression and Bladder Hypertrophy through Akt and MAPK Pathways during Cystitis", The Journal of Biological Chemistry, 2010; pp. 4206-4212 (Year: 2010).* www.healthline.com—"What is Cystitis?", obtained Sep. 21, 2019; pp. 1-14 (Year: 2019).*

(Continued)

*Primary Examiner* — Lianko G Garyu
(74) *Attorney, Agent, or Firm* — Harness, Dickey & Pierce, P.L.C.

(57) ABSTRACT

The present invention refers to the use of protein kinase inhibitors and more specifically to the use of inhibitors of the protein kinase c-Jun amino terminal kinase, JNK inhibitor sequences, chimeric peptides, or of nucleic acids encoding same as well as pharmaceutical compositions containing same, for the treatment of various diseases or disorders strongly related to JNK signaling.

8 Claims, 83 Drawing Sheets
Specification includes a Sequence Listing.

(56) References Cited

U.S. PATENT DOCUMENTS

| | | |
|---|---|---|
| 7,034,109 B2 | 4/2006 | Bonny |
| 7,148,215 B2 | 12/2006 | Ratcliffe et al. |
| 7,166,692 B2 | 1/2007 | Karas |
| 7,538,091 B2 | 5/2009 | Bonny |
| 7,635,681 B2 | 12/2009 | Bonny |
| 7,803,749 B2 | 9/2010 | Bonny |
| 7,943,574 B2 | 5/2011 | Bonny |
| 8,063,012 B2 | 11/2011 | Watt et al. |
| 8,080,517 B2 | 12/2011 | Bonny |
| 8,183,339 B1 | 5/2012 | Bonny |
| 8,236,924 B2 | 8/2012 | Bonny |
| 8,278,413 B2 | 10/2012 | Bonny |
| 8,569,447 B2 | 10/2013 | Bonny |
| 8,748,395 B2 | 6/2014 | Bonny |
| 8,981,052 B2 | 3/2015 | Bonny |
| 9,006,185 B2 | 4/2015 | Bonny |
| 9,150,618 B2 | 10/2015 | Combette et al. |
| 9,180,159 B2 | 11/2015 | Bonny |
| 9,290,538 B2 | 3/2016 | Bonny |
| 9,610,330 B2 | 4/2017 | Bonny |
| 9,624,267 B2 | 4/2017 | Bonny |
| 2002/0042423 A1 | 4/2002 | Richert et al. |
| 2002/0090696 A1 | 7/2002 | Miller et al. |
| 2002/0103229 A1 | 8/2002 | Bhagwat et al. |
| 2003/0100549 A1 | 5/2003 | Salituro et al. |
| 2003/0104622 A1 | 6/2003 | Robbins et al. |
| 2003/0108539 A1 | 6/2003 | Bonny |
| 2003/0124113 A1 | 7/2003 | Hillman et al. |
| 2003/0148395 A1 | 8/2003 | Liu et al. |
| 2003/0220480 A1 | 11/2003 | Bonny |
| 2004/0058875 A1 | 3/2004 | Gamache |
| 2004/0082509 A1 | 4/2004 | Bonny |
| 2004/0265879 A1 | 12/2004 | Iversen et al. |
| 2005/0019366 A1 | 1/2005 | Zeldis |
| 2005/0043241 A1 | 2/2005 | Bonny |
| 2005/0059597 A1 | 3/2005 | Tymianski |
| 2005/0106695 A1 | 5/2005 | Bonny |
| 2006/0094753 A1 | 5/2006 | Pang et al. |
| 2006/0166881 A1 | 7/2006 | Hotchkiss et al. |
| 2006/0178310 A1 | 8/2006 | Bonny |
| 2006/0223807 A1 | 10/2006 | Davis et al. |
| 2006/0258706 A1 | 11/2006 | Saindane |
| 2006/0270646 A1 | 11/2006 | Graczyk et al. |
| 2007/0003531 A1 | 1/2007 | Mukherji et al. |
| 2007/0015779 A1 | 1/2007 | Griffin et al. |
| 2007/0060514 A1 | 3/2007 | Bonny |
| 2008/0008749 A1 | 1/2008 | Pearlman et al. |
| 2008/0051410 A1 * | 2/2008 | Watterson ............... A61K 31/50 514/252.02 |
| 2008/0274956 A1 | 11/2008 | Bonny et al. |
| 2009/0281036 A1 | 11/2009 | Meyer |
| 2009/0305968 A1 | 12/2009 | Bonny |
| 2010/0098635 A1 | 4/2010 | Lambing et al. |
| 2010/0216716 A1 | 8/2010 | Bonny |
| 2010/0256041 A1 | 10/2010 | Bonny et al. |
| 2010/0331335 A1 | 12/2010 | Sham et al. |
| 2011/0052566 A1 | 3/2011 | Rosenblum et al. |
| 2011/0183888 A1 * | 7/2011 | Bonny ................... A61K 38/28 514/1.5 |
| 2012/0058137 A1 | 3/2012 | Bonny |
| 2012/0071483 A1 | 3/2012 | Cohen et al. |
| 2012/0101046 A1 | 4/2012 | Hirai et al. |
| 2012/0142584 A1 | 6/2012 | Bonny |
| 2012/0148590 A1 | 6/2012 | Bonny |
| 2012/0258982 A1 | 10/2012 | Cheung et al. |
| 2012/0328609 A1 | 12/2012 | Lewcock et al. |
| 2014/0057834 A1 | 2/2014 | Bonny |
| 2014/0309400 A1 | 10/2014 | Combette et al. |
| 2015/0133393 A1 | 5/2015 | Combette et al. |
| 2016/0089413 A1 | 3/2016 | Combette et al. |
| 2016/0115200 A1 | 4/2016 | Combette et al. |
| 2016/0199444 A1 | 7/2016 | Combette et al. |
| 2016/0264630 A1 | 9/2016 | Bonny |
| 2017/0056466 A1 | 3/2017 | Combette et al. |
| 2017/0128516 A1 | 5/2017 | Combette et al. |
| 2017/0137481 A1 | 5/2017 | Combette et al. |
| 2017/0290877 A1 | 10/2017 | Combette et al. |
| 2017/0320917 A1 | 11/2017 | Bonny |
| 2018/0170983 A1 | 6/2018 | Combette et al. |
| 2019/0060392 A1 | 2/2019 | Combette et al. |

FOREIGN PATENT DOCUMENTS

| | | |
|---|---|---|
| CN | 1738901 B | 5/2010 |
| EP | 84691 A1 | 8/1983 |
| EP | 0375040 | 12/1989 |
| EP | 0679716 A1 | 11/1995 |
| EP | 0897002 A2 | 2/1999 |
| EP | 1364949 A1 | 11/2003 |
| EP | 1676574 A2 | 7/2006 |
| EP | 2627346 A1 | 8/2013 |
| FR | 2767323 A1 | 2/1999 |
| JP | 58-146538 | 9/1983 |
| JP | 02-221294 | 4/1990 |
| JP | 2002534479 A | 10/2002 |
| JP | 2003511071 A | 3/2003 |
| JP | 2003531871 A | 10/2003 |
| JP | 2004-66595 A | 3/2004 |
| JP | 2004-516811 A | 6/2004 |
| JP | 2005-525096 A | 8/2005 |
| JP | 2006-501165 A | 1/2006 |
| JP | 2006-502719 A | 1/2006 |
| JP | 2006-512143 A | 4/2006 |
| JP | 2007-503617 A | 2/2007 |
| JP | 2008-519785 A | 6/2008 |
| JP | 2011-524861 A | 9/2011 |
| JP | 2012/513427 A | 6/2012 |
| JP | 5485265 B2 | 5/2014 |
| JP | 5711666 B2 | 5/2015 |
| JP | 2015/197193 A | 11/2015 |
| JP | 5824085 B2 | 11/2015 |
| WO | 92/18138 A1 | 10/1992 |
| WO | 93/18759 A1 | 9/1993 |
| WO | 94/04562 A1 | 3/1994 |
| WO | 94/04686 | 3/1994 |
| WO | 94/05311 A1 | 3/1994 |
| WO | 94/23751 A1 | 10/1994 |
| WO | 95/34295 | 12/1995 |
| WO | 96/34093 | 10/1996 |
| WO | 97/05265 | 2/1997 |
| WO | 97/10836 | 3/1997 |
| WO | 98/11907 | 3/1998 |
| WO | 98/23781 A1 | 6/1998 |
| WO | 98/44106 A1 | 10/1998 |
| WO | 98/47913 A1 | 10/1998 |
| WO | 98/49188 | 11/1998 |
| WO | 98/51325 A2 | 11/1998 |
| WO | 98/51825 A1 | 11/1998 |
| WO | 98/52614 | 11/1998 |
| WO | 99/07728 A2 | 2/1999 |
| WO | 99/16787 A1 | 4/1999 |
| WO | 99/20624 A1 | 4/1999 |
| WO | 99/49879 | 10/1999 |
| WO | 99/50282 A2 | 10/1999 |
| WO | 99/58561 A1 | 11/1999 |
| WO | 99/67284 A2 | 12/1999 |
| WO | 00/12587 A2 | 3/2000 |
| WO | 00/41719 A1 | 7/2000 |
| WO | 01/10888 A1 | 2/2001 |
| WO | 01/13957 A2 | 3/2001 |
| WO | 01/15511 A2 | 3/2001 |
| WO | 01/27268 | 4/2001 |
| WO | 01/39784 | 6/2001 |
| WO | 2001/043774 A1 | 6/2001 |
| WO | 01/82975 | 11/2001 |
| WO | 2001/098324 A1 | 12/2001 |
| WO | 02/31109 A2 | 4/2002 |
| WO | 02/32437 | 4/2002 |
| WO | 02/061105 A2 | 8/2002 |
| WO | 02/062396 A2 | 8/2002 |
| WO | 02/065986 A2 | 8/2002 |
| WO | 02/069930 A1 | 9/2002 |
| WO | 02/081504 A2 | 10/2002 |
| WO | 02/081505 A2 | 10/2002 |

(56) References Cited

FOREIGN PATENT DOCUMENTS

| WO | 03/008553 | | 1/2003 | | |
|---|---|---|---|---|---|
| WO | 03/057725 | | 7/2003 | | |
| WO | 03/075917 | A1 | 9/2003 | | |
| WO | 03/103698 | A1 | 12/2003 | | |
| WO | 03/103718 | A2 | 12/2003 | | |
| WO | 03/106491 | | 12/2003 | | |
| WO | 20041022580 | A2 | 3/2004 | | |
| WO | 2004026406 | A1 | 4/2004 | | |
| WO | 20041035793 | A1 | 4/2004 | | |
| WO | 20041037196 | | 5/2004 | | |
| WO | 20041045535 | A2 | 6/2004 | | |
| WO | 2004/060318 | A2 | 7/2004 | | |
| WO | 20041054501 | A2 | 7/2004 | | |
| WO | 20041070052 | A2 | 8/2004 | | |
| WO | 20041092339 | A2 | 10/2004 | | |
| WO | 20051084158 | A2 | 9/2005 | | |
| WO | 2005/097116 | A1 | 10/2005 | | |
| WO | 20061001582 | | 1/2006 | | |
| WO | 2006/021458 | A2 | 3/2006 | | |
| WO | 20061050930 | | 5/2006 | | |
| WO | 2007/031098 | A1 | 3/2007 | | |
| WO | 20071031280 | | 3/2007 | | |
| WO | 2008/028860 | A1 | 3/2008 | | |
| WO | 2008/095943 | A1 | 8/2008 | | |
| WO | 2008/094208 | A3 | 10/2008 | | |
| WO | 20091137602 | | 11/2009 | | |
| WO | 2009/143864 | A1 | 12/2009 | | |
| WO | 2009/143865 | A1 | 12/2009 | | |
| WO | 20091144037 | | 12/2009 | | |
| WO | 20091144038 | | 12/2009 | | |
| WO | WO 2009143865 | A1 | * | 12/2009 | ............ A61K 38/28 |
| WO | 20101065850 | | 6/2010 | | |
| WO | 2010072405 | A1 | 7/2010 | | |
| WO | 2010072406 | A1 | 7/2010 | | |
| WO | 2010091310 | A1 | 8/2010 | | |
| WO | 2010/113753 | A1 | 10/2010 | | |
| WO | 2011/082328 | A1 | 7/2011 | | |
| WO | 2011/160653 | A1 | 12/2011 | | |
| WO | 2011/160827 | A2 | 12/2011 | | |
| WO | 2012/048721 | A1 | 4/2012 | | |
| WO | 2012/048893 | A1 | 4/2012 | | |
| WO | 20131091670 | | 6/2013 | | |
| WO | 20131091896 | | 6/2013 | | |
| WO | 2014/206426 | A1 | 12/2014 | | |
| WO | 2014206564 | A1 | 12/2014 | | |
| WO | 2015197193 | A3 | 2/2016 | | |

OTHER PUBLICATIONS

Nori et al., "Intracellular targeting of polymer-bound drugs for cancer chemotherapy," Advanced Drug Delivery Reviews, 57(4):609-636 (2005).
Okitsu et al., "Protein transduction domains enable isolated islets to efficiently internalize the target protein," Transplantation Proceedings, 35(1):479 (2003).
Pan et al., "Small peptide inhibitor of JNKs protects against MPTP-induced nigral dopaminergic injury via inhibiting the JNK-signaling pathway," Laboratory Investigation, 90(2):156-167 (2010).
Parkinson's Disease: Challenges, Progress, and Promise, National Institute of Neurological Disorders and Stroke, National Institutes of Health Publication No. 05-5595, <http://www.ninds.nih.gov/disorders/parkinsons_disease/parkinsons_research_pr.htm> (2004).
Penco et al., "Identification of an import signal for, and the nuclear localization of, human lactoferrin," Biotechnology and Applied Biochemistry, 34(Pt 3):151-159 (2001).
Hruby et al., "Design of Novel Synthetic Peptides Including Cyclic Conformationally and Topgraphically Constrained Analogs," Methods in Molecular Biology, vol. 35, Chapter 11, Peptide Synthesis Protocols, Pennington/Dunn (Eds.), Humana Press Inc., Totowa, NJ, USA, pp. 201-239 (1994).
Pennington et al., "Solid-Phase Synthesis of Peptides Containing the CH2NH Reduced Bond Surrogate," Methods in Molecular Biology, vol. 35, Chapter 12, Peptide Synthesis Protocols, Pennington/Dunn (Eds.), Humana Press Inc., Totowa, NJ, USA, pp. 241-247 (1994).
Pirvola et al., "Rescue of hearing, auditory hair cells, and neurons by CEP-1347/KT7515, an inhibitor of c-Jun N-terminal kinase activation," 20(1):43-50 (2000).
Prantner et al., "Synthesis and characterization of a Gd-DOTA-D-permeation peptide for magnetic resonance relaxation enhancement of intracellular targets," Molecular Imaging, 2(4):333-341 (2003).
Guichard et al.; Horvath et al.; Hruby et al., Peptides 1996: Proceedings of the twenty-fourth European Peptide Symposium, Sep. 8-13, 1996, Edinburgh, Scotland; Ramage/Epton (Eds.), The European Peptide Society, Mayflower Scientific Ltd., Kingswinford, pp. 447-450 and 483-486 (1996).
Du et al., "JNK inhibition reduces apoptosis and neovascularization in a murine model of age-related macular degeneration," Proc Natl Acad Sci USA, 110(6):2377-2382 (2013).
Ramanathan et al., "Targeting the sodium-dependent multivitamin transporter (SMVT) for improving the oral absorption properties of a retro-inverso Tat nonapeptide," Pharmaceutical Research, 18(7):950-956 (2001).
Ribeiro et al., "Heme oxygenase-1 fused to a TAT peptide transduces and protects pancreatic beta-cells," Biochemical and Biophysical Research Communications, 305(4):876-881 (2003).
Rickels et al., "Phage display selection of ligand residues important for Src homology 3 domain binding specificity," Proc Natl Acad Sci U S A., 92(24):10909-10913 (1995).
Robinson et al., "Properties and structure-activity studies of cyclic beta-hairpin peptidomimetics based on the cationic antimicrobial peptide protegrin I," Bioorganic & Medicinal Chemistry, 13(6):2055-2064 (2005).
Roduit et al., "MAP kinase pathways in UV-induced apoptosis of retinal pigment epithelium ARPE19 cells," Apoptosis, 13(3):343-353 (2008).
Rojas et al., "Controlling epidermal growth factor (EGF)-stimulated Ras activation in intact cells by a cell-permeable peptide mimicking phosphorylated EGF receptor," Journal of Biological Chemistry, 271(44):27456-27461 (1996).
Roy et al., "Role of the JNK signal transduction pathway in inflammatory bowel disease," World Journal of Gastroenterol, 14(2):200-202 (2008).
Ruben et al., "Structural and functional characterization of human immunodeficiency virus tat protein," Journal of Virology, 63(1):1-8 (1989).
Rudikoff et al., "Single amino acid substitution altering antigen-binding specificity," Proc Natl Acad Sci U S A, 79 (6):1979-1983 (1982).
Rudinger, "Characteristics of the Amino Acids as Components of a Peptide Hormone Sequence," Peptide Hormones, University Park Press, Baltimore, pp. 1-7 (1976).
Saito et al., "Contribution of peptide backbone atoms to binding of an antigenic peptide to class I major histocompatibility complex molecule," Molecular Immunology, 34(16-17):1133-1145 (1997).
Schimmer et al., "The BH3 domain of BAD fused to the Antennapedia peptide induces apoptosis via its alpha helical structure and independent of Bcl-2," Cell Death and Differentiation, 8(7):725-733 (2001).
Schinzel et al., "The phosphate recognition site of *Escherichia coli* maltodextrin phosphorylase," FEBS Letters, 286 (1-2):125-128 (1991).
Schwarze et al., "In vivo protein transduction: delivery of a biologically active protein into the mouse," Science, 285 (5433):1569-1572 (1999).
Sebestyen et al., "DNA vector chemistry: the covalent attachment of signal peptides to plasmid DNA," Nature Biotechnology, 16(1):80-85 (1998).
Sakane et al., "Current Concepts: Behcet's disease," The New England Journal of Medicine, 341(17):1284-1291, (1999).
Ohelke et al., Van Regenmortel et al., Saito et al., Peptide Science—Present and Future, Edited by Y. Shimonishi, Kluwer Academic Publishers, Dordrecht, The Netherlands, pp. 782-787 and 805-807 (1999).
Smilek et al., "A single amino acid change in a myelin basic protein peptide confers the capacity to prevent rather than induce experimental autoimmune encephalomyelitis," Proc Natl Acad Sci U S A, 88(21):9633-9637 (1991).

(56) References Cited

OTHER PUBLICATIONS

Stevens et al., "Efficient generation of major histocompatibility complex class I-peptide complexes using synthetic peptide libraries," The Journal of Biological Chemistry, 273(5):2874-2884 (1998).
Stevens et al., "Peptide length preferences for rat and mouse MHC class I molecules using random peptide libraries," European Journal of Immunology, 28(4):1272-1279 (1998).
Noguchi et al., "Effect of JNK Inhibitor During Islet Isolation and Transplantation," Transplantation proceedings, 40 (2):379-381 (2008).
Noguchi et al., "Cell Permeable Peptide of JNK Inhibitor Prevents Islet Apoptosis Immediately After Isolation and Improves Islet Graft Function," American Journal of Transplantation, 5(8):1848-1855 (2005).
Torchilin et al., "Fluorescence microscopy to follow the targeting of liposomes and micelles to cells and their intracellular fate," Advanced Drug Delivery Reviews, 57(1):95-109 (2005).
Torgerson et al., "Regulation of NF-kappa B, AP-1, NFAT, and STAT1 nuclear import in T lymphocytes by noninvasive delivery of peptide carrying the nuclear localization sequence of NF-kappa B p50," Journal of Immunology, 161 (11):6084-6092 (1998).
Touchard et al., "A peptide inhibitor of c-Jun N-terminal kinase for the treatment of endotoxin-induced uveitis," nvestigative Ophthalmology & Visual Science, 51(9):4683-4693 (2010).
Iyer et al., "RDP58, a rationally designed peptide, inhibits multiple forms of pathogenic inflammation through the inhibition of p38MAPK and JNK," Biopolymers, vol. 71, No. 3, 061, p. 298 (2013).
Van Regenmortel et al., "D-peptides as immunogens and diagnostic reagents," Current Opinion of Biotechnology, 9 (4):377-382 (1998).
Vives et al., "A truncated HIV-1 Tat protein basic domain rapidly translocates through the plasma membrane and accumulates in the cell nucleus," Journal of Biological Chemistry, 272(25):16010-16017 (1997).
Vives et al., "Structure-activity relationship study of the plasma membrane translocating potential of a short peptide from HIV-1 Tat protein," Letters in Peptide Science, 4(4):429-436 (1997).
Vocero-Akbani et al., "Killing HIV-infected cells by transduction with an HIV protease-activated caspase-3 protein," Nature Medicine, 5(1):29-33 (1999).
Voet, "Abnormal Hemoglobins," Biochemistry Second Edition, John Wiley & Sons, Inc., USA, pp. 235-241 (1995).
Wadia et al., "Delivery of Novel Anti-Cancer Peptides by Protein Transduction Domains," American Pharmaceutical Review, 7(3):65-69 (2004).
Waldmeier et al., "Recent clinical failures in Parkinson's disease with apoptosis inhibitors underline the need for a paradigm shift in drug discovery for neurodegenerative diseases," Biochemical Pharmacology, 72(10):1197-206 (2006).
Walsh et al., "Erythrocyte survival is promoted by plasma and suppressed by a Bak-derived BH3 peptide that interacts with membrane-associated Bcl-X(L)," Blood, 99(9):3439-3448 (2002).
Wender et al., "TThe design, synthesis, and evaluation of molecules that enable or enhance cellular uptake: peptoid molecular transporters," Proc Natl Acad Sci U S A, 97(24):13003-13008 (2000).
Whitmarsh et al., "A mammalian scaffold complex that selectively mediates MAP kinase activation," Science, 281 (5383):1671-1674 (1998).
Whitmarsh et al., "Transcription factor AP-1 regulation by mitogen-activated protein kinase signal transduction pathways," Journal of Molecular Medicine, 74(10):589-607 (1996).
Wilson, "Preventing Nerve Cell Death in ALS," Internet document—<http://www.als.caJ_news/57.aspx>, 2 pages (Dec. 5, 2001).
Wishart et al., "A single mutation converts a novel phosphotyrosine binding domain into a dual-specificity phosphatase," The Journal of Biological Chemistry, 270(45):26782-26785 (1995).
Kelekar et al., "Bcl-2-family proteins: the role of the BH3 domain in apoptosis," Trends Cell Biol., 8(8):324-330 (1998).
Killick et al, "Clusterin regulates ß-amyloid toxicity via Dickkopf-1-driven induction of the wnt-PCP-JNK pathway," Mol Psychiatry., 19(1):88-98 (2014).

Bost et al., "The Jun kinase 2 isoform is preferentially required for epidermal growth factor-induced transformation of human A549 lung carcinoma cells," Molecular and Cellular Biology, 19(3): 1938-1949 (1999).
Chang Lufen et al., JNK1 is required for maintenance of neuronal microtubules and controls phosphorylation of microtubule-associated proteins, Developmental Cell, 4(4): 521-533 (2003).
Hunot Stephan et al., "JNK-mediated induction of cyclooxygenase 2 is required for neurodegeneration in a mouse model of Parkinson's disease," Proceedings of the National Academy of Sciences of the United States of America,101 (2): 665-670 (2004).
Jaeschke et al., "Disruption of the Jnk2 (Mapk9) gene reduces destructive insulitis and diabetes in a mouse model of type I diabetes," Proceedings of the National Academy of Sciences of the United States of America, 102(19): 6931-6935 (2005).
Kaneto et al., "Possible novel therapy for diabetes with cell-permeable JNK-inhibitory peptide," Nature Medicine, 10(10):1128-1132 (2004).
Parenteau et al., "Free uptake of cell-penetrating peptides by fission yeast," FEBS Letters 579: 4873-4878 (2005).
Polyakov et al., "Novel Tat-peptide chelates for direct transduction of technetium-99m and rhenium into human cells for imaging and radiotherapy" Bioconjugate Chem., 11: 762-771 (2000).
Saar et al., "Cell-penetrating peptides: a comparative membrane toxicity study," Analytical Biochemistry, 345(1):55-65 (2005).
Sabapathy, "Role of the JNK pathway in human diseases," Progress in Molecular Biology and Translational Science, 106:145-169 (2012).
Salh, "c-Jun N-terminal kinases as potential therapeutic targets," Expert Opin Ther Targets, 11(10):1339-1353 (2007).
Seki et al., "A liver full of JNK: signaling in regulation of cell function and disease pathogenesis, and clinical approaches," Gastroenterology, 143(2):307-320 (2012).
Sumara et al., "Jnking atherosclerosis," Cellular and Molecular Life Sciences, Birkhäuser Verlag, 62(21): 2487-2494 (2005).
Tachibana et al., "JNK1 is required to preserve cardiac function in the early response to pressure overload, Biochemical and Biophysical Research Communications," 343(4): 1060-1066 (2006).
Westwick et al., "Activatin of Jun kinase is an early event in hepatic regeneration," The Journal of the Clinical Investigation, 95(2): 803-810 (1995).
Hommes et al., "Inhibition of stress-activated MAP kinases induces clinical improvement in moderate to severe Crohn's disease," Gastroenterology, 122(1):7-14 (2002).
Mitsuyama et al., "Pro-inflammatory signaling by Jun-N-terminal kinase in inflammatory bowel disease," Int J Mol Med., 17(3):449-55 (2006).
Qin et al., "TAT Protein Transduction Domains : New Promise for Protein Therapy," Chinese Journal of Biochemistry and Molecular Biology, 23(7): 519-524 (2007) (Abstract Translated).
Bogoyevitch et al., "Taking the cell by stealth or storm? Protein transduction domains (PTDs) as versatile vectors for delivery," DNA Cell Biol., 21(12):879-894 (2002).
InVivoGen, Inc., SP600125: MAP Kinase Inhibitor—Autophagy Inhibitor—JNK inhibitor, Downloaded Jun. 9, 2014.
Witkowski et al., "Conversion of a beta-ketoacyl synthase to a malonyl decarboxylase by replacement of the active-site cysteine with glutamine," Biochemistry, 38(36):11643-11650 (1999).
Ahmed et al., "Basal cancer cell survival involves JNK2 suppression of a novel JNK1/c-Jun/Bcl-3 apoptotic network," PLoS One, 4(10):e7305 (2009).
Yamamoto et al., "Molecular design of bioconjugated cell adhesion peptide with a water-soluble polymeric modifier for enhancement of antimetastatic effect," Current Drug Targets, 3(2):123-130 (2002).
Yang et al., "Differential targeting of MAP kinases to the ETS-domain transcription factor Elk-1," The EMBO Journal, 17(6):1740-1749 (1998).
Yasuda et al., "The JIP group of mitogen-activated protein kinase scaffold proteins," Molecular and Cellular Biology, 19(10):7245-7254 (1999).
Zhang et al., "Preparation of functionally active cell-permeable peptides by single-step ligation of two peptide modules," —Proceedings of National Academy of Sciences, 95(16):9184-9189 (1998).

(56) References Cited

OTHER PUBLICATIONS

Zoukhri et al., "c-Jun NH2-terminal kinase mediates interleukin-1beta-induced inhibition of lacrimal gland secretion," Journal of Neurochemistry, 96(1):126-135 (2006).
Chemical Abstracts Database, Accession No. 133:204452 CA, (Sep. 29, 2000) 3 pages.
Chemical Abstracts Accession No. 2004:27781 and CAS Registry File CN 647864-97-9.
GenBank Database Accession No. AAD20443 (Mar. 17, 1999) 2 pages.
GenBank Database Accession No. AAD22543 (Mar. 1, 2006) 2 pages.
GenBank Database Accession No. AF074091 (Mar. 17, 1999) 2 pages.
GenBank Database Accession No. AF108959 (Mar. 1, 2006) 2 pages.
GenBank Database Accession No. AF218778 (Mar. 2, 2006) 2 pages.
GenBank Database Accession No. PH0878 (May 30, 1997) 1 page.
Database WPI, Thompson Scientific, Accession Number: 2010-M79716, 3 pages (2010).
Bowie et al., "Deciphering the message in protein sequences: tolerance to amino acid substitutions," Science, 247 (4948): 1306-1310 (1990).
Patel M. et al, "Getting into the brain—approaches to enhance brain drug delivery", CNS Drugs, v23(1):35-58 (2009).
Hirt et al., "D-JNKI1, a cell-penetrating c-Jun-N-terminal kinase inhibitor, protects against cell death in severe cerebral ischemia," Stroke, 35(7): 1738-1743 (2004).
Kugler et al., "MAP kinase pathways involved in glioblastoma response to erucylphosphocholine," International Journal of Oncology, 25(6):1721-1727 (2004).
Stedman's Online Dictionary Definition of "inflammation", Obtained from www.pdrel.com, last viewed on Dec. 18, 2010, 2 pages.
Wang et al., "A single amino acid determines lysophospholipid specificity of the S1P1 (EDG1) and LPA1 (EDG2) phospholipid growth factor receptors," Journal of Biological Chemistry, 276(52): 49213-49220 (2001).
Wells, "Additivity of mutational effects in proteins," Biochemistry, 29(37): 8509-8517 (1990).
Tan et al., "Selective inhibition of ErbB2-overexpressing breast cancer in vivo by a novel TAT-based ErbB2-targeting signal transducers and activators of transcription 3-blocking peptide," Cancer Res., 66:3764-3772 (2008).
De Paiva et al., "Essential role for c-Jun N-terminal kinase 2 in corneal epithelial response to desiccating stress," Arch Ophthalmol., 127(12): 1625-1631 (2009).
Aarts et al., "Treatment of ischemic brain damage by perturbing NMDA receptor—PSD-95 protein interactions," Science, 298(5594):846-850 (2002).
Abaza et al., "Effects of amino acid substitutions outside an antigenic site on protein binding to monoclonal antibodies of predetermined specificity obtained by peptide immunization: demonstration with region 94-100 (antigenic site 3) of myoglobin," Journal of Protein Chemistry, 11(5):433-444 (1992).
Asanuma et al., "Protection against malonate-induced ischemic brain injury in rat by a cell-permeable peptidic c-Jun N-terminal kinase inhibitor, (L)-HIV-TAT48-57-PP-JBD20, observed by the apparent diffusion coefficient mapping magnetic resonance imaging method," Neurosci Lett., 359(1-2):57-60 (2004) (only abstract).
Aldrian-Herrada et al., "A peptide nucleic acid (PNA) is more rapidly internalized in cultured neurons when coupled to a retro-inverso delivery peptide. The antisense activity depresses the target mRNA and protein in magnocellular oxytocin neurons," Nucleic Acids Research, 26(21):4910-4916 (1998).
Assi et al., "The specific JNK inhibitor SP600125 targets tumour necrosis factor-alpha production and epithelial cell apoptosis in acute murine colitis," Immunology, 118(1):112-121 (2006).
Barr et al., "Identification of the Critical Features of a Small Peptide Inhibitor of JNK Activity," Science, 282 (5389):642-643 (1998).
Berendsen, "A Glimpse of the Holy Grail?" Science, 282:642-643 (1998).
Bessalle et al., "All-D-magainin: chirality, antimicrobial activity and proteolytic resistance," FEBS Letters, 274(1-2):151-155 (1990).
Bonny et al., "Cell-Permeable Peptide Inhibitors of JNK: Novel Blockers of Beta-Cell Death," Diabetes, 50(1):77-82 (2001).
Bonny et al., "A JIP-1-Related Nuclear Protein Present in Insulin-Secreting Cells," Journal of Biological Chemistry, 273(4):1843-1846 (1998).
Bonny et al., "Pancreatic-specific expression of the glucose transporter type 2 gene: identification of cis-elements and islet-specific trans-acting factors," Molecular Endrocrinology, 9(10)1413-1426 (1995).
Bonny et al., "Targeting the JNK pathway as a therapeutic protective strategy for nervous system diseases," Reviews of Neuroscience, 16(1):57-67 (2005).
Borsello et al., "A peptide inhibitor of c-Jun N-terminal kinase protects against excitotoxicity and cerebral ischemia," Nature Medicine, 9(9):1180-1186 (2003).
Borsello et al., "Use of cell-permeable peptides to prevent neuronal degeneration," Trends in Molecular Medicine, 10(5):239-244 (2004).
Bradley et al., "Limits of cooperativity in a structurally modular protein: response of the Notch ankyrin domain to analogous alanine substitutions in each repeat," Journal of Molecular Biology, 324(2):373-386 (2002).
Branden et al., "A Peptide Nucleic Acid-Nuclear Localization Signal Fusion that Mediates Nuclear Transport of DNA," Nature Biotechnology, 17(8):784-787 (1999).
Branden et al., Introduction to Protein Structure, Second Edition, Garland Publishing Inc., New York, p. 382 (1999).
Branden et al., Introduction to Protein Structure, Garland Publishing Inc., New York, p. 2471(1999).
Cardazo et al., "Cell-permeable peptides induce dose- and length-dependent cytotoxic effects," Biochimica Biophysica Acta., 1768(9):2222-2234 (2007).
Chaloin et al., "Design of carrier peptide-oligonucleotide conjugates with rapid membrane translocation and nuclear localization properties," Biochemical and Biophysical Research Communications, 243(2):601-608 (1998).
Creighton T., "Protein—Protein Interactions," Encyclopedia of Molecular Biology, vol. 1, John Wiley and Sons, Inc., pp. 2027-2033 (1997).
Derossi et al., "Cell internalization of the third helix of the Antennapedia homeodomain is receptor-independent," The Journal of Biological Chemistry, 271(30):18188-18193 (1996).
Designing Custom Peptides, Sigma Genosys, <http://www.sigmagenosys.com/peptide_design.asp>, 2 pages (Dec. 16, 2004).
Database UniProt, Retrieved from EBI, Database Accession No. Q9WVI9, Abstract (Feb. 28, 2003).
Dickens et al., "A cytoplasmic inhibitor of the JNK signal transduction pathway," Science, 277(5326):693-696 (1997).
Dietz et al., "Delivery of Bioactive Molecules into the Cell: The Trojan Horse Approach," Molecular and Cellular Neuroscience, 27(2):85-131 (2004).
Dominguez-Bendala et al., "TAT-mediated neurogenin 3 protein transduction stimulates pancreatic endocrine differentiation in vitro," Diabetes, 54(3):720-726 (2005).
Fawell et al., "Tat-mediated delivery of heterologous proteins into cells," Proc Natl Acad Sci USA, 91(2):664-668 (1994 ).
Fornoni et al., "The L-Isoform but not D-Isoforms of a JNK Inhibitory Peptide Protects Pancreatic β-cells," Biochemical and Biophysical Research Communications, 354(1):227-233 (2007).
Frankel et al., "Cellular Uptake of the Tat Protein from Human Immunodeficiency Virus," Cell, 55(6):1189-1193 (1998).
Ferrandi et al., "Inhibition of c-Jun N-terminal kinase decreases cardiomyocyte apoptosis and infarct size after myocardial ischemia and reperfusion in anaesthetized rats," British Journal of Pharmacology, 142(6): 953-960 (2004).
Futaki et al., "Arginine-rich peptides. An abundant source of membrane-permeable peptides having potential as carriers for intracellular protein delivery," The Journal of Biological Chemistry, 276(8):5836-5840 (2001).

(56) References Cited

OTHER PUBLICATIONS

Gammon et al., "Quantitative analysis of permeation peptide complexes labeled with Technetium-99m: chiral and sequence-specific effects on net cell uptake," Bioconjugate Chemistry, 14(2):368-376 (2003).
Gotthardt et al., "Interactions of the low density lipoprotein receptor gene family with cytosolic adaptor and scaffold proteins suggest diverse biological functions in cellular communication and signal transduction," The Journal of Biological Chemistry, 275(33):25616-25624 (2000).
Guichard et al., "Antigenic mimicry of natural L-peptides with retro-inverso-peptidomimetics," Proc Natl Acad Sci USA, 91(21):9765-9769 (1994).
Gunaseelan et al., "Synthesis of poly(ethylene glycol)-based saquinavir prodrug conjugates and assessment of release and anti-HIV-1 bioactivity using a novel protease inhibition assay," Bioconjugate Chemistry, 15(6):1322-1333 (2004).
Gura, "Systems for identifying new drugs are often faulty," Science, 278(5340):1041-1042 (1997).
Hawiger, "Noninvasive intracellular delivery of functional peptides and proteins," Current Opinion in Chemical Biology, 3(1):89-94 (1999).
Hayashi et al., "Development of oligoarginine-drug conjugates linked to new peptidic self-cleavable spacers toward effective intestinal absorption," Bioorganic and Medicinal Chemistry Letters, 17(18):5129-5132 (2007).
Heemskerk et al., "From chemical to drug: neurodegeneration drug screening and the ethics of clinical trials," Nature Neuroscience, Suppl:1027-1029 (2002).
Herve et al., "On the immunogenic properties of retro-inverso peptides. Total retro-inversion of T-cell epitopes causes a loss of binding to MHC II molecules," Molecular Immunology, 34(2):157-163 (1997).
EMBL Sequence Database Accession No. R85141 (Aug. 17, 1995).
Ho et al., "Synthetic protein transduction domains: enhanced transduction potential in vitro and in vivo," Cancer Research, 61(2):474-477 (2001).
Holinger et al., "Bak BH3 peptides antagonize Bcl-xL function and induce apoptosis through cytochrome c-independent activation of caspases," The Journal of Biological Chemistry, 274(19):13298-13304 (1999).
Holzberg et al., "Disruption of the c-JUN-JNK complex by a cell-permeable peptide containing the c-JUN delta domain induces apoptosis and affects a distinct set of interleukin-1-induced inflammatory genes," The Journal of Biological Chemistry, 278(41):40213-40223 (2003).
Houghten, "General method for the rapid solid-phase synthesis of large numbers of peptides: specificity of antigen-antibody interaction at the level of individual amino acids," Proc Natl Acad Sci USA, 82(15):5131-5135 (1985).
Huq et al., "Specific recognition of HIV-1 TAR RNA by a D-Tat peptide," 4(11):881-882, Nature Structural Biology (1997).
Johnson et al., "The c-jun kinase/stress-activated pathway: regulation, function and role in human disease," Biochimica et Biophysica Acta, 1773(8):1341-1348 (2007).
Pinilla et al., "The Versatility of Nonsupport-Bound Combinatorial Libraries," Chapter 5, Combinatorial Peptide and Nonpeptide Libraries—A Handbook, Edited by Günther Jung, John Wiley & Sons, pp. 139-171 (1997).
Spatola et al., "Cyclic Peptide Libraries: Recent Developments," Chapter 11, Combinatorial Peptide and Nonpeptide Libraries—A Handbook, Edited by Günther Jung, John Wiley & Sons, pp. 327-347 (1996).
Adele-Biassette et al.—Neuronal Apoptosis does not Correlate with Dementia in HIV Infection but is Related to Microglial Activation and Axonal Damage—Neuropathology and Applied Neurobiology—1999—pp. 123-133—vol. 25—Blackwell Science Ltd.—USA.
Adler et al., "Regulation of JNK Signaling by GSTp," The EMBO Journal, 18(5):1321-1334 (1999).
Brady et al., "Reflections on a Peptide," Nature, 368(6473):692-693 (1994).
Briand et al., "A retro-inverso peptide corresponding to the GH loop of foot-and-mouth disease virus elicits high levels of long-lasting protective neutralizing antibodies," Proc Natl Acad Sci USA, 94(23):12545-12550 (1997).
Brugidou et al., "The Retro-Inverso Form of a Homeobox-Derived Short Peptide is Rapidly Internalized by Cultured Neurons: A New Basis for an Efficient Intracellular Delivery System," Biochemical and Biophysical Research Communications, 214(2):685-693 (1995).
Chie et al., "Identification of the site of inhibition of oncogenic ras-p21-induced signal transduction by a peptide from a ras effector domain," Journal of Protein Chemistry, 18(8):881-884 (1999).
Chorev et al., "A Dozen Years of Retro-Inverso Peptidomimetics," Accounts of Chemical Research, 26:266-273 (1993).
Chorev et al., "Recent developments in retro peptides and proteins—an ongoing topochemical exploration," Trends in Biotechnology, 13(10):438-445 (1995).
Dang et al., "Nuclear and nucleolar targeting sequences of c-erb-A, c-myb, N-myc, p53, HSP70, and HIV tat proteins," Journal of Biological Chemistry, 264(30):18019-18023 (1989).
Ausubel et al., "Using synthetic oligonucleotides as probes," Current protocols in Molecular Biology, Supplement 2, Apr. 1988, John Wiley & Sons Inc., New York, pp. 6.4.01-6.4.1 0.
Elliott et al., "Intercellular trafficking and protein delivery by a herpesvirus structural protein," Cell, 88(2):223-233 (1997).
Frankel et al., "Activity of Synthetic Peptides from the Tat Protein of Human Immunodeficiency Virus Type 1," Proc Natl Acad Sci USA, 86(19):7397-7401 (1989).
Giorello et al., Inhibition of cancer cell growth and c-Myc transcriptional activity by a c-Myc helix 1-type peptide fused to an internalization sequence, Cancer Research, 58(16):3654-3659 (1998).
Guichard et al., "Partially modified retro-inverso pseudopeptides as non-natural ligands for the human class I histocompatibility molecule HLA-A2," Journal of Medicinal Chemistry, 39(10):2030-2039 (1996).
Hauber et al., "Mutational analysis of the conserved basic domain of human immunodeficiency virus tat protein," Journal of Virology, 63(3):1181-1187 (1989).
Inhibit.Dictionary.com, The American Heritage@ Stedman's Medical Dictionary, Houghton Mifflin Company, USA, One Page, Internet document: http://dictionary.reference.com/browse/inhibit, Accessed on Oct. 10, 2007.
Jackson et al., "Heat shock induces the release of fibroblast growth factor 1 from NIH 3T3 cells," Proc Natl Acad Sci USA, 89(22)10691-10695 (1992).
Jameson et al., "A rationally designed CD4 analogue inhibits experimental allergic encephalomyelitis," Nature, 368 (6473):744-746 (1994).
Kennedy et al., "Role of JNK in tumor development.," Cell Cycle, 2(3):199-201 (2003).
Kida et al., "Design and synthesis of a Tat-related gene transporter: a tool for carrying the adenovirus vector into cells," Bioorganic and Medicinal Chemistry Letters, 16(3):743-745 (2006).
Kieber-Emmons et al., "Therapeutic Peptides and Peptidomimetics," Current Opinion in Biotechnology, 8:435-441 (1997).
Kisselev, "Polypeptide release factors in prokaryotes and eukaryotes: same function, different structure," Structure, 10(1):8-9 (2002).
Kuan et al., "A critical role of neural-specific JNK3 for ischemic apoptosis," Proceedings of the National Academy of Sciences USA, 100(25): 15184-15189 (2003).
Lebleu "Delivering information-rich drugs—prospects and challenges," Trends in Biotechnology, 14(4):109-110 (1996).
Lee et al., "c-Jun N-terminal Kinasa (JNK) Mediates Feedback Inhibition of the Insulin Signaling Cascade," The Journal of Biological Chemistry, 278(5):2896-2902 (2003).
Lewis et al., "Lymphoma Cell Uptake of Radiometal—and Fluorescent-Labelled BCL-2 Antisense PNA Conjugates is Mediated by a Retro-Inverso Delivery Peptide," Journal of Label Compounds and Radiopharmaceuticals, 46(S1) p. S13 (2003).
Li, "Specificity and versatility of SH3 and other proline-recognition domains: structural basis and implications for cellular signal transduction," Biochemical Journal, 390(Pt 3):641-653 (2005).

(56) References Cited

OTHER PUBLICATIONS

Lim et al., "Penetration enhancement in mouse skin and lipolysis in adipocytes by TAT-GKH, a new cosmetic ingredient," Journal of Cosmetic Science, 54(5):483-491 (2003).
Lin et al., "Inhibition of nuclear translocation of transcription factor NF-kappa B by a synthetic peptide containing a cell membrane-permeable motif and nuclear localization sequence," Journal of Biological Chemistry, 270(24):14255-14258 (1995).
Lloyd-Williams et al., "Formation of Disulfide Bridges," Chapter 5, Chemical Approaches to the Synthesis of Peptides and Proteins, CRC Press LLC, USA, pp. 209-236 (1997).
Lloyd-Williams et al., "Peptide Libraries," Chapter 6, Chemical Approaches to the Synthesis of Peptides and Proteins, CRC Press LLC, USA, pp. 237 and 264-267 (1997).
Mann et al., "Endocytosis and targeting of exogenous HIV-1 Tat protein," The EMBO Journal, 10(7):1733-1739 (1991).
Marino et al., "Inhibition of Experimental Autoimmune Encephalomyelitis in SJL Mice by Oral Administration of Retro-Inverso Derivative of Encephalitogenic Epitope P87-99," European Journal of Immunology, 29:2560-2566 (1999).
Marks et al., "Protein Targeting by Tyrosine- and Di-leucine-based Signals: Evidence for Distinct Saturable Components," The Journal of Cell Biology, 135(2):341-354 (1996).
Mayer, "SH3 domains: complexity in moderation," Journal of Cell Science, 114(Pt 7):1253-1263 (2001).
Mazur et al., "Identification and expression of the TREX1 and TREX2 cDNA sequences encoding mammalian 3'->5' exonucleases," The Journal of Biological Chemistry, 274(28):19655-19660 (1999).
Melikov et al., "Arginine-rich cell penetrating peptides: from endosomal uptake to nuclear delivery," Cellular and Molecular Life Sciences, 62(23):2739-2749 (2005).
Messer, "MBC 3320 Posterier Pituitary Hormones," Vasopression and Oxytocin, pp. 1-5, <http://www.neurosci.pharm.utoledo.edu/MBC3320/vasopressin.htm> —USA (Apr. 3, 2000).
Mi et al., "Characterization of a class of cationic peptides able to facilitate efficient protein transduction in vitro and in vivo," Molecular Therapy, 2(4):339-347 (2000).
Milano et al., "A peptide inhibitor of c-Jun NH2-terminal kinase reduces myocardial ischemia-reperfusion injury and infarct size in vivo," American Journal of Physiology, 292(4):H1828-H1835 (2007).
Mooi et al., "Regulation and Structure of an Escherichia Coli Gene Coding for an Outer Membrane Protein involved in Export of K88ab Fimbrial Subunits," Nucleic Acids Research, 14(6):2443-2457 (1996).
Moon et al., "Bcl-2 Overexpression Attenuates SP600125-induced Apoptosis in Human Leukemia U937 Cells," Cancer Letters, 264:316-325 (2008).
Mooser et al. "Genomic Organization, Fine-Mapping, and Expression of the Human Islet-Brain 1 (IB1)/C-Jun-Amino-Terminal Kinase Interacting Protein-1 (JIP-1) Gene," Genomics, 55:202-208 (1999).
Moulin et al. "Islet-brain (IB)/JNK-interacting proteins (JIPs): future targets for the treatment of neurodegenerative diseases?" Current Neurovascular Research, 1(2):111-127 (2004).
Nagahara et al., "Transduction of Full-Length TAT Fusion Proteins into Mammalian Cells: TAT-p27Kip1 Induces Cell Migration," Nature Medicine, 4(12):1449-1452 (1998).
Negri et al., "Design of a Novel Peptide Inhibitor of the JNK Signaling Pathway," Diabetes, Abstract Book, 61st Scientific Sessions, Jun. 22-26, 2001, Pennsylvania Convention Center, Philadelphia, PA, vol. 50, Supplement No. 2, p. A294, 1217-P (2001).
Neundorf et al., "Detailed analysis concerning the biodistribution and metabolism of human calcitonin-derived cell-penetrating peptides," Bioconjugate Chemistry, 19(8):596-1603 (2008).
Ngo et al., "Computational Complexity, Protein Structure Prediction, and the Levinthal Paradox," The Protein Folding Problem and Tertiary Structure Prediction, Merz et al. (Editors), Birkhauser Boston, USA, pp. 433 and 492-495 (1994).
Noguchi et al., "Regulation of c-Myc through phosphorylation at Ser-62 and Ser-71 by c-Jun N-terminal kinase," Journal of Biological Chemistry, 274(46):32580-32587 (1999).
Nori et al., "Tat-conjugated synthetic macromolecules facilitate cytoplasmic drug delivery to human ovarian carcinoma cells," Bioconjugate Chemistry, 14(1):44-50 (2002).
Chen et al., "The Role of c-Jun N-terminal Kinase (JNK) in Apoptosis Induced by Ultraviolet C and gamma Radiation," J. of Bio. Chem., 271(50):31929-31936 (1996).
133:204452, Interaction of native RNAs with Tat peptides. Chemical Abstracs Database Sep. 29, 2000:1-3.
Branden and Tooze, Prediction; Engineering and Design of Protein Structures. Introduction to Protein Structure, 1991:247.
Hillier et al, Homo sapiens cDNA done. EMBL Sequence Database, 1995 R85141.
International Search Report and Written Opinion dated Apr. 27, 2010 issued in PCT/EP2009/009229.
International Search Report and Written Opinion dated Jun. 2, 2010 issued in PCT/EP2009/009228.
Q9WVI9, JIPI_Mouse Standard; PRT; 707 AA. Database UniProt 2003.
Bennett, Brydon L., et al., "SP600125, an anthrapyrazolone inhibitor of Jun N-terminal kinase," PNAS, 98(24):13681-13686, Nov. 20, 2001.
Saito and Paterson, Contribution of Peptide Backbone Atoms to Binding of an Antigenic Peptide to Class I Major Histocompatibility Complex Molecule. Molecular Immunology 1997 Nov.-Dec.; 34(16-17):1133-1145.
Selective Dimerisation of Cysteines to form Heterodimers. NJE Feb. 3, 1997.
Garg, "Successful Management of Uveitis in a Patient with Unilateral Multifocal Choroiditis", Insert to Retina Today, pp. 1-8 (2019).
Tsuyoshi et al., Behcet's disease. NE J Med. 1999:1284-1291.
Cui et al., JNK pathway: diseases and therapeutic potential. Acta Pharmacol Sin. May 2007;28(5):601-608.
Josephson et al., High-Efficiency Intracellular Magnetic Labeling with Novel Superparamagnetic-Tat Peptide Conjugates. Bioconjug Chem. Mar.-Apr. 1999;10(2):186-191.
Moschos et al., Lung Delivery Studies Using siRNA Conjugated to TAT(48-60) and Penetratin Reveal Peptide Induced Reduction in Gene Expression and Induction of Innate Immunity. Bioconjug Chem. Sep.-Oct. 2007:18 (5):1450-1459.
Dickens et al., Database—UNIPROT—Retrieved from EBI—Database Accession No. Q9WVI9—Abstracts—32-28-2003—Document No. XP-002366175—USA.
Agrawal, Vishal and Kishan, KV. Radha—Promiscuous Binding Nature of SH3 Domains to their Target Proteins—Protein and Peptide Letters—2002—pp. 185-193—vol. 9—No. 3—Bentham Science Publishers Ltd.—USA.
Guichard et al., Chapters 165 and 166; Gur'Yanov et al., Chapter 167; In R. Ramage and R. Epton (eds.), Peptides 1996 : Proceedings of the Twenty-Fourth European Peptide Symposium (Sep. 8-13, 1996, Edinburgh, Scotland), European Peptide Society, Mayflower Scientific Ltd., United Kingdom), pp. 447-451 (1998).
Horvath et al., Chapter 183; Hruby et al., Chapter 184; In R. Ramage and R. Epton (eds.), Peptides 1996 : Proceedings of the Twenty-Fourth European Peptide Symposium (Sep. 8-13, 1996, Edinburgh, Scotland), European Peptide Society, Mayflower Scientific Ltd., United Kingdom), pp. 483-486 (1996).
Tournier et al.—Mitogen-Activated Protein Kinase Kinase 7 is an Activator of the c-Jun NH2—Terminal Kinase—Cell Biology—Proceedings of the National Academy of Science—Jul. 1997—pp. 7337-7342—vol. 94—National Academy of Science—USA.
Wyszko et al., "Interaction of Native RNAs with Tat Peptides," RNA Biochemistry and Biotechnology, NATO Science Series, 70:277-290 (1999); Chemical Abstracts Database Accession Na 133:204452.
NCBI Sequence Viewer—Accession No. AAD20443—Reports—Islet—Brain 1 (Homo Sapiens)—Two References—Mooser et al.—Mar. 17, 1999—2 pages—USA.
NCBI Sequence Viewer—Accession No. AAD22543—Reports—Islet—Brain 1 (Rattus Norvegicus)—Three References—Bonny et al.—Mar. 1, 2006—2 pages—USA.
NCBI Sequence Viewer—Accession No. AF074091—Reports—Homo Sapiens Islet—Brain 1 mRNA—Complete Cds.—Two References—Mooser et al.—Mar. 17, 1999—2 pages—USA.

(56) References Cited

OTHER PUBLICATIONS

NCBI Sequence Viewer—Accession No. AF108959—Reports—Rattus Norvegicus Islet—Brain 1 (IB1) mRNA—Complete Cds.—Three References—Bonny et al.—Mar. 1, 2006—2 pages—USA.
NCBI Sequence Viewer—Accession No. AF218778—Reports—Homo Sapiens Islet—Brain 2 mRNA—Complete Cds—Three References—Kristensen et al.—Mar. 2, 2006—2 pages—USA.
Conti et al., "Atherosclerosis: a chronic inflammatory disease mediated by mast cells", Central European Journal of Immunology, 2015, pp, 380-386 (Year: 2015).
Rovina et al., "Inflammation and Immune Response in COPD: Where Do We Stand ? ", Mediators of Inflammation, 2013, pp. 1 -9 Year: 2013).
Murdoch et al., "Chronic inflammation and asthma", Mutation Research, 2010, pp. 24-39 (Year: 2010).
Donath et al.,Type 2 diabetes as an inflammatory disease, Nature Reviews—immunology, 2011, pp. 98-107 (Year: 2011).
Todd et al., "GeneticProtection from the Inflammatory Disease Type 1 Diabetes in Humans and Animal Models", Immunity, pp. 387-395 (Year: 2001).
Dugan et al., "Role of c -Jun N- terminal Kinase (JNK) activation in micturition reflexes in cyclophosphamide (CYP)—induced cystitis in female rats," Journal of Molecular Neuroscience, 54(3):360-369 (2014).
Juszczak et al., "Animal models of overactive bladder: Cyclophosphamide (CYP)—induced cystitis in rats", N46, EAU 3rd North Eastern European Meeting (NEEM)/ European Urology Supplements 8 (2009) 583-584 (Year: 2009).
Cerbone et al., "AS601245, an anti -inflammatory JNK inhibitor, and clofibrate have a synergistic effect in inducing cell responses and in affecting the gene expression profile in CaCo -2 colon cancer cells," PPAR Research, 2012: 269751, 1-16 (2012).
Budur et al., "A pharmacogenetics supported clinica trial to delay onset of mild cognitive impairment due to Alzheimer's disease using low dose pioglitazone: the tomorrow study," Neuropsychopharmacology, 39: S342 (2014).
Bloch et al., "Increased ERK and JNK activation and decreased ERK/JNK ratio are associated with long-term organ damage in patients with systemic lupus erythematosus," Rheumatology 53: 1034-1042 (2014).
Barichello et al., "Dexamethasone treatment reverses cognitive impairment but increases brain oxidative stress in rats submitted to pneumococcal meningitis," Oxidative Medicine and Cellular Longevity, 1-7 (2011).
Aisen et al., "A randomized controlled trial of prednisone in Alzheimer's disease," Neurology, 54: 588-593 (2000).
Melino et al., "The effect of the JNK inhibitor, JIP peptide, on human T lymphocyte proliferation and cytokine production," 181(10): 7300-7306 (2008).
Wang et al., "JNK inhibition as a potential strategy in treating Parkinson's disease," Drug News Perspect., 17 (10):646-654 (2004).
Weston et al., "The JNK signal transduction pathway," Curr. Opin. Cell Biol., 19(2):142-149, (2007).
Soejima et al., "Activation of MKK4 (SEK1), JNK, and C-Jun in Labial Salivary Infiltrating T Cells in Patients With Sjogren's Syndrome," Rheumatology International, 27(4): 329-333 (2006).
Shimazawa et al., "Inhibitor of double stranded RNA-dependent protein kinase protects against cell damage induced by ER stress," Neurosci Lett., 409(3):192-195 (2006).
Nakamura et al., "Expression of mitogen activated protein kinases in labial salivary glands of patients with Sjogren's syndrome," Annals of the Rheumatic Diseases, 58(6):382-385 (1999).
Manning et al., "Targeting JNK for therapeutic benefit: from junk to gold?" Nature Reviews Drug Discovery, 2: 554-565 (2003).
Hanyu et al., "Pioglitazone improved cognition in a pilot study on patients with Alzheimer's disease and mild cognitive impairment with diabetes mellitus," Journal of the American Geriatrics Society, 57(1):177-179 (2009).
Janin, "Protein—Protein Interactions" Encyclopedia of Molecular Biology (Creighton, ed.) 2027-2033 (1999).

Hruby et al., "Design of Potent and Specific Melanotropin Agonists and Antagonists: Investigating Ligands for New Receptors," Peptides (Ramage et al, ed) 485-486 (1996).
Horvath et al., "Somatostatin Octa- and Heptapeptides, Structural and Biological Characteristics," Peptides (Ramage et al, ed) 483-484 (1996).
Fujita et al.—Prophylactic or Therapeutic Agent for Retinal Diseases and Method for Preventing or Treating Retinal Diseases, Each Comprising JNK (C-JUN N-Terminal Kinase)-Inhibiting Peptide, and Use of the Peptide—International Application No. PCT/JP2010/55208—Santen Pharmaceutical Co., Lid.—Database WPI—Thompson Scientific—pp. 1-4—XP-002643212—USA.
Kishan, KV. Radha and Agrawal, Vishal—SH3-like Fold Proteins are Structurally Conserved and Functionally Divergent—Current Protein and Peptide Science—1995—pp. 143-150—vol. 6—Bentham Science Publishers Ltd.—USA.
Duby et al. (Contributors)—Using Synthetic Oligonucleotides as Probes—Current Protocols in Molecular Biology—Supplement 2—Apr. 1988—pp. 6.4.1-6.4.10—John Wiley & Sons—Document No. XP 002044485—USA.
NCBI Sequence Viewer—Accession No. AAF32323—Reports—Islet-Brain 2 (Homo Sapiens)—Two References—Negri et al.—Feb. 9, 2000—2 pages—USA.
Van Regenmortel et al., "Peptide analogues as vaccines and immunomodulators," Peptide Science—Present and Future (Shimonishi, ed) 784-787 (1999).
Neidle, S. ed., "Cancer Drug Design and Discovery," Elsevier/Academic Press, 427-431 (2008).
Auerbach et al., "Angiogenesis assays: Problems arid pitfalls," Cancer and Metastasis Reviews, 19: 167-172 (2000).
Jain, R., "Barriers to Drug Delivery in Solid Tumors," Scientific American, 58-65 (1994).
Sporn et al., "Chemoprevention of cancer," Carcinogenesis, 21: 525-530 (2000).
Thoren et al, —The Antennapedia Peptide Penetratin Translocates across Lipid Bilayers—The First Direct Observation—FEBS Letters—2000—pp. 265-268—No. 482—Federation of European Biochemical Societies—Elsevier Science B.V.—Europe.
Fischer, P.M.—The Design, Synthesis and Application of Stereochemical and Directional Peptide Isomers: A Critical Review—Current Protein and Peptide Science—2003—pp. 339-356—vol. 4—Bentham Science Publishes Ltd.—United Kingdom.
Pennington, Michael W. and Dunn, Ben M. {Editors)—Chapter 11—Design of Novel Synthetic Peptides including Cyclic Conformationally and Topgraphically Constrained Analogs—Hruby, Victor and Bonner, G. Gregg—Methods in Molecular Biology—vol. 35—Peptide Synthesis Protocols—1994—pp. 201-239—Humana Press Inc,—USA.
Guichard et al., "Mimicry of an Immunodominant Epitope of Foot and Mouth Disease Virus with Retro-inverson Isomers: A New Approach in the Design of Peptide Based Vaccines," Peptides (Ramage et al. ed) 447-448 (1996).
Guichard et al., Partially Modified Retro-inverson Psudopeptides as Non-natural Ligands for the Human Class I Histocompatibility Molecule, HLA-A2, Peptides (Ramage et al. ed) 449-450 (1996).
Multifocal choroiditis, "National Center of Advancing Translational Science," https : / /rarediseases.info.nih/gov/diseases /9824 /multifocal-choroiditis; 5 pages (2017).
Theoretical p1 /Mw average of the amino acid sequence DQSRPVQPFLNLTTPRKPRPPRRRQRRKKRG; http: //web.expasy.org /cgi- bin /compute_pi /pi_tool; obtained Sep. 20, 2017; p. 1 (2017).
Sclip A et al. c-Jun N-terminal kinase regulates soluble Abeta oligomers and cognitive impairment in AD mouse model. J. Biol. Chem. 286(51), 43871-43880. (Year: 2011).
TgCRND8 Research Model, Alzforum, www.alzforum.org /research -models /tgcrnd8, retrieved Nov. 25, 2018. (Year: 2018).
XG -102 C-Terminal acid, Compound Summary for CID 72941992, PubChem, pubchem.ncbi.nlm.nih.gov / compound /72941992#section =Top, retrieved Nov. 24, 2018. (Year: 2018).
Sclip A et al. c -Jun N- terminal kinase has a key role in Alzheimer disease synaptic dysfunction in vivo, Cell Death and Disease, 5, e1019. Published online Jan. 23, 2014. (Year: 2014).

(56) References Cited

OTHER PUBLICATIONS

Sharma N et al. SP600125, a competitive inhibitor of JNK attenuates streptozotocin induced neurocognitive deficit arid oxidative stress in rats. Pharmacology, Biochemistry and Behavior, 96, 386-394. (Year: 2010).
Office Action dated Feb. 1, 2016 issued in U.S. Appl. No. 14/367,706, 24 pages.
Office Action dated Mar. 21, 2014 issued in U.S. Appl. No. 13/141,314, 21 pages.
Office Action dated Jul. 31, 2014 issued in U.S. Appl. No. 13/141,314, 17 pages.
Office Action dated Aug. 27, 2015 issued in U.S. Appl. No. 13/141,314, 9 pages.
Office Action dated Aug. 16, 2018 issued in U.S. Appl. No. 15/321,893, 8 pages.
Office Action dated Dec. 4, 2017 issued in U.S. Appl. No. 15/321,904, 14 pages.
Office Action dated Nov. 29, 2018 issued in U.S. Appl. No. 15/737,480, 16 pages.
Office Action dated Jan. 30, 2019 issued in U.S. Appl. No. 15/628,771, 17 pages.
Office Action dated Aug. 24, 2017 issued in U.S. Appl. No. 15/516,943, 14 pages.
Office Action dated Jun. 15, 2018 issued in U.S. Appl. No. 15/516,943, 9 pages.
Office Action dated Jan. 10, 2019 issued in U.S. Appl. No. 15/516,943, 10 pages.
Office Action dated Aug. 8, 2019 issued in U.S. Appl. No. 15/516,943, 11 pages.
Office Action dated Dec. 11, 2013 issued in U.S. Appl. No. 14/035,450, 9 pages.
Office Action dated Sep. 24, 2014 issued in U.S. Appl. No. 14/035,450, 7 pages.
Office Action dated Apr. 27, 2015 issued in U.S. Appl. No. 14/035,450, 10 pages.
Office Action dated Aug. 31, 2015 issued in U.S. Appl. No. 14/035,450, 10 pages.
Office Action dated May 2, 2016 issued in U.S. Appl. No. 14/035,450, 10 pages.
Office Action dated Oct. 23, 2017 in U.S. Appl. No. 15/217,326, 21 pages.
Office Action dated May 13, 2018 in U.S. Appl. No. 15/217,326, 16 pages.
Office Action dated Feb. 7, 2019 in U.S. Appl. No. 15/217,326, 14 pages.
Office Action dated Jan. 26, 2017 in U.S. Appl. No. 14/849,374, 19 pages.
Office Action dated Sep. 26, 2017 in U.S. Appl. No. 14/849,374, 16 pages.
Office Action dated Mar. 29, 2017 in U.S. Appl. No. 15/045,058, 43 pages.
Office Action dated Jul. 22, 2015 in U.S. Appl. No. 14/144,938, 12 pages.
Office Action dated Dec. 28, 2010 in U.S. Appl. No. 12/066,657, 27 pages.
Office Action dated Jun. 28, 2010 in U.S. Appl. No. 12/066,657, 9 pages.
Office Action dated Jul. 19, 2012 in U.S. Appl. No. 12/066,657, 13 pages.
Office Action dated Jul. 8, 2011 in U.S. Appl. No. 12/101,911, 14 pages.
Office Action dated Aug. 29, 2006 in U.S. Appl. No. 10/457,614, 21 pages.
Office Action dated Oct. 12, 2007 in U.S. Appl. No. 10/457,614, 17 pages.
Office Action dated Oct. 31, 2019 issued in U.S. Appl. No. 15/934,735, 9 pages.
Nih, "Panuveitis", https://rarediseases.info.nih.gov/diseases/8577/panuveitis; 2016, pp. 1-7 (2016).
Saito et al., "Contribution of peptide backbone atoms to binding of antigenic peptide to class I major histocompatibility complex molecule," Peptide Science—Present and Future (Shimonishi, ed.) 805-807 (1999).
Barr et al., Identification of the Critical Features of a Small Peptide inhibitor of JNK Activity. The Journal of Biochemical Chemistry Mar. 29, 2002; 277(13):10987-10997.
Office Action dated Apr. 8, 2019 issued in U.S. Appl. No. 15/934,735, 8 pages.

\* cited by examiner

Peptide sequences, Human, Mouse and Rat

```
                       :  :     **. :
A   IB2       :  IPSPSVEEPHKHRPTTLRL--TTLGAQDS
    IB1       :  PGTGCGDTYRPKRPTTLNLFPQVPRSQDT
    c-Jun     :  GAYGYSNPKILKQSMTLNLADPVGNLKPH
    ATF2      :  TNEDHLAVHKHKHEMTLKFGPARNDSVIV

:  . ***** *    **:
B   L-IB1(s)  :  ---RPKRPTTLNLFPQVPRSQD
    L-IB1     :  DTYRPKRPTTLNLFPQVPRSQDT
                       °  °  °

C   L-TAT      :  NH2-GRKKRRQRRR-COOH
    L-TAT-IB1(s): NH2-GRKKRRQRRRPP---RPKRPTTLNLFPQVPRSQD-COOH
    L-TAT-IB1  :  NH2-GRKKRRQRRPPDTYRPKRPTTLNLFPQVPRSQDT-COOH

D-TAT      :  NH2-RRRQRRKKRG-COOH
    D-TAT-IB1(s): NH2--DQSRPVQPFLNLTTPRKPR---PPRRRQRRKKRG-COOH
    D-TAT-IB1  :  NH2-TDQSRPVQPFLNLTTPRKPRYTDPPRRRQRRKKRG-COOH
```

Fig. 1

Generic Sequences, Human, Mouse and Rat

L-generic-TAT(s)      : $NH_2-X_n^b-RKKRRQRRR-X_n^b-COOH$
L-TAT-IB (generic) (s): $NH_2-X_n^b-RKKRRQRRR-X_n^b-X_n^a-RPTTLXLXXXXXQD-X_n^b-COOH$
L-TAT-IB (generic)    : $NH_2-XXXXXXXRKKRRQRRRXXXXXXXXXXXRPTTLXLXXXXXXXQDS/TX-COOH$ D-generic-TAT(s)      : $NH_2-X_n^b-RRRQRRKKR-X_n^b-COOH$
D-TAT-IB (generic) (s): $NH_2-X_n^b-DQXXXXXLXLTTPR-X_n^a-X_n^b-RRRQRRKKR-X_n^b-COOH$
D-TAT-IB (generic)    : $NH_2-XT/SDQXXXXXLXLTTPRXXXXXXXXXXRRRQRRKKRXXXXXXX-COOH$

Fig. 2

A
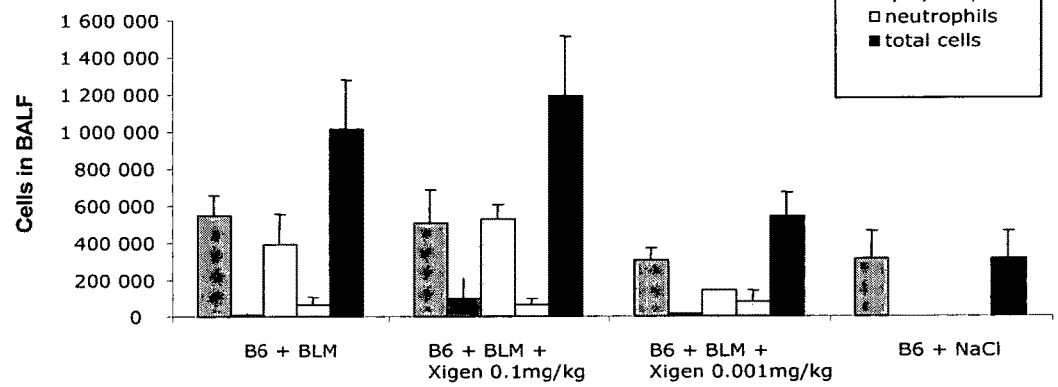
B
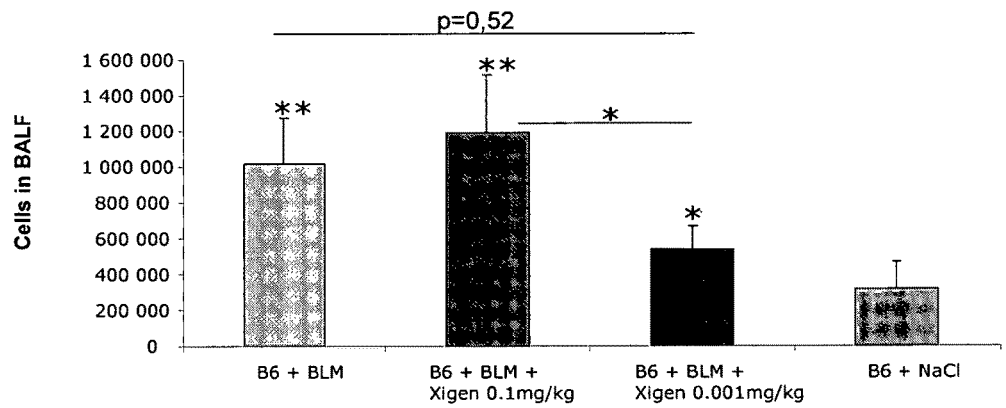
C
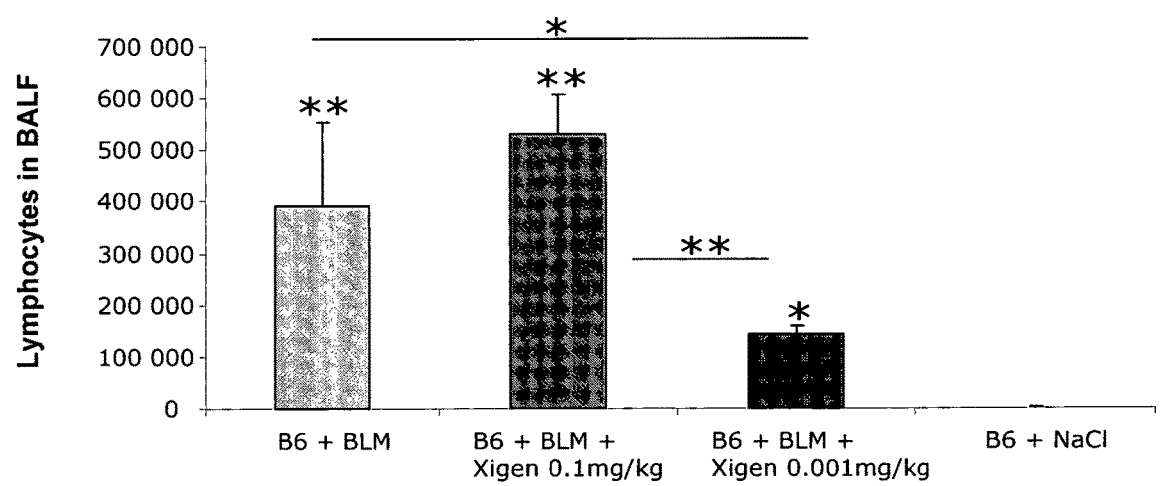
Fig. 10

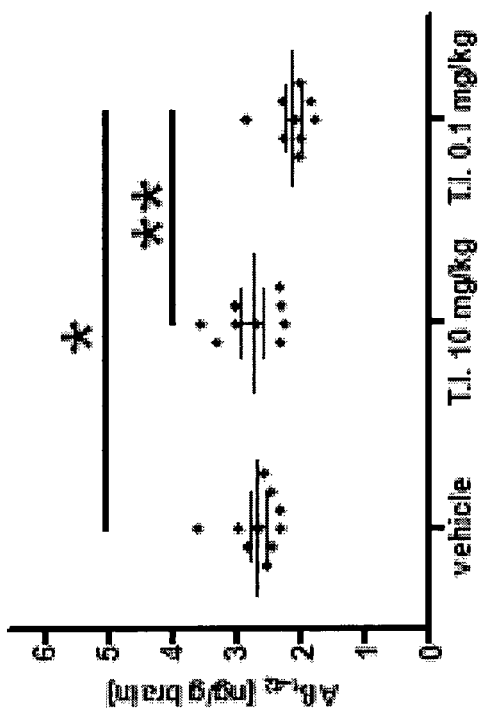
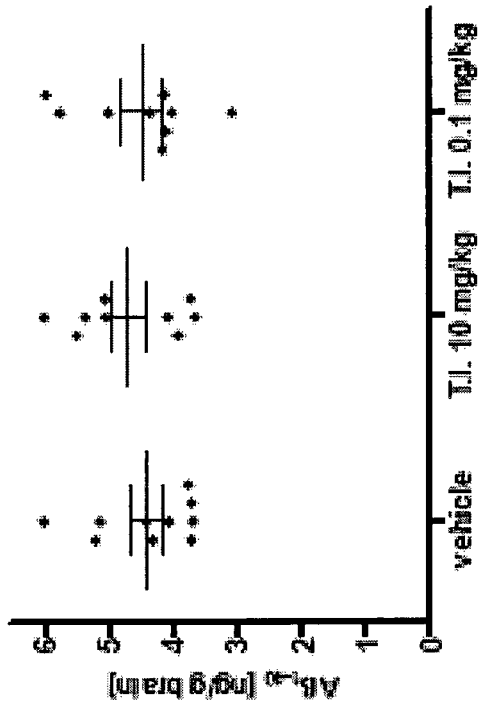
Fig. 11

Macrophage
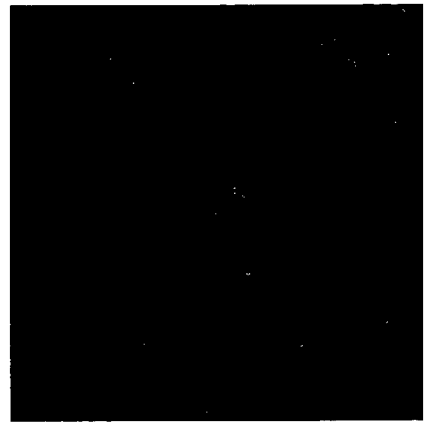
DMEM Control
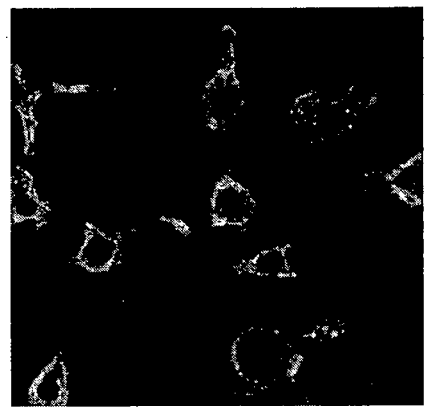
XG-102
Fig. 24

```
ccgccccagc tcagtccgaa ccccgcggcg gcggcggcct cctccacacg cctccacctc    60
cgccgccgcc gccgccgccg ccgcctcccg cgccgctctc cgcccggatg gccaggctga   120
gcccgggaat ggcggagcga gagagcggcc tgagcggggg tgccgcgtcc ccaccggccg   180
cttccccatt cctgggactg cacatcgcgt cgcctcccaa tttcaggctc acccatgata   240
tcagcctgga ggagtttgag gatgaagacc tttcggagat cactgatgag tgtggcatca   300
gcctgcagtg caaagacacc ttgtctctcc ggcccccgcg cgccgggcta ctgtctgcgg   360
gtagcagcgg tagcgcgggg agccggctgc aggcggagat gctgcagatg gacctgatcg   420
acgcggcaag tgacactccg ggcgccgagg acgacgaaga ggacgacgac gagctcgctg   480
cccaacggcc aggagtgggg ccttccaaag ccgagtctgg ccaggagccg gcgtctcgca   540
gccagggtca gggccagggc cccggcacag gctgcggaga cacctaccgg cccaagaggc   600
ctaccacgct caaccttttc ccgcaggtgc cgcggtctca ggacacgctg aataataact   660
ctttaggcaa aaagcacagt tggcaggacc gtgtgtctcg atcatcctcc cctctgaaga   720
caggggagca gacgcctcca catgaacata tctgcctgag tgatgagctg ccgccccagg   780
gcagtcctgt tcccacccag gatcgtggca cttccaccga cagcccttgt cgccgtactg   840
cagccaccca gatggcacct ccaagtggtc cccctgccac tgcacctggt ggccggggcc   900
actcccatcg agatcggtcc atatcagcag atgtgcggct cgaggcgact gaggagatct   960
acctgacccc agtgcagagg ccccagacc ctgcagaacc cacctccacc ttcttgccac  1020
ccactgagag ccggatgtct gtcagctcgg atcctgaccc tgccgcttac tctgtaactg  1080
cagggcgacc gcacccttcc atcagtgaag aggatgaggg cttcgactgt ctgtcatccc  1140
cagagcaagc tgagccacca ggtggagggt ggcggggaag cctcggggag ccaccaccgc  1200
ctccacgggc ctcactgagc tcggacacca gcgcactgtc ctacgactct gtcaagtaca  1260
cactggtggt ggatgagcat gcccagcttg agttggtgag cctgcggcca tgttttggag  1320
attacagtga cgaaagcgac tctgccactg tctatgacaa ctgtgcctct gcctcctcgc  1380
cctacgagtc agccattggt gaggaatatg aggaggcccc tcaaccccgg cctcccacct  1440
gcctgtcaga ggactccaca ccggatgagc ctgacgtcca cttctctaag aagtttctga  1500
atgtcttcat gagtggccgc tctcgttcct ccagtgccga gtcctttggg ctgttctcct  1560
gtgtcatcaa tggggaggag catgagcaaa cccatcgggc tatattcagg tttgtgcctc  1620
ggcatgaaga tgaacttgag ctggaagtgg acgaccctct gctggtggag ctgcaggcag  1680
```

Fig. 29

```
aagactattg gtatgaggcc tataacatgc gcactggagc ccgtggtgtc tttcctgcct    1740
actatgccat tgaggtcacc aaggagcctg agcacatggc agcccttgcc aaaaacagcg    1800
actggattga ccagttccgg gtgaagttcc tgggctctgt ccaggttcct tatcacaagg    1860
gcaatgatgt cctctgtgct gctatgcaaa agatcgccac cacccgccgg ctcaccgtgc    1920
actttaaccc gccctccagc tgtgtccttg aaatcagcgt taggggtgtc aagataggtg    1980
tcaaagctga tgaagctcag gaggccaagg gaaataaatg tagccacttt ttccagctaa    2040
aaaacatctc tttctgtggg taccatccaa agaacaacaa gtactttggg tttatcacta    2100
agcaccctgc tgaccaccgg tttgcctgcc atgtctttgt gtctgaagat tccaccaaag    2160
ccctggcaga gtctgtgggg cgtgcatttc agcagttcta caagcaattt gtggaatata    2220
cctgtcctac agaagatatc tacttggagt agcagcaacc cccctctctg cagcccctca    2280
gccccaggcc agtactagga cagctgactg ctgacaggat gttgtactgc cacgagagaa    2340
tgggggagtg agggctgttg gggtcggggg gcagggggttt ggggagaggc agatgcagtt    2400
tattgtaata tatggggtta gattaatcta tggaggacag tacaggctct ctcggggctg    2460
gggaagggca gggctggggt gggggtcagg catctggcca caaaggggtc ccctagggac    2520
agaggcgctg caccatcctg ggcttgtttc atactagagg ccctggcttt ctggctcttg    2580
ggtcctgcct tgacaaagcc cagccacctg gaagtgtcac cttcccttgt ccacctcacc    2640
cagtgccctg agctcatgct gagcccaagc acctccgaag gactttccag taaggaaatg    2700
gcaacatgtg acagtgagac cctgttctca tctgtggggc tccggcagct ccgaccccca    2760
gcctggccag cacgctgacc ctggcaagct tgtgtgttca agaaggaga gggccacagc    2820
aagccctgcc tgccagggaa ggttccctct cagctggccc cagccaactg gtcactgtct    2880
tgtcacctgg ctactactat taaagtgcca tttcttgtct gaaaaaaaaa aaaaaaaaa    2940
aaaaaactc gag                                                       2953
```

Fig. 29 (cont.)

Met Ala Arg Leu Ser Pro Gly Met Ala Glu Arg Glu Ser Gly Leu Ser
1               5                   10                  15

Gly Gly Ala Ala Ser Pro Pro Ala Ala Ser Pro Phe Leu Gly Leu His
        20              25              30

Ile Ala Ser Pro Pro Asn Phe Arg Leu Thr His Asp Ile Ser Leu Glu
        35              40              45

Glu Phe Glu Asp Glu Asp Leu Ser Glu Ile Thr Asp Glu Cys Gly Ile
    50              55              60

Ser Leu Gln Cys Lys Asp Thr Leu Ser Leu Arg Pro Pro Arg Ala Gly
65              70              75              80

Leu Leu Ser Ala Gly Ser Ser Gly Ser Ala Gly Ser Arg Leu Gln Ala
            85              90              95

Glu Met Leu Gln Met Asp Leu Ile Asp Ala Ala Ser Asp Thr Pro Gly
            100             105             110

Ala Glu Asp Asp Glu Glu Asp Asp Glu Leu Ala Ala Gln Arg Pro
        115             120             125

Gly Val Gly Pro Ser Lys Ala Glu Ser Gly Gln Glu Pro Ala Ser Arg
    130             135             140

Ser Gln Gly Gln Gly Gln Gly Pro Gly Thr Gly Cys Gly Asp Thr Tyr
145             150             155             160

Arg Pro Lys Arg Pro Thr Thr Leu Asn Leu Phe Pro Gln Val Pro Arg
            165             170             175

Ser Gln Asp Thr Leu Asn Asn Asn Ser Leu Gly Lys Lys His Ser Trp
            180             185             190

Gln Asp Arg Val Ser Arg Ser Ser Ser Pro Leu Lys Thr Gly Glu Gln
        195             200             205

Thr Pro Pro His Glu His Ile Cys Leu Ser Asp Glu Leu Pro Pro Gln
    210             215             220

Gly Ser Pro Val Pro Thr Gln Asp Arg Gly Thr Ser Thr Asp Ser Pro
225             230             235             240

Cys Arg Arg Thr Ala Ala Thr Gln Met Ala Pro Pro Ser Gly Pro Pro
            245             250             255

Fig. 30

Ala Thr Ala Pro Gly Gly Arg Gly His Ser His Arg Asp Arg Ser Ile
              260                 265                 270

Ser Ala Asp Val Arg Leu Glu Ala Thr Glu Glu Ile Tyr Leu Thr Pro
        275                 280                 285

Val Gln Arg Pro Pro Asp Pro Ala Glu Pro Thr Ser Thr Phe Leu Pro
    290             295                 300

Pro Thr Glu Ser Arg Met Ser Val Ser Ser Asp Pro Asp Pro Ala Ala
305             310                 315                 320

Tyr Ser Val Thr Ala Gly Arg Pro His Pro Ser Ile Ser Glu Glu Asp
            325                 330                 335

Glu Gly Phe Asp Cys Leu Ser Ser Pro Glu Gln Ala Glu Pro Pro Gly
            340                 345                 350

Gly Gly Trp Arg Gly Ser Leu Gly Glu Pro Pro Pro Pro Arg Ala
            355                 360                 365

Ser Leu Ser Ser Asp Thr Ser Ala Leu Ser Tyr Asp Ser Val Lys Tyr
    370                 375                 380

Thr Leu Val Val Asp Glu His Ala Gln Leu Glu Leu Val Ser Leu Arg
385                 390                 395                 400

Pro Cys Phe Gly Asp Tyr Ser Asp Glu Ser Asp Ser Ala Thr Val Tyr
                405                 410                 415

Asp Asn Cys Ala Ser Ala Ser Ser Pro Tyr Glu Ser Ala Ile Gly Glu
            420             425                 430

Glu Tyr Glu Glu Ala Pro Gln Pro Arg Pro Pro Thr Cys Leu Ser Glu
        435                 440                 445

Asp Ser Thr Pro Asp Glu Pro Asp Val His Phe Ser Lys Lys Phe Leu
    450             455                 460

Asn Val Phe Met Ser Gly Arg Ser Arg Ser Ser Ala Glu Ser Phe
465                 470                 475                 480

Gly Leu Phe Ser Cys Val Ile Asn Gly Glu Glu His Glu Gln Thr His
                485             490                 495

Arg Ala Ile Phe Arg Phe Val Pro Arg His Glu Asp Glu Leu Glu Leu
            500             505                 510

Fig. 30 (cont.)

Glu Val Asp Asp Pro Leu Leu Val Glu Leu Gln Ala Glu Asp Tyr Trp
            515                 520                 525

Tyr Glu Ala Tyr Asn Met Arg Thr Gly Ala Arg Gly Val Phe Pro Ala
    530                 535                 540

Tyr Tyr Ala Ile Glu Val Thr Lys Glu Pro Glu His Met Ala Ala Leu
545                 550                 555                 560

Ala Lys Asn Ser Asp Trp Ile Asp Gln Phe Arg Val Lys Phe Leu Gly
                565                 570                 575

Ser Val Gln Val Pro Tyr His Lys Gly Asn Asp Val Leu Cys Ala Ala
            580                 585                 590

Met Gln Lys Ile Ala Thr Thr Arg Arg Leu Thr Val His Phe Asn Pro
    595                 600                 605

Pro Ser Ser Cys Val Leu Glu Ile Ser Val Arg Gly Val Lys Ile Gly
610                 615                 620

Val Lys Ala Asp Glu Ala Gln Glu Ala Lys Gly Asn Lys Cys Ser His
625                 630                 635                 640

Phe Phe Gln Leu Lys Asn Ile Ser Phe Cys Gly Tyr His Pro Lys Asn
            645                 650                 655

Asn Lys Tyr Phe Gly Phe Ile Thr Lys His Pro Ala Asp His Arg Phe
            660                 665                 670

Ala Cys His Val Phe Val Ser Glu Asp Ser Thr Lys Ala Leu Ala Glu
        675                 680                 685

Ser Val Gly Arg Ala Phe Gln Gln Phe Tyr Lys Gln Phe Val Glu Tyr
    690                 695                 700

Thr Cys Pro Thr Glu Asp Ile Tyr Leu Glu
705                 710

Fig. 30 (cont.)

```
Met Ala Glu Arg Glu Ser Gly Gly Leu Gly Gly Gly Ala Ala Ser Pro
 1               5                  10                 15

Pro Ala Ala Ser Pro Phe Leu Gly Leu His Ile Ala Ser Pro Pro Asn
             20                  25              30

Phe Arg Leu Thr His Asp Ile Ser Leu Glu Glu Phe Glu Asp Glu Asp
         35                  40              45

Leu Ser Glu Ile Thr Asp Glu Cys Gly Ile Ser Leu Gln Cys Lys Asp
     50              55                  60

Thr Leu Ser Leu Arg Pro Pro Arg Ala Gly Leu Leu Ser Ala Gly Gly
 65              70                  75                  80

Gly Gly Ala Gly Ser Arg Leu Gln Ala Glu Met Leu Gln Met Asp Leu
             85                  90                  95

Ile Asp Ala Thr Gly Asp Thr Pro Gly Ala Glu Asp Asp Glu Glu Asp
             100             105                 110

Asp Asp Glu Glu Arg Ala Ala Arg Arg Pro Gly Ala Gly Pro Pro Lys
         115             120                 125

Ala Glu Ser Gly Gln Glu Pro Ala Ser Arg Gly Gln Gly Gln Ser Gln
     130             135                 140

Gly Gln Ser Gln Gly Pro Gly Ser Gly Asp Thr Tyr Arg Pro Lys Arg
 145             150                 155                 160

Pro Thr Thr Leu Asn Leu Phe Pro Gln Val Pro Arg Ser Gln Asp Thr
             165                 170             175

Leu Asn Asn Asn Ser Leu Gly Lys Lys His Ser Trp Gln Asp Arg Val
             180             185                 190

Ser Arg Ser Ser Ser Pro Leu Lys Thr Gly Glu Gln Thr Pro Pro His
     195             200                 205

Glu His Ile Cys Leu Ser Asp Glu Leu Pro Pro Gln Ser Gly Pro Ala
     210             215                 220

Pro Thr Thr Asp Arg Gly Thr Ser Thr Asp Ser Pro Cys Arg Arg Ser
 225             230                 235                 240

Thr Ala Thr Gln Met Ala Pro Pro Gly Gly Pro Pro Ala Ala Pro Pro
             245                 250                 255
```

Fig. 31

Gly Gly Arg Gly His Ser His Arg Asp Arg Ile His Tyr Gln Ala Asp
         260                 265                 270

Val Arg Leu Glu Ala Thr Glu Glu Ile Tyr Leu Thr Pro Val Gln Arg
         275                 280                 285

Pro Pro Asp Ala Ala Glu Pro Thr Ser Ala Phe Leu Pro Pro Thr Glu
         290                 295                 300

Ser Arg Met Ser Val Ser Ser Asp Pro Asp Pro Ala Ala Tyr Pro Ser
305                 310                 315                 320

Thr Ala Gly Arg Pro His Pro Ser Ile Ser Glu Glu Glu Glu Gly Phe
             325                 330                 335

Asp Cys Leu Ser Ser Pro Glu Arg Ala Glu Pro Pro Gly Gly Gly Trp
             340                 345                 350

Arg Gly Ser Leu Gly Glu Pro Pro Pro Pro Arg Ala Ser Leu Ser
             355                 360                 365

Ser Asp Thr Ser Ala Leu Ser Tyr Asp Ser Val Lys Tyr Thr Leu Val
    370                 375                 380

Val Asp Glu His Ala Gln Leu Glu Leu Val Ser Leu Arg Pro Cys Phe
385                 390                 395                 400

Gly Asp Tyr Ser Asp Glu Ser Asp Ser Ala Thr Val Tyr Asp Asn Cys
                405                 410                 415

Ala Ser Val Ser Ser Pro Tyr Glu Ser Ala Ile Gly Glu Glu Tyr Glu
             420                 425                 430

Glu Ala Pro Arg Pro Gln Pro Pro Ala Cys Leu Ser Glu Asp Ser Thr
         435                 440                 445

Pro Asp Glu Pro Asp Val His Phe Ser Lys Lys Phe Leu Asn Val Phe
    450                 455                 460

Met Ser Gly Arg Ser Arg Ser Ser Ala Glu Ser Phe Gly Leu Phe
465                 470                 475                 480

Ser Cys Ile Ile Asn Gly Glu Glu Gln Glu Gln Thr His Arg Ala Ile
             485                 490                 495

Phe Arg Phe Val Pro Arg His Glu Asp Glu Leu Glu Leu Glu Val Asp
             500                 505                 510

Fig. 31 (cont.)

```
Asp Pro Leu Leu Val Glu Leu Gln Ala Glu Asp Tyr Trp Tyr Glu Ala
        515                 520                 525

Tyr Asn Met Arg Thr Gly Ala Arg Gly Val Phe Pro Ala Tyr Tyr Ala
    530                 535                 540

Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
                565                 570                 575

Val Pro Tyr His Lys Gly Asn Asp Val Leu Cys Ala Ala Met Gln Lys
            580                 585                 590

Ile Ala Thr Arg Arg Leu Thr Val His Phe Asn Pro Pro Ser Ser
        595                 600                 605

Cys Val Leu Glu Ile Ser Val Arg Gly Val Lys Ile Gly Val Lys Ala
        610                 615                 620

Asp Asp Ser Gln Glu Ala Lys Gly Asn Lys Cys Ser His Phe Phe Gln
625                 630                 635                 640

Leu Lys Asn Ile Ser Phe Cys Gly Tyr His Pro Lys Asn Asn Lys Tyr
                645                 650                 655

Phe Gly Phe Ile Thr Lys His Pro Ala Asp His Arg Phe Ala Cys His
            660                 665                 670

Val Phe Val Ser Glu Asp Ser Thr Lys Ala Leu Ala Glu Ser Val Gly
        675                 680                 685

Arg Ala Phe Gln Gln Phe Tyr Lys Gln Phe Val Glu Tyr Thr Cys Pro
        690                 695                 700

Thr Glu Asp Ile Tyr Leu Glu
705                 710
```

Fig. 31 (cont.)

| | |
|---|---|
| atggcggagc gagaaagcgg cggcctggga gggggggccg cgtccccgcc cgccgcctcc | 60 |
| ccgttcctgg ggctgcacat cgcttcgcct cccaatttca ggctcaccca tgacatcagc | 120 |
| ctggaggagt ttgaggatga agacctctcg gagatcactg atgagtgtgg catcagctta | 180 |
| cagtgcaaag acaccctgtc cttacggccc ccgcgcgccg ggctgctctc tgcgggcggc | 240 |
| ggcggcgcgg ggagccggtt gcaggccgag atgctgcaga tggacctgat cgacgcgacg | 300 |
| ggggacactc ccggggccga ggacgacgag gaggacgacg acgaggagcg cgcggcccgg | 360 |
| cggccgggag cggggccgcc caaggccgag tccggccagg agccggcgtc ccgcggccag | 420 |
| ggccagagcc aaggccagag ccagggcccg ggcagcgggg acacgtaccg gcccaagcgg | 480 |
| cccaccacgc tcaacctctt tccgcaggtg ccgcggtctc aggacacact gaataataat | 540 |
| tctctgggca aaaagcacag ttggcaggat cgggtgtctc gatcatcctc acccctgaag | 600 |
| acaggggagc agacaccacc gcatgaacac atctgcctga gcgatgagct gccccccag | 660 |
| agcggccccg cccccaccac agatcgaggc acctccaccg acagcccttg ccgccgcagc | 720 |
| acagccaccc agatggcacc tccgggtggt cccctgctg ccccgcctgg gggtcggggc | 780 |
| cactcgcatc gagaccgaat ccactaccag gccgatgtgc gactagaggc cactgaggag | 840 |
| atctacctga ccccagtgca gaggccccca gacgctgcag agcccacctc cgccttcctg | 900 |
| ccgcccactg agagccggat gtcagtcagc tccgatccag accctgccgc ctaccctcc | 960 |
| acggcagggc ggccgcaccc ctccatcagt gaagaggaag agggcttcga ctgcctgtcg | 1020 |
| tccccagagc gggctgagcc cccaggcgga gggtggcggg ggagcctggg ggagccgccg | 1080 |
| ccacctccac gggcctctct gagctcggac accagcgccc tgtcctatga ctctgtcaag | 1140 |
| tacacgctgg tggtagatga gcatgcacag ctggagctgg tgagcctgcg gccgtgcttc | 1200 |
| ggagactaca gtgacgagag tgactctgcc accgtctatg acaactgtgc ctccgtctcc | 1260 |
| tcgccctatg agtcggccat cggagaggaa tatgaggagg ccccgcggcc ccagccccct | 1320 |
| gcctgcctct ccgaggactc cacgcctgat gaacccgacg tccatttctc caagaaattc | 1380 |
| ctgaacgtct tcatgagtgg ccgctcccgc tcctccagtg ctgagtcctt cgggctgttc | 1440 |
| tcctgcatca tcaacgggga ggagcaggag cagacccacc gggccatatt caggtttgtg | 1500 |
| cctcgacacg aagacgaact tgagctggaa gtggatgacc ctctgctagt ggagctccag | 1560 |
| gctgaagact actggtacga ggcctacaac atgcgcactg gtgcccgggg tgtctttcct | 1620 |
| gcctattacg ccatcgaggt caccaaggag cccgagcaca tggcagccct ggccaaaaac | 1680 |
| agtgactggg tggaccagtt ccgggtgaag ttcctgggct cagtccaggt tccctatcac | 1740 |

Fig. 32

```
aagggcaatg acgtcctctg tgctgctatg caaaagattg ccaccacccg ccggctcacc    1800
gtgcacttta acccgccctc cagctgtgtc ctggagatca gcgtgcgggg tgtgaagata    1860
ggcgtcaagg ccgatgactc ccaggaggcc aaggggaata aatgtagcca cttttccag    1920
ttaaaaaaca tctctttctg cggatatcat ccaaagaaca acaagtactt tgggttcatc    1980
accaagcacc ccgccgacca ccggtttgcc tgccacgtct ttgtgtctga agactccacc    2040
aaagccctgg cagagtccgt ggggagagca ttccagcagt tctacaagca gtttgtggag    2100
tacacctgcc ccacagaaga tatctacctg gagtag                              2136
```

Fig. 32 (cont.)

Effect of XG-102 (DJNK inhibitor) on JNK activation during isolation

**Effect of XG-102 (DJNK inhibitor) on c-fos gene expression
(Measured by Realtime RTPCr)**

XG-1 02 increases islet viability (OCR/DNA) measured after 7 days of culture

**Each point represents a different isolation

***Without DJNK 1 of 5 (20%) consecutive isolations met the release criteria. With DJNKi 6/6 (100%) consecutive isolations met the release criteria and were successfully transplanted into an NHP

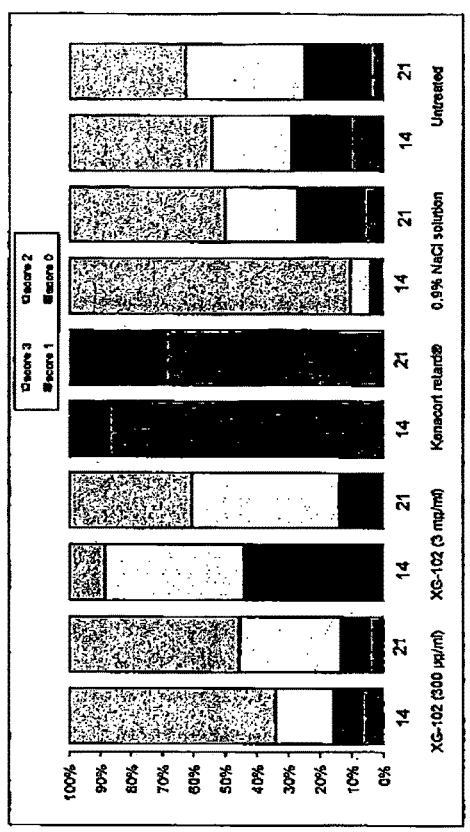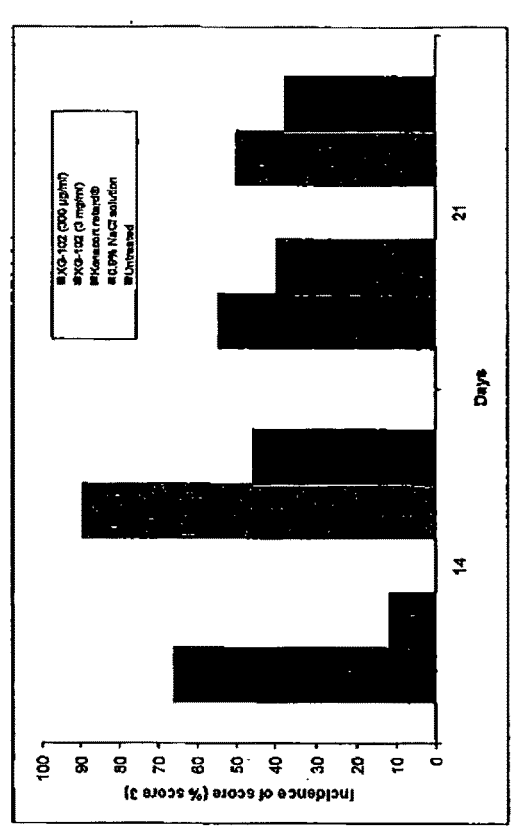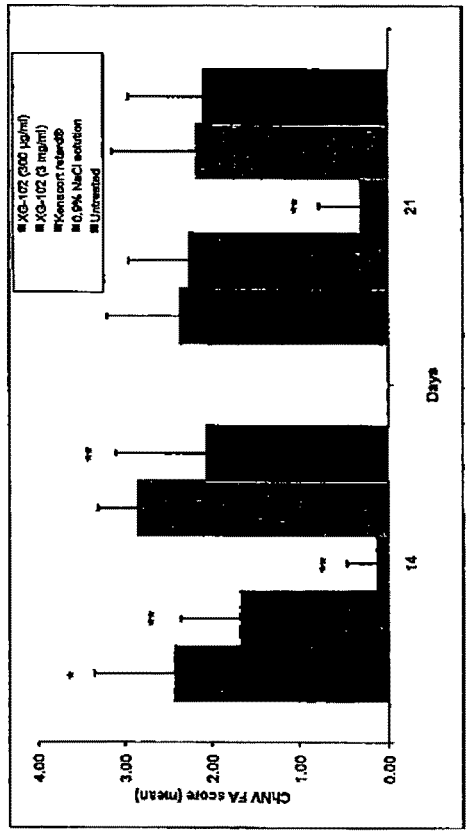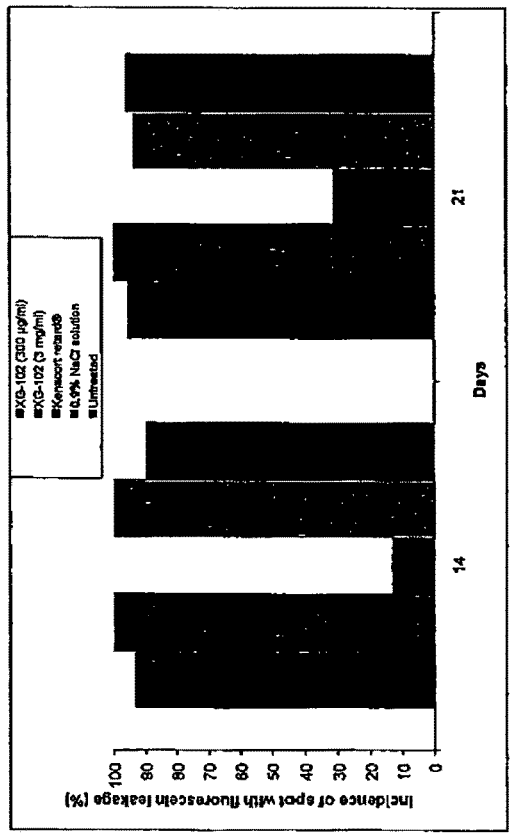
Fig. 39

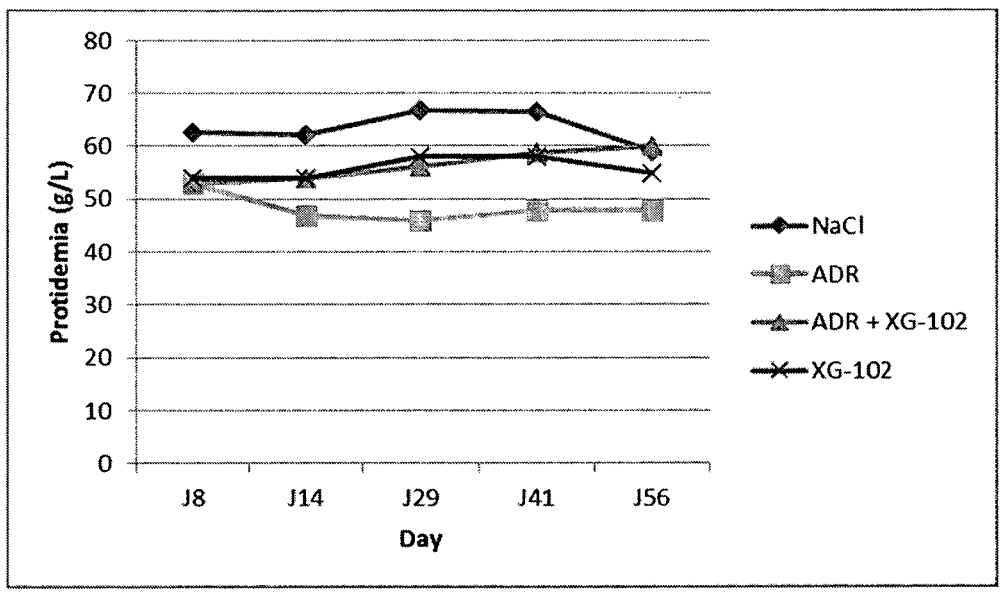
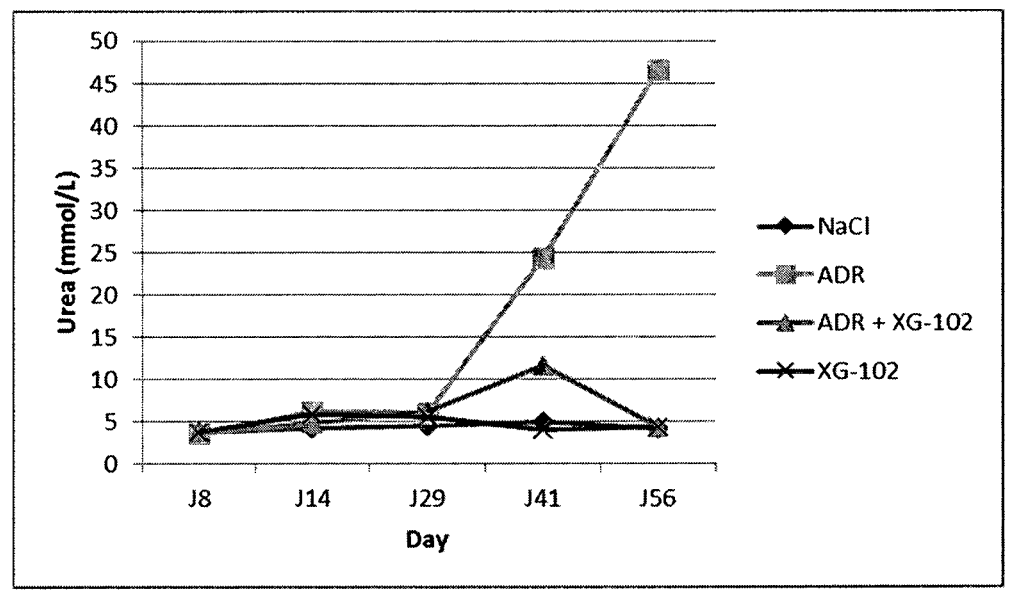
Fig. 48

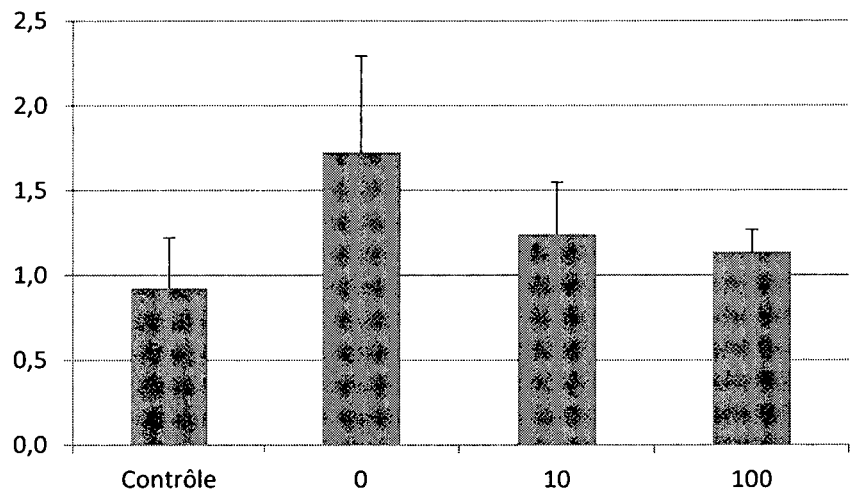
A
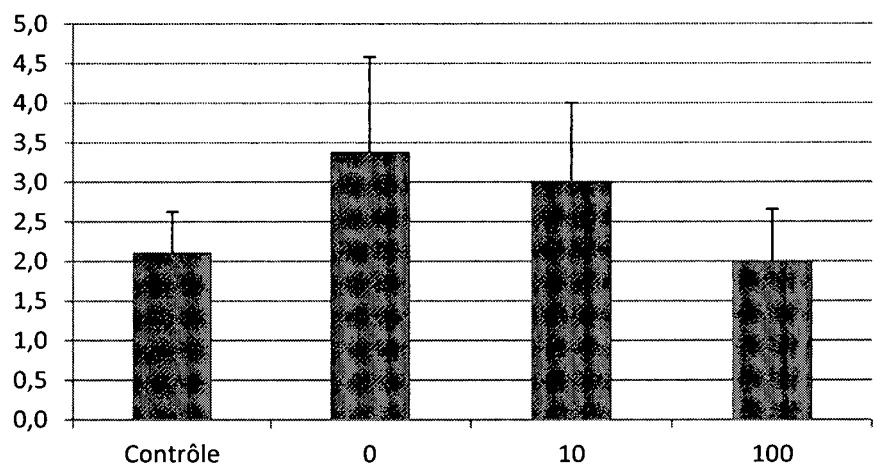
B
Fig. 56

| | 90 µg XG-102 (N=47) | | 900 µg XG-102 (N=48) | | Dexamethasone (N=50) | | Exact Chi-square test P values | |
|---|---|---|---|---|---|---|---|---|
| | Total # events | # patients (%) | Total # events | # patients (%) | Total # events | # patients (%) | 90µg XG-102 vs. Dexamethasone | 900µg XG-102 vs. Dexamethasone |
| Adverse event summary | 78 | 31 (66.0%) | 69 | 32 (66.7%) | 55 | 29 (58.0%) | 0.531 | 0.410 |
| Adverse event up to 24 hours after the subconjunctival injection of study treatment | 31 | 16 (34.0%) | 19 | 13 (27.1%) | 19 | 15 (30.0%) | 0.828 | 0.825 |
| Adverse event after 24 hours after the subconjunctival injection of study treatment | 47 | 27 (57.4%) | 50 | 24 (50.0%) | 36 | 19 (38.0%) | 0.068 | 0.309 |
| Serious adverse event summary | 4 | 4 (8.5%) | 3 | 3 (6.3%) | 2 | 2 (4.0%) | 0.426 | 0.674 |
| Serious adverse event up to 24 hours after the subconjunctival injection of study treatment | 1 | 1 (2.1%) | 0 | 0 (0.0%) | 0 | 0 (0.0%) | 0.485 | 0.309 |
| Serious adverse event after 24 hours after the subconjunctival injection of study treatment | 3 | 3 (6.4%) | 3 | 3 (6.3%) | 2 | 2 (4.0%) | 0.671 | 0.674 |

Data are number of patients (%), N=Number of patients in each group, #=number, µg=microgram, %=percentage.

Fig. 64

| | 90 μg XG-102 (N=47) | | 900 μg XG-102 (N=48) | | Dexamethasone (N=50) | | Exact Chi-square test P values | |
|---|---|---|---|---|---|---|---|---|
| | Total # events | # patients (%) | Total # events | # patients (%) | Total # events | # patients (%) | 90μg XG-102 vs. Dexamethasone | 900μg XG-102 vs. Dexamethasone |
| Cardiac disorders | | | | | | | | |
| Tachycardia | 2 | 2 (4.3%) | 0 | 0 (0.0%) | 1 | 1 (2.0%) | 0.610 | 1.000 |
| Eye disorders | | | | | | | | |
| Cataract | 2 | 2 (4.3%) | 3 | 3 (6.3%) | 4 | 4 (8.0%) | 0.678 | 1.000 |
| Conjunctival hyperaemia | 1 | 1 (2.1%) | 3 | 3 (6.3%) | 2 | 2 (4.0%) | 1.000 | 0.674 |
| Corneal oedema | 4 | 4 (8.5%) | 2 | 2 (4.2%) | 5 | 5 (10.0%) | 1.000 | 0.436 |
| Cyclitic membrane | 3 | 3 (6.4%) | 1 | 1 (2.1%) | 1 | 1 (2.0%) | 0.352 | 1.000 |
| Eye inflammation | 5 | 5 (10.6%) | 2 | 2 (4.2%) | 0 | 0 (0.0%) | 0.024 | 0.237 |
| Eye pain | 3 | 2 (4.3%) | 8 | 7 (14.6%) | 1 | 1 (2.0%) | 0.610 | 0.029 |
| Eyelid oedema | 5 | 5 (10.6%) | 2 | 2 (4.2%) | 1 | 1 (2.0%) | 0.105 | 0.613 |
| Hyphaema | 1 | 1 (2.1%) | 2 | 2 (4.2%) | 1 | 1 (2.0%) | 1.000 | 0.613 |
| Macular oedema | 2 | 2 (4.3%) | 4 | 4 (8.3%) | 3 | 3 (6.0%) | 1.000 | 0.712 |
| Punctate keratitis | 3 | 3 (6.4%) | 2 | 2 (4.2%) | 3 | 3 (6.0%) | 1.000 | 1.000 |
| Retinal detachment | 2 | 2 (4.3%) | 3 | 3 (6.3%) | 2 | 2 (4.0%) | 1.000 | 0.674 |
| Uveitive keratitis | 3 | 3 (6.4%) | 2 | 2 (4.2%) | 1 | 1 (2.0%) | 0.352 | 0.613 |
| Vitreous haemorrhage | 1 | 1 (2.1%) | 1 | 1 (2.1%) | 1 | 1 (2.0%) | 1.000 | 1.000 |
| Investigations | | | | | | | | |
| Aspartate Transaminase increased | 1 | 1 (2.1%) | 1 | 1 (2.1%) | 1 | 1 (2.0%) | 1.000 | 1.000 |
| Blood creatine phosphokinase increased | 2 | 2 (4.3%) | 2 | 2 (4.2%) | 4 | 4 (8.0%) | 0.678 | 0.678 |
| Blood creatinine increased | 0 | 0 (0.0%) | 2 | 2 (4.2%) | 1 | 1 (2.0%) | 1.000 | 0.613 |
| Blood pressure increased | 1 | 1 (2.1%) | 2 | 2 (4.2%) | 1 | 1 (2.0%) | 1.000 | 0.613 |
| Gamma-glutamyltransferase increased | 0 | 0 (0.0%) | 3 | 3 (6.3%) | 0 | 0 (0.0%) | | 0.114 |
| Intraocular pressure increased | 12 | 11 (23.4%) | 6 | 5 (10.4%) | 8 | 7 (14.0%) | 0.299 | 0.760 |
| White blood cell count increased | 0 | 0 (0.0%) | 3 | 3 (6.3%) | 0 | 0 (0.0%) | | 0.114 |
| Nervous system disorders | | | | | | | | |
| Headache | 2 | 2 (4.3%) | 1 | 1 (2.1%) | 0 | 0 (0.0%) | 0.232 | 0.490 |
| Surgical and medical procedures | | | | | | | | |
| Retinal operation | 1 | 1 (2.1%) | 2 | 2 (4.2%) | 0 | 0 (0.0%) | 0.485 | 0.237 |

Data are number of patients(%), N=Number of patients in each group, #=number t, μg=microgram, %=percentage. For two patients - FR-01-0001(XG-102 90 μg) and FR-01-0015 (dexamethasone), Intraocular Hypertension was coded as 'Ocular hypertension'. SOC - EYE

Fig. 65

| | 90 μg XG-102 (N=47) | | 900 μg XG-102 (N=48) | | Dexamethasone (N=50) | | Exact Chi-square test P values | |
|---|---|---|---|---|---|---|---|---|
| | Total # events | # patients (%) | Total # events | # patients (%) | Total # events | # patients (%) | 90μg XG-102 vs. Dexamethasone | 900μg XG-102 vs. Dexamethasone |
| Eye disorders | 2 | 2 (4.3%) | 1 | 1 (2.1%) | 2 | 2 (4.0%) | 1.000 | 1.000 |
| Lens dislocation | 0 | 0 (0.0%) | 1 | 1 (2.1%) | 0 | 0 (0.0%) | | 0.490 |
| Retinal detachment | 0 | 0 (0.0%) | 0 | 0 (0.0%) | 2 | 2 (4.0%) | 0.495 | 0.495 |
| Retinal oedema | 1 | 1 (2.1%) | 0 | 0 (0.0%) | 0 | 0 (0.0%) | 0.485 | |
| Choroidal haematoma | 1 | 1 (2.1%) | 0 | 0 (0.0%) | 0 | 0 (0.0%) | 0.485 | |
| Investigations | 1 | 1 (2.1%) | 0 | 0 (0.0%) | 0 | 0 (0.0%) | 0.485 | |
| Intraocular pressure increased | 1 | 1 (2.1%) | 0 | 0 (0.0%) | 0 | 0 (0.0%) | 0.485 | |
| Surgical and medical procedures | 1 | 1 (2.1%) | 2 | 2 (4.2%) | 0 | 0 (0.0%) | 0.485 | 0.237 |
| Retinal operation | 1 | 1 (2.1%) | 2 | 2 (4.2%) | 0 | 0 (0.0%) | 0.485 | 0.237 |

*Data are number of patients (%), N=Number of patients in each group, n=number, μg=microgram, %=percentage.*

Fig. 66

| Group | Treatment | | | | Body weight ± SD (g) | | | | MBWC ± SD (%) | |
|---|---|---|---|---|---|---|---|---|---|---|
| | substance | Dose (mg/kg/inj) | Route of administration | Treatment schedule | D0 | D10 | D42 | D94 | D10 to D42 | D10 to D94 |
| 1 | Vehicle | - | IV | (Q4Dx4)x2 | 22.4 ± 1.2 | 22.1 ± 1.6 | 25.9 ± 1.4 | 27.8 ± 3.4 | +17.7 ± 9.7 | +25.7 ± 15.9 |
| 2 | XG-102 | 1 | IV | (Q4Dx4)x2 | 22.4 ± 1.0 | 22.0 ± 1.7 | 25.6 ± 1.7 | 28.0 ± 0.9 | +17.1 ± 10.1 | +28.2 ± 11.9 |

| Group | Body weight ± SD (g) | | | | MBWC ± SD (%) | |
|---|---|---|---|---|---|---|
| | D0 | D10 | D42 | D94 | D10 to D42 | D10 to D94 |
| XG-102 1mg/kg | NS | NS | NS | NS | NS | NS |

Fig. 70

| Group | Treatment | | | | Body weight ± SD (g) | | | | MBWC ± SD (%) | |
|---|---|---|---|---|---|---|---|---|---|---|
| | substance | Dose (mg/kg/inj) | Route of administration | Treatment schedule | D0 | D10 | D41 | D67 | D10 to D41 | D10 to D67 |
| 1 | Vehicle | - | IV | (Q4Dx4)x2 | 19.7 ± 1.4 | 20.9 ± 1.5 | 23.4 ± 1.8 | 23.6 ± 1.8 | +11.7 ± 3.1 | +13.0 ± 5.8 |
| 2 | XG-102 | 0.1 | IV | (Q4Dx4)x2 | 19.4 ± 1.2 | 21.0 ± 1.3 | 23.3 ± 1.1 | 23.9 ± 1.1 | +11.4 ± 3.9 | +15.0 ± 4.1 |
| 3 | XG-102 | 1 | IV | (Q4Dx4)x2 | 19.4 ± 1.2 | 21.0 ± 1.3 | 23.4 ± 1.5 | 25.1 ± 1.7 | +11.2 ± 5.0 | +21.7 ± 6.8 |
| 4 | XG-102 | 5 | IV | (Q4Dx4)x2 | 19.6 ± 1.1 | 21.1 ± 1.3 | 23.8 ± 1.4 | 25.2 ± 1.4 | +12.8 ± 3.2 | +19.6 ± 7.4 |

Fig. 72

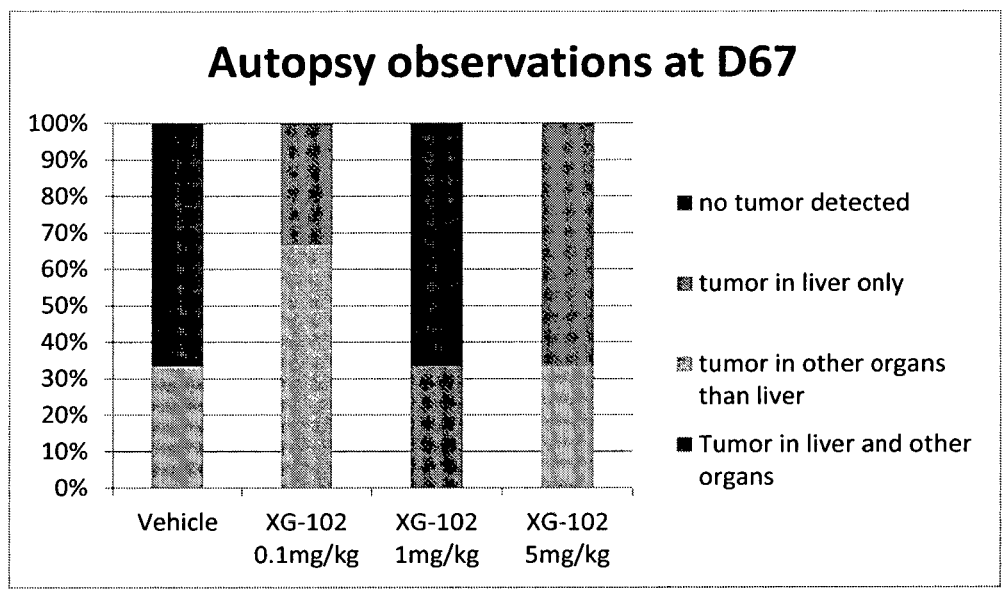
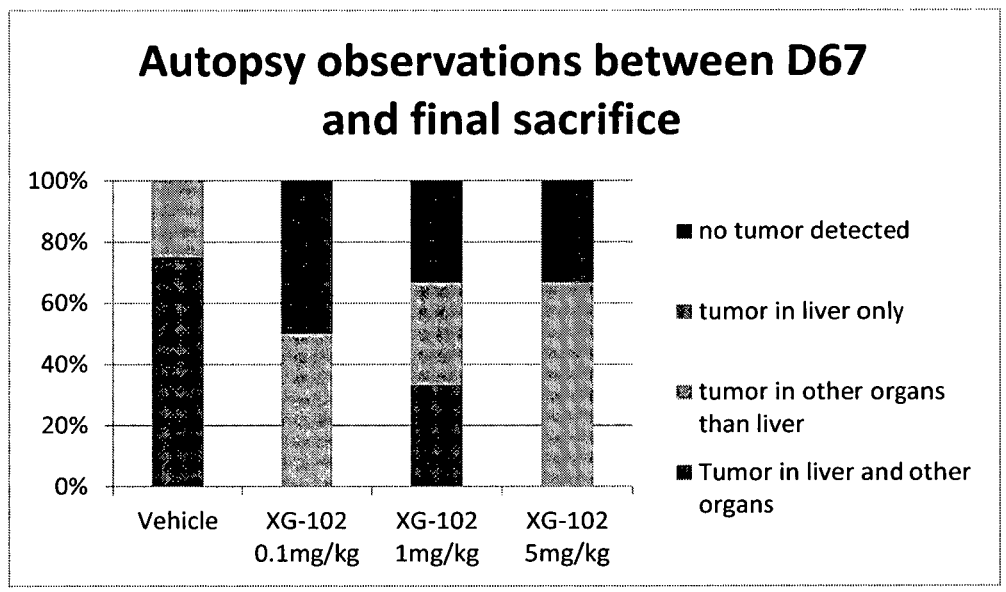
Fig. 74

USE OF CELL-PERMEABLE PEPTIDE INHIBITORS OF THE JNK SIGNAL TRANSDUCTION PATHWAY FOR THE TREATMENT OF VARIOUS DISEASES

SEQUENCE LISTING SUBMISSION VIA EFS-WEB

A computer readable text file, entitled "067802-5033_SequenceListing.txt," created on or about 26 Feb. 2016, with a file size of about 210 kb contains the sequence listing for this application and is hereby incorporated by reference in its entirety.

The present invention refers to the use of protein kinase inhibitors and more specifically to the use of inhibitors of the protein kinase c-Jun amino terminal kinase, JNK inhibitor sequences, chimeric peptides, or of nucleic acids encoding same as well as pharmaceutical compositions containing same, for the treatment of various novel diseases or disorders strongly related to JNK signaling.

The c-Jun amino terminal kinase (JNK) is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These receptors can include cytokine receptors, serpentine receptors and receptor tyrosine kinases. In mammalian cells, JNK has been implicated in biological processes such as oncogenic transformation and mediating adaptive responses to environmental stress. JNK has also been associated with modulating immune responses, including maturation and differentiation of immune cells, as well as effecting programmed cell death in cells identified for destruction by the immune system. This unique property makes JNK signaling a promising target for developing pharmacological intervention. Among several neurological disorders, JNK signaling is particularly implicated in ischemic stroke and Parkinson's disease, but also in other diseases as mentioned further below. Furthermore, the mitogen-activated protein kinase (MAPK) p38alpha was shown to negatively regulate the cell proliferation by antagonizing the JNK-dun-pathway. The mitogen-activated protein kinase (MAPK) p38alpha therefore appears to be active in suppression of normal and cancer cell proliferation and, as a further, demonstrates the involvement of JNK in cancer diseases (see e.g. Hui et al., Nature Genetics, Vol 39, No. 6, June 2007). It was also shown, that c-Jun N-terminal Kinase (JNK) is involved in neuropathic pain produced by spinal nerve ligation (SNL), wherein SNL induced a slow and persistent activation of JNK, in particular JNK1, whereas p38 mitogen-activated protein kinase activation was found in spinal microglia after SNL, which had fallen to near basal level by 21 days (Zhuang et al., The Journal of Neuroscience, Mar. 29, 2006, 26(13):3551-3560)).

Inhibition or interruption of JNK signaling pathway, particularly the provision of inhibitors of the JNK signaling pathway, thus appears to be a promising approach in combating disorders strongly related to JNK signaling. However, there are only a few inhibitors of the JNK signaling pathway known so far.

Inhibitors of the JNK signaling pathway as already known in the prior art, particularly include e.g. upstream kinase inhibitors (for example, CEP-1347), small chemical inhibitors of JNK (SP600125 and AS601245), which directly affect kinase activity e.g. by competing with the ATP-binding site of the protein kinase, and peptide inhibitors of the interaction between JNK and its substrates (D-JNKI and I-JIP) (see e.g. Kuan et al., Current Drug Targets—CNS & Neurological Disorders, February 2005, vol. 4, no. 1, pp. 63-67(5)).

The upstream kinase inhibitor CEP-1347 (KT7515) is a semisynthetic inhibitor of the mixed lineage kinase family. CEP-1347 (KT7515) promotes neuronal survival at dosages that inhibit activation of the c-Jun amino-terminal kinases (JNKs) in primary embryonic cultures and differentiated PC12 cells after trophic withdrawal and in mice treated with 1-methyl-4-phenyl tetrahydropyridine. Further, CEP-1347 (KT7515) can promote long term-survival of cultured chick embryonic dorsal root ganglion, sympathetic, ciliary and motor neurons (see e.g. Borasio et al., Neuroreport. 9(7): 1435-1439, May 11th 1998).

The small chemical JNK inhibitor SP600125 was found to reduce the levels of c-Jun phosphorylation, to protect dopaminergic neurons from apoptosis, and to partly restore the level of dopamine in MPTP-induced PD in C57BL/6N mice (Wang et al., Neurosci Res. 2004 February; 48(2); 195-202). These results furthermore indicate that JNK pathway is the major mediator of the neurotoxic effects of MPTP in vivo and inhibiting JNK activity may represent a new and effective strategy to treat PD.

A further example of small chemical inhibitors is the aforementioned JNK-Inhibitor AS601245. AS601245 inhibits the JNK signalling pathway and promotes cell survival after cerebral ischemia. In vivo, AS601245 provided significant protection against the delayed loss of hippocampal CA1 neurons in a gerbil model of transient global ischemia. This effect is mediated by JNK inhibition and therefore by c-Jun expression and phosphorylation (see e.g. Carboni et al., J Pharmacol Exp Ther. 2004 July; 310(1):25-32. Epub 2004 Feb. 26).

A third class of inhibitors of the JNK signaling pathway represent peptide inhibitors of the interaction between JNK and its substrates, as mentioned above. As a starting point for construction of such JNK inhibitor peptides a sequence alignment of naturally occurring JNK proteins may be used. Typically, these proteins comprise JNK binding domains (JBDs) and occur in various insulin binding (IB) proteins, such as IB1 or IB2. The results of such an exemplary sequence alignment is e.g. a sequence alignment between the JNK binding domains of IB1 [SEQ ID NO: 13], IB2 [SEQ ID NO: 14], c-Jun [SEQ ID NO: 15] and ATF2 [SEQ ID NO: 16] (see e.g. FIGS. 1A-1C). Such an alignment reveals a partially conserved 8 amino acid sequence (see e.g. FIG. 1A). A comparison of the JBDs of IB1 and IB2 further reveals two blocks of seven and three amino acids that are highly conserved between the two sequences.

Sequences constructed on basis of such an alignment are e.g. disclosed in WO 01/27268 or in WO 2007/031280. WO 2007/031280 and WO 01/27268 disclose small cell permeable fusion peptides, comprising a so-called TAT cell permeation sequence derived from the basic trafficking sequence of the HIV-TAT protein and a minimum 20 amino acid inhibitory sequence of IB1. Both components are covalently linked to each other. Exemplary (and at present the only) inhibitors of the MAPK-JNK signaling pathway disclosed in both WO 2007/031280 and WO 01/27268, are e.g. L-JNKI1 (JNK-inhibitor peptide composed of L amino acids) or the protease resistant D-JNKI1 peptides (JNK-inhibitor peptide composed of non-native D amino acids). These JNK-inhibitor (JNKI) peptides are specific for JNK (JNK1, JNK2 and JNK3). In contrast to those small compound inhibitors as discussed above, the inhibitor sequences in WO 2007/031280 or WO 01/27268, e.g. JNKI1, rather inhibit the interaction between JNK and its substrate. By its trafficking sequence derived from TAT, the fusion peptide is efficiently transported into cells. Due to the novel properties obtained by the trafficking component the fusion peptides are actively transported into cells, where they remain effective until proteolytic degradation.

However, peptides according to WO 2007/031280 or WO 01/27268 have only shown to be active in a particularly limited number of diseases, particularly non-malignant or immunological-related cell proliferative diseases.

One object of the present invention is thus, to identify further diseases, which can be combated with JNK inhibitor peptides. Another object of the present invention is to provide (the use of) new JNK inhibitor peptides and derivatives thereof for the treatment of those diseases and of diseases not yet or already known to be strongly related to JNK signaling.

This object is solved by the use of a JNK inhibitor sequence, preferably as defined herein, typically comprising less than 150 amino acids in length for the preparation of a pharmaceutical composition for treating various inflammatory or non-inflammatory diseases strongly related to JNK signaling in a subject, wherein the diseases or disorders are selected from the following groups:

(a) encephalomyelitis, in particular acute disseminated encephalomyelitis, spondylitis, in particular ankylosing spondylitis, antisynthetase syndrome, dermatitis, in particular atopic dermatitis or contact dermatitis, hepatitis, in particular autoimmune hepatitis, autoimmune peripheral neuropathy, pancreatitis, in particular autoimmune pancreatitis, Behçet's disease, Bickerstaff's encephalitis, Blau syndrome, Coeliac disease, Chagas disease, polyneuropathy, in particular chronic inflammatory demyelinating polyneuropathy, osteomyelitis, in particular chronic recurrent multifocal osteomyelitis, Churg-Strauss syndrome, Cogan syndrome, giant-cell arteritis, CREST syndrome, vasculitis, in particular cutaneous small-vessel vasculitis and urticarial vasculitis, dermatitis herpetiformis, dermatomyositis, systemic scleroderma, Dressler's syndrome, drug-induced lupus erythematosus, discoid lupus erythematosus, enthesitis, eosinophilic fasciitis, eosinophilic gastroenteritis, erythema nodosum, Idiopathic pulmonary fibrosis, gastritis, Grave's disease, Guillain-barré syndrome, Hashimoto's thyroiditis, Henoch-Schonlein purpura, Hidradenitis suppurativa, Idiopathic inflammatory demyelinating diseases, myositis, in particular inclusion body myositis, cystitis, in particular interstitial cystitis, Kawasaki disease, Lichen planus, lupoid hepatitis, Majeed syndrome, Ménière's disease, microscopic polyangiitis, mixed connective tissue disease, myelitis, in particular neuromyelitis optica, thyroiditis, in particular Ord's thyroiditis, rheumatism, in particular palindromic rheumatism, Parsonage-Turner syndrome, pemphigus vulgaris, perivenous encephalomyelitis, polyarteritis nodosa, polymyalgia, in particular polymyalgia rheumatica, polymyositis, cirrhosis, in particular primary biliary cirrhosis, cholangitis, in particular primary sclerosing cholangitis, progressive inflammatory neuropathy, Rasmussen's encephalitis, relapsing polychondritis, arthritis, in particular reactive arthritis (Reiter disease) and rheumatoid arthritis, rheumatic fever, sarcoidosis, Schnitzler syndrome, serum sickness, spondyloarthropathy, Takayasu's arteritis, Tolosa-Hunt syndrome, transverse myelitis, and Wegener's granulomatosis, (b) eye inflammatory diseases, in particular selected from uveitis, scleritis, corneal surgery, conjunctivitis, non-infectious keratitis, iritis, chorioretinal inflammation, inflammatory diseases damaging the retina of the eye (retinopathy), in particular diabetic retinopathy, arterial hypertension induced hypertensive retinopathy, radiation induced retinopathy, sun-induced solar retinopathy, trauma-induced retinopathy, e.g. Purtscher's retinopathy, retinopathy of prematurity (ROP) and hyperviscosity-related retinopathy, (c) Addison's disease, Agammaglobulinemia, Alopecia areata, Amytrophic lateral sclerosis, Antiphospholipid syndrome, Atopic allergy, Autoimmune aplastic anemia, Autoimmune cardiomyopathy, Autoimmune enteropathy, Autoimmune hemolytic anemia, Autoimmune inner ear, disease, Autoimmune lymphoproliferative syndrome, Autoimmune polyendocrine syndrome, Autoimmune progesterone dermatitis, Idiopathic thrombocytopenic purpura, Autoimmune urticaria, Balo concentric sclerosis, Bullous pemphigoid, Castleman's disease, Cicatricial pemphigoid, Cold agglutinin disease, Complement component 2 deficiency associated disease, Cushing's syndrome, Dagos disease, Adiposis dolorosa, Eosinophilic pneumonia, Epidermolysis bullosa acquisita, Hemolytic disease of the newborn, Cryoglobulinemia, Evans syndrome, Fibrodysplasia ossificans progressive, Gastrointestinal pemphigoid, Goodpasture's syndrome, Hashimoto's encephalopathy, Gestational pemphigoid, Hughes-stovin syndrome, Hypogammaglobulinemia, Lambert-eaton myasthenic syndrome, Lichen sclerosus, Morphea, Pityriasis lichenoides et varioliformis acuta, Myasthenia gravis, Narcolepsy, Neuromyotonia, Opsoclonus myoclonus syndrome, Paraneoplastic cerebellar degeneration, Paroxysmal nocturnal hemoglobinuria, Parry-romberg syndrome, Pernicious anemia, POEMS syndrome, Pyoderma gangrenosum, Pure red cell aplasia, Raynaud's phenomenon, Restless legs syndrome, Retroperitoneal fibrosis, Autoimmune polyendocrine syndrome type 2, Stiff person syndrome, Susac's syndrome, Febrile neutrophilic dermatosis, Sydenham's chorea, Thrombocytopenia, and vitiligo, (d) arthritis, in particular juvenile idiopathic arthritis, psoriastic arthritis and rheumatoid arthritis, and arthrosis, and osteoarthritis, (e) skin diseases in particular selected from psoriasis, eczema, dermatitis, acne, mouth ulcers, erythema, lichen plan, sarcoidose, vascularitis, adult linear IgA disease (f) tauopathies, amyloidoses and prion diseases, (g) polypes.

(h) inflammatory diseases of the mouth or the jaw bone, in particular pulpitis, periimplantitis, periodontitis, gingivitis, stomatitis, mucositis, desquamative disorders, temporomandibular joint disorder, (i) osteonecrosis (j) age-related macular degeneration (AMD), in particular the wet or the dry form of age-related macular degeneration, and cataract (k) fibrotic diseases and/or disorders particularly selected from lung, heart, liver, bone marrow, mediastinum, retroperitoneum, skin, intestine, joint, and shoulder fibrosis, (l) kidney diseases and/or disorders in particular selected from glomerulonephritis in general, in particular membrano-proliferative glomerulonephritis, mesangio-proliferative glomerulonephritis, rapidly progressive glomerulonephritis, nephrophathies in general, in particular membranous nephropathy or diabetic nephropathy, nephritis in general, in particular lupus nephritis, pyelonephritis, interstitial nephritis, tubulointerstitial nephritis, chronic nephritis or acute nephritis, and minimal change disease and focal segmental glomerulosclerosis, (m) sympathetic ophthalmia (n) kidney, heart, lung, pancreas, liver, blood cell, bone marrow, cornea, accidental severed limb, in particular fingers, hand, foot, face, nose, bone, cardiac valve, blood vessel or intestine transplant rejection reaction, (o) Corticobasal degeneration, progressive supranuclear palsy, schizophrenia, inherited Kreutzfeld Jacob, motor neurone disease, spinocerebellar ataxia/atrophie, dementia, in particular frontotemporal dementia, dementia with lewy bodies, multiple system atrophy, hereditary spastic paraparesis, Friedreich's ataxiea, Charcot Marie toot, and (p) the disease is a hereditary or non-hereditary metabolic disease, in particular selected from the group of metabolic disorders of the carbohydrate metabolism, e.g., glycogen storage disease, disorders of amino acid metabolism, e.g., phenylketonuria, maple syrup urine disease, glutaric acidemia type 1, urea Cycle Disorder or urea Cycle Defects, e.g., carbamoyl phosphate synthetase I deficiency, disorders of organic acid metabolism (organic acidurias), e.g., alcaptonuria, disorders of fatty acid oxidation and mitochondrial metabolism, e.g., medium-chain acyl-coenzyme A dehydrogenase deficiency (often shortened to MCADD.), disorders of porphyrin metabolism, e.g. acute intermittent porphyria, disorders of purine or pyrimidine metabolism, e.g., Lesch-Nyhan syndrome, Disorders of steroid metabolism, e.g., lipoid congenital adrenal hyperplasia, or congenital adrenal hyperplasia, disorders of mitochondrial function, e.g., Kearns-Sayre syndrome, disorders of peroxisomal function. e.g., Zellweger syndrome, or lysosomal storage disorders, e.g., Gaucher's disease or Niemann Pick disease.

According to one preferred embodiment, the disorder/disease to be treated is AMD, the wet or the dry form, and cataract.

According to one preferred embodiment, the disorder/disease to be treated is retinopathy, in particular diabetic retinopathy.

According to one preferred embodiment, the disorder/disease to be treated is psoriasis.

According to another preferred embodiment, the disorder/disease to be treated is a graft rejection or transplant rejection reaction, in particular a liver, lung, kidney, pancreas, skin or heart transplant graft rejection, e.g. graft versus host or host versus graft.

According to still another preferred embodiment, the disorder/disease to be treated is glomerulonephritis.

Moreover, in the following further diseases to be treated are disclosed:

The JNK inhibitors of the present invention may be used for example for the treatment of inflammatory diseases including for example acute inflammation as well as chronic inflammation. The JNK inhibitors of the present invention may be used to treat any type of tissue inflammation, e.g. inflammation in the eye, inflammation in the mouth, inflammation of the respiratory system including in particular the lung, inflammation of the skin, inflammation within the cardiovascular system, inflammation of the brain, inflammation in the ear, etc. Some non-limiting examples for such inflammatory disease states are mucositis, stomatitis, peri-implantitis, retinitis, chorioiditis, keratoconjunctivitis sicca, inflammatory bowel diseases (IBD), uveitis (e.g. anterior uveitis, intermediate uveitis, posterior uveitis), periodontitis, COPD, asthma, pulpitis, rheumatoid arthritis, osteoarthritis, Crohn's disease, psoriatic arthritis, vasculitis, interstitial cystitis; acute inflammation at a site of infection or wound, meningitis, encephalitis, pneumonia, pharyngitis, tonsillitis, otitis (including otitis media), vasculitis, synovitis, enteritis, Crohn's disease, ulcerative colitis, graft rejection etc.

The JNK inhibitors as disclosed herein may for example be used in methods of treatment of ear diseases (in particular diseases of the inner ear), hearing loss (in particular acute hearing loss), damaged hair cell stereocilia, hair cell apoptosis, noise trauma, otitis, otitis media etc. Hearing loss and associated hair cell apoptosis are non-limiting examples for disorders resulting from stress situations for cells in which JNK inhibition can modulate the stress response and for example block apoptosis.

The JNK inhibitors of the present invention may also be used for the treatment of metabolic disorders, for example for the treatment of diabetes (type 1 or type 2, in particular type 1), Fabry disease, Gaucher disease, hypothermia, hyperthermia hypoxia, lipid histiocytosis, lipidoses, metachromatic leukodystrophy, mucopolysaccharidosis, Niemann Pick disease, obesity, and Wolman's disease. Hypothermia, hyperthermia and hypoxia are again non-limiting examples for stress situations for cells in which JNK inhibition can modulate the stress response and for example block apoptosis.

Likewise, the JNK inhibitors of the present invention may be used for the treatment of neural, neuronal and/or neurodegenerative diseases, respectively. Examples for such diseases are for example Alexander disease, Alzheimer's disease, amyotrophic lateral sclerosis (ALS), apoplexy, Ataxia Telangiectasia, cut or otherwise disrupted axons, axotomy, brain lesions, CMT (Charcot-Marie-Tooth), corticobasal degeneration, dementia, diseases or disorders of the nervous system, dystonia, epilepsy, Farber's disease, Friedreich ataxia (SCA), gangliosidoses, Guillain-Barré syndrome, hereditary spastic paraplegia, Hirschsprung's disease, human immunodeficiency virus dementia, Huntington's disease, infarct of the brain, ischemic stroke, Krabbe disease, Lennox Gastaut Syndrome, lissencephaly, multiple sclerosis, myelodysplastic syndromes, myelopathy, AIDS-related neurodegenerative diseases, neurofibromatosis type 2 (NF-2), neurolatyerism, neuronal apoptosis, neuronal death, neuropathic pain, neuropathy, chemotherapy induced neuropathy, diabetes induced neuropathy, NMDA-induced neurotoxicity, pain, Parkinson's disease, parkinsonism, Pick's Disease, polyneuropathy, progressive supranuclear palsy, Sandhoff disease, spina bifida, stroke, Tay Sachs, TBI (diffuse axonal injury), treatment of dark neurone induced for example by an inflammatory pain, West Syndrome, spinal muscular atrophy etc.

With respect to autoimmune disorders, the JNK inhibitor peptides of the present invention may for example be used in a method of treatment of autoimmune diseases of the CNS, auto-inflammatory diseases, Celiac disease; Sjogren's syndrome, systemic lupus erythematosus etc.

Examples for bone diseases which may be treated with the JNK inhibitors of the present invention are for example arthritis, disc herniation, fibrodysplasia ossificans progressiva (FOP), osteoarthritis, osteopetrosis, osteoporosis, in particular diabetes induced osteoporosis, Paget's Disease, rheumatoid arthritis, etc.

Examples for skin diseases which may be treated with the JNK inhibitors of the present invention are for example psoriasis and lupus erythematosus.

Diseases of the eye, which may be treated with the JNK inhibitors of the present invention involve for example age-related macular degeneration (AMD); angioid streaks; anterior ischemic optic neuropathy; anterior uveitis; cataract, in particular age related cataract; central exudative chorioretinopathy; central serous chorioretinopathy; chalazion; chorioderemia; chorioiditis; choroidal sclerosis; conjunctivitis; cyclitis; diabetic retinopathy; dry eye syndrome; endophthalmitis; episcleritis; eye infection; fundus albipunctatus; gyrate atrophy of choroid and retina; hordeolum; inflammatory diseases of the blephara; inflammatory diseases of the choroid; inflammatory diseases of the ciliary body; inflammatory diseases of the conjunctiva; inflammatory diseases of the cornea; inflammatory diseases of the iris; inflammatory diseases of the lacrimal gland; inflammatory diseases of the orbital bone; inflammatory diseases of the sclera; inflammatory diseases of the vitreous body; inflammatory diseases of the uvea; inflammatory diseases of the retina; intermediate uveitis; irititis; keratitis; Leber's disease; multifocal choroiditis; myositis of the eye muscle; neovascular maculopathy (e.g. caused by high myopia, tilted disc syndrome, choroidal osteoma or the like); NMDA induced retinotoxicity; non-chronic or chronic inflammatory eye diseases; Oguchi's disease; optic nerve disease; orbital phlegmon; panophtalmitis; panuveitis; post caspule opacification; posterior capsule opacification (PCO) (a cataract after-surgery complication); posterior uveitis; proliferative vitreoretinopathy; retinal artery occlusion; retinal detachment, retinal diseases; retinal injuries; retinal macroaneurysm; retinal pigment epithelium detachment; retinal vein occlusion; retinitis; retinitis pigmentosa; retinitis punctata albescens; retinopathy, in particular retinopathy of prematurity and diabetic retinopathy; scleritis; Stargardt's disease; treatment of inflamed ocular wounds and/or ocular wound edges; treatment of intraocular inflammation after eye surgery or trauma; uveitis; vitelliform macular dystrophy; etc.

Exemplary diseases of the mouth which may be treated with the JNK inhibitors as disclosed herein are periodontitis, in particular chronic periodontitis; mucositis; oral desquamative disorders, oral liquen planus, pemphigus vulgaris, pulpitis; stomatitis; temporomandibular joint disorder, peri-implantitis etc.

The present invention is also suitable for use in the treatment of diseases resulting in loss of bladder function (e.g., urinary incontinence, overactive bladder, interstitial cystitis, or bladder cancer).

Another field of use is the treatment of pain, in particular neuropathic, incident, breakthrough, psychogenic, or phantom pain, all of these types of pain either in the acute or chronic form.

Likewise the JNK inhibitors of the present invention may—as already previously proposed for other JNK inhibitors—be used for the treatment of proliferative diseases like cancer and tumor diseases, such as acusticus neurinoma lung carcinomas; acute lymphocytic leukemia (L1, L2, L3); acute lymphoid leukaemia (ALL); acute myelogenous leukemia (AML); adenocarcinomas; anal carcinoma; bronchial carcinoma; cervix carcinoma; cervical cancer; astrocytoma; basalioma; cancer with Bcr-Abl transformation; bladder cancer; blastomas; bone cancer; brain metastases; brain tumours; breast cancer; Burkitt's lymphoma; carcinoids; cervical cancer; chronic lymphocytic leukaemia (CLL); chronic myeloid leukaemia (CML); colon cancer; colon carcinoma; corpus carcinoma; craniopharyngeomas; CUP syndrome; virus-induced tumours; EBV-induced B cell lymphoma; endometrium carcinoma; erytholeukemia (M6); esophagus cancer; gallbladder cancer; gastrointestinal cancer; gastrointestinal stromal tumors; gastrointestinal tumours; genitourinary cancer; glaucoma; glioblastoma; gliomas; head/neck tumours; hepatitis B-induced tumours; hepatocell or hepatocellular carcinomas; hepatomas; herpes virus-induced tumours; Hodgkin's syndrome; HTLV-1-induced lymphomas; HTLV-2-induced lymphomas; insulinomas; intestinal cancer; Kaposi's sarcoma; kidney cancer; kidney carcinomas; laryngeal cancer; leukemia; lid tumour; liver cancer; liver metastases; lung cancer; lymphoid cancer; lymphomas; malignant melanomas; mammary carcinomas; mantle cell lymphoma; medulloblastoma; megakaryoblastic leukemia (M7); melanoma, in particular malignant melanoma; meningioma; mesothelioma; monocytic leukemia (MS); multiple myeloma; mycosis fungoides; myeloblastic leukemia (M1); myeloblastic leukemia (M2); myelomonocytic leukemia (M4); neurinoma; non-Hodgkin's lymphomas; non-small cell carcinoma; non-small cell carcinoma of the lung; oesophageal cancer; oesophageal carcinoma; oligodendroglioma; ovarian cancer; ovarian carcinoma; pancreatic cancer; pancreatic carcinoma; papilloma virus-induced carcinomas; penis cancer; pituitary tumour; plasmocytoma; promyelocytic leukemia (M3); prostate cancer; prostate tumours; rectal tumours; rectum carcinoma; renal-cell carcinoma; retinoblastoma; sarcomas; Schneeberger's disease; small cell lung carcinomas; small intestine cancer; small intestine tumours; soft tissue tumours; spinalioma; squamous cell carcinoma; stomach cancer; testicular cancer; throat cancer; thymoma; thyroid cancer; thyroid carcinoma; tongue cancer; undifferentiated AML (MO); urethral cancer; uterine cancer; vaginal cancer; Von Hippel Lindau disease; vulval cancer; Wilms' Tumor; Xeroderma pigmentosum; etc.

Since JNK signalling is also involved in many cardiovascular diseases and disorders, the use of JNK inhibitors in the treatment of such diseases has already been suggested in the past. The inhibitors of the present invention may be used accordingly, e.g. for the treatment of cardiovascular diseases such as arterial hypertension; arteriosclerosis; arteriosclerotic lesions; Behcet's syndrome; bifurcations of blood vessels; cardiac hypertrophy; cardiavascular hypertrophy; cardiomyopathies, in particular chemotherapy induced cardiomyopathies; cerebral ischemia; coronary heart diseases; dilatation of the abdominal aorta; focal cerebral ischemia; global cerebral ischemia; heart hypertrophy; infrarenal aneurism hypertension; ischemia; myocardial infarct, in particular acute myocardial infarction; myocarditis; reperfusion; restenosis; vasculitis; Wegener's granulomatosis; etc.

The JNK inhibitors of the present invention may in the context of cardiovascular diseases also be used complementary to coronary artery bypass graft surgery (CABG surgery); percutaneous transluminal coronary angioplasty (PTCA); and/or stent treatment, for example to prevent or treat intimal hyperplasia resulting from said (surgical) treatment.

Diseases of the respiratory system and in particular lung diseases which may be treated effectively with the JNK inhibitors of the present invention are for example acute respiratory distress syndrome (ARDS); asthma; chronic illnesses involving the respiratory system; chronic obstructive pulmonary disease (COPD); cystic fibrosis; inflammatory lung diseases; pneumonia; pulmonary fibrosis; etc.

Like the inhibitors in the prior art the inhibitors of the present invention may also be used to treat disease of the intestinal tract, e.g. colitis (e.g. atypical colitis, chemical colitis; collagenous colitis, distal colitis, diversion colitis; fulminant colitis, indeterminate colitis, infectious colitis, ischemic colitis, lymphocytic colitis, or microscopic colitis), Crohn's disease, gastroenteritis, Hirschsprung's disease, inflammatory digestive diseases; inflammatory bowel disease (IBD), Morbus Crohn, non-chronic or chronic digestive diseases, non-chronic or chronic inflammatory digestive diseases; regional enteritis; ulcerative colitis etc.

The JNK inhibitors of the present invention may also serve as therapeutic agent for the treatment of infectious diseases resulting from e.g. bacterial or viral infection. The JNK inhibitors as disclosed herein may for example prevent or ameliorate inflammatory reactions caused by said infections. Examples for such diseases states, which are not considered to be limiting, are viral encephalitis; viral induced cancers (e.g. as mentioned above), human immunodeficiency virus dementia, meningitis, meningoencephalitis, encephalomyelitis, tonsillitis, etc.

There are many other diseases, disease states and disorders for which the JNK inhibitors of the present invention can be used as treatment, for example Aarskog syndrome, acetaminophen hepatotoxicity; Alder-Reilly anomaly; alopecia areata; alpha-1-antitrypsin deficiency; anaphylaxis; apoptosis; apoptotic cell death; atypical hemolytic uremic syndrome; basopenia; basophilia; bipolar disorders; burns; cellular shear stress; Chedial-Higashi syndrome; DNA damage due to chemotherapeutic drugs; cholestasis; chromosome 11, Partial Monosomy 11 q; chromosome 22, Trisomy Mosaic; chronic granulomatous disease; hepatitis, such as chronic or fulminant hepatitis; clinical depression; common variable hypogammaglobulinemia; congenital C3 deficiency; CTL protection from activation-induced cell death (AICD); deafness; depression and depressive disorders (in particular prevention of depressive disorders develop on a background of cytokine-induced sickness behaviour), DiGeorge's syndrome; diseases caused by defective apoptosis; diseases of the liver; diseases of the spine; diseases of the uterus; diseases states and symptoms due to exposure to DNA damaging agents and/or ionizing radiation and resulting cellular stress; Down Syndrome; Duchenne muscular dystrophy; ectodermal dysplasias; endometriosis; eosinopenia; eosinophilia; exocitoxic cell death; fetal alcohol syndrome; fibrosis; fibrotic disease; formation of fibrous tissue; free radicals (leading to cellular stress); graft rejection; Graft versus host Disease, in particular skin graft versus host; hair loss; hemolytic uremic syndrome; hepatotoxicity; hyperalgesia, such as diabetes induced hyperalgesia; hyperthermia; hypoglycemia; hypothyroidism; idiopathic hypereosinophilic syndrome; IgA nephropathy; infantile sex-linked agammaglobulinemia; inflammatory pain; infrarenal aneyrism; islet regeneration; islet transplantation; Job's syndrome (hyper-IgE); lazy leukocyte syndrome; leukocyte glucose-6-phosphate dehydrogenase deficiency; leukodystrophy; leukopenia; lymphocytic leukocytosis; lymphocytopenia; lymphocytosis; major depression; mania; maniac depression; Marfan syndrome; mastocytosis; May Hegglin Anomaly; membranoproliferative glomerulonephritis Type II; monocytopenia; monocytosis; myeloperoxidase deficiency-benign; myopathies; neutropenia; neutrophilia; Nezelof's syndrome; organ transplantation; oxidative stress injuries; Pelger-Huet anomaly; polycystic kidney diseases; post-dialysis syndrome; radiation syndromes; radiotherapy; renal diseases; renal failure; rescuing CTL from activation induced cell death; severe combined immunodeficiency disease; transplant rejection; transplantation; trisomy; unipolar depression; UV-induced injuries; Wiskott Aldrich syndrome; wound healing; etc.

The inventors of the present invention consider temporomandibular joint disorder, mucositis, stomatitis, oral liquen planus (desquamative disorder), Pemphigus vulgaris (desquamative disorder), periodontitis, chronic periodontitis, pulpitis, peri-implantitis, uveitis (anterior uveitis, intermediate uveitis, posterior uveitis), keratoconjunctivitis sicca (dry eye syndrome), coronary artery bypass graft surgery (CABG surgery), acute myocardial infarction, prevention of intimal hyperplasia following percutaneous transluminal coronary angioplasty (PTCA), prevention of intimal hyperplasia following stent placement, atherosclerosis, COPD, asthma, rheumatoid arthritis, osteoarthritis, Crohn's disease, inflammatory bowel disease (IBD), psoriasis, diabetes, stroke, Parkinson's disease, Alzheimer's disease, systemic lupus erythematosus, and vasculitis, in particular Wegener's granulomatosis, to be particularly useful for treatment with the JNK inhibitors of the present invention.

According to another aspect of the present invention, a inhibitor sequence comprising less than 150 amino acids in length for the (in vitro) treatment of a tissue or organ transplant prior its transplantation. Usually, a transplant originating from brain-dead donors is typically not subjected to WIT has 8-12 hrs of CIT (time needed for transportation from the procurement hospital to the isolation lab. It was found that such transplants may be pre-treated by the JNK inhibitors according to the present invention in order improve their viability and functionality until transplanted to host. For that aspect of the invention, the transplant is a kidney, heart, lung, pancreas, liver, blood cell, bone marrow, cornea, accidental severed limb, in particular fingers, hand, foot, face, nose, bone, cardiac valve, blood vessel or intestine transplant, preferably a kidney, heart, pancreas or skin transplant.

Since JNK inhibitor sequences as known in the art only proved usability for a limited number of diseases, it was a surprising finding that JNK inhibitor sequences as defined herein may be used and are suitable for the treatment of diseases or disorders strongly related to JNK signaling as mentioned above. This was neither obvious nor suggested by the prior art, even though JNK inhibitor sequences in general have been known from the art.

Typically, a JNK inhibitor sequence as defined above may be derived from a human or rat IB1 sequence, preferably from an amino acid sequence as defined or encoded by any of sequences according to SEQ ID NO: 102 (depicts the IB1 cDNA sequence from rat and its predicted amino acid sequence), SEQ ID NO: 103 (depicts the IB1 protein sequence from rat encoded by the exon-intron boundary of the rIB1 gene-splice donor), SEQ ID NO: 104 (depicts the IB1 protein sequence from *Homo sapiens*), or SEQ ID NO: 105 (depicts the IB1 cDNA sequence from *Homo sapiens*), more preferably from an amino acid sequence as defined or encoded by any of sequences according to SEQ ID NO: 104 (depicts the IB1 protein sequence from *Homo sapiens*), or SEQ ID NO: 105 (depicts the IB1 cDNA sequence from *Homo sapiens*), or from any fragments or variants thereof. In other words, the JNK inhibitor sequence comprises a fragment, variant, or variant of such fragment of a human or rat IB1 sequence. Human or rat IB sequences are defined or encoded, respectively, by the sequences according to SEQ ID NO: 102, SEQ ID NO: 103, SEQ ID NO: 104 or SEQ ID NO: 105.

Preferably, such a JNK inhibitor sequence as used herein comprises a total length of less than 150 amino acid residues, preferably a range of 5 to 150 amino acid residues, more preferably 10 to 100 amino acid residues, even more preferably 10 to 75 amino acid residues and most preferably a range of 10 to 50 amino acid residues, e.g. 10 to 30, 10 to 20, or 10 to 15 amino acid residues.

More preferably, such a JNK inhibitor sequence and the above ranges may be selected from any of the above mentioned sequences, even more preferably from an amino acid sequence as defined according to SEQ ID NO: 104 or as encoded by SEQ ID NO: 105, even more preferably in the region between nucleotides 420 and 980 of SEQ ID NO: 105 or amino acids 105 and 291 of SEQ ID NO: 104, and most preferably in the region between nucleotides 561 and 647 of SEQ ID NO: 105 or amino acids 152 and 180 of SEQ ID NO: 104.

According to a particular embodiment, a JNK inhibitor sequence as used herein typically binds JNK and/or inhibits the activation of at least one JNK activated transcription factor, e.g. c-Jun or ATF2 (see e.g. SEQ ID NOs: 15 and 16, respectively) or Elk1.

Likewise, the JNK inhibitor sequence as used herein preferably comprises or consists of at least one amino acid sequence according to any one of SEQ ID NOs: 1 to 4, 13 to 20 and 33 to 100, or a fragment, derivative or variant thereof. More preferably, the JNK inhibitor sequence as used herein may contain 1, 2, 3, 4 or even more copies of an amino acid sequence according to SEQ ID NOs: 1 to 4, 13 to 20 and 33 to 100, or a variant, fragment or derivative thereof. If present in more than one copy, these amino acid sequences according to SEQ ID NOs: 1 to 4, 13 to 20 and 33 to 100, or variants, fragments, or derivatives thereof as used herein may be directly linked with each other without any linker sequence or via a linker sequence comprising 1 to 10, preferably 1 to 5 amino acids. Amino acids forming the linker sequence are preferably selected from glycine or proline as amino acid residues. More preferably, these amino acid sequences according to SEQ ID NOs: 1 to 4, 13 to 20 and 33 to 100, or fragments, variants or derivatives thereof, as used herein, may be separated by each other by a hinge of two, three or more proline residues.

The JNK inhibitor sequences as used herein may be composed of L-amino acids, D-amino acids, or a combination of both. Preferably, the JNK inhibitor sequences as used herein comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the JNK inhibitor sequences as used herein in a blockwise, a non-blockwise or in an alternate manner.

According to one preferred embodiment the JNK inhibitor sequences as used herein may be exclusively composed of L-amino acids. The JNK inhibitor sequences as used herein may then comprise or consist of at least one "native JNK inhibitor sequence" according to SEQ ID NO: 1 or 3. In this context, the term "native" or "native JNK inhibitor sequence(s)" is referred to non-altered JNK inhibitor sequences according to any of SEQ ID NOs: 1 or 3, as used herein, entirely composed of L-amino acids.

Accordingly, the JNK inhibitor sequence as used herein may comprise or consist of at least one (native) amino acid sequence $NH_2-X_n^b-X_n^a$-RPTTLXLXXXXXXXQD-$X_n^b$—COOH (L-IB generic (s)) [SEQ ID NO: 3] and/or the JNK binding domain (JBDs) of IB1 XRPTTLX-LXXXXXXXQDS/TX (L-IB (generic)) [SEQ ID NO: 19]. In this context, each X typically represents an amino acid residue, preferably selected from any (native) amino acid residue. $X_n^a$ typically represents one amino acid residue, preferably selected from any amino acid residue except serine or threonine, wherein n (the number of repetitions of X) is 0 or 1. Furthermore, each $X_n^b$ may be selected from any amino acid residue, wherein n (the number of repetitions of X) is 0-5, 5-10, 10-15, 15-20, 20-30 or more, provided that if n (the number of repetitions of X) is 0 for $X_n^a$, $X_n^b$ does preferably not comprise a serine or threonine at its C-terminus, in order to avoid a serine or threonine at this position. Preferably, $X_n^b$ represents a contiguous stretch of peptide residues derived from SEQ ID NO: 1 or 3. $X_n^a$ and $X_n^b$ may represent either D or L amino acids. Additionally, the JNK inhibitor sequence as used herein may comprise or consist of at least one (native) amino acid sequence selected from the group comprising the JNK binding domain of IB1 DTYRPKRPTTLNLFPQVPRSQDT (L-IB1) [SEQ ID NO: 17]. More preferably, the JNK inhibitor sequence as used herein further may comprise or consist of at least one (native) amino acid sequence $NH_2$-RPKRPTTLNLF-PQVPRSQD-COOH (L-IB1(s)) [SEQ ID NO: 1]. Furthermore, the JNK inhibitor sequence as used herein may comprise or consist of at least one (native) amino acid sequence selected from the group comprising the JNK binding domain of IB1 L-IB1(s1) ($NH_2$-TLNLFPQVPR-SQD-COOH, SEQ ID NO: 33); L-IB1(s2) ($NH_2$-TTLNLF-PQVPRSQ-COOH, SEQ ID NO: 34); L-IB1(s3) ($NH_2$-PTTLNLFPQVPRS-COOH, SEQ ID NO: 35); L-IB1(s4) ($NH_2$-RPTTLNLFPQVPR-COOH, SEQ ID NO: 36); L-IB1 (s5) ($NH_2$-KRPTTLNLFPQVP-COOH, SEQ ID NO: 37); L-IB1(s6) ($NH_2$-PKRPTTLNLFPQV-COOH, SEQ ID NO: 38); L-IB1(s7) ($NH_2$-RPKRPTTLNLFPQ-COOH, SEQ ID NO: 39); L-IB1(s8) ($NH_2$-LNLFPQVPRSQD-COOH, SEQ ID NO: 40); L-IB1(s9) ($NH_2$-TLNLFPQVPRSQ-COOH, SEQ ID NO: 41); L-IB1(s10) ($NH_2$-TTLNLFPQVPRS-COOH, SEQ ID NO: 42); L-IB1(s11) ($NH_2$-PTTLNLF-PQVPR-COOH, SEQ ID NO: 43); L-IB1(s12) ($NH_2$-RPT-TLNLFPQVP-COOH, SEQ ID NO: 44); L-IB1(s13) ($NH_2$-KRPTTLNLFPQV-COOH, SEQ ID NO: 45); L-IB1(s14) ($NH_2$-PKRPTTLNLFPQ-COOH, SEQ ID NO: 46); L-IB1 (s15) ($NH_2$-RPKRPTTLNLFP-COOH, SEQ ID NO: 47); L-IB1(s16) ($NH_2$-NLFPQVPRSQD-COOH, SEQ ID NO: 48); L-IB1(s17) ($NH_2$-LNLFPQVPRSQ-COOH, SEQ ID NO: 49); L-IB1(s18) ($NH_2$-TLNLFPQVPRS-COOH, SEQ ID NO: 50); L-IB1(s19) ($NH_2$-TTLNLFPQVPR-COOH, SEQ ID NO: 51); L-IB1(s20) ($NH_2$-PTTLNLFPQVP-COOH, SEQ ID NO: 52); L-IB1(s21) ($NH_2$-RPTTLNLF-PQV-COOH, SEQ ID NO: 53); L-IB1(s22) ($NH_2$-KRPT-TLNLFPQ-COOH, SEQ ID NO: 54); L-IB1(s23) ($NH_2$-PKRPTTLNLFP-COOH, SEQ ID NO: 55); L-IB1(s24) ($NH_2$-RPKRPTTLNLF-COOH, SEQ ID NO: 56); L-IB1 (s25) ($NH_2$-LFPQVPRSQD-COOH, SEQ ID NO: 57); L-IB1(s26) ($NH_2$-NLFPQVPRSQ-COOH, SEQ ID NO: 58); L-IB1(s27) ($NH_2$-LNLFPQVPRS-COOH, SEQ ID NO: 59); L-IB1(s28) ($NH_2$-TLNLFPQVPR-COOH, SEQ ID NO: 60); L-IB1(s29) ($NH_2$-TTLNLFPQVP-COOH, SEQ ID NO: 61); L-IB1(s30) ($NH_2$-PTTLNLFPQV-COOH, SEQ ID NO: 62); L-IB1(s31) ($NH_2$-RPTTLNLFPQ-COOH, SEQ ID NO: 63); L-IB1(s32) ($NH_2$-KRPTTLNLFP-COOH, SEQ ID NO: 64); L-IB1(s33) ($NH_2$-PKRPTTLNLF-COOH, SEQ ID NO: 65); and L-IB1(s34) ($NH_2$-RPKRPTTLNL-COOH, SEQ ID NO: 66).

Additionally, the JNK inhibitor sequence as used herein may comprise or consist of at least one (native) amino acid sequence selected from the group comprising the (long) JNK binding domain (JBDs) of IB1 PGTGCGDTYRPKRPT-TLNLFPQVPRSQDT (IB1-long) [SEQ ID NO: 13], the (long) JNK binding domain of IB2 IPSPSVEEPHKHRPT-TLRLTTLGAQDS (IB2-long) [SEQ ID NO: 14], the JNK binding domain of c-Jun GAYGYSNPKILKQSMTLN-LADPVGNLKPH (c-Jun) [SEQ ID NO: 15], the JNK binding domain of ATF2 TNEDHLAVHKHKHEMTLKF-GPARNDSVIV (ATF2) [SEQ ID NO: 16] (see e.g. FIG. 1A-1C). In this context, an alignment revealed a partially conserved 8 amino acid sequence (see e.g. FIG. 1A) and a further comparison of the JBDs of IB1 and IB2 revealed two blocks of seven and three amino acids that are highly conserved between the two sequences.

According to another preferred embodiment the JNK inhibitor sequences as used herein may be composed in part or exclusively of D-amino acids as defined above. More preferably, these JNK inhibitor sequences composed of D-amino acids are non-native D retro-inverso sequences of the above (native) JNK inhibitor sequences. The term "retro-inverso sequences" refers to an isomer of a linear peptide sequence in which the direction of the sequence is reversed and the chirality of each amino acid residue is inverted (see e.g. Jameson et al., Nature, 368, 744-746 (1994); Brady et al., Nature, 368, 692-693 (1994)). The advantage of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence or peptide as used according to the present invention may be converted into an D retro-inverso sequence or peptide by synthesizing a reverse of the sequence or peptide for the corresponding native L-amino acid sequence or peptide.

The D retro-inverso sequences as used herein and as defined above have a variety of useful properties. For example, D retro-inverso sequences as used herein enter cells as efficiently as L-amino acid sequences as used herein, whereas the D retro-inverso sequences as used herein are more stable than the corresponding L-amino acid sequences.

Accordingly, the JNK inhibitor sequences as used herein may comprise or consist of at least one D retro-inverso sequence according to the amino acid sequence $NH_2$—$X_n^b$-DQXXXXXXXLXLTTPR-$X_n^a$—$X_n^b$—COOH (D-IB1 generic (s)) [SEQ ID NO: 4] and/or XS/TDQXXXXXXX-LXLTTPRX (D-IB (generic)) [SEQ ID NO: 20]. As used in this context, X, $X_n^a$ and $X_n^b$ are as defined above (preferably, representing D amino acids), wherein $X_n^b$ preferably represents a contiguous stretch of residues derived from SEQ ID NO: 2 or 4. Additionally, the JNK inhibitor sequences as used herein may comprise or consist of at least one D retro-inverso sequence according to the amino acid sequence comprising the JNK binding domain (JBDs) of IB1 TDQS-RPVQPFLNLTTPRKPRYTD (D-IB1) [SEQ ID NO: 18]. More preferably, the JNK inhibitor sequences as used herein may comprise or consist of at least one D retro-inverso sequence according to the amino acid sequence $NH_2$-DQS-RPVQPFLNLTTPRKPR-COOH (D-IB1(s)) [SEQ ID NO: 2]. Furthermore, the JNK inhibitor sequences as used herein may comprise or consist of at least one D retro-inverso sequence according to the amino acid sequence comprising the JNK binding domain (JBDs) of IB1 D-IB1(s1) ($NH_2$-QPFLNLTTPRKPR-COOH, SEQ ID NO: 67); D-IB1(s2) ($NH_2$-VQPFLNLTTPRKP-COOH, SEQ ID NO: 68); D-IB1 (s3) ($NH_2$-PVQPFLNLTTPRK-COOH, SEQ ID NO: 69); D-IB1(s4) ($NH_2$-RPVQPFLNLTTPR-COOH, SEQ ID NO: 70); D-IB1(s5) ($NH_2$-SRPVQPFLNLTTP-COOH, SEQ ID NO: 71); D-IB1(s6) ($NH_2$-QSRPVQPFLNLTT-COOH, SEQ ID NO: 72); D-IB1(s7) ($NH_2$-DQSRPVQPFLNLT-COOH, SEQ ID NO: 73); D-IB1(s8) ($NH_2$-PFLN-LTTPRKPR-COOH, SEQ ID NO: 74); D-IB1(s9) ($NH_2$-QPFLNLTTPRKP-COOH, SEQ ID NO: 75); D-IB1(s10) ($NH_2$-VQPFLNLTTPRK-COOH, SEQ ID NO: 76); D-IB1 (s11) ($NH_2$-PVQPFLNLTTPR-COOH, SEQ ID NO: 77); D-IB1(s12) ($NH_2$-RPVQPFLNLTTP-COOH, SEQ ID NO: 78); D-IB1(s13) ($NH_2$-SRPVQPFLNLTT-COOH, SEQ ID NO: 79); D-IB1(s14) ($NH_2$-QSRPVQPFLNLT-COOH, SEQ ID NO: 80); D-IB1(s15) ($NH_2$-DQSRPVQPFLNL-COOH, SEQ ID NO: 81); D-IB1(s16) ($NH_2$-FLNLTTPRKPR-COOH, SEQ ID NO: 82); D-IB1(s17) ($NH_2$-LTTPRKP-COOH, SEQ ID NO: 83); D-IB1(s18) ($NH_2$-QPFLNLTTPRK-COOH, SEQ ID NO: 84); D-IB1(s19) ($NH_2$-VQPFLNLTTPR-COOH, SEQ ID NO: 85); D-IB1 (s20) ($NH_2$-PVQPFLNLTTP-COOH, SEQ ID NO: 86); D-IB1(s21) ($NH_2$-RPVQPFLNLTT-COOH, SEQ ID NO: 87); D-IB1(s22) ($NH_2$-SRPVQPFLNLT-COOH, SEQ ID NO: 88); D-IB1(s23) ($NH_2$-QSRPVQPFLNL-COOH, SEQ ID NO: 89); D-IB1(s24) ($NH_2$-DQSRPVQPFLN-COOH, SEQ ID NO: 90); D-IB1(s25) ($NH_2$-DQSRPVQPFL-COOH, SEQ ID NO: 91); D-IB1(s26) ($NH_2$-QSRPVQP-FLN-COOH, SEQ ID NO: 92); D-IB1(s27) ($NH_2$-SRPVQP-FLNL-COOH, SEQ ID NO: 93); D-IB1(s28) ($NH_2$-RPVQPFLNLT-COOH, SEQ ID NO: 94); D-IB1(s29) ($NH_2$-PVQPFLNLTT-COOH, SEQ ID NO: 95); D-IB1(s30) ($NH_2$-VQPFLNLTTP-COOH, SEQ ID NO: 96); D-IB1(s31) ($NH_2$-QPFLNLTTPR-COOH, SEQ ID NO: 97); D-IB1(s32) ($NH_2$-PFLNLTTPRK-COOH, SEQ ID NO: 98); D-IB1(s33) ($NH_2$-FLNLTTPRKP-COOH, SEQ ID NO: 99); and D-IB1 (s34) ($NH_2$-LNLTTPRKPR-COOH, SEQ ID NO: 100).

The JNK inhibitor sequences as used herein and as disclosed above are presented in Table 1 (SEQ ID NO:s 1-4, 13-20 and 33-100). The table presents the name of the JNK inhibitor sequences as used herein, as well as their sequence identifier number, their length, and amino acid sequence. Furthermore, Table 1 shows sequences as well as their generic formulas, e.g. for SEQ ID NO's: 1, 2, 5, 6, 9 and 11 and SEQ ID NO's: 3, 4, 7, 8, 10 and 12, respectively. Table 1 furthermore discloses the chimeric sequences SEQ ID NOs: 9-12 and 23-32 (see below), L-IB1 sequences SEQ ID NOs: 33 to 66 and D-IB1 sequences SEQ ID NOs: 67 to 100.

TABLE 1

| SEQUENCE/PEPTIDE NAME | SEQ ID NO | AA | SEQUENCE |
|---|---|---|---|
| L-IB1(s) | 1 | 19 | RPKRPTTLNLFPQVPRSQD ($NH_2$-RPKRPTTLNLFPQVPRSQD-COOH) |
| D-IB1(s) | 2 | 19 | DQSRPVQPFLNLTTPRKPR ($NH_2$-DQSRPVQPFLNLTTPRKPR-COOH) |
| L-IB(generic)(s) | 3 | 19 | $NH_2$-$X_n^b$-$X_n^a$-RPTTLXLXXXXXXXQD-$X_n^b$-COOH |
| D-IB(generic)(s) | 4 | 19 | $NH_2$-$X_n^b$-DQXXXXXXXLXLTTPR-$X_n^a$-$X_n^b$-COOH |

TABLE 1-continued

| SEQUENCE/PEPTIDE NAME | SEQ ID NO | AA | SEQUENCE |
|---|---|---|---|
| L-TAT | 5 | 10 | GRKKRRQRRR (NH$_2$-GRKKRRQRRR-COOH) |
| D-TAT | 6 | 10 | RRRQRRKKRG (NH$_2$-RRRQRRKKRG-COOH) |
| L-generic-TAT(s) | 7 | 11 | NH$_2$-X$_n^b$-RKKRRQRRR-X$_n^b$-COOH |
| D-generic-TAT(s) | 8 | 11 | NH$_2$-X$_n^b$-RRRQRRKKR-X$_n^b$-COOH |
| L-TAT-IB1(s) | 9 | 31 | GRKKRRQRRRPPRPKRPTTLNLFPQVPRSQD (NH$_2$-GRKKRRQRRRPPRPKRPTTLNLFPQVPRSQD-COOH) |
| L-TAT-IB(generic)(s) | 10 | 29 | NH$_2$-X$_n^b$-RKKRRQRRR-X$_n^b$-X$_n^a$-RPTTLXLXXXXXXXQD-X$_n^b$-COOH |
| D-TAT-IB1(s) | 11 | 31 | DQSRPVQPFLNLTTPRKPRPPRRRQRRKKRG (NH$_2$-DQSRPVQPFLNLTTPRKPRPPRRRQRRKKRG-COOH) |
| D-TAT-IB(generic)(s) | 12 | 29 | NH$_2$-X$_n^b$-DQXXXXXXXLXLTTPR-X$_n^a$-X$_n^b$-RRRQRRKKR-X$_n^b$-COOH |
| IB1-long | 13 | 29 | PGTGCGDTYRPKRPTTLNLFPQVPRSQDT (NH$_2$-PGTGCGDTYRPKRPTTLNLFPQVPRSQDT-COOH) |
| IB2-long | 14 | 27 | IPSPSVEEPHKHRPTTLRLTTLGAQDS (NH$_2$-IPSPSVEEPHKHRPTTLRLTTLGAQDS-COOH) |
| c-Jun | 15 | 29 | GAYGYSNPKILKQSMTLNLADPVGNLKPH (NH$_2$-GAYGYSNPKILKQSMTLNLADPVGNLKPH-COOH) |
| ATF2 | 16 | 29 | TNEDHLAVHKHKHEMTLKFGPARNDSVIV (NH$_2$-TNEDHLAVHKHKHEMTLKFGPARNDSVIV-COOH) |
| L-IB1 | 17 | 23 | DTYRPKRPTTLNLFPQVPRSQDT (NH$_2$-DTYRPKRPTTLNLFPQVPRSQDT-COOH) |
| D-IB1 | 18 | 23 | TDQSRPVQPFLNLTTPRKPRYTD (NH$_2$-TDQSRPVQPFLNLTTPRKPRYTD-COOH) |
| L-IB(generic) | 19 | 19 | XRPTTLXLXXXXXXXQDS/TX (NH$_2$-XRPTTLXLXXXXXXXQDS/TX-COOH) |
| D-IB(generic) | 20 | 19 | XS/TDQXXXXXXXLXLTTPRX (NH$_2$-XS/TDQXXXXXXXLXLTTPRX-COOH) |
| L-generic-TAT | 21 | 17 | XXXXRKKRRQRRRXXXX (NH$_2$-XXXXRKKRRQRRRXXXX-COOH) |
| D-generic-TAT | 22 | 17 | XXXXRRRQRRKKRXXXX (NH$_2$-XXXXRRRQRRKKRXXXX-COOH) |
| L-TAT-IB1 | 23 | 35 | GRKKRRQRRRPPDTYRPKRPTTLNLFPQVPRSQDT (NH$_2$-GRKKRRQRRRPPDTYRPKRPTTLNLFPQVPRSQDT-COOH) |
| L-TAT-IB(generic) | 24 | 42 | XXXXXXXRKKRRQRRRXXXXXXXXRPTTLXLXXXXXXXQDS/TX (NH$_2$-XXXXXXXRKKRRQRRRXXXXXXXXRPTTLXLXXXXXXXQDS/TX-COOH) |
| D-TAT-IB1 | 25 | 35 | TDQSRPVQPFLNLTTPRKPRYTDPPRRRQRRKKRG (NH$_2$-TDQSRPVQPFLNLTTPRKPRYTDPPRRRQRRKKRG-COOH) |
| D-TAT-IB(generic) | 26 | 42 | XT/SDQXXXXXXXLXLTTPRXXXXXXXXRRRQRRKKRXXXXXXX (NH$_2$-XT/SDQXXXXXXXLXLTTPRXXXXXXXXRRRQRRKKRXXXXXXX-COOH) |
| L-TAT-IB1(s1) | 27 | 30 | RKKRRQRRRPPRPKRPTTLNLFPQVPRSQD (NH$_2$-RKKRRQRRRPPRPKRPTTLNLFPQVPRSQD-COOH) |
| L-TAT-IB1(s2) | 28 | 30 | GRKKRRQRRRX$_n^c$RPKRPTTLNLFPQVPRSQD (NH$_2$-GRKKRRQRRRX$_n^c$RPKRPTTLNLFPQVPRSQD-COOH) |
| L-TAT-IB1(s3) | 29 | 29 | RKKRRQRRRX$_n^c$RPKRPTTLNLFPQVPRSQD (NH$_2$-RKKRRQRRRX$_n^c$RPKRPTTLNLFPQVPRSQD-COOH) |
| D-TAT-IB1(s1) | 30 | 30 | DQSRPVQPFLNLTTPRKPRPPRRRQRRKKR (NH$_2$-DQSRPVQPFLNLTTPRKPRPPRRRQRRKKR-COOH) |
| D-TAT-IB1(s2) | 31 | 30 | DQSRPVQPFLNLTTPRKPRX$_n^c$RRRQRRKKRG (NH$_2$-DQSRPVQPFLNLTTPRKPRX$_n^c$RRRQRRKKRG-COOH) |

TABLE 1-continued

| SEQUENCE/PEPTIDE NAME | SEQ ID NO | AA | SEQUENCE |
| --- | --- | --- | --- |
| D-TAT-IB1(s3) | 32 | 29 | DQSRPVQPFLNLTTPRKPRX$_n$°RRRQRRKKR<br>(NH$_2$-DQSRPVQPFLNLTTPRKPRX$_n$°RRRQRRKKR-COOH) |
| L-IB1(s1) | 33 | 13 | TLNLFPQVPRSQD<br>(NH$_2$-TLNLFPQVPRSQD-COOH) |
| L-IB1(s2) | 34 | 13 | TTLNLFPQVPRSQ<br>(NH$_2$-TTLNLFPQVPRSQ-COOH) |
| L-IB1(s3) | 35 | 13 | PTTLNLFPQVPRS<br>(NH$_2$-PTTLNLFPQVPRS-COOH) |
| L-IB1(s4) | 36 | 13 | RPTTLNLFPQVPR<br>(NH$_2$-RPTTLNLFPQVPR-COOH) |
| L-IB1(s5) | 37 | 13 | KRPTTLNLFPQVP<br>(NH$_2$-KRPTTLNLFPQVP-COOH) |
| L-IB1(s6) | 38 | 13 | PKRPTTLNLFPQV<br>(NH$_2$-PKRPTTLNLFPQV-COOH) |
| L-IB1(s7) | 39 | 13 | RPKRPTTLNLFPQ<br>(NH$_2$-RPKRPTTLNLFPQ-COOH) |
| L-IB1(s8) | 40 | 12 | LNLFPQVPRSQD<br>(NH$_2$-LNLFPQVPRSQD-COOH) |
| L-IB1(s9) | 41 | 12 | TLNLFPQVPRSQ<br>(NH$_2$-TLNLFPQVPRSQ-COOH) |
| L-IB1(s10) | 42 | 12 | TTLNLFPQVPRS<br>(NH$_2$-TTLNLFPQVPRS-COOH) |
| L-1B1(s11) | 43 | 12 | PTTLNLFPQVPR<br>(NH$_2$-PTTLNLFPQVPR-COOH) |
| L-IB1(s12) | 44 | 12 | RPTTLNLFPQVP<br>(NH$_2$-RPTTLNLFPQVP-COOH) |
| L-IB1(s13) | 45 | 12 | KRPTTLNLFPQV<br>(NH$_2$-KRPTTLNLFPQV-COOH) |
| L-IB1(s14) | 46 | 12 | PKRPTTLNLFPQ<br>(NH$_2$-PKRPTTLNLFPQ-COOH) |
| L-IB1(s15) | 47 | 12 | RPKRPTTLNLFP<br>(NH$_2$-RPKRPTTLNLFP-COOH) |
| L-IB1(s16) | 48 | 11 | NLFPQVPRSQD<br>(NH$_2$-NLFPQVPRSQD-COOH) |
| L-IB1(s17) | 49 | 11 | LNLFPQVPRSQ<br>(NH$_2$-LNLFPQVPRSQ-COOH) |
| L-IB1(s18) | 50 | 11 | TLNLFPQVPRS<br>(NH$_2$-TLNLFPQVPRS-COOH) |
| L-IB1(s19) | 51 | 11 | TTLNLFPQVPR<br>(NH$_2$-TTLNLFPQVPR-COOH) |
| L-IB1(s20) | 52 | 11 | PTTLNLFPQVP<br>(NH$_2$-PTTLNLFPQVP-COOH) |
| L-IB1(s21) | 53 | 11 | RPTTLNLFPQV<br>(NH$_2$-RPTTLNLFPQV-COOH) |
| L-IB1(s22) | 54 | 11 | KRPTTLNLFPQ<br>(NH$_2$-KRPTTLNLFPQ-COOH) |
| L-IB1(s23) | 55 | 11 | PKRPTTLNLFP<br>(NH$_2$-PKRPTTLNLFP-COOH) |
| L-IB1(s24) | 56 | 11 | RPKRPTTLNLF<br>(NH$_2$-RPKRPTTLNLF-COOH) |
| L-IB1(s25) | 57 | 10 | LFPQVPRSQD<br>(NH$_2$-LFPQVPRSQD-COOH) |

TABLE 1-continued

| SEQUENCE/PEPTIDE NAME | SEQ ID NO | AA | SEQUENCE |
|---|---|---|---|
| L-IB1(s26) | 58 | 10 | NLFPQVPRSQ (NH$_2$-NLFPQVPRSQ-COOH) |
| L-IB1(s27) | 59 | 10 | LNLFPQVPRS (NH$_2$-LNLFPQVPRS-COOH) |
| L-IB1(s28) | 60 | 10 | TLNLFPQVPR (NH$_2$-TLNLFPQVPR-COOH) |
| L-IB1(s29) | 61 | 10 | TTLNLFPQVP (NH$_2$-TTLNLFPQVP-COOH) |
| L-IB1(s30) | 62 | 10 | PTTLNLFPQV (NH$_2$-PTTLNLFPQV-COOH) |
| L-IB1(s31) | 63 | 10 | RPTTLNLFPQ (NH$_2$-RPTTLNLFPQ-COOH) |
| L-IB1(s32) | 64 | 10 | KRPTTLNLFP (NH$_2$-KRPTTLNLFP-COOH) |
| L-IB1(s33) | 65 | 10 | PKRPTTLNLF (NH$_2$-PKRPTTLNLF-COOH) |
| L-IB1(s34) | 66 | 10 | RPKRPTTLNL (NH$_2$-RPKRPTTLNL-COOH) |
| D-IB1(s1) | 67 | 13 | QPFLNLTTPRKPR (NH$_2$-QPFLNLTTPRKPR-COOH) |
| D-IB1(s2) | 68 | 13 | VQPFLNLTTPRKP (NH$_2$-VQPFLNLTTPRKP-COOH) |
| D-IB1(s3) | 69 | 13 | PVQPFLNLTTPRK (NH$_2$-PVQPFLNLTTPRK-COOH) |
| D-IB1(s4) | 70 | 13 | RPVQPFLNLTTPR (NH$_2$-RPVQPFLNLTTPR-COOH) |
| D-IB1(s5) | 71 | 13 | SRPVQPFLNLTTP (NH$_2$-SRPVQPFLNLTTP-COOH) |
| D-IB1(s6) | 72 | 13 | QSRPVQPFLNLTT (NH$_2$-QSRPVQPFLNLTT-COOH) |
| D-IB1(s7) | 73 | 13 | DQSRPVQPFLNLT (NH$_2$-DQSRPVQPFLNLT-COOH) |
| D-IB1(s8) | 74 | 12 | PFLNLTTPRKPR (NH$_2$-PFLNLTTPRKPR-COOH) |
| D-IB1(s9) | 75 | 12 | QPFLNLTTPRKP (NH$_2$-QPFLNLTTPRKP-COOH) |
| D-IB1(s10) | 76 | 12 | VQPFLNLTTPRK (NH$_2$-VQPFLNLTTPRK-COOH) |
| D-IB1(s11) | 77 | 12 | PVQPFLNLTTPR (NH$_2$-PVQPFLNLTTPR-COOH) |
| D-IB1(s12) | 78 | 12 | RPVQPFLNLTTP (NH$_2$-RPVQPFLNLTTP-COOH) |
| D-IB1(s13) | 79 | 12 | SRPVQPFLNLTT (NH$_2$-SRPVQPFLNLTT-COOH) |
| D-IB1(s14) | 80 | 12 | QSRPVQPFLNLT (NH$_2$-QSRPVQPFLNLT-COOH) |
| D-IB1(s15) | 81 | 12 | DQSRPVQPFLNL (NH$_2$-DQSRPVQPFLNL-COOH) |
| D-IB1(s16) | 82 | 11 | FLNLTTPRKPR (NH$_2$-FLNLTTPRKPR-COOH) |
| D-IB1(s17) | 83 | 11 | PFLNLTTPRKP (NH$_2$-PFLNLTTPRKP-COOH) |

TABLE 1-continued

| SEQUENCE/PEPTIDE NAME | SEQ ID NO | AA | SEQUENCE |
|---|---|---|---|
| D-1B1(s18) | 84 | 11 | QPFLNLTTPRK (NH$_2$-QPFLNLTTPRK-COOH) |
| D-1B1(s19) | 85 | 11 | VQPFLNLTTPR (NH$_2$-VQPFLNLTTPR-COOH) |
| D-1B1(s20) | 86 | 11 | PVQPFLNLTTP (NH$_2$-PVQPFLNLTTP-COOH) |
| D-IB1(s21) | 87 | 11 | RPVQPFLNLTT (NH$_2$-RPVQPFLNLTT-COOH) |
| D-IB1(s22) | 88 | 11 | SRPVQPFLNLT (NH$_2$-SRPVQPFLNLT-COOH) |
| D-IB1(s23) | 89 | 11 | QSRPVQPFLNL (NH$_2$-QSRPVQPFLNL-COOH) |
| D-IB1(s24) | 90 | 11 | DQSRPVQPFLN (NH$_2$-DQSRPVQPFLN-COOH) |
| D-IB1(s25) | 91 | 10 | DQSRPVQPFL (NH$_2$-DQSRPVQPFL-COOH) |
| D-IB1(s26) | 92 | 10 | QSRPVQPFLN (NH$_2$-QSRPVQPFLN-COOH) |
| D-IB1(s27) | 93 | 10 | SRPVQPFLNL (NH$_2$-SRPVQPFLNL-COOH) |
| D-IB1(s28) | 94 | 10 | RPVQPFLNLT (NH$_2$-RPVQPFLNLT-COOH) |
| D-IB1(s29) | 95 | 10 | PVQPFLNLTT (NH$_2$-PVQPFLNLTT-COOH) |
| D-IB1(s30) | 96 | 10 | VQPFLNLTTP (NH$_2$-VQPFLNLTTP-COOH) |
| D-IB1(s31) | 97 | 10 | QPFLNLTTPR (NH$_2$-QPFLNLTTPR-COOH) |
| D-IB1(s32) | 98 | 10 | PFLNLTTPRK (NH$_2$-PFLNLTTPRK-COOH) |
| D-IB1(s33) | 99 | 10 | FLNLTTPRKP (NH$_2$-FLNLTTPRKP-COOH) |
| D-IB1(s34) | 100 | 10 | LNLTTPRKPR (NH$_2$-LNLTTPRKPR-COOH) |

According to another preferred embodiment, the JNK inhibitor sequence as used herein comprises or consists of at least one variant, fragment and/or derivative of the above defined native or non-native amino acid sequences according to SEQ ID NOs: 1-4, 13-20 and 33-100. Preferably, these variants, fragments and/or derivatives retain biological activity of the above disclosed native or non-native JNK inhibitor sequences as used herein, particularly of native or non-native amino acid sequences according to SEQ ID NOs: 1-4, 13-20 and 33-100, i.e. binding JNK and/or inhibiting the activation of at least one JNK activated transcription factor, e.g. c-Jun, ATF2 or Elk1. Functionality may be tested by various tests, e.g. binding tests of the peptide to its target molecule or by biophysical methods, e.g. spectroscopy, computer modeling, structural analysis, etc. Particularly, an JNK inhibitor sequence or variants, fragments and/or derivatives thereof as defined above may be analyzed by hydrophilicity analysis (see e.g. Hopp and Woods, 1981. Proc Natl Acad Sci USA 78: 3824-3828) that can be utilized to identify the hydrophobic and hydrophilic regions of the peptides, thus aiding in the design of substrates for experimental manipulation, such as in binding experiments, or for antibody synthesis. Secondary structural analysis may also be performed to identify regions of an JNK inhibitor sequence or of variants, fragments and/or derivatives thereof as used herein that assume specific structural motifs (see e.g. Chou and Fasman, 1974, Biochem 13: 222-223). Manipulation, translation, secondary structure prediction, hydrophilicity and hydrophobicity profiles, open reading frame prediction and plotting, and determination of sequence homologies can be accomplished using computer software programs available in the art. Other methods of structural analysis include, e.g. X-ray crystallography (see e.g. Engstrom, 1974. Biochem Exp Biol 11: 7-13), mass spectroscopy and gas chromatography (see e.g. METHODS IN PROTEIN SCIENCE, 1997, J. Wiley and Sons, New York, N.Y.) and computer modeling (see e.g. Fletterick and Zoller, eds., 1986. Computer Graphics and Molecular Modeling, In: CURRENT COMMUNICATIONS IN MOLECULAR BIOLOGY, Cold Spring Harbor Laboratory Press, Cold Spring Harbor, N.Y.) may also be employed.

Accordingly, the JNK inhibitor sequence as used herein may comprise or consist of at least one variant of (native or non-native) amino acid sequences according to SEQ ID NOs: 1-4, 13-20 and 33-100. In the context of the present invention, a "variant of a (native or non-native) amino acid sequence according to SEQ ID NOs: 1-4, 13-20 and 33-100" is preferably a sequence derived from any of the sequences according to SEQ ID NOs: 1-4, 13-20 and 33-100, wherein the variant comprises amino acid alterations of the amino acid sequences according to SEQ ID NOs: 1-4, 13-20 and 33-100. Such alterations typically comprise 1 to 20, preferably 1 to 10 and more preferably 1 to 5 substitutions, additions and/or deletions of amino acids according to SEQ ID NOs: 1-4, 13-20 and 33-100, wherein the variant exhibits a sequence identity with any of the sequences according to SEQ ID NOs: 1-4, 13-20 and 33-100 of at least about 30%, 50%, 70%, 80%, 90%, 95%, 98% or even 99%.

If variants of (native or non-native) amino acid sequences according to SEQ ID NOs: 1-4, 13-20 and 33-100 as defined above and used herein are obtained by substitution of specific amino acids, such substitutions preferably comprise conservative amino acid substitutions.

Conservative amino acid substitutions may include synonymous amino acid residues within a group which have sufficiently similar physicochemical properties, so that a substitution between members of the group will preserve the biological activity of the molecule (see e.g. Grantham, R. (1974), Science 185, 862-864). It is evident to the skilled person that amino acids may also be inserted and/or deleted in the above-defined sequences without altering their function, particularly if the insertions and/or deletions only involve a few amino acids, e.g. less than twenty, and preferably less than ten, and do not remove or displace amino acids which are critical to functional activity. Moreover, substitutions shall be avoided in variants as used herein, which lead to additional threonines at amino acid positions which are accessible for a phosphorylase, preferably a kinase, in order to avoid inactivation of the JNK-inhibitor sequence as used herein or of the chimeric peptide as used herein in vivo or in vitro.

Preferably, synonymous amino acid residues, which are classified into the same groups and are typically exchangeable by conservative amino acid substitutions, are defined in Table 2.

TABLE 2

Preferred Groups of Synonymous Amino Acid Residues

| Amino Acid | Synonymous Residue |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, (Thr), Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, (Thr), Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, (Thr), Arg, Gln |
| Asn | Gln, Asp, Ser, Asn |
| Lys | Glu, Gln, His, Arg, Lys |

TABLE 2-continued

Preferred Groups of Synonymous Amino Acid Residues

| Amino Acid | Synonymous Residue |
|---|---|
| Asp | Glu, Asn, Asp |
| Glu | Asp, Lys, Asn, Gln, His, Arg, Glu |
| Met | Phe, Ile, Val, Leu, Met |
| Trp | Trp |

A specific form of a variant of SEQ ID NOs: 1-4, 13-20 and 33-100 as used herein is a fragment of the (native or non-native) amino acid sequences according to SEQ ID NOs: 1, 1-4, 13-20 and 33-100" as used herein, which is typically altered by at least one deletion as compared to SEQ ID NOs 1-4, 13-20 and 33-100. Preferably, a fragment comprises at least 4 contiguous amino acids of any of SEQ ID NOs: 1-4, 13-20 and 33-100, a length typically sufficient to allow for specific recognition of an epitope from any of these sequences. Even more preferably, the fragment comprises 4 to 18, 4 to 15, or most preferably 4 to 10 contiguous amino acids of any of SEQ ID NOs: 1-4, 13-20 and 33-100, wherein the lower limit of the range may be 4, or 5, 6, 7, 8, 9, or 10. Deleted amino acids may occur at any position of SEQ ID NOs: 1-4, 13-20 and 33-100, preferably N- or C-terminally.

Furthermore, a fragment of the (native or non-native) amino acid sequences according to SEQ ID NOs: 1-4, 13-20 and 33-100, as described above, may be defined as a sequence sharing a sequence identity with any of the sequences according to SEQ ID NOs: 1-4, 13-20 and 33-100 as used herein of at least about 30%, 50%, 70%, 80%, 90%, 95%, 98%, or even 99%.

The JNK inhibitor sequences as used herein may further comprise or consist of at least one derivative of (native or non-native) amino acid sequences according to SEQ ID NOs: 1-4, 13-20 and 33-100 as defined above. In this context, a "derivative of an (native or non-native) amino acid sequence according to SEQ ID NOs: 1-4, 13-20 and 33-100" is preferably an amino acid sequence derived from any of the sequences according to SEQ ID NOs: 1-4, 13-20 and 33-100, wherein the derivative comprises at least one modified L- or D-amino acid (forming non-natural amino acid(s)), preferably 1 to 20, more preferably 1 to 10, and even more preferably 1 to 5 modified L- or D-amino acids. Derivatives of variants or fragments also fall under the scope of the present invention.

"A modified amino acid" in this respect may be any amino acid which is altered e.g. by different glycosylation in various organisms, by phosphorylation or by labeling specific amino acids. Such a label is then typically selected from the group of labels comprising:

(i) radioactive labels, i.e. radioactive phosphorylation or a radioactive label with sulphur, hydrogen, carbon, nitrogen, etc.;
(ii) colored dyes (e.g. digoxygenin, etc.);
(iii) fluorescent groups (e.g. fluorescein, etc.);
(iv) chemoluminescent groups;
(v) groups for immobilization on a solid phase (e.g. His-tag, biotin, strep-tag, flag-tag, antibodies, antigen, etc.); and
(vi) a combination of labels of two or more of the labels mentioned under (i) to (v).

In the above context, an amino acid sequence having a sequence "sharing a sequence identity" of at least, for example, 95% to a query amino acid sequence of the present invention, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted.

For sequences without exact correspondence, a "% identity" of a first sequence may be determined with respect to a second sequence. In general, these two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length.

Methods for comparing the identity and homology of two or more sequences, particularly as used herein, are well known in the art. Thus for instance, programs available in the Wisconsin Sequence Analysis Package, version 9.1 (Devereux et al., 1984, Nucleic Acids Res. 12, 387-395), for example the programs BESTFIT and GAP, may be used to determine the % identity between two polynucleotides and the % identity and the % homology between two polypeptide sequences. BESTFIT uses the "local homology" algorithm of (Smith and Waterman (1981), J. Mol. Biol. 147, 195-197.) and finds the best single region of similarity between two sequences. Other programs for determining identity and/or similarity between sequences are also known in the art, for instance the BLAST family of programs (Altschul et al., 1990, J. Mol. Biol. 215, 403-410), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U. S. A 85, 2444-2448).

JNK-inhibitor sequences as used according to the present invention and as defined above may be obtained or produced by methods well-known in the art, e.g. by chemical synthesis or by genetic engineering methods as discussed below. For example, a peptide corresponding to a portion of an JNK inhibitor sequence as used herein including a desired region of said JNK inhibitor sequence, or that mediates the desired activity in vitro or in vivo, may be synthesized by use of a peptide synthesizer.

JNK inhibitor sequence as used herein and as defined above, may be furthermore be modified by a trafficking sequence, allowing the JNK inhibitor sequence as used herein and as defined above to be transported effectively into the cells. Such modified JNK inhibitor sequence are preferably provided and used as chimeric sequences.

According to a second aspect the present invention therefore provides the use of a chimeric peptide including at least one first domain and at least one second domain, for the preparation of a pharmaceutical composition for treating diseases or disorders strongly related to JNK signaling as defined above in a subject, wherein the first domain of the chimeric peptide comprises a trafficking sequence, while the second domain of the chimeric peptide comprises an JNK inhibitor sequence as defined above, preferably of any of sequences according to SEQ ID NO: 1-4, 13-20 and 33-100 or a derivative or a fragment thereof.

Typically, chimeric peptides as used according to the present invention have a length of at least 25 amino acid residues, e.g. 25 to 250 amino acid residues, more preferably 25 to 200 amino acid residues, even more preferably 25 to 150 amino acid residues, 25 to 100 and most preferably amino acid 25 to 50 amino acid residues.

As a first domain the chimeric peptide as used herein preferably comprises a trafficking sequence, which is typically selected from any sequence of amino acids that directs a peptide (in which it is present) to a desired cellular destination. Thus, the trafficking sequence, as used herein, typically directs the peptide across the plasma membrane, e.g. from outside the cell, through the plasma membrane, and into the cytoplasm. Alternatively, or in addition, the trafficking sequence may direct the peptide to a desired location within the cell, e.g. the nucleus, the ribosome, the endoplasmic reticulum (ER), a lysosome, or peroxisome, by e.g. combining two components (e.g. a component for cell permeability and a component for nuclear location) or by one single component having e.g. properties of cell membrane transport and targeted e.g. intranuclear transport. The trafficking sequence may additionally comprise another component, which is capable of binding a cytoplasmic component or any other component or compartment of the cell (e.g. endoplasmic reticulum, mitochondria, gloom apparatus, lysosomal vesicles). Accordingly, e.g. the trafficking sequence of the first domain and the JNK inhibitor sequence of the second domain may be localized in the cytoplasm or any other compartment of the cell. This allows to determine localization of the chimeric peptide in the cell upon uptake.

Preferably, the trafficking sequence (being included in the first domain of the chimeric peptide as used herein) has a length of 5 to 150 amino acid sequences, more preferably a length of 5 to 100 and most preferably a length of from 5 to 50, 5 to 30 or even 5 to 15 amino acids.

More preferably, the trafficking sequence (contained in the first domain of the chimeric peptide as used herein) may occur as a continuous amino acid sequence stretch in the first domain. Alternatively, the trafficking sequence in the first domain may be splitted into two or more fragments, wherein all of these fragments resemble the entire trafficking sequence and may be separated from each other by 1 to 10, preferably 1 to 5 amino acids, provided that the trafficking sequence as such retains its carrier properties as disclosed above. These amino acids separating the fragments of the trafficking sequence may e.g. be selected from amino acid sequences differing from the trafficking sequence. Alternatively, the first domain may contain a trafficking sequence composed of more than one component, each component with its own function for the transport of the cargo JNK inhibitor sequence of the second domain to e.g. a specific cell compartment.

The trafficking sequence as defined above may be composed of L-amino acids, D-amino acids, or a combination of both. Preferably, the trafficking sequence (being included in the first domain of the chimeric peptide as used herein) may comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the JNK trafficking sequences in a blockwise, a non-blockwise or in an alternate manner.

According to one alternative embodiment, the trafficking sequence of the chimeric peptide as used herein may be exclusively composed of L-amino acids. More preferably, the trafficking sequence of the chimeric peptide as used herein comprises or consists of at least one "native" trafficking sequence as defined above. In this context, the term "native" is referred to non-altered trafficking sequences, entirely composed of L-amino acids.

According to another alternative embodiment the trafficking sequence of the chimeric peptide as used herein may be exclusively composed of D-amino acids. More preferably, the trafficking sequence of the chimeric peptide as used herein may comprise a D retro-inverso peptide of the sequences as presented above.

The trafficking sequence of the first domain of the chimeric peptide as used herein may be obtained from naturally occurring sources or can be produced by using genetic engineering techniques or chemical synthesis (see e.g. Sambrook, J., Fritsch, E. F., Maniatis, T. (1989) Molecular cloning: A laboratory manual. 2nd edition. Cold Spring Harbor Laboratory Press, Cold Spring Harbor, N.Y.).

Sources for the trafficking sequence of the first domain may be employed including, e.g. native proteins such as e.g. the TAT protein (e.g. as described in U.S. Pat. Nos. 5,804,604 and 5,674,980, each of these references being incorporated herein by reference), VP22 (described in e.g. WO 97/05265; Elliott and O'Hare, Cell 88: 223-233 (1997)), non-viral proteins (Jackson et al, Proc. Natl. Acad. Sci. USA 89: 10691-10695 (1992)), trafficking sequences derived from Antennapedia (e.g. the antennapedia carrier sequence) or from basic peptides, e.g. peptides having a length of 5 to 15 amino acids, preferably 10 to 12 amino acids and comprising at least 80%, more preferably 85% or even 90% basic amino acids, such as e.g. arginine, lysine and/or histidine. Furthermore, variants, fragments and derivatives of one of the native proteins used as trafficking sequences are disclosed herewith. With regard to variants, fragments and derivatives it is referred to the definition given above for JNK inhibitor sequences as used herein. Variants, fragments as well as derivatives are correspondingly defined as set forth above for JNK inhibitor sequences as used herein. Particularly, in the context of the trafficking sequence, a variant or fragment or derivative may be defined as a sequence sharing a sequence identity with one of the native proteins used as trafficking sequences as defined above of at least about 30%, 50%, 70%, 80%, 90%, 95%, 98%, or even 99%.

In a preferred embodiment of the chimeric peptide as used herein, the trafficking sequence of the first domain comprises or consists of a sequence derived from the human immunodeficiency virus (HIV)1 TAT protein, particularly some or all of the 86 amino acids that make up the TAT protein.

For a trafficking sequence (being included in the first domain of the chimeric peptide as used herein), partial sequences of the full-length TAT protein may be used forming a functionally effective fragment of a TAT protein, i.e. a TAT peptide that includes the region that mediates entry and uptake into cells. As to whether such a sequence is a functionally effective fragment of the TAT protein can be determined using known techniques (see e.g. Franked et al., Proc. Natl. Acad. Sci, USA 86: 7397-7401 (1989)). Thus, the trafficking sequence in the first domain of the chimeric peptide as used herein may be derived from a functionally effective fragment or portion of a TAT protein sequence that comprises less than 86 amino acids, and which exhibits uptake into cells, and optionally the uptake into the cell nucleus. More preferably, partial sequences (fragments) of TAT to be used as carrier to mediate permeation of the chimeric peptide across the cell membrane, are intended to comprise the basic region (amino acids 48 to 57 or 49 to 57) of full-length TAT.

According to a more preferred embodiment, the trafficking sequence (being included in the first domain of the chimeric peptide as used herein) may comprise or consist of an amino acid sequence containing TAT residues 48-57 or 49 to 57, and most preferably a generic TAT sequence $NH_2$—$X_n^b$-RKKRRQRRR-$X_n^b$—COOH (L-generic-TAT (s)) [SEQ ID NO: 7] and/or XXXXRKKRRQ RRRXXXX (L-generic-TAT) [SEQ ID NO: 21], wherein X or $X_n^b$ is as defined above. Furthermore, the number of "$X_n^b$" residues in SEQ ID NOs:8 is not limited to the one depicted, and may vary as described above. Alternatively, the trafficking sequence being included in the first domain of the chimeric peptide as used herein may comprise or consist of a peptide containing e.g. the amino acid sequence $NH_2$-GRK-KRRQRRR-COOH (L-TAT) [SEQ ID NO: 5].

According to another more preferred embodiment the trafficking sequence (being included in the first domain of the chimeric peptide as used herein) may comprise a D retro-inverso peptide of the sequences as presented above, i.e. the D retro-inverso sequence of the generic TAT sequence having the sequence $NH_2$—$X_n^b$-RRRQRRKKR-$X_n^b$—COOH (D-generic-TAT (s)) [SEQ ID NO: 8] and/or XXXXRRRQRRKKRXXXX (D-generic-TAT) [SEQ ID NO: 22]. Also here, $X_n^b$ is as defined above (preferably representing D amino acids). Furthermore, the number of "$X_n^b$" residues in SEQ ID NOs:8 is not limited to the one depicted, and may vary as described above. Most preferably, the trafficking sequence as used herein may comprise the D retro-inverso sequence $NH_2$-RRRQRRKKRG-COOH (D-TAT) [SEQ ID NO: 6].

According to another embodiment the trafficking sequence being included in the first domain of the chimeric peptide as used herein may comprise or consist of variants of the trafficking sequences as defined above. A "variant of a trafficking sequence" is preferably a sequence derived from a trafficking sequence as defined above, wherein the variant comprises a modification, for example, addition, (internal) deletion (leading to fragments) and/or substitution of at least one amino acid present in the trafficking sequence as defined above. Such (a) modification(s) typically comprise(s) 1 to 20, preferably 1 to 10 and more preferably 1 to 5 substitutions, additions and/or deletions of amino acids. Furthermore, the variant preferably exhibits a sequence identity with the trafficking sequence as defined above, more preferably with any of SEQ ID NOs: 5 to 8 or 21-22, of at least about 30%, 50%, 70%, 80%, 90%, 95%, 98% or even 99%.

Preferably, such a modification of the trafficking sequence being included in the first domain of the chimeric peptide as used herein leads to a trafficking sequence with increased or decreased stability. Alternatively, variants of the trafficking sequence can be designed to modulate intracellular localization of the chimeric peptide as used herein. When added exogenously, such variants as defined above are typically designed such that the ability of the trafficking sequence to enter cells is retained (i.e. the uptake of the variant of the trafficking sequence into the cell is substantially similar to that of the native protein used a trafficking sequence). For example, alteration of the basic region thought to be important for nuclear localization (see e.g. Dang and Lee, J. Biol. Chem. 264: 18019-18023 (1989); Hauber et al., J. Virol. 63: 1181-1187 (1989); et al., J. Virol. 63: 1-8 (1989)) can result in a cytoplasmic location or partially cytoplasmic location of the trafficking sequence, and therefore, of the JNK inhibitor sequence as component of the chimeric peptide as used herein. Additional to the above, further modifications may be introduced into the variant, e.g. by linking e.g. cholesterol or other lipid moieties to the trafficking sequence to produce a trafficking sequence having increased membrane solubility. Any of the above disclosed variants of the trafficking sequences being included in the first domain of the chimeric peptide as used herein can be produced using techniques typically known to a skilled person (see e.g. Sambrook, J., Fritsch, E. F., Maniatis, T. (1989) Molecular cloning: A laboratory manual. 2nd edition. Cold Spring Harbor Laboratory, Cold Spring Harbor, N.Y.)

As a second domain the chimeric peptide as used herein typically comprises an JNK inhibitor sequence, selected from any of the JNK inhibitor sequences as defined above, including variants, fragments and/or derivatives of these JNK inhibitor sequences.

Both domains, i.e. the first and the second domain(s), of the chimeric peptide as used herein, may be linked such as to form a functional unit. Any method for linking the first and second domain(s) as generally known in the art may be applied.

According to one embodiment, the first and the second domain(s) of the chimeric peptide as used herein are preferably linked by a covalent bond. A covalent bond, as defined herein, may be e.g. a peptide bond, which may be obtained by expressing the chimeric peptide as defined above as a fusion protein. Fusion proteins, as described herein, can be formed and used in ways analogous to or readily adaptable from standard recombinant DNA techniques, as described below. However, both domains may also be linked via side chains or may be linked by a chemical linker moiety.

The first and/or second domains of the chimeric peptide as used herein may occur in one or more copies in said chimeric peptide. If both domains are present in a single copy, the first domain may be linked either to the N-terminal or the C-terminal end of the second domain. If present in multiple copies, the first and second domain(s) may be arranged in any possible order. E.g. the first domain can be present in the chimeric peptide as used herein in a multiple copy number, e.g. in two, three or more copies, which are preferably arranged in consecutive order. Then, the second domain may be present in a single copy occurring at the N- or C-terminus of the sequence comprising the first domain. Alternatively, the second domain may be present in a multiple copy number, e.g. in two, three or more copies, and the first domain may be present in a single copy. According to both alternatives, first and second domain(s) can take any place in a consecutive arrangement. Exemplary arrangements are shown in the following: e.g. first domain-first domain-first domain-second domain; first domain-first domain-second domain-first domain; first domain-second domain-first domain-first domain; or e.g. second domain-first domain-first domain-first domain. It is well understood for a skilled person that these examples are for illustration purposes only and shall not limit the scope of the invention thereto. Thus, the number of copies and the arrangement may be varied as defined initially.

Preferably, the first and second domain(s) may be directly linked with each other without any linker. Alternatively, they may be linked with each other via a linker sequence comprising 1 to 10, preferably 1 to 5 amino acids. Amino acids forming the linker sequence are preferably selected from glycine or proline as amino acid residues. More preferably, the first and second domain(s) may be separated by each other by a hinge of two, three or more proline residues between the first and second domain(s).

The chimeric peptide as defined above and as used herein, comprising at least one first and at least one second domain, may be composed of L-amino acids, D-amino acids, or a combination of both. Therein, each domain (as well as the linkers used) may be composed of L-amino acids, D-amino acids, or a combination of both (e.g. D-TAT and L-IB1(s) or L-TAT and D-IB1(s), etc.). Preferably, the chimeric peptide as used herein may comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the chimeric peptide as used herein in a blockwise, a non-blockwise or in an alternate manner.

According to a specific embodiment the chimeric peptide as used herein comprises or consists of the L-amino acid chimeric peptides according to the generic L-TAT-IB peptide $NH_2$—$X_n^b$-RKKRRQRRR-$X_n^b$—$X_n^a$-RPTTLX-LXXXXXXXQD-$X_n^b$—COOH (L-TAT-IB (generic) (s)) [SEQ ID NO: 10], wherein X, $X_n^a$ and $X_n^b$ are preferably as defined above. More preferably, the chimeric peptide as used herein comprises or consists of the L-amino acid chimeric peptide $NH_2$-GRKKRRQRRRPPRPKRPTTLNLFPQVPR-SQD-COOH (L-TAT-IB1 (s)) [SEQ ID NO: 9]. Alternatively or additionally, the chimeric peptide as used herein comprises or consists of the L-amino acid chimeric peptide sequence GRKKRRQRRR PPDTYRPKRP TTLNLFPQVP RSQDT (L-TAT-IB1) [SEQ ID NO: 23], or XXXXXXXXRKK RRQRRRXXXX XXXXRPTTLX LXXXXXXXQD S/TX (L-TAT-IB generic) [SEQ ID NO: 24], wherein X is preferably also as defined above, or the chimeric peptide as used herein comprises or consists of the L-amino acid chimeric peptide sequence RKKRRQRRRP-PRPKRPTTLNLFPQVPRSQD (L-TAT-IB1(s1)) [SEQ ID NO: 27], GRKKRRQRRRX$_n^c$RPKRPTTLNLFPQVPR-SQD (L-TAT-IB1(s2)) [SEQ ID NO: 28], or RKKRRQR-RRX$_n^c$RPKRPTTLNLFPQVPRSQD (L-TAT-IB1(s3)) [SEQ ID NO: 29]. In this context, each X typically represents an amino acid residue as defined above, more preferably $X_n^c$ represents a contiguous stretch of peptide residues, each X independently selected from each other from glycine or proline, e.g. a monotonic glycine stretch or a monotonic proline stretch, wherein n (the number of repetitions of $X_n^c$) is typically 0-5, 5-10, 10-15, 15-20, 20-30 or even more, preferably 0-5 or 5-10. $X_n^c$ may represent either D or L amino acids.

According to an alternative specific embodiment the chimeric peptide as used herein comprises or consists of D-amino acid chimeric peptides of the above disclosed L-amino acid chimeric peptides. Exemplary D retro-inverso chimeric peptides according to the present invention are e.g. the generic D-TAT-IB peptide $NH_2$—$X_n^b$-DQXXXXXXX-LXLTTPR-$X_n^a$—$X_n^b$-RRRQRRKKR-$X_n^b$—COOH (D-TAT-IB (generic) (s)) [SEQ ID NO: 12]. Herein, X, $X_n^a$ and $X_n^b$ are preferably as defined above (preferably representing D amino acids). More preferably, the chimeric peptide as used herein comprises or consists of D-amino acid chimeric peptides according to the TAT-IB1 peptide $NH_2$-DQSRPVQPFLNLTTPRKPRPPRRRQRRKKRG-COOH (D-TAT-IB1(s)) [SEQ ID NO: 11]. Alternatively or additionally, the chimeric peptide as used herein comprises or consists of the D-amino acid chimeric peptide sequence TDQSRPVQPFLNLTTPRKPRYTDPPRRRQRRKKRG (D-TAT-IB1) [SEQ ID NO: 25], or XT/SDQXXXXXXX-LXLTTPRXXXXXXXXXRRRQRRKKRXXXXXXX (D-TAT-IB generic) [SEQ ID NO: 26], wherein X is preferably also as defined above, or the chimeric peptide as used herein comprises or consists of the D-amino acid chimeric peptide sequence DQSRPVQPFLNLTTPRKPRPPRRRQR-RKKR (D-TAT-IB1(s1)) [SEQ ID NO: 30], DQSRPVQP- FLNLTTPRKPRX$_n^c$RRRQRRKKRG (D-TAT-IB1(s2)) [SEQ ID NO: 31], or DQSRPVQPFLNLTTPRKPRX$_n^c$RRRQRRKKR (D-TAT-IB1(s3)) [SEQ ID NO: 32]. X$_n^c$ may be as defined above.

The first and second domain(s) of the chimeric peptide as defined above may be linked to each other by chemical or biochemical coupling carried out in any suitable manner known in the art, e.g. by establishing a peptide bond between the first and the second domain(s) e.g. by expressing the first and second domain(s) as a fusion protein, or e.g. by cross-linking the first and second domain(s) of the chimeric peptide as defined above.

Many known methods suitable for chemical crosslinking of the first and second domain(s) of the chimeric peptide as defined above are non-specific, i.e. they do not direct the point of coupling to any particular site on the transport polypeptide or cargo macromolecule. As a result, use of non-specific crosslinking agents may attack functional sites or sterically block active sites, rendering the conjugated proteins biologically inactive. Thus, preferably such crosslinking methods are used, which allow a more specific coupling of the first and second domain(s).

In this context, one way to increasing coupling specificity is a direct chemical coupling to a functional group present only once or a few times in one or both of the first and second domain(s) to be crosslinked. For example, cysteine, which is the only protein amino acid containing a thiol group, occurs in many proteins only a few times. Also, for example, if a polypeptide contains no lysine residues, a crosslinking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity. Cysteine residues may be replaced when they occur in parts of a polypeptide sequence where their participation in a crosslinking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for crosslinking purposes. When a cysteine residue is introduced, introduction at or near the amino or carboxy terminus is preferred. Conventional methods are available for such amino acid sequence modifications, wherein the polypeptide of interest is produced by chemical synthesis or via expression of recombinant DNA.

Coupling of the first and second domain(s) of the chimeric peptide as defined above and used herein can also be accomplished via a coupling or conjugating agent. There are several intermolecular crosslinking reagents which can be utilized (see for example, Means and Feeney, CHEMICAL MODIFICATION OF PROTEINS, Holden-Day, 1974, pp. 39-43). Among these reagents are, for example, N-succinimidyl 3-(2-pyridyldithio) propionate (SPDP) or N,N'-(1,3-phenylene) bismaleimide (both of which are highly specific for sulfhydryl groups and form irreversible linkages); N, N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups). Other crosslinking reagents useful for this purpose include: p,p'-difluoro-m, m'-dinitrodiphenylsulfone which forms irreversible crosslinkages with amino and phenolic groups); dimethyl adipimidate (which is specific for amino groups); phenol-1,4 disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Crosslinking reagents used for crosslinking the first and second domain(s) of the chimeric peptide as defined above may be homobifunctional, i.e. having two functional groups that undergo the same reaction. A preferred homobifunctional crosslinking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible crosslinking of polypeptides that contain cysteine residues.

Crosslinking reagents used for crosslinking the first and second domain(s) of the chimeric peptide as defined above may also be heterobifunctional. Heterobifunctional crosslinking agents have two different functional groups, for example an amine-reactive group and a thiol-reactive group, that will crosslink two proteins having free amines and thiols, respectively. Examples of heterobifunctional crosslinking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl)butyrate ("SMPB"), an extended chain analog of MBS. The succinimidyl group of these crosslinkers reacts with a primary amine, and the thiol-reactive maleimide forms a covalent bond with the thiol of a cysteine residue.

Crosslinking reagents suitable for crosslinking the first and second domain(s) of the chimeric peptide as defined above often have low solubility in water. A hydrophilic moiety, such as a sulfonate group, may thus be added to the crosslinking reagent to improve its water solubility. In this respect, Sulfo-MBS and Sulfo-SMCC are examples of crosslinking reagents modified for water solubility, which may be used according to the present invention.

Likewise, many crosslinking reagents yield a conjugate that is essentially non-cleavable under cellular conditions. However, some crosslinking reagents particularly suitable for crosslinking the first and second domain(s) of the chimeric peptide as defined above contain a covalent bond, such as a disulfide, that is cleavable under cellular conditions. For example, Traut's reagent, dithiobis(succinimidylpropionate) ("DSP"), and N-succinimidyl 3-(2-pyridyldithio)propionate ("SPDP") are well-known cleavable crosslinkers. The use of a cleavable crosslinking reagent permits the cargo moiety to separate from the transport polypeptide after delivery into the target cell. Direct disulfide linkage may also be useful.

Numerous crosslinking reagents, including the ones discussed above, are commercially available. Detailed instructions for their use are readily available from the commercial suppliers. A general reference on protein crosslinking and conjugate preparation is: Wong, CHEMISTRY OF PROTEIN CONJUGATION AND CROSSLINKING, CRC Press (1991).

Chemical crosslinking of the first and second domain(s) of the chimeric peptide as defined above may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the crosslinking reagent, such as in "long-chain SPDP" (Pierce Chem. Co., Rockford, Ill., cat. No. 21651 H).

Furthermore, variants, fragments or derivatives of one of the above disclosed chimeric peptides may be used herein. With regard to fragments and variants it is generally referred to the definition given above for JNK inhibitor sequences.

Particularly, in the context of the present invention, a "variant of a chimeric peptide" is preferably a sequence derived from any of the sequences according to SEQ ID NOs: 9 to 12 and 23 to 32, wherein the chimeric variant comprises amino acid alterations of the chimeric peptides according to SEQ ID NOs: 9 to 12 and 23 to 32 as used herein. Such alterations typically comprise 1 to 20, preferably 1 to 10 and more preferably 1 to 5 substitutions, additions and/or deletions (leading to fragments) of amino acids according to SEQ ID NOs: 9 to 12 and 23 to 32, wherein the altered chimeric peptide as used herein exhibits a sequence identity with any of the sequences according to SEQ ID NOs: 9-12 and 23 to 32 of at least about 30%, 50%, 70%, 80%, or 95%, 98%, or even 99%. Preferably, these variants retain the biological activity of the first and the second domain as contained in the chimeric peptide as used herein, i.e. the trafficking activity of the first domain as disclosed above and the activity of the second domain for binding JNK and/or inhibiting the activation of at least one JNK activated transcription factor.

Accordingly, the chimeric peptide as used herein also comprises fragments of the afore disclosed chimeric peptides, particularly of the chimeric peptide sequences according to any of SEQ ID NOs: 9 to 12 and 23 to 32. Thus, in the context of the present invention, a "fragment of the chimeric peptide" is preferably a sequence derived any of the sequences according to SEQ ID NOs: 9 to 12 and 23 to 32, wherein the fragment comprises at least 4 contiguous amino acids of any of SEQ ID NOs: 9 to 12 and 23 to 32. This fragment preferably comprises a length which is sufficient to allow specific recognition of an epitope from any of these sequences and to transport the sequence into the cells, the nucleus or a further preferred location. Even more preferably, the fragment comprises 4 to 18, 4 to 15, or most preferably 4 to 10 contiguous amino acids of any of SEQ ID NOs: 9 to 12 and 23 to 32. Fragments of the chimeric peptide as used herein further may be defined as a sequence sharing a sequence identity with any of the sequences according to any of SEQ ID NOs: 99 to 12 and 23 to 32 of at least about 30%, 50%, 70%, 80%, or 95%, 98%, or even 99%.

Finally, the chimeric peptide as used herein also comprises derivatives of the afore disclosed chimeric peptides, particularly of the chimeric peptide sequences according to any of SEQ ID NOs: 9 to 12 and 23 to 32.

The present invention additionally refers to the use of nucleic acid sequences encoding JNK inhibitor sequences as defined above, chimeric peptides or their fragments, variants or derivatives, all as defined above, for the preparation of a pharmaceutical composition for treating diseases or disorders strongly related to JNK signaling as defined above in a subject. A preferable suitable nucleic acid encoding an JNK inhibitor sequence as used herein is typically chosen from human IB1 nucleic acid (GenBank Accession No. (AF074091), rat IB1 nucleic acid (GenBank Accession No. AF 108959), or human IB2 (GenBank Accession No AF218778) or from any nucleic acid sequence encoding any of the sequences as defined above, i.e. any sequence according to SEQ ID NO: 1-26.

Nucleic acids encoding the JNK inhibitor sequences as used herein or chimeric peptides as used herein may be obtained by any method known in the art (e.g. by PCR amplification using synthetic primers hybridizable to the 3'- and 5'-termini of the sequence and/or by cloning from a cDNA or genomic library using an oligonucleotide sequence specific for the given gene sequence).

Additionally, nucleic acid sequences are disclosed herein as well, which hybridize under stringent conditions with the appropriate strand coding for a (native) JNK inhibitor sequence or chimeric peptide as defined above. Preferably, such nucleic acid sequences comprise at least 6 (contiguous) nucleic acids, which have a length sufficient to allow for specific hybridization. More preferably, such nucleic acid sequences comprise 6 to 38, even more preferably 6 to 30, and most preferably 6 to 20 or 6 to 10 (contiguous) nucleic acids.

"Stringent conditions" are sequence dependent and will be different under different circumstances. Generally, stringent conditions can be selected to be about 5° C. lower than the thermal melting point (TM) for the specific sequence at a defined ionic strength and pH. The TM is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

"High stringency conditions" may comprise the following, e.g. Step 1: Filters containing DNA are pretreated for 8 hours to overnight at 65° C. in buffer composed of 6*SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5-20*10$^6$ cpm of $^{32}$P-labeled probe. Step 3: Filters are washed for 1 hour at 37° C. in a solution containing 2*SSC, 0.01% PVP, 0.01% Ficoll, and 0.01% BSA. This is followed by a wash in 0.1*SSC at 50° C. for 45 minutes. Step 4: Filters are autoradiographed. Other conditions of high stringency that may be used are well known in the art (see e.g. Ausubel et al., (eds.), 1993, Current Protocols in Molecular Biology, John Wiley and Sons, NY; and Kriegler, 1990, Gene Transfer and Expression, a Laboratory Manual, Stockton Press, NY).

"Moderate stringency conditions" can include the following: Step 1: Filters containing DNA are pretreated for 6 hours at 55° C. in a solution containing 6*SSC, 5*Denhardt's solution, 0.5% SDS and 100 mg/ml denatured salmon sperm DNA. Step 2: Filters are hybridized for 18-20 hours at 55° C. in the same solution with 5-20*10$^6$ cpm $^{32}$P-labeled probe added. Step 3: Filters are washed at 37° C. for 1 hour in a solution containing 2*SSC, 0.1% SDS, then washed twice for 30 minutes at 60° C. in a solution containing 1*SSC and 0.1% SDS. Step 4: Filters are blotted dry and exposed for autoradiography. Other conditions of moderate stringency that may be used are well-known in the art (see e.g. Ausubel et al., (eds.), 1993, Current Protocols in Molecular Biology, John Wiley and Sons, NY; and Kriegler, 1990, Gene Transfer and Expression, a Laboratory Manual, Stockton Press, NY).

Finally, "low stringency conditions" can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5-20×106 cpm $^{32}$P-labeled probe. Step 3: Filters are washed for 1.5 hours at 55 C in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g. as employed for cross-species hybridizations). See e.g. Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

The nucleic acid sequences as defined above according to the present invention can be used to express peptides, i.e. an JNK inhibitor sequence as used herein or an chimeric peptide as used herein for analysis, characterization or therapeutic use; as markers for tissues in which the corresponding peptides (as used herein) are preferentially expressed (either constitutively or at a particular stage of tissue differentiation or development or in disease states). Other uses for these nucleic acids include, e.g. molecular weight markers in gel electrophoresis-based analysis of nucleic acids.

According to a further embodiment of the present invention, expression vectors may be used for the above purposes for recombinant expression of one or more JNK inhibitor sequences and/or chimeric peptides as defined above. The term "expression vector" is used herein to designate either circular or linear DNA or RNA, which is either double-stranded or single-stranded. It further comprises at least one nucleic acid as defined above to be transferred into a host cell or into a unicellular or multicellular host organism. The expression vector as used herein preferably comprises a nucleic acid as defined above encoding the JNK inhibitor sequence as used herein or a fragment or a variant thereof, or the chimeric peptide as used herein, or a fragment or a variant thereof. Additionally, an expression vector according to the present invention preferably comprises appropriate elements for supporting expression including various regulatory elements, such as enhancers/promoters from viral, bacterial, plant, mammalian, and other eukaryotic sources that drive expression of the inserted polynucleotide in host cells, such as insulators, boundary elements, LCRs (e.g. described by Blackwood and Kadonaga (1998), Science 281, 61-63) or matrix/scaffold attachment regions (e.g. described by Li, Harju and Peterson, (1999), Trends Genet. 15, 403-408). In some embodiments, the regulatory elements are heterologous (i.e. not the native gene promoter). Alternately, the necessary transcriptional and translational signals may also be supplied by the native promoter for the genes and/or their flanking regions.

The term "promoter" as used herein refers to a region of DNA that functions to control the transcription of one or more nucleic acid sequences as defined above, and that is structurally identified by the presence of a binding site for DNA-dependent RNA-polymerase and of other DNA sequences, which interact to regulate promoter function. A functional expression promoting fragment of a promoter is a shortened or truncated promoter sequence retaining the activity as a promoter. Promoter activity may be measured by any assay known in the art (see e.g. Wood, de Wet, Dewji, and DeLuca, (1984), Biochem Biophys. Res. Commun. 124, 592-596; Seliger and McElroy, (1960), Arch. Biochem. Biophys. 88, 136-141) or commercially available from Promega®).

An "enhancer region" to be used in the expression vector as defined herein, typically refers to a region of DNA that functions to increase the transcription of one or more genes. More specifically, the term "enhancer", as used herein, is a DNA regulatory element that enhances, augments, improves, or ameliorates expression of a gene irrespective of its location and orientation vis-à-vis the gene to be expressed, and may be enhancing, augmenting, improving, or ameliorating expression of more than one promoter.

The promoter/enhancer sequences to be used in the expression vector as defined herein, may utilize plant, animal, insect, or fungus regulatory sequences. For example, promoter/enhancer elements can be used from yeast and other fungi (e.g. the GAL4 promoter, the alcohol dehydrogenase promoter, the phosphoglycerol kinase promoter, the alkaline phosphatase promoter). Alternatively, or in addition, they may include animal transcriptional control regions, e.g. (i) the insulin gene control region active within pancreatic beta-cells (see e.g. Hanahan, et al., 1985. Nature 315: 115-122); (ii) the immunoglobulin gene control region active within lymphoid cells (see e.g. Grosschedl, et al., 1984, Cell 38: 647-658); (iii) the albumin gene control region active within liver (see e.g. Pinckert, et al., 1987. Genes and Dev 1: 268-276; (iv) the myelin basic protein gene control region active within brain oligodendrocyte cells (see e.g. Readhead, et al., 1987, Cell 48: 703-712); and (v) the gonadotropin-releasing hormone gene control region active within the hypothalamus (see e.g. Mason, et al., 1986, Science 234: 1372-1378), and the like.

Additionally, the expression vector as defined herein may comprise an amplification marker. This amplification marker may be selected from the group consisting of, e.g. adenosine deaminase (ADA), dihydrofolate reductase (DHFR), multiple drug resistance gene (MDR), ornithine decarboxylase (ODC) and N-(phosphonacetyl)-L-aspartate resistance (CAD).

Exemplary expression vectors or their derivatives suitable for the present invention particularly include, e.g. human or animal viruses (e.g. vaccinia virus or adenovirus); insect viruses (e.g. baculovirus); yeast vectors; bacteriophage vectors (e.g. lambda phage); plasmid vectors and cosmid vectors.

The present invention additionally may utilize a variety of host-vector systems, which are capable of expressing the peptide coding sequence(s) of nucleic acids as defined above. These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Preferably, a host cell strain, suitable for such a host-vector system, may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptide. Moreover, different host cells possess characteristic and specific mechanisms for the translational and post-translational processing and modification (e.g. glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an non-glycosylated core peptide; whereas expression within mammalian cells ensures "native" glycosylation of a heterologous peptide.

The present invention further provides the use of antibodies directed against the JNK inhibitor sequences and/or chimeric peptides as described above, for preparing a pharmaceutical composition for the treatment of diseases or disorders strongly related to JNK signaling as defined herein. Furthermore, efficient means for production of antibodies specific for JNK inhibitor sequences according to the present invention, or for chimeric peptides containing such an inhibitor sequence, are described and may be utilized for this purpose.

According to the invention, JNK inhibitor sequences and/or chimeric peptides as defined herein, as well as, fragments, variants or derivatives thereof, may be utilized as immunogens to generate antibodies that immunospecifically bind these peptide components. Such antibodies include, e.g. polyclonal, monoclonal, chimeric, single chain, Fab fragments and a Fab expression library. In a specific embodiment the present invention provides antibodies to chimeric peptides or to JNK inhibitor sequences as defined above. Various procedures known within the art may be used for the production of these antibodies.

By way of example, various host animals may be immunized for production of polyclonal antibodies by injection with any chimeric peptide or JNK inhibitor sequence as defined above. Various adjuvants may be used thereby to increase the immunological response which include, but are not limited to, Freund's (complete and incomplete) adjuvant, mineral gels (e.g. aluminum hydroxide), surface active substances (e.g. lysolecithin, pluronic polyols, polyanions, peptides, oil emulsions, dinitrophenol, etc.), CpG, polymers, Pluronics, and human adjuvants such as Bacille Calmette-Guerin and *Corynebacterium parvum*.

For preparation of monoclonal antibodies directed towards an chimeric peptide or a JNK inhibitor sequence as defined above, any technique may be utilized that provides for the production of antibody molecules by continuous cell line culture. Such techniques include, but are not limited to, the hybridoma technique (see Kohler and Milstein, 1975. Nature 256: 495-497); the trioma technique; the human B-cell hybridoma technique (see Kozbor, et al., 1983, Immunol Today 4: 72) and the EBV hybridoma technique to produce human monoclonal antibodies (see Cole, et al., 1985. In: Monoclonal Antibodies and Cancer Therapy, Alan R. Liss, Inc., pp. 77-96). Human monoclonal antibodies may be utilized in the practice of the present invention and may be produced by the use of human hybridomas (see Cote, et al., 1983. Proc Natl Acad Sci USA 80: 2026-2030) or by transforming human B-cells with Epstein Barr Virus in vitro (see Cole, et al, 1985. In: Monoclonal Antibodies and Cancer Therapy (Alan R. Liss, Inc., pp. 77-96).

According to the invention, techniques can be adapted for the production of single-chain antibodies specific to the JNK inhibitor sequences and/or chimeric peptides (see e.g. U.S. Pat. No. 4,946,778) as defined herein. In addition, methods can be adapted for the construction of Fab expression libraries (see e.g. Huse et al., 1989. Science 246: 1275-1281) to allow rapid and effective identification of monoclonal Fab fragments with the desired specificity for these JNK inhibitor sequences and/or chimeric peptides. Non-human antibodies can be "humanized" by techniques well known in the art (see e.g. U.S. Pat. No. 5,225,539). Antibody fragments that contain the idiotypes to a JNK inhibitor sequences and/or chimeric peptide as defined herein may be produced by techniques known in the art including, e.g. (i) a F(ab')2 fragment produced by pepsin digestion of an antibody molecule; (ii) a Fab fragment generated by reducing the disulfide bridges of an F(ab')$_2$ fragment; (iii) a Fab fragment generated by the treatment of the antibody molecule with papain and a reducing agent and (iv) Fv fragments.

In one embodiment of this invention, methods, that may be utilized for the screening of antibodies and which possess the desired specificity include, but are not limited to, enzyme-linked immunosorbent assay (ELISA) and other immunologically-mediated techniques known within the art. In a specific embodiment, selection of antibodies that are specific to a particular epitope of an JNK inhibitor sequence and/or an chimeric peptide as defined herein (e.g. a fragment thereof typically comprising a length of from 5 to 20, preferably 8 to 18 and most preferably 8 to 11 amino acids) is facilitated by generation of hybridomas that bind to the fragment of an JNK inhibitor sequence and/or an chimeric peptide, as defined herein, possessing such an epitope. These antibodies that are specific for an epitope as defined above are also provided herein.

The antibodies as defined herein may be used in methods known within the art referring to the localization and/or quantification of an JNK inhibitor sequence (and/or correspondingly to a chimeric peptide as defined above), e.g. for use in measuring levels of the peptide within appropriate physiological samples, for use in diagnostic methods, or for use in imaging the peptide, and the like.

The JNK inhibitor sequences, chimeric peptides, nucleic acids, vectors, host cells and/or antibodies as defined according to the invention can be formulated in a pharmaceutical composition, which may be applied in the prevention or treatment of any of the diseases as defined herein, particularly in the prevention or treatment of diseases or disorders strongly related to JNK signaling as defined herein. Typically, such a pharmaceutical composition used according to the present invention includes as an active component, e.g.: (i) any one or more of the JNK inhibitor sequences and/or chimeric peptides as defined above, and/or variants, fragments or derivatives thereof, particularly JNK inhibitor sequences according to any of sequences of SEQ ID NOs: 1 to 4 and 13 to 20 and 33-100 and/or chimeric peptides according to any of sequences of SEQ ID NOs: 9 to 12 and 23 to 32, and/or JNK inhibitor sequences according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions; and/or (ii) nucleic acids encoding an JNK inhibitor sequence and/or an chimeric peptide as defined above and/or variants or fragments thereof, and/or (iii) cells comprising any one or more of the JNK inhibitor sequences and/or chimeric peptides, and/or variants, fragments or derivatives thereof, as defined above and/or (iv) cells transfected with a vector and/or nucleic acids encoding an JNK inhibitor sequence and/or an chimeric peptide as defined above and/or variants or fragments thereof.

According to a preferred embodiment, such a pharmaceutical composition as used according to the present invention typically comprises a safe and effective amount of a component as defined above, preferably of at least one JNK inhibitor sequence according to any of sequences of SEQ ID NOs: 1 to 4 and 13 to 20 and 33-100 and/or at least one chimeric peptide according to any of sequences of SEQ ID NOs: 9 to 12 and 23 to 32, and/or at least one JNK inhibitor sequence according to any of sequences of SEQ ID NOs: 1 to 4 and 13 to 20 and 33-100 comprising a trafficking sequence according to any of SEQ ID NOs: 5-8 and 21 to 22, or variants or fragments thereof within the above definitions, or at least one nucleic acids encoding same, or at least one vector, host cell or antibody as defined above.

The inventors of the present invention additionally found, that the JNK-inhibitor sequence and the chimeric peptide, respectively, as defined herein, exhibit a particular well uptake rate into cells involved in the diseases of the present invention. Therefore, the amount of a JNK-inhibitor sequence and chimeric peptide, respectively, in the pharmaceutical composition to be administered to a subject, may—without being limited thereto—have a very low dose. Thus, the dose may be much lower than for peptide drugs known in the art, such as DTS-108 (Florence Meyer-Losic et al., Clin Cancer Res., 2008, 2145-53). This has several positive aspects, for example a reduction of potential side reactions and a reduction in costs.

Preferably, the dose (per kg bodyweight) is in the range of up to 10 mmol/kg, preferably up to 1 mmol/kg, more preferably up to 100 µmol/kg, even more preferably up to 10 µmol/kg, even more preferably up to 1 µmol/kg, even more preferably up to 100 nmol/kg, most preferably up to 50 nmol/kg.

Thus, the dose range may preferably be from about 1 pmol/kg to about 1 mmol/kg, from about 10 pmol/kg to about 0.1 mmol/kg, from about 10 pmol/kg to about 0.01 mmol/kg, from about 50 pmol/kg to about 1 pmol/kg, from about 100 pmol/kg to about 500 nmol/kg, from about 200 pmol/kg to about 300 nmol/kg, from about 300 pmol/kg to about 100 nmol/kg, from about 500 pmol/kg to about 50 nmol/kg, from about 750 pmol/kg to about 30 nmol/kg, from about 250 pmol/kg to about 5 nmol/kg, from about 1 nmol/kg to about 10 nmol/kg, or a combination of any two of said values.

In this context, prescription of treatment, e.g. decisions on dosage etc. when using the above pharmaceutical composition is typically within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980. Accordingly, a "safe and effective amount" as defined above for components of the pharmaceutical compositions as used according to the present invention means an amount of each or all of these components, that is sufficient to significantly induce a positive modification of diseases or disorders strongly related to JNK signaling as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of such a component will vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The pharmaceutical compositions according to the invention can be used according to the invention for human and also for veterinary medical purposes.

The pharmaceutical composition as used according to the present invention may furthermore comprise, in addition to one of these substances, a (compatible) pharmaceutically acceptable carrier, excipient, buffer, stabilizer or other materials well known to those skilled in the art.

In this context, the expression "(compatible) pharmaceutically acceptable carrier" preferably includes the liquid or non-liquid basis of the composition. The term "compatible" means that the constituents of the pharmaceutical composition as used herein are capable of being mixed with the pharmaceutically active component as defined above and with one another component in such a manner that no interaction occurs which would substantially reduce the pharmaceutical effectiveness of the composition under usual use conditions. Pharmaceutically acceptable carriers must, of course, have sufficiently high purity and sufficiently low toxicity to make them suitable for administration to a person to be treated.

If the pharmaceutical composition as used herein is provided in liquid form, the pharmaceutically acceptable carrier will typically comprise one or more (compatible) pharmaceutically acceptable liquid carriers. The composition may comprise as (compatible) pharmaceutically acceptable liquid carriers e.g. pyrogen-free water; isotonic saline or buffered (aqueous) solutions, e.g. phosphate, citrate etc. buffered solutions, vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid, etc. Particularly for injection of the pharmaceutical composition as used herein, a buffer, preferably an aqueous buffer, may be used.

If the pharmaceutical composition as used herein is provided in solid form, the pharmaceutically acceptable carrier will typically comprise one or more (compatible) pharmaceutically acceptable solid carriers. The composition may comprise as (compatible) pharmaceutically acceptable solid carriers e.g. one or more compatible solid or liquid fillers or diluents or encapsulating compounds may be used as well, which are suitable for administration to a person. Some examples of such (compatible) pharmaceutically acceptable solid carriers are e.g. sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulphate, etc.

The precise nature of the (compatible) pharmaceutically acceptable carrier or other material may depend on the route of administration. The choice of a (compatible) pharmaceutically acceptable carrier may thus be determined in principle by the manner in which the pharmaceutical composition as used according to the invention is administered. The pharmaceutical composition as used according to the invention can be administered, for example, systemically. Routes for administration include, for example, parenteral routes (e.g. via injection), such as intravenous, intramuscular, subcutaneous, intradermal, or transdermal routes, etc., enteral routes, such as oral, or rectal routes, etc., topical routes, such as nasal, or intranasal routes, etc., or other routes, such as epidermal routes or patch delivery.

The suitable amount of the pharmaceutical composition to be used can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those, which are suitable for use in lotions, creams, gels and the like. If the compound is to be administered perorally, tablets, capsules and the like are the preferred unit dose form. The pharmaceutically acceptable carriers for the preparation of unit dose forms, which can be used for oral administration are well known in the prior art. The choice thereof will depend on secondary considerations such as taste, costs and storability, which are not critical for the purposes of the present invention, and can be made without difficulty by a person skilled in the art.

Pharmaceutical compositions for oral administration may be in tablet, capsule, powder or liquid form. A tablet may include a solid carrier as defined above, such as gelatin, and optionally an adjuvant. Liquid pharmaceutical compositions for oral administration generally may include a liquid carrier as defined above, such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount or a "therapeutically effective amount" (as the case may be), this being sufficient to show benefit to the individual. The actual amount administered, and rate and time-course of administration, will depend on the nature and severity of what is being treated.

Prevention and/or treatment of a disease as defined herein typically includes administration of a pharmaceutical composition as defined above. The term "modulate" includes the suppression of expression of JNK when it is over-expressed in any of the above diseases. It also includes suppression of phosphorylation of c-jun, ATF2 or NFAT4 in any of the above diseases, for example, by using at least one JNK inhibitor sequence according to any of sequences of SEQ ID NOs: 1 to 4 and 13 to 20 and 33-100 and/or at least one chimeric peptide according to any of sequences of SEQ ID NOs: 9 to 12 and 23 to 32, and/or at least one JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions, as a competitive inhibitor of the natural c-jun, ATF2 and NFAT4 binding site in a cell. The term "modulate" also includes suppression of hetero- and homomeric complexes of transcription factors made up of, without being limited thereto, c-jun, ATF2, or NFAT4 and their related partners, such as for example the AP-1 complex that is made up of c-jun, AFT2 and c-fos. When a disease or disorder strongly related to JNK signaling as defined above is associated with JNK overexpression, such suppressive JNK inhibitor sequences can be introduced to a cell. In some instances, "modulate" may then include the increase of JNK expression, for example by use of an IB peptide-specific antibody that blocks the binding of an IB-peptide to JNK, thus preventing JNK inhibition by the IB-related peptide.

Prevention and/or treatment of a subject with the pharmaceutical composition as disclosed above may be typically accomplished by administering (in vivo) an ("therapeutically effective") amount of said pharmaceutical composition to a subject, wherein the subject may be e.g. any mammal, e.g. a human, a primate, mouse, rat, dog, cat, cow, horse or pig. The term "therapeutically effective" means that the active component of the pharmaceutical composition is of sufficient quantity to ameliorate the disease or disorder strongly related to JNK signaling as defined above.

Accordingly, any peptide as defined above, e.g. at least one JNK inhibitor sequence according to any of sequences of SEQ ID NOs: 1 to 4 and 13 to 20 and 33-100 and/or at least one chimeric peptide according to any of sequences of SEQ ID NOs: 9 to 12 and 23 to 32, and/or at least one JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions, may be utilized in a specific embodiment of the present invention to treat diseases or disorders strongly related to JNK signaling as defined above, e.g. by modulating activated JNK signaling pathways.

However, the above defined peptides may be also encoded by nucleic acids, which then may form part of the inventive pharmaceutical compositions, e.g. for use in gene therapy. In this context, gene therapy refers to therapy that is performed by administration of a specific nucleic acid as defined above to a subject, e.g. by way of a pharmaceutical composition as defined above, wherein the nucleic acid(s) exclusively comprise(s) L-amino acids. In this embodiment of the present invention, the nucleic acid produces its encoded peptide(s), which then serve(s) to exert a therapeutic effect by modulating function of the disease or disorder. Any of the methods relating to gene therapy available within the art may be used in the practice of the present invention (see e.g. Goldspiel, et al., 1993. Clin Pharm 12: 488-505).

In a preferred embodiment, the nucleic acid as defined above and as used for gene therapy is part of an expression vector encoding and expressing any one or more of the IB-related peptides as defined above within a suitable host, i.e. an JNK inhibitor sequence according to any of sequences of SEQ ID NOs: 1 to 4 and 13 to 20 and 33-100 and/or a chimeric peptide according to any of sequences of SEQ ID NOs: 9 to 12 and 23 to 32, and/or an JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions. In a specific embodiment, such an expression vector possesses a promoter that is operably-linked to coding region(s) of a JNK inhibitor sequence. The promoter may be defined as above, e.g. inducible or constitutive, and, optionally, tissue-specific.

In another specific embodiment, a nucleic acid molecule as defined above is used for gene therapy, in which the coding sequences of the nucleic acid molecule (and any other desired sequences thereof) as defined above are flanked by regions that promote homologous recombination at a desired site within the genome, thus providing for intra-chromosomal expression of these nucleic acids (see e.g. Koller and Smithies, 1989. Proc Natl Acad Sci USA 86: 8932-8935).

Delivery of the nucleic acid as defined above according to the invention into a patient for the purpose of gene therapy, particular in the context of the above mentioned diseases or disorders strongly related to JNK signaling as defined above may be either direct (i.e. the patient is directly exposed to the nucleic acid or nucleic acid-containing vector) or indirect (i.e. cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, e.g. constructing the nucleic acid as part of an appropriate nucleic acid expression vector and administering the same in a manner such that it becomes intracellular (e.g. by infection using a defective or attenuated retroviral or other viral vector; see U.S. Pat. No. 4,980,286); directly injecting naked DNA; using microparticle bombardment (e.g. a "GeneGun"; Biolistic, DuPont); coating the nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see e.g. Wu and Wu, 1987.) Biol Chem 262: 4429-4432), which can be used to "target" cell types that specifically express the receptors of interest, etc.

An additional approach to gene therapy in the practice of the present invention involves transferring a gene (comprising a nucleic acid as defined above) into cells in in vitro tissue culture by such methods as electroporation, lipofection, calcium phosphate-mediated transfection, viral infection, or the like. Generally, the method of transfer includes the concomitant transfer of a selectable marker to the cells. The cells are then placed under selection pressure (e.g. antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including e.g. transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methods that ensure that the necessary developmental and physiological functions of the recipient cells are not disrupted by the transfer. See e.g. Loeffler and Behr, 1993. Meth Enzymol 217: 599-618. The chosen technique should provide for the stable transfer of the nucleic acid to the cell, such that the nucleic acid is expressible by the cell. Preferably, the transferred nucleic acid is heritable and expressible by the cell progeny.

In preferred embodiments of the present invention, the resulting recombinant cells may be delivered to a patient by various methods known within the art including, e.g. injection of epithelial cells (e.g. subcutaneously), application of recombinant skin cells as a skin graft onto the patient, and intravenous injection of recombinant blood cells (e.g. hematopoietic stem or progenitor cells). The total amount of cells that are envisioned for use depend upon the desired effect, patient state, and the like, and may be determined by one skilled within the art. Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, Cell 71: 973-985), hematopoietic stem or progenitor cells, e.g. as obtained from bone marrow, umbilical cord blood, peripheral blood, fetal liver, and the like. In a preferred embodiment, the cells utilized for gene therapy are autologous to the patient.

Alternatively and/or additionally, for treating diseases as mentioned herein targeting therapies may be used to deliver the JNK inhibitor sequences, chimeric peptides, and/or nucleic acids as defined above more specifically to certain types of cell, by the use of targeting systems such as (a targeting) antibody or cell specific ligands. Antibodies used for targeting are typically specific for cell surface proteins of cells associated with any of the diseases as defined below. By way of example, these antibodies may be directed to cell surface antibodies such as e.g. B cell-associated surface proteins such as MHC class II DR protein, CD18 (LFA-1 beta chain), CD45RO, CD40 or Bgp95, or cell surface proteins selected from e.g. CD2, CD4, CD5, CD7, CD8, CD9, CD10, CD13, CD16, CD19, CD20, CD21, CD22, CD23, CD24, CD25, CD30, CD33, CD34, CD38, CD39, CD4, CD43, CD45, CD52, CD56, CD68, CD71, CD138, etc. Targeting constructs may be typically prepared by covalently binding the JNK inhibitor sequences, chimeric peptides, and nucleic acids as defined herein according to the invention to an antibody specific for a cell surface protein or by binding to a cell specific ligand. Proteins may e.g. be bound to such an antibody or may be attached thereto by a peptide bond or by chemical coupling, crosslinking, etc. The targeting therapy may then be carried out by administering the targeting construct in a pharmaceutically efficient amount to a patient by any of the administration routes as defined below, e.g. intraperitoneal, nasal, intravenous, oral and patch delivery routes. Preferably, the JNK inhibitor sequences, chimeric peptides, or nucleic acids as defined herein according to the invention, being attached to the targeting antibodies or cell specific ligands as defined above, may be released in vitro or in vivo, e.g. by hydrolysis of the covalent bond, by peptidases or by any other suitable method. Alternatively, if the JNK inhibitor sequences, chimeric peptides, or nucleic acids as defined herein according to the invention are attached to a small cell specific ligand, release of the ligand may not be carried out. If present at the cell surface, the chimeric peptides may enter the cell upon the activity of its trafficking sequence. Targeting may be desirable for a variety of reasons; for example if the JNK inhibitor sequences, chimeric peptides, and nucleic acids as defined herein according to the invention are unacceptably toxic or if it would otherwise require a too high dosage.

Instead of administering the JNK inhibitor sequences and/or chimeric peptides as defined herein according to the invention directly, they could be produced in the target cells by expression from an encoding gene introduced into the cells, e.g. from a viral vector to be administered. The viral vector typically encodes the JNK inhibitor sequences and/or chimeric peptides as defined herein according to the invention. The vector could be targeted to the specific cells to be treated. Moreover, the vector could contain regulatory elements, which are switched on more or less selectively by the target cells upon defined regulation. This technique represents a variant of the VDEPT technique (virus-directed enzyme prodrug therapy), which utilizes mature proteins instead of their precursor forms.

Alternatively, the JNK inhibitor sequences and/or chimeric peptides as defined herein could be administered in a precursor form by use of an antibody or a virus. These JNK inhibitor sequences and/or chimeric peptides may then be converted into the active form by an activating agent produced in, or targeted to, the cells to be treated. This type of approach is sometimes known as ADEPT (antibody-directed enzyme prodrug therapy) or VDEPT (virus-directed enzyme prodrug therapy); the former involving targeting the activating agent to the cells by conjugation to a cell-specific antibody, while the latter involves producing the activating agent, e.g. a JNK inhibitor sequence or the chimeric peptide, in a vector by expression from encoding DNA in a viral vector (see for example, EP-A-415731 and WO 90/07936).

According to a further embodiment, the JNK inhibitor sequences, chimeric peptides, nucleic acid sequences or antibodies to JNK inhibitor sequences or to chimeric peptides as defined herein, e.g. an JNK inhibitor sequence according to any of sequences of SEQ ID NOs: 1 to 4 and 13 to 20 and 33-100 and/or a chimeric peptide according to any of sequences of SEQ ID NOs: 9 to 12 and 23 to 32, and/or an JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions, may be utilized in (in vitro) assays (e.g. immunoassays) to detect, prognose, diagnose, or monitor various conditions and disease states selected from diseases or disorders strongly related to JNK signaling as defined above, or monitor the treatment thereof. The immunoassay may be performed by a method comprising contacting a sample derived from a patient with an antibody to an JNK inhibitor sequence, a chimeric peptide, or a nucleic acid sequence, as defined above, under conditions such that immunospecific-binding may occur, and subsequently detecting or measuring the amount of any immunospecific-binding by the antibody. In a specific embodiment, an antibody specific for an JNK inhibitor sequence, a chimeric peptide or a nucleic acid sequence may be used to analyze a tissue or serum sample from a patient for the presence of JNK or a JNK inhibitor sequence; wherein an aberrant level of JNK is indicative of a diseased condition. The immunoassays that may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, fluorescent immunoassays, complement-fixation assays, immunoradiometric assays, and protein-A immunoassays, etc. Alternatively, (in vitro) assays may be performed by delivering the JNK inhibitor sequences, chimeric peptides, nucleic acid sequences or antibodies to JNK inhibitor sequences or to chimeric peptides, as defined above, to target cells typically selected from e.g. cultured animal cells, human cells or micro-organisms, and to monitor the cell response by biophysical methods typically known to a skilled person. The target cells typically used therein may be cultured cells (in vitro) or in vivo cells, i.e. cells composing the organs or tissues of living animals or humans, or microorganisms found in living animals or humans.

The present invention additionally provides the use of kits for diagnostic or therapeutic purposes, particular for the treatment, prevention or monitoring of diseases or disorders strongly related to JNK signaling as defined above, wherein the kit includes one or more containers containing JNK inhibitor sequences, chimeric peptides, nucleic acid sequences and/or antibodies to these JNK inhibitor sequences or to chimeric peptides as defined above, e.g. an anti-JNK inhibitor sequence antibody to an JNK inhibitor sequence according to any of sequences of SEQ ID NOs: 1 to 4 and 13 to 20 and 33-100, to a chimeric peptide according to any of sequences of SEQ ID NOs: 9 to 12 and 23 to 32, to an JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or to or variants or fragments thereof within the above definitions, or such an anti-JNK inhibitor sequence antibody and, optionally, a labeled binding partner to the antibody. The label incorporated thereby into the antibody may include, but is not limited to, a chemiluminescent, enzymatic, fluorescent, colorimetric or radioactive moiety. In another specific embodiment, kits for diagnostic use in the treatment, prevention or monitoring of diseases or disorders strongly related to JNK signaling as defined above are provided which comprise one or more containers containing nucleic acids that encode, or alternatively, that are the complement to, an JNK inhibitor sequence and/or a chimeric peptide as defined above, optionally, a labeled binding partner to these nucleic acids, are also provided. In an alternative specific embodiment, the kit may be used for the above purposes as a kit, comprising one or more containers, a pair of oligonucleotide primers (e.g. each 6-30 nucleotides in length) that are capable of acting as amplification primers for polymerase chain reaction (PCR; see e.g. Innis, et al., 1990. PCR PROTOCOLS, Academic Press, Inc., San Diego, Calif.), ligase chain reaction, cyclic probe reaction, and the like, or other methods known within the art used in context with the nucleic acids as defined above. The kit may, optionally, further comprise a predetermined amount of a purified JNK inhibitor sequence as defined above, a chimeric peptide as defined above, or nucleic acids encoding these, for use as a diagnostic, standard, or control in the assays for the above purposes.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

DESCRIPTION OF FIGURES

FIGS. 1A-C are diagrams showing alignments of conserved JBD domain regions in the indicated transcription factors. JNK inhibitor sequences used herein were identified by carrying out sequence alignments. The results of this alignment are exemplarily shown in FIGS. 1A-1C. FIG. 1A depicts the region of highest homology between the JBDs of IB1, IB2, c-Jun and ATF2. Panel B depicts the amino acid sequence of the JBDs of L-IB1(s) and L-IB1 for comparative reasons. Fully conserved residues are indicated by asterisks, while residues changed to Ala in the GFP-JBD$_{23}$Mut vector are indicated by open circles. FIG. 1C shows the amino acid sequences of chimeric proteins that include a JNK inhibitor sequence and a trafficking sequence. In the example shown, the trafficking sequence is derived from the human immunodeficiency virus (HIV) TAT polypeptide, and the JNK inhibitor sequence is derived from an IB1(s) polypeptide. Human, mouse, and rat sequences are identical in Panels B and C.

FIG. 2 is a diagram showing sequences of generic TAT-IB fusion peptides from human, mouse and rat.

FIG. 10 describes the results of the histology in the treatment of Chronic Obstructive Pulmonary Disease (COPD) using an animal model of Bleomycin induced acute lung fibrosis. 3 µm sections of lungs were stained with haematoxylin and eosin. Inflammatory cells accumulation, fibrotic areas, loss of lung architecture were observed 10 days after BLM administration. As can be seen, a decrease of these parameters is observed after administration of XG-102 at the low dose (0.001 mg/kg) but not with the high dose (0.1 mg/kg).

FIG. 11 shows the effects of a treatment with XG-102 (SEQ ID NO: 11) on brain $A\beta_{1-40}$ and $A\beta_{1-42}$ levels determined by ELISA. The Graphs represent the $A\beta_{1-40}$ (left) and $A\beta_{1-42}$ (right) levels determined by ELISA in different brain homogenate fractions with Triton 40 and Triton 42. Data are represented as scattered dot plot with individual values (black) and group mean±SEM. Significant differences are marked with asterisks (* p<0.05; ** p<0.01). Significant group differences were observed only in Triton X-100 fraction for $A\beta_{1-42}$.

FIG. 24 Primary cultured macrophages were incubated with XG-102 (SEQ ID NO: 11) and extensively washed. Presence of XG-102 (SEQ ID NO: 11) was revealed using a specific antibody against XG-102. XG-102 is strongly incorporated into primary macrophages.

FIG. 29 shows the IB1 cDNA sequence from rat and its predicted amino acid sequence (SEQ ID NO:102)

FIG. 30 shows the IB1 protein sequence from rat encoded by the exon-intron boundary of the rIB1 gene-splice donor (SEQ ID NO:103)

FIG. 31 shows the IB1 protein sequence from *Homo sapiens* (SEQ ID NO:104)

FIG. 32 shows the IB1 cDNA sequence from *Homo sapiens* (SEQ ID NO:105)

FIG. 41 (C) Incidence of ChNV formation ten minutes after fluorescein injection at day 14 and 21, for five groups (XG-102 300 microgramm/ml, XG-102 3 mg/ml, Kencort retard, 0.9% NaCl solution, untreated).

FIG. 41 (D) Incidence of fluorescein leakage extend at day 14 and day 21; for five groups (XG-102 300 microgramm/ml, XG-102 3 mg/ml, Kencort retard, 0.9% NaCl solution, untreated)

FIG. 41 It is shown that XG-102 does not evoke any adverse effect as to proteinuria. The ELISA assay was used to determine the albumin concentration for group 1, group 4 and group 5 as a function of the observation period (day 5, 8, 11, 14, 17, 20, 23, 26, 29, 32, 25, 38, 41)

FIG. 48 shows the renal function assessed by protidemia (A) and urea level (B) of rats in an Adriamycin (ADR)-induced nephropathy model on Days 8, 14, 29, 41 and 56 after ADR administration. Groups No. 1 ("ADR") and No. 2 ("ADR+XG-102") have been treated on Day 0 with ADR to induce necropathy, whereas groups No. 3 ("NaCl") and No. 4 ("XG-102") received 0.9% NaCL. Moreover, groups Nos. 2 and 4 have been treated on Day 0 with XG-102, whereas groups Nos. 1 and 3 received vehicle (0.9% NaCl).

FIG. 56 shows that XG-102 dose-dependently decreased JNK (A) and PAF2 (B) phosphorylation induced by 15-min ischemia in an experiment evaluating the dose-response to XG-102 in islet isolation/transplantation (Example 22). Isolation of rat islets has been carried out either immediately after animal sacrifice or after a 15-minute period of warm ischemia. JNK activation has been assessed by western blot at the end of the isolation process. As negative controls, JNK activation has been assessed on unprocessed rat pancreases.

FIG. 64 shows for the study of Example 27 the overview of reported adverse events (serious and non-serious) by dose group.

FIG. 65 shows for the study of Example 27 the summary of the AEs (sorted by MedDRA SOC and PT term) which were reported for at least 2% of patients randomized to either of the three study groups.

FIG. 66 shows for the study of Example 27 the overview of the reported serious adverse events (SAEs).

FIG. 70 shows for Example 30 the tolerance of mice to XG-102. Mean body weights and MBWC±SD are indicated. MBWC % corresponds to variation of mean body weight between the considered day and day of first treatment (D10). Statistical analysis was performed with the Bonferroni-Dunn test, taking vehicle treated group as reference.

FIG. 72 shows for Example 31 the tolerance of mice to XG-102 and XG-414 treatments, alone or in combination. Mean body weights and mean body weight changes±SD are indicated. MBWC % corresponds to variation of mean body weight between the considered day and day of first treatment (D10).

FIG. 74 shows for Example 31 the tumor invasion observed by microscopic evaluation of mice sacrificed at D67 or between D67 and final sacrifice as histogram representations. The level of tumor take was classified in 4 different categories specified in the figure legend.

EXAMPLES

Figure 3:
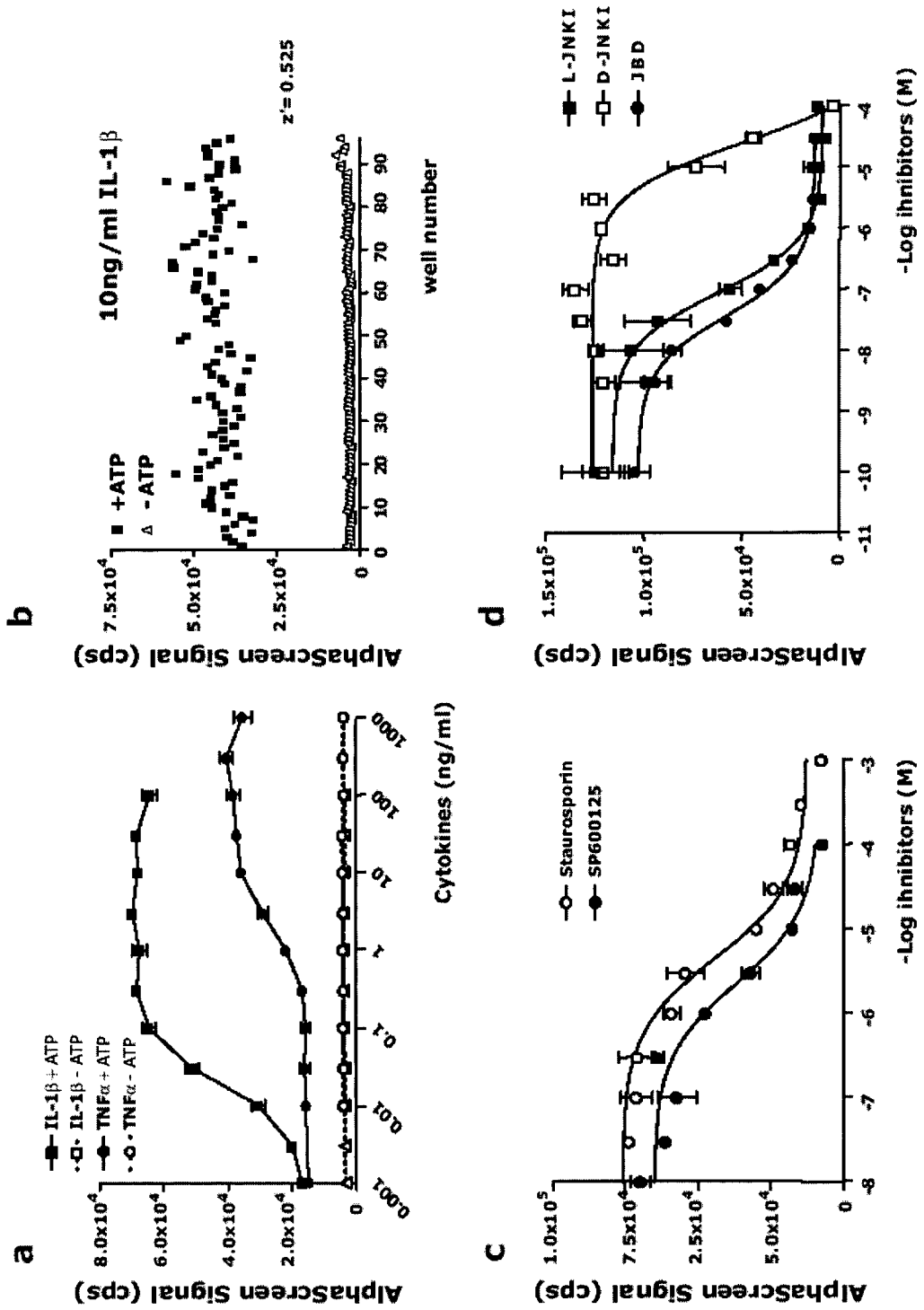
FIG. 3 depicts the results of the inhibition of endogeneous JNK-activity in HepG2 cells using fusion peptides according to SEQ ID NOs: 9 and 11 in an one-well approach. As can be seen from FIG. 3, particularly panel d in FIG. 3, D-TAT-IB1(s) according to SEQ ID NO: 11 (here abbreviated as D-JNKI) effectively inhibits JNK activity, even better than L-TAT-IB1(s) according to SEQ ID NO: 9 (here abbreviated as L-JNKI).

Example 1: Identification of JNK Inhibitor Sequences

Amino acid sequences important for efficient interaction with JNK were identified by sequence alignments between known JNK binding domain JBDs. A sequence comparison between the JBDs of IB1 [SEQ ID NO: 13], IB2 [SEQ ID NO: 14], c-Jun [SEQ ID NO: 15] and ATF2 [SEQ ID NO: 16] defined a weakly conserved 8 amino acid sequence (see FIG. 1A). Since the JBDs of IB1 and IB2 are approximately 100 fold as efficient as c-Jun or ATF2 in binding JNK (Dickens et al. Science 277: 693 (1997), it was reasoned that conserved residues between IB1 and IB2 must be important to confer maximal binding. The comparison between the JBDs of IB1 and IB2 defined two blocks of seven and three amino acids that are highly conserved between the two sequences.

These two blocks are contained within a peptide sequence of 19 amino acids in L-IB1(s) [SEQ ID NO: 1] and are also shown for comparative reasons in a 23 aa peptide sequence derived from IB1 [SEQ ID NO: 17]. These sequences are shown in FIG. 1B, dashes in the L-IB1 sequence indicate a gap in the sequence in order to align the conserved residues with L-IB1(s).

Example 2: Preparation of JNK Inhibitor Fusion Proteins

JNK inhibitor fusion proteins according to SEQ ID NO: 9 were synthesized by covalently linking the C-terminal end of SEQ ID NO: 1 to a N-terminal 10 amino acid long carrier peptide derived from the HIV-TAT4g 57 (Vives et al., J Biol. Chem. 272: 16010 (1997)) according to SEQ ID NO: 5 via a linker consisting of two proline residues. This linker was used to allow for maximal flexibility and prevent unwanted secondary structural changes. The basic constructs were also prepared and designated L-IB1(s) (SEQ ID NO: 1) and L-TAT [SEQ ID NO: 5], respectively.

All-D retro-inverso peptides according to SEQ ID NO: 11 were synthesized accordingly. The basic constructs were also prepared and designated D-IB1(s) [SEQ ID NO: 2] and D-TAT [SEQ ID NO: 6], respectively.

All D and L fusion peptides according to SEQ ID NOs: 9, 10, 11 and 12 were produced by classical Fmock synthesis and further analysed by Mass Spectrometry. They were finally purified by HPLC. To determine the effects of the proline linker, two types of TAT peptide were produced one with and one without two prolines. The addition of the two prolines did not appear to modify the entry or the localization of the TAT peptide inside cells. Generic peptides showing the conserved amino acid residues are given in FIG. 2.

Example 3: Inhibition of Cell Death by JBD19

Effects of the 19 aa long JBD sequence of IB1(s) on JNK biological activities were studied. The 19 aa sequence was linked N-terminal to the Green Fluorescent Protein (GFP JBD19 construct), and the effect of this construct on pancreatic beta-cell apoptosis induced by IL1 was evaluated. This mode of apoptosis was previously shown to be blocked by transfection with $JBD_{1-280}$ whereas specific inhibitors of ERK1/2 or p38 as known in the art did not protect.

Oligonucleotides corresponding to JBD19 and comprising a conserved sequence of 19 amino acids as well as a sequence mutated at the fully conserved regions were synthesized and directionally inserted into the EcoRI and SalI sites of the pEGFP-N1 vector encoding the Green Fluorescent Protein (GFP) (from Clontech). Insulin producing TC-3 cells were cultured in RPMI 1640 medium supplemented with 10% Fetal Calf Serum, 100 µg/mL Streptomycin, 100 units/mL Penicillin and 2 mM Glutamine. Insulin producing TC-3 cells were transfected with the indicated vectors and IL-1 (10 ng/mL) was added to the cell culture medium. The number of apoptotic cells was counted at 48 hours after the addition of IL-1 using an inverted fluorescence microscope. Apoptotic cells were discriminated from normal cells by the characteristic "blebbing out" of the cytoplasm and were counted after two days.

GFP is Green Fluorescent protein expression vector used as a control; JBD19 is the vector expressing a chimeric GFP linked to the 19 aa sequence derived from the JBD of IB1; JBD19Mut is the same vector as GFP-JBD19, but with a JBD mutated at four conserved residues shown as FIG. 1B; and $JBD_{1-280}$ is the GFP vector linked to the entire JBD (aa 1-280). The GFP-JBD19 expressing construct prevented IL-1 induced pancreatic-cell apoptosis as efficiently as the entire $JBD_{1-280}$.

As additional controls, sequences mutated at fully conserved IB1(s) residues had greatly decreased ability to prevent apoptosis.

Example 4: Cellular Import of TAT-IB1(s) Peptides

The ability of the L- and D-enantiomeric forms of TAT and TAT-IB1(s) peptides ("TAT-IB peptides") to enter cells was evaluated. L-TAT, D-TAT, L-TAT-IB1(s), and D-TAT-IB1(s) peptides [SEQ ID NOs: 5, 6, 9 and 12, respectively] were labeled by N-terminal addition of a glycine residue conjugated to fluorescein. Labeled peptides (1 µM) were added to TC-3 cell cultures, which were maintained as described in Example 3. At predetermined times cells were washed with PBS and fixed for five minutes in ice-cold methanol-acetone (1:1) before being examined under a fluorescence microscope. Fluorescein-labeled BSA (1 µM, 12 moles/mole BSA) was used as a control. Results demonstrated that all the above fluorescein labeled peptides had efficiently and rapidly (less than five minutes) entered cells once added to the culture medium. Conversely, fluorescein labeled bovine serum albumin (1 µM BSA, 12 moles fluorescein/mole BSA) did not enter the cells.

A time course study indicated that the intensity of the fluorescent signal for the L-enantiomeric peptides decreased by 70% following a 24 hours period. Little to no signal was present at 48 hours. In contrast, D-TAT and D-TAT-IB1(s) were extremely stable inside the cells.

Fluorescent signals from these all-D retro-inverso peptides were still very strong 1 week later, and the signal was only slightly diminished at 2 weeks post treatment.

Example 5: In Vitro Inhibition of c-JUN, ATF2 and Elk1 Phosphorylation

The effects of the peptides on JNKs-mediated phosphorylation of their target transcription factors were investigated in vitro. Recombinant and non activated JNK1, JNK2 and JNK3 were produced using a TRANSCRIPTION AND TRANSLATION rabbit reticulocyte lysate kit (Promega) and used in solid phase kinase assays with c-Jun, ATF2 and Elk1, either alone or fused to glutathione-S-transferase (GST), as substrates. Dose response studies were performed wherein L-TAT or L-TAT-IB1(s) peptides (0-25 µM) were mixed with the recombinant JNK1, JNK2, or JNK3 kinases in reaction buffer (20 mM Tris-acetate, 1 mM EGTA, 10 mM p-nitrophenyl-phosphate (pNPP), 5 mM sodium pyrophosphate, 10 mM p-glycerophosphate, 1 mM dithiothreitol) for 20 minutes. The kinase reactions were then initiated by the addition of 10 mM $MgCl_2$ and 5 pCi $^{33}$P-dATP and 1 µg of either GST-Jun (aa 1-89), GST-AFT2 (aa 1-96) or GST-ELK1 (aa 307-428). GST-fusion proteins were purchased from Stratagene (La Jolla, Calif.).

Ten µL of glutathione-agarose beads were also added to the mixture. Reaction products were then separated by SDS-PAGE on a denaturing 10% polyacrylamide gel. Gels were dried and subsequently exposed to X-ray films (Kodak). Nearly complete inhibition of c-Jun, ATF2 and Elk1 phosphorylation by JNKs was observed at TAT-IB(s) peptide doses as low as 2.5 µM. However, a marked exception was the absence of TAT-IB(s) inhibition of JNK3 phosphorylation of Elk1. Overall, the TAT-IB1(s) peptide showed superior effects in inhibiting JNK family phosphorylation of their target transcription factors. The ability of D-TAT, D-TAT-IB1(s) and L-TAT-IB1(s) peptides (0-250 µM dosage study) to inhibit GST-Jun (aa 1-73) phosphorylation by recombinant JNK1, JNK2, and JNK3 by were analyzed as described above. Overall, D-TAT-IB1(s) peptide decreased JNK-mediated phosphorylation of c-Jun, but at levels approximately 10-20 fold less efficiently than L-TAT-IB1(s).

Example 6: Inhibition of c-JUN Phosphorylation by Activated JNKs

The effects of the L-TAT or L-TAT-IB1(s) peptides as defined herein on JNKs activated by stressful stimuli were evaluated using GST-Jun to pull down JNKs from UV-light irradiated HeLa cells or IL-1 treated PTC cells. PTC cells were cultured as described above. HeLa cells were cultured in DMEM medium supplemented with 10% Fetal Calf Serum, 100 µg/mL Streptomycin, 100 units/ml Penicillin and 2 mM Glutamine. One hour prior to being used for cell extract preparation, PTC cells were activated with IL-1 as described above, whereas HeLa cells were activated by UV-light (20 J/m$^2$). Cell extracts were prepared from control, UV-light irradiated HeLa cells and IL-1 treated TC-3 cells by scraping the cell cultures in lysis buffer (20 mM Tris-acetate, 1 mM EGTA, 1% Triton X-100, 10 mM p-nitrophenyl-phosphate, 5 mM sodium pyrophosphate, 10 mMP-glycerophosphate, 1 mM dithiothreitol). Debris was removed by centrifugation for five minutes at 15,000 rpm in an SS-34 Beckman rotor. One-hundred µg extracts were incubated for one hour at room temperature with one µg GST-jun (amino acids 1-89) and 10 µL of glutathione-agarose beads (Sigma). Following four washes with the scraping buffer, the beads were resuspended in the same buffer supplemented with L-TAT or L-TAT-IB1(s) peptides (25 µM) for 20 minutes. Kinase reactions were then initiated by addition of 10 mM MgCl$_2$ and 5 pCi $^{33}$P-gamma-dATP and incubated for 30 minutes at 30° C.

Reaction products were then separated by SDS-PAGE on a denaturing 10% polyacrylamide gel. Gels were dried and subsequently exposed to X-ray films (Kodak). The TAT-IB(s) peptides efficiently prevented phosphorylation of c-Jun by activated JNKs in these experiments.

Example 7: In Vivo Inhibition of c-JUN Phosphorylation by TAT-IB(s) Peptides as Defined Herein To determine whether the cell-permeable peptides as defined herein could block JNK signaling in vivo, we used a heterologous GAL4 system. HeLa cells, cultured as described above, were co-transfected with the 5×GAL-LUC reporter vector together with the GAL-Jun expression construct (Stratagene) comprising the activation domain of c-Jun (amino acids 1-89) linked to the GAL4 DNA-binding domain. Activation of JNK was achieved by the co-transfection of vectors expressing the directly upstream kinases MKK4 and MKK7 (see Whitmarsh et al., Science 285: 1573 (1999)). Briefly, 3×10$^5$ cells were transfected with the plasmids in 3.5-cm dishes using DOTAP (Boehringer Mannheim) following instructions from the manufacturer. For experiments involving GAL-Jun, 20 ng of the plasmid was transfected with 1 µg of the reporter plasmid pFR-Luc (Stratagene) and 0.5 µg of either MKK4 or MKK7 expressing plasmids. Three hours following transfection, cell media were changed and TAT and TAT-IB1(s) peptides (1 µM) were added. The luciferase activities were measured 16 hours later using the "Dual Reporter System" from Promega after normalization to protein content. Addition of TAT-IB1(s) peptide blocked activation of c-Jun following MKK4 and MKK7 mediated activation of JNK. Because HeLa cells express JNK1 and JNK2 isoforms but not JNK3, we transfected cells with JNK3. Again, the TAT-IB(s) peptide inhibited JNK2 mediated activation of c-Jun.

Example 8: Synthesis of all-D Retro-Inverso IB(s) Peptides and Variants Thereof Peptides of the invention may be all-D amino acid peptides synthesized in reverse to prevent natural proteolysis (i.e. all-D retro-inverso peptides). An all-D retro-inverso peptide of the invention would provide a peptide with functional properties similar to the native peptide, wherein the side groups of the component amino acids would correspond to the native peptide alignment, but would retain a protease resistant backbone.

Retro-inverso peptides of the invention are analogs synthesized using D-amino acids by attaching the amino acids in a peptide chain such that the sequence of amino acids in the retro-inverso peptide analog is exactly opposite of that in the selected peptide which serves as the model. To illustrate, if the naturally occurring TAT protein (formed of L-amino acids) has the sequence GRKKRRQRRR [SEQ ID NO: 5], the retro-inverso peptide analog of this peptide (formed of D-amino acids) would have the sequence RRRQRRKKRG [SEQ ID NO: 6]. The procedures for synthesizing a chain of D-amino acids to form the retro-inverso peptides are known in the art (see e.g. Jameson et al., Nature, 368, 744-746 (1994); Brady et al., Nature, 368, 692-693 (1994); Guichard et al., J. Med. Chem. 39, 2030-2039 (1996)). Specifically, the retro-peptides according to SEQ ID NOs 2, 4, 6, 8, 11-12, 18, 20, 22 and 25-26, were produced by classical F-mock synthesis and further analyzed by Mass Spectrometry. They were finally purified by HPLC.

Since an inherent problem with native peptides is degradation by natural proteases and inherent immunogenicity, the heterobivalent or heteromultivalent compounds of this invention will be prepared to include the "retro-inverso isomer" of the desired peptide. Protecting the peptide from natural proteolysis should therefore increase the effectiveness of the specific heterobivalent or heteromultivalent compound, both by prolonging half-life and decreasing the extent of the immune response aimed at actively destroying the peptides.

Example 9: Long Term Biological Activity of all-D Retro-Inverso IB(s) Peptides and Variants Thereof Long term biological activity is predicted for the D-TAT-IB(s) retro-inverso containing peptide heteroconjugate (see chimeric sequences above) when compared to the native L-amino acid analog owing to protection of the D-TAT-IB(s) peptide from degradation by native proteases, as shown in Example 5.

Inhibition of IL-1 induced pancreatic beta-cell death by the D-TAT-IB1(s) peptide was analyzed. TC-3 cells were incubated as described above for 30 minutes with one single addition of the indicated peptides (1, μM), then IL-1 (10 ng/ml) was added.

Apoptotic cells were then counted after two days of incubation with IL-1 by use of Propidium Iodide and Hoechst 33342 nuclear staining. A minimum of 1,000 cells were counted for each experiment. Standard Error of the Means (SEM) are indicated, n=5. The D-TAT-IB1 peptide decreased IL-1 induced apoptosis to a similar extent as L-TAT-IB peptides.

Long term inhibition of IL-1P induced cell-death by the D-TAT-IB1 peptide was also analyzed. TC-3 cells were incubated as above for 30 minutes with one single addition of the indicated peptides (1 μM), then IL-1 (10 ng/ml) was added, followed by addition of the cytokine every two days. Apoptotic cells were then counted after 15 days of incubation with IL-1 by use of propidium iodide and Hoechst 33342 nuclear staining. Note that one single addition of the TAT-IB1 peptide does not confer long-term protection. A minimum of 1.000 cells were counted for each experiment. As a result, D-TAT-IB1(s), but not L-TAT-IB1(s), was able to confer long term (15 day) protection.

Example 10: Suppression of JNK Transcription Factors by L-TAT-IB1(s) Peptides as Used According to the Present Invention Gel retardation assays were carried out with an AP-1 doubled labeled probe (5'-CGC TTG ATG AGT CAG CCG GAA-3' (SEQ ID NO: 101). HeLa cell nuclear extracts that were treated or not for one hour with 5 ng/ml/TNF-α, as indicated. TAT and L-TAT-IB1(s) peptides as used according to the present invention were added 30 minutes before TNF-alpha. Only the part of the gel with the specific AP-1 DNA complex (as demonstrated by competition experiments with non-labeled specific and non-specific competitors) is shown.

L-TAT-IB1(s) peptides as used according to the present invention decrease the formation of the AP-1 DNA binding complex in the presence of TNF-alpha.

Example 11: Inhibition of Endogenous JNK Activity in HepG2 Cells Using an all-in One Well Approach (See FIG. 3)

HepG2 cells were seeded at 3,000 cells/well the day prior the experiment. Then, increasing concentrations of either interleukin-1 [IL-1 beta v)] or tumor necrosis factor [TNFalpha] (a) were added to activate JNK for 30 minutes. Cells were lysed in 20 mM Hepes, 0.5% Tween pH 7.4 and processed for AlphaScreen JNK. (b) Z' for the JNK activity induced by 10 ng/ml IL-1 and measured in 384 wells/plate (n=96). (c) Inhibition of endogenous IL-1 beta-induced JNK activity with chemical JNK inhibitors [staurosporin and SP600125]. (d) Effect of peptidic inhibitors L-TAT-IB1(s) according to SEQ ID NO: 9 [here abbreviated as L-JNKi (v)) and D-TAT-IB1(s) according to SEQ ID NO: 11 (here abbreviated as D-JNKi) and JBDs (corresponds to L-JNKI without the TAT sequence)] on IL-1 dependent JNK activity. All panels are representative of three independent experiments (n=3).

Methods: Alphascreen Kinase Assay
Principle:

AlphaScreen is a non-radioactive bead-based technology used to study biomolecular interactions in a microplate format. The acronym ALPHA stands for Amplified Luminescence Proximity Homogenous Assay. It involves a biological interaction that brings a "donor" and an "acceptor" beads in close proximity, then a cascade of chemical reactions acts to produce an amplified signal. Upon laser excitation at 680 nm, a photosensitizer (phthalocyanine) in the "donor" bead converts ambient oxygen to an excited singlet state. Within its 4 μsec half-life, the singlet oxygen molecule can diffuse up to approximately 200 nm in solution and if an acceptor bead is within that proximity, the singlet oxygen reacts with a thioxene derivative in the "acceptor" bead, generating chemiluminescence at 370 nm that further activates fluorophores contained in the same "acceptor" bead. The excited fluorophores subsequently emit light at 520-620 nm. In the absence of an acceptor bead, singlet oxygen falls to ground state and no signal is produced.

Kinase reagents (B-GST-cJun, anti P-cJun antibody and active JNK3) were first diluted in kinase buffer (20 mM Tris-HCl pH 7.6, 10 mM MgCl$_2$, 1 mM DTT, 100 μM Na$_3$VO$_4$, 0.01% Tween-20) and added to wells (15 μl). Reactions were then incubated in presence of 10 μM of ATP for 1 h at 23° C. Detection was performed by an addition of 10 μl of beads mix (Protein A acceptor 20 μg/ml and Streptavidin donor 20 μg/ml), diluted in detection buffer (20 mM Tris-HCl pH 7.4, 20 mM NaCl, 80 mM EDTA, 0.3% BSA), followed by an another one-hour incubation at 23° C. in the dark. For measurement of JNK endogenous activity, kinase assays were performed as described above except active JNK3 was replaced by cells lysates and reaction kinase components were added after the cells lysis. B-GST-cjun and P-cJun antibody were used at the same concentrations whereas ATP was used at 50 μM instead of 10 μM. AlphaScreen signal was analyzed directly on the Fusion or En Vision apparatus.

Example 12: Determining the Activity of all-D Retro-Inverso IB(s) Peptides and Variants Thereof in the Treatment of Viral Infections—Varicella-Zoster Virus (VZV)

Determination of the activity of IB(s) peptides and all-D retro-inverso IB(s) peptides as used according to the present invention was tested using the JNK inhibitor peptide XG-102 (SEQ ID NO: 11) as a test compound in cultured host cells (human foreskin fibroblasts (HFFs)). Viruses are obligate intracellular parasites that require a functional cell environment to complete their lifecycle; dying cells do not support virus replication. Additionally, inhibitors of cell functions may be toxic to cells, which could non-specifically prevent virus growth. Thus, sick or dying host cells could exhibit nonspecifically reduced virus titers. Since this may falsify the results, a cytotoxicity assay was carried out first, determining the tolerance of the cultured cells to the test compound. Subsequently, a plaque reduction assay was carried out and then activity of the JNK inhibitor peptide XG-102 (SEQ ID NO: 11) was tested with respect to Viral Zoster Virus (VZV) in infected cells.

Figure 4:
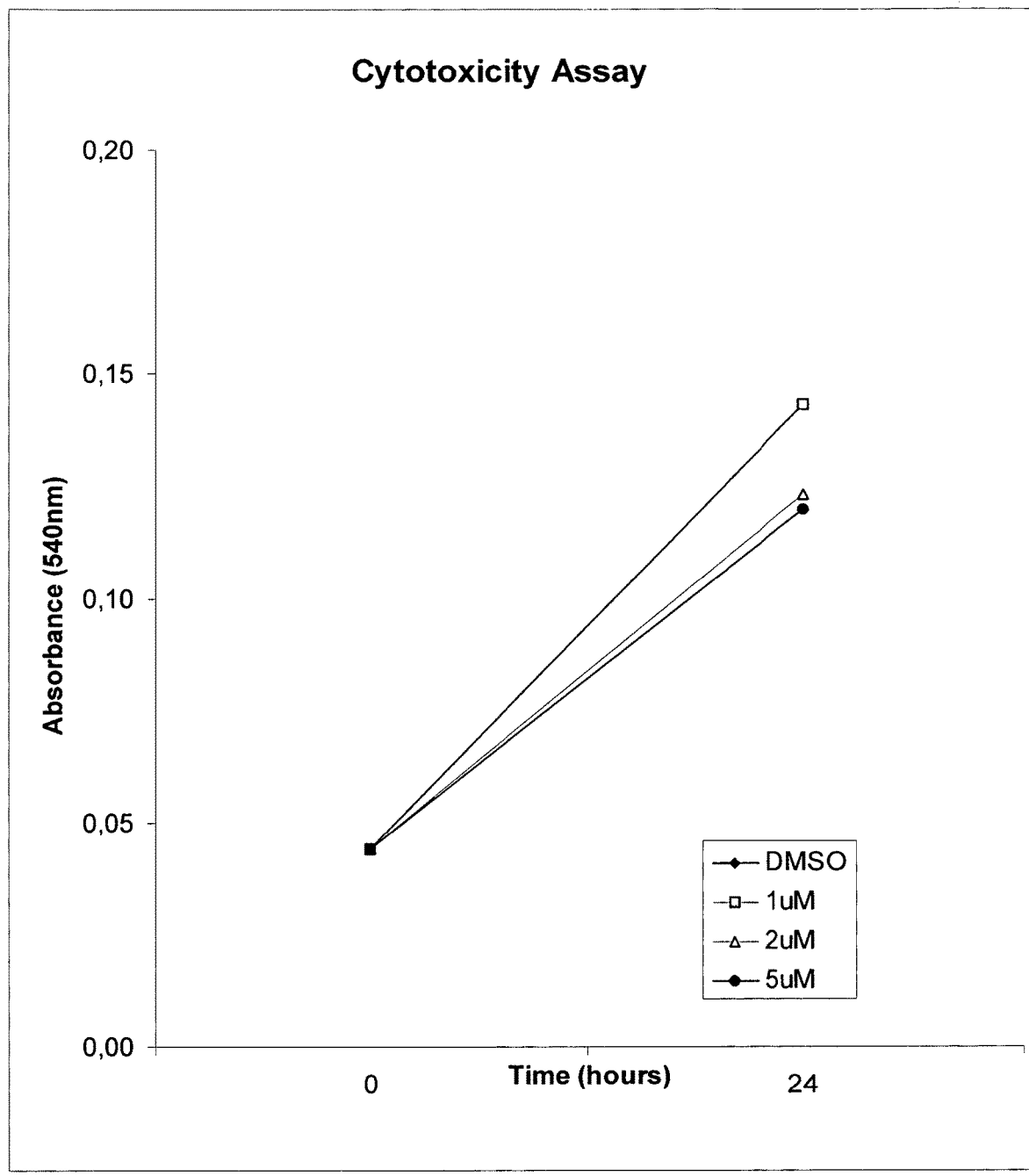
FIG. 4 shows the result of the cytotoxicity assay with a chimeric JNK inhibitor sequence according to SEQ ID NO: 11, also termed XG-102 (see Example 12). As can be seen, XG-102 (SEQ ID NO: 11) is not cytotoxic for HFFs. HFFs were seeded in 96-well tissue culture plates. Medium containing DMSO (same level as the 5 µM drug), or XG-102 at 1, 2, and 5 µM was added for 24 h. Neutral Red was briefly added, the cells were fixed, then the dye was extracted. Absorbance was measured at 540 nm. No difference was observed between DMSO and 1 µM XG-102.

A) Determination of the Cytotoxicity of all-D Retro-Inverso IB(s) Peptides:

For determination of toxicity, cultured cells (human foreskin fibroblasts (HFFs)) were seeded in 96-well tissue culture plates. Medium containing DMSO (same level as 5 μM XG-102 (SEQ ID NO: 11)), or XG-102 (SEQ ID NO: 11) was added at several concentrations of (1, 2, and 5 μM) for 24 h. Subsequently, a Neutral Red assay was carried out. Neutral Red colorimetric assays for cytotoxicity assays (in sets of 6 replicates) were used to set the maximum dose for subsequent efficacy assays (as performed in Taylor et al., 2004, J. Virology, 78:2853-2862). Live cells absorb Neutral Red and, accordingly, the level of absorbance is a quantitative measure of cell viability and number. Neutral Red uptake is directly proportional to the number of cells and also reflects normal endocytosis. Therefore, a brief pulse of Neutral Red was added to the medium at 0 or 24 hours. After fixation and extraction, dye was added and the amount of dye in each sample was measured in an ELISA plate reader at 540 nm (see FIG. 4). No cytotoxicity was observed with any amount of XG-102 (SEQ ID NO: 11), and cell growth was not restricted compared to the DMSO diluent alone (control). Thus the standard concentration of 1 µM had no evident effects on HFF cells, and higher doses would also be well tolerated.

B) Plaque Reduction Assay to Evaluate the Antiviral Effects of XG-102 (SEQ ID NO: 11) Against Varicella-Zoster Virus (VZV)

Figure 5:
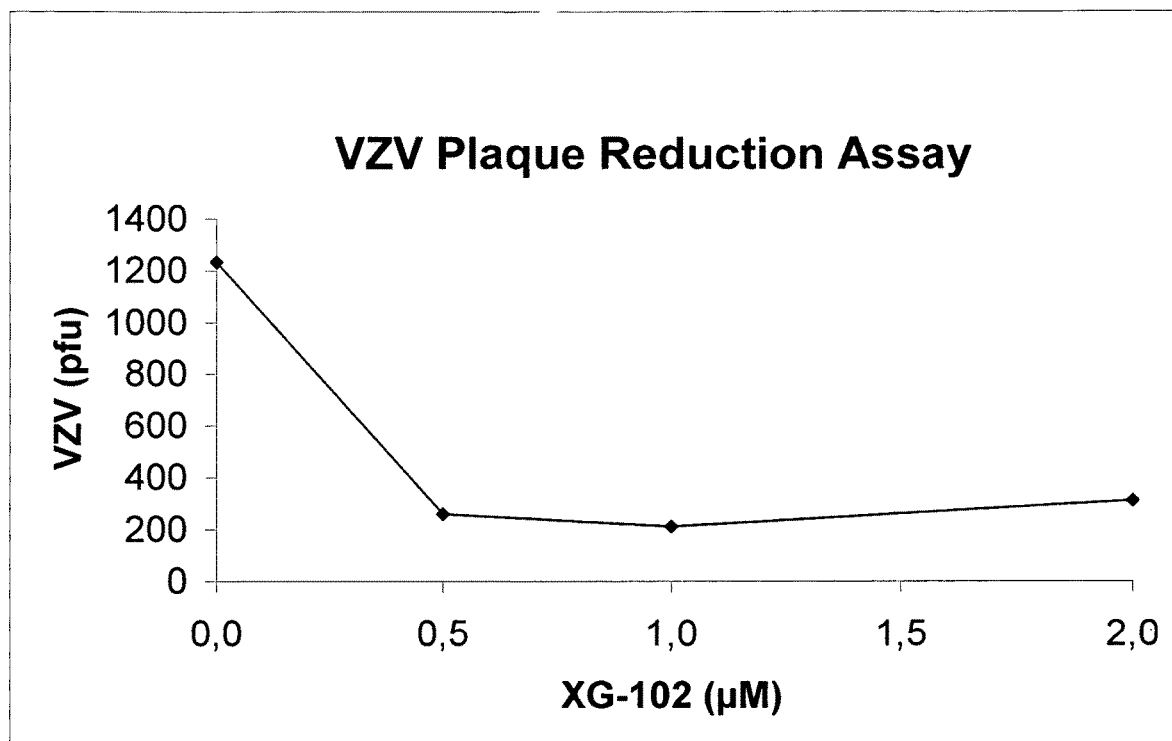
FIG. 5 depicts the results of the plaque reduction assay carried out for testing activity of a chimeric JNK inhibitor sequence according to SEQ ID NO: 11, also termed XG-102 against Varizella Zoster Virus (VZV) (see Example 12). As can be seen, XG-102 (SEQ ID NO: 11) is a potent inhibitor of Varizella Zoster Virus (VZV), particularly at concentrations of 0.5 µM and 1 µM

To determine whether XG-102 (SEQ ID NO: 11) had a dose-dependent antiviral effect, a range of concentrations surrounding the standard 1 µM dose were tested. In this plaque reduction assay, confluent human foreskin fibroblasts (HFFs) in 24-well plates were inoculated with VZV-infected HFFs at a ratio of 1:100 (multiplicity of infection MOI=0.01) and adsorbed to the cells for 2 hours. The excess virus was washed out, and medium containing 0 (DMSO only), 0.5, 1, or 2 µM XG-102 (SEQ ID NO: 11) was added. One sample was taken at this time to measure the initial level of infection; wherein each well contained ~150 pfu. After 24 hours, duplicate wells were trypsinized, and then the cell suspensions were titered on MeWo cell monolayers in triplicate to determine the number of VZV-infected cells in each sample. During unrestricted growth, VZV usually increases by 10-fold over 1 day because it propagates by cell-cell spread. This is what was observed for the cultures treated with DMSO alone, which yielded 1200±430 pfu (FIG. 5). The results of the determination were as follows:

| XG-102 (SEQ ID NO: 11) | Spread of VZV (pfu) ± SD |
|---|---|
| 0 µM (DMSO) | 1233 ± 432 |
| 0.5 µM | 260 ± 53 |
| 1.0 µM | 212 ± 48 |
| 2.0 µM | 312 ± 79 |

XG-102 (SEQ ID NO: 11) had thus a strong antiviral effect at all the concentrations tested, with VZV yields near 200-300 pfu. Using the graph of these results to interpolate the $EC_{50}$, it was calculated that approximately 0.3 µM XG-102 (SEQ ID NO: 11) caused VZV yield to decrease by 50%.

From the cytotoxicity and efficacy data, a preliminary Selective Index ($Tox/EC_{50}$) of 5.0 µM/0.3 µM was calculated, which gives a value of ~17, wherein the true SI is considered even higher, since the concentration of XG-102 (SEQ ID NO: 11) was not yet approached that would kill 50% of the cells.

C) Measurement of Varicella-Zoster Virus (VZV) Replication in Human Foreskin Fibroblasts (HFFs) with XG-102 (SEQ ID NO: 11)

To determine the minimum effective dose of XG-102 that prevents varicella-zoster virus (VZV) replication in human foreskin fibroblasts (HFFs) with XG-102 (SEQ ID NO: 11) confluent monolayers of HFFs were inoculated with VZV-BAC-Luc strain for 2 h, then treated for 24 h with XG-102 (SEQ ID NO: 11) in concentrations of 0.25, 0.5, or 1.0 µM or with the negative control (XG-100, 1.0 µM). Virus yield was measured by luciferase assay. Samples were in triplicate and the average luminescence is shown; error bars represent the standard deviation of the mean.

Figure 6:
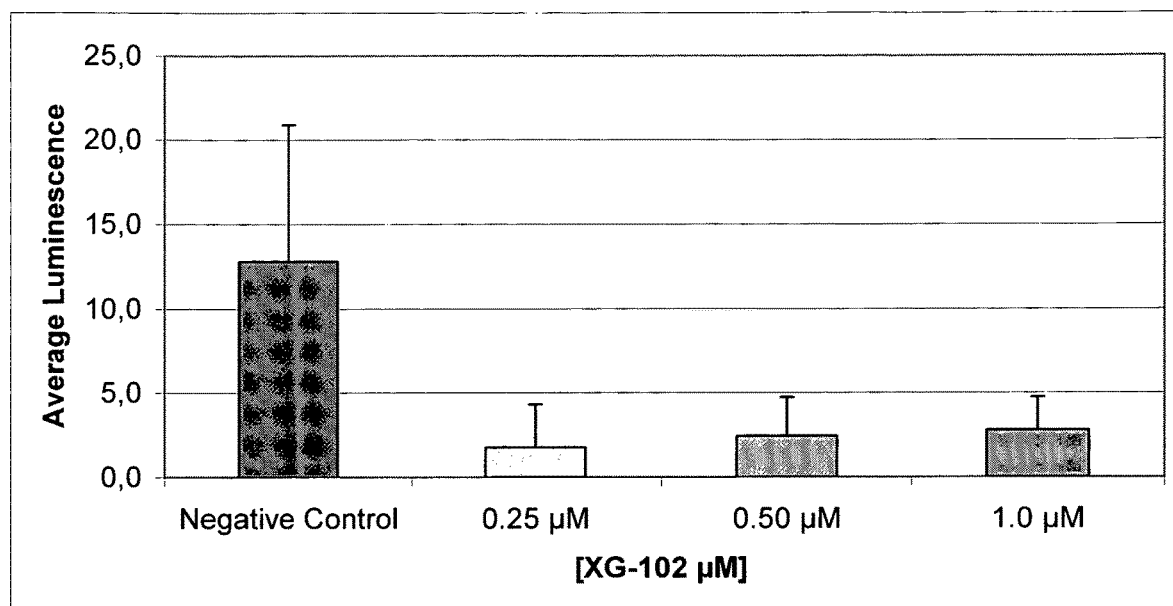
FIG. 6 shows the results of the inhibition of Varizella Zoster Virus (VZV) in cultured human fibroblasts using a chimeric JNK inhibitor sequence according to SEQ ID NO: 11, also termed XG-102 (see Example 12). As can be seen, VZV shows a significant sensitivity to XG-102 (SEQ ID NO: 11). VZV replication was normal in the presence of the negative control (XG-100, the Tat peptide alone). XG-102 (SEQ ID NO: 11) thus prevented VZV replication already at the lowest concentration tested of 0.25 µM.

As a result, VZV replication was normal in the presence of the negative control (the Tat peptide alone). XG-102 (SEQ ID NO: 11) prevented VZV replication at the lowest concentration tested, 0.25 µM. The minimum effective dose could not be determined in this experiment. While it is not yet known why VZV depends on JNK activity during infection, there appears to be a critical requirement for this enzyme. A low concentration (0.25 µM) of XG-102 (SEQ ID NO: 11) is thus sufficient to completely block VZV spread in culture. One possible explanation for this effect is that this amount of XG-102 (SEQ ID NO: 11) binds to all the JNK molecules in the infected cells. Alternatively, 0.25 µM XG-102 (SEQ ID NO: 11) may reduce JNK activity below a threshold level that is optimal for VZV replication. The results of this experiment are summarized in FIG. 6.

Example 13: Determining the Activity of all-D Retro-Inverso IB(s) Peptides and Variants Thereof in the Treatment of Chronic Obstructive Pulmonary Disease (COPD)

In order to determine the activity of the exemplary all-D retro-inverso IB(s) peptide XG-102 (SEQ ID NO: 11) in the treatment of Chronic Obstructive Pulmonary Disease (COPD) XG-102 (SEQ ID NO: 11) is used in an animal model of Bleomycin induced acute lung inflammation and fibrosis. The protocol of bleomycin induced inflammation and fibrosis has been described before in the literature. The aim of the Experiment was to investigate the effect of XG-102 (SEQ ID NO: 11) by subcutaneous (s.c.) route on neutrophil recruitment in broncho alveolar lavage (BAL) and lung in bleomycin induced inflammation and fibrosis:

at 1 day after a single bleomycin administration (10 mg/kg)

and at day 10 with the development of fibrosis

1) Method and Experimental Approach

The test compound XG-102 (SEQ ID NO: 11) at two doses and vehicle control were given s.c. with a single intranasal administration of bleomycin and mice were analyzed after 1 and 10 days. The animals used in the model were 10 C57BL/6 mice (8 weeks old) per group. The experimental groups included vehicle, 0.001 mg/kg XG-102 (SEQ ID NO: 11) and 0.1 mg/kg XG-102 (SEQ ID NO: 11), and the treatment consisted of repeated sub-cutaneous administration of XG-102 (SEQ ID NO: 11), prior to bleomycin administration then every 3 days. Acute lung inflammation at 24 h was monitored by BAL lavage, cytology, cell counts, and lung myeloperoxidase activity. The effect of the compound was compared with vehicle controls. Lung fibrosis was assessed histologically using hematoxylin and eosin staining at day 10 after the single dose of bleomycin.

1.1) Bleomycin Administration

Bleomycin sulfate in saline (10 mg/kg body weight) from Bellon Laboratories (Montrouge, France) or saline were given through the airways by nasal instillation in a volume of 40 µL under light ketamine-xylasine anesthesia. The groups for Bleomycin administration for both bleomycin induced inflammation and fibrosis included: Vehicle, 0.001 mg/kg XG-102 (SEQ ID NO: 11) and 0.1 mg/kg XG-102 (SEQ ID NO: 11). The route for bleomycin induced inflammation was subcutaneous (s.c.) route, and administration occurred as a single dose. The route for bleomycin induced fibrosis was subcutaneous (s.c.) route, and administration occurred 3 times in 10 days.

1.2) Bronchoalveolar Lavage Fluid (BALF)

After incision of the trachea, a plastic cannula was inserted and airspaces were washed using 0.3 ml of PBS solution, heated to 37° C. The samples collected were dispatched in 2 fractions: the first one (1 ml corresponding to the 2 first lavages) was used for mediator measurement and the second one for the cell determination (4 ml). The first fraction was centrifuged (600 g for 10 min) and supernatant was fractionated and kept at −80° C. until mediator determination. The cell pellet was then resuspended in 0.4 ml sterile NaCl, 0.9%, and pooled with the second fraction and was used for cell counts.

1.3) Lung Homogenization

After BAL the whole lung was removed and placed inside a microtube (Lysing matrix D, Q Bio Gene, Illkrich, France) with 1 ml of PBS, total lung tissue extract was prepared using a Fastprep® system (FP120, Q Bio Gene, Illkrich, France), the extract was then centrifuged and the supernatant stored at −80° C. before mediator measurement and collagen assay with Sircol Collagen Assay (France Biochem Division, France).

1.4) Cell Count and Determination

Total cell count was determined in BAL fluid using a Malassez hemocytometer. Differential cell counts were performed on cytospin preparations (Cytospin 3, Thermo Shandon) after staining with MGG Diff-quick (Dade Behring AG). Differential cell counts were made on 200 cells using standard morphological criteria.

1.5) TNF Measurement

TNF level in BALF was determined using ELISA assay kits (Mouse DuoSet, R&D system, Minneapolis, USA) according to manufacturer's instructions. Results are reported as pg/ml.

1.6) MPO-Measurement

MPO-levels were measured upon administration of XG-102. MPO was not significantly induced after bleomycin in this experiment. Furthermore, XG-102 had no effect on MPO levels in the lung.

1.7) Histology

After BAL and lung perfusion, the large lobe was fixed in 4% buffered formaldehyde for standard microscopic analysis. 3-m sections were stained with hematoxylin and eosin (H&E).

2.) Results

A) First Study: Bleomycin (BLM) Induced Acute Lung Inflammation

Groups: Vehicle, XG-102 (SEQ ID NO: 11) 0.001 mg/kg and XG-102 (SEQ ID NO: 11) 0.1 mg/kg Route: s.c. route, single dose a) Cell Recruitment in Bronchoalveolar Lavage Space At 0.1 mg/kg, XG-102 (SEQ ID NO: 11) reduces significantly the neutrophil recruitment and the number of total cells recruited during the inflammatory stage. At 0.001 mg/kg, XG-102 (SEQ ID NO: 11) has no effect on neutrophil recruitment or other cell types into the bronchoalveolar space (one representative experiment with n=5 mice per group; *, p<0.05; **, p<0.001).

b) Cell Recruitment in Lung Using MPO in Lung Homogenization

Myeloperoxidase (MPO) plays an important role in host defense systems. This 140 kDa protein, composed of two heavy chains of 53 kDa and two light chains of 15 kDa, was first discovered in the 1960s. The release of MPO from the granules of neutrophils and monocytes in response to the activation of leukocytes allows the conversion of hydrogen peroxide and chloride ions into hypochlorous acid (HOCl), a strong oxidizing agent. Although MPO serves an important purpose in the defense system, various studies show that MPO also plays a role in several inflammatory conditions, wherein an elevated MPO level e.g. has been linked to coronary artery diseases. Furthermore, tissue MPO levels reflect the state of activation of neutrophils and gives an indication on neutrophil tissue infiltration.

Figure 7:
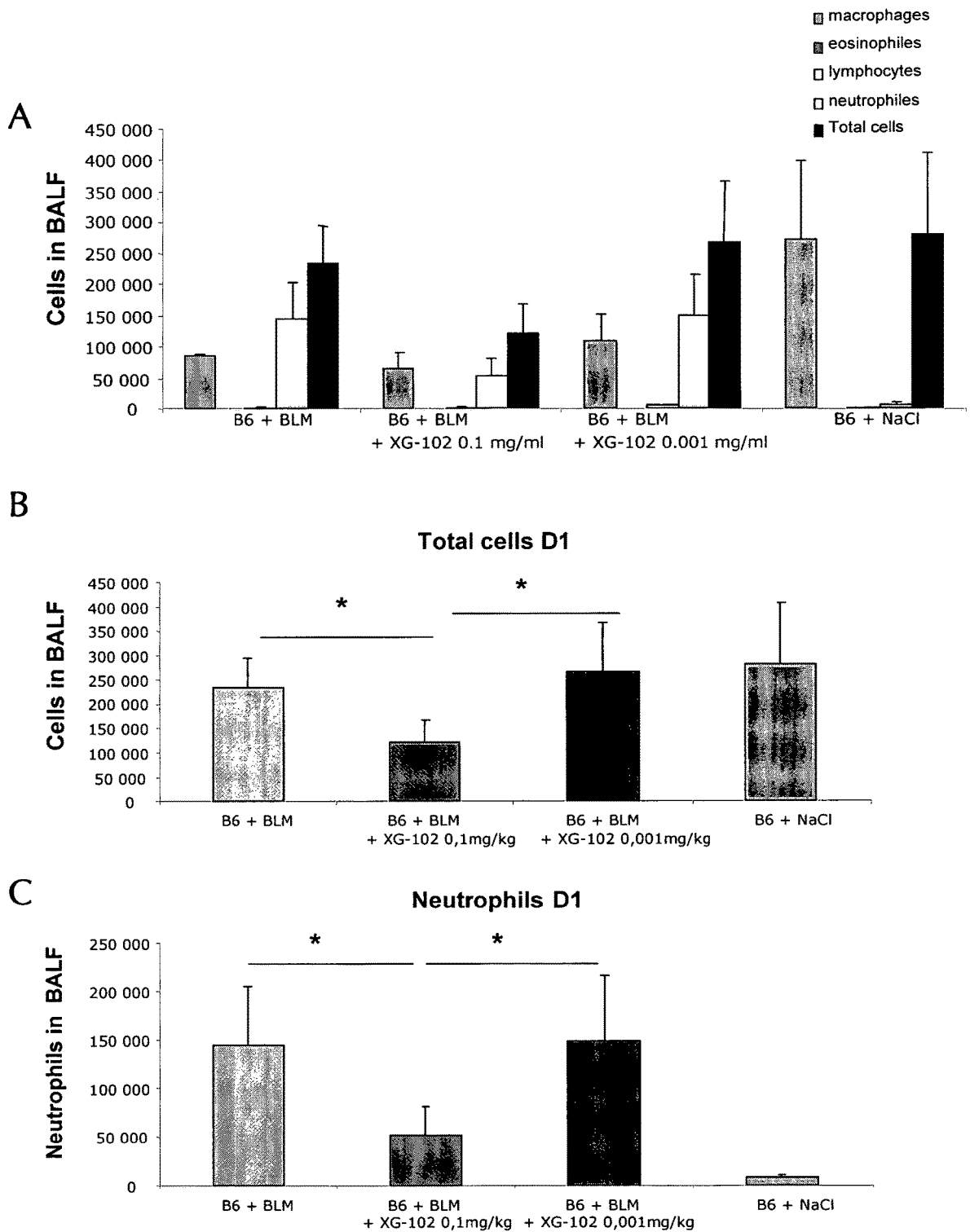
FIG. 7 depicts the activity of XG-102 (SEQ ID NO: 11) on cell recruitment in lung using MPO in lung homogenization in the treatment of Chronic Obstructive Pulmonary Disease (COPD) using an animal model of Bleomycin induced acute lung inflammation. As can be seen, MPO was not significantly induced after bleomycin administration. XG-102 (SEQ ID NO: 11) had thus only little effect on the MPO levels in the lung.

In the present experiment, MPO was not significantly induced after bleomycin administration. XG-102 (SEQ ID NO: 11) had thus no effect on the MPO levels in the lung (see FIG. 7).

c) TNF Measurement

Figure 8:
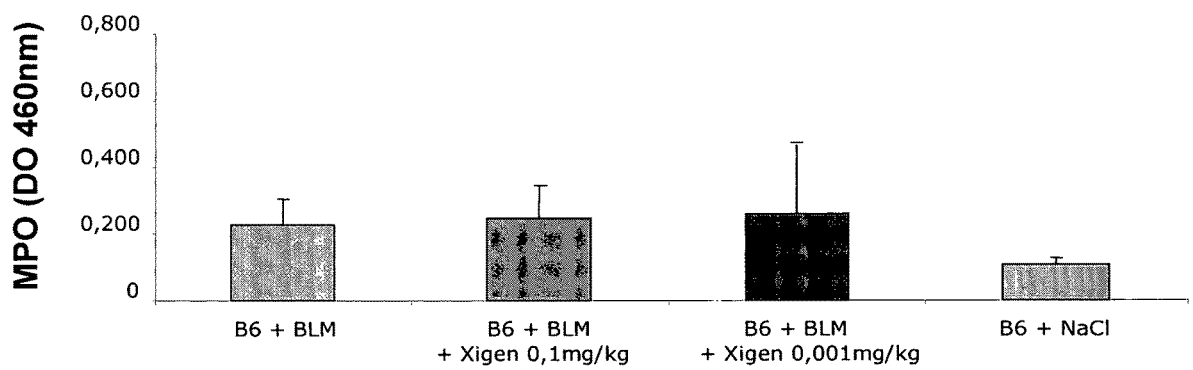
FIG. 8 depicts the activity of XG-102 (SEQ ID NO: 11) on TNF levels in the treatment of Chronic Obstructive Pulmonary Disease (COPD) using an animal model of Bleomycin induced acute lung fibrosis. When measuring TNF levels, a trend to reduction of the TNF level in BALF after administration of XG-102 (SEQ ID NO: 11) was observed in the BLM model. TNF levels are very low after BLM.

When measuring TNF levels, a trend to reduction of the TNF level in BALF after administration of XG-102 (SEQ ID NO: 11) was observed, although TNF levels were very low after BLM administration (see FIG. 8).

d) Conclusion

It could be observed that at 0.1 mg/kg, XG-102 (SEQ ID NO: 11) decreases the neutrophil and total cell recruitment into the bronchoalveolar space and induces a trend to decrease the TNF level. Moreover, the study of the histological slides showed a decrease of the inflammatory cell accumulation in the peribronchial space. It can thus be concluded that XG-102 (SEQ ID NO: 11) reduces the Bleomycin-induced inflammation.

According to the acquired results, the experiment was additionally performed in a fibrosis model.

B) Second Study: Bleomycin (BLM) Induced Lung Fibrosis

Figure 9:
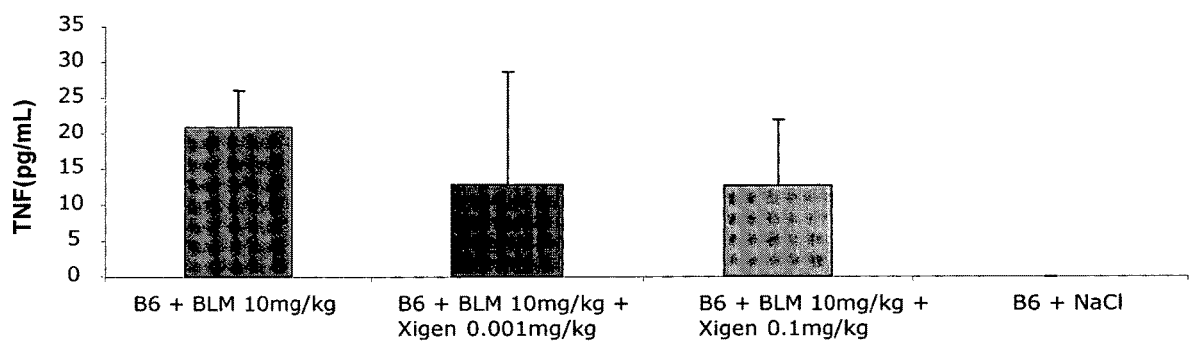
FIG. 9 depicts the activity of XG-102 (SEQ ID NO: 11) on cell recruitment in bronchoalveolar lavage space in the treatment of Chronic Obstructive Pulmonary Disease (COPD) using an animal model of Bleomycin induced acute lung fibrosis. At 0.1 mg/kg, XG-102 (SEQ ID NO: 11) reduces significantly the lymphocyte recruitment and the number of total cells recruited during the inflammatory stage characterised at this point by the lymphocytes recruitment. At 0.1 mg/kg, XG-102 (SEQ ID NO: 11) enhances the lymphocytes recruitment or the number of total cell into the bronchoalveolar space (n=5 mice per group; *, p<0.05; **, p<0.001).

Groups: Vehicle, XG-102 (SEQ ID NO: 11) 0.001 mg/kg and XG-102 (SEQ ID NO: 11) 0.1 mg/kg Route: s.c. route, 3 times in 10 days a) Cell Recruitment in Bronchoalveolar Lavage Space At 0.001 mg/kg, XG-102 (SEQ ID NO: 11) reduced significantly the lymphocyte recruitment and the number of total cells recruited during the inflammatory stage characterised at this point by the lymphocytes recruitment. At 0.1 mg/kg, XG-102 (SEQ ID NO: 11) had no effect (n=5 mice per group; *, p<0.05; **, p<0.001) (see FIG. 9).

a) Histology

3 μm sections of lungs were stained with haematoxylin and eosin. Inflammatory cells accumulation, fibrotic areas, loss of lung architecture were observed 10 days after BLM administration. A decrease of these parameters was observed after administration of XG-102 at the low dose (0.001 mg/kg) but not with the high dose (0.1 mg/kg) (see FIG. 10).

b) Conclusion:

It can be concluded that XG-102 (SEQ ID NO: 11) administered 3 times at the low dose of 0.001 mg/kg decreases the Bleomycin-induced later inflammation, in particular the lymphocytes recruitment observed at this time. Moreover, the test substance administered 3 times at this dose attenuates the Bleomycin-induced fibrosis. Less extended fibrotic areas with a more conserved lung structure could be observed.

Example 14: Determining the Activity of all-D Retro-Inverso IB(s) Peptides and Variants Thereof in the Treatment of Alzheimer's Disease In order to determine the activity of the exemplary all-D retro-inverso IB(s) peptide XG-102 (SEQ ID NO: 11) in Alzheimer's disease, XG-102 (SEQ ID NO: 11) was evaluated in the hAPP-transgenic mice model overexpressing APP751 with London and Swedish mutations using the behavioral Morris Water Maze test as well as immunohistological tests measuring plaque load and ELISA tests measuring β-amyloid$_{1-40}$ and β-amyloid$_{1-42}$ levels in the brain of mice.

A) Methods i) Introduction

The study was designed to evaluate the efficacy of the test substance (XG-102, SEQ ID NO: 11) on behavioral, biochemical and histological markers using 5 months (±2 weeks) old female hAPP Tg mice. Therefore, mice were treated every two or three weeks up to 4 months and in the end of the treatment period behavior was evaluated in the Morris Water Maze. At sacrifice brain, CSF and blood were collected. Aβ40 and Aβ42 levels were determined in four different brain homogenate fractions as well as in CSF of Tg mice. Plaque load was quantified in the cortex and the hippocampus of 8 Tg animals per treatment group.

ii) Animals

Female Tg mice with a C57BL/6×DBA background and an age of 5 months (±2 week) were randomly assigned to treatment groups 1 to 3 (n=12). Animals were subjected to administration of vehicle or XG-102 (SEQ ID NO: 11) in two different concentrations beginning at 5 months of age and continued for up to 4 months with subcutaneous (s.c.) applications every second or third week. All animals which were used for the present study had dark eyes and were likely to perceive the landmarks outside the MWM pool. However, it had to be excluded that seeing abilities of an animal were poor, which was controlled in the visible platform training, the so called pretest, before treatment start for all animals including reserves enclosed to the study. In case a seeing handicap for a specific animal would have been affirmed, the mouse would have been excluded from the study.

iii) Animal Identification and Housing

Mice were individually identified by ear markings. They were housed in individual ventilated cages (IVCs) on standardized rodent bedding supplied by Rettenmaier®. Each cage contained a maximum of five mice. Mice were kept according to the JSW Standard Operating Procedures (SOP GEN011) written on the basis of international standards. Each cage was identified by a colored card indicating the study number, sex, the individual registration numbers (IRN) of the animals, date of birth, as well as the screening date and the treatment group allocation. The temperature during the study was maintained at approximately 24° C. and the relative humidity was maintained at approximately 40-70%. Animals were housed under a constant light-cycle (12 hours light/dark). Normal tap water was available to the animals ad libitum.

iv) Treatment

Forty female hAPP transgenic mice were treated with either 0.1 mg/kg b.w./every two weeks or 10 mg/kg b.w./every three weeks of the test substance XG-102 (SEQ ID NO: 11) in two different dosages (n=12/group) or treated with the vehicle (n=12) s.c. once every three weeks over four months.

v) Morris Water Maze (MWM)

The Morris Water Maze (MWM) task was conducted in a black circular pool of a diameter of 100 cm. Tap water was filled in with a temperature of 22±1° C. and the pool was virtually divided into four sectors. A transparent platform (8 cm diameter) was placed about 0.5 cm beneath the water surface. During the whole test session, except the pretest, the platform was located in the southwest quadrant of the pool. One day before the 4 days lasting training session animals had to perform a so called "pre-test" (two 60 sec lasting trials) to ensure that the seeing abilities of each animal were normal. Only animals that fulfilled this task were enclosed to the MWM testing. In the MWM task each mouse had to perform three trials on four consecutive days. A single trial lasted for a maximum of maximum one minute. During this time, the mouse had the chance to find the hidden, diaphanous target. If the animal could not find a "way" out of the water, the investigator guided to or placed the mouse on the platform. After each trial mice were allowed to rest on the platform for 10-15 sec. During this time, the mice had the possibility to orientate in the surrounding. Investigations took place under dimmed light conditions, to prevent the tracking system from negative influences (Kaminski; PCS, Biomedical Research Systems). On the walls surrounding the pool, posters with black, bold geometric symbols (e.g. a circle and a square) were fixed which the mice could use the symbols as landmarks for their orientation. One swimming group per trial consisted of five to six mice, so that an intertrial time of about five to ten minutes was ensured. For the quantification of escape latency (the time [second]—the mouse needed to find the hidden platform and therefore to escape from the water), of pathway (the length of the trajectory [meter] to reach the target) and of the abidance in the goal quadrant a computerized tracking system was used. The computer was connected to a camera placed above the centre of the pool. The camera detected the signal of the light emitting diode (LED), which was fixed with a little hairgrip on the mouse's tail. One hour after the last trial on day 4 the mice had to fulfill a so-called probe trial. At this time, the platform was removed from the pool and during the one-minute probe trial; the experimenter counted the number of crossings over the former target position. Additionally the abidance in this quadrant as well as the three other quadrants was calculated. Through out this trial a mouse could not get any, howsoever-natured, clue from the platform.

vi) Tissue Sampling

At the end of the treatment period, and following all behavioral testing, all remaining mice (n=28) were sacrificed. Therefore, all mice were sedated by standard inhalation anesthesia (Isofluran, Baxter) as described in SOP MET030. Cerebrospinal fluid (CSF) was obtained by blunt dissection and exposure of the foramen magnum. Upon exposure, a Pasteur pipette was inserted to the approximate depth of 0.3-1 mm into the foramen magnum. CSF was collected by suctioning and capillary action until flow fully ceases. Two aliquots of each sample were immediately frozen and kept at −80° C. until ready for further analysis with ELISA technique. After CSF sampling, each mouse was placed in dorsal recumbence, thorax was opened and a 26-gauge needle attached to a 1 cc syringe was inserted into the right cardiac ventricular chamber. Light suction was applied to the needle and blood was collected into EDTA and consequently used to obtain plasma. To get plasma, blood samples from each mouse were spun at 1,750 rpm (700 g) for 10 minutes in a centrifuge (GS—6R Beckman) using a rotor with swing buckets (GH—3.8 Beckman). Plasma was frozen and stored at −20° C. until further analysis. After blood sampling transgenic mice were intracardially perfused with 0.9% sodium chloride. Brains were rapidly removed the cerebellum was cut off. The right hemispheres of all mice were immersion fixed in freshly produced 4% Paraformaldehyde/PBS (pH 7.4) for one hour at room temperature. Thereafter brains were transferred to a 15% sucrose PBS solution for 24 hours to ensure cryoprotection. On the next day brains were frozen in isopentane and stored at −80° C. until used for histological investigations (SOP MET042). The left hemispheres were weighed and frozen in liquid nitrogen and stored at −80° C. for biochemical analysis.

vii) Determination of $A\beta_{1-40}$ and $A\beta_{1-42}$

In four different brain homogenate fractions of each Tg mouse as well as in CSF samples the $A\beta_{1-40}$ and $A\beta_{1-42}$ levels were evaluated with ELISA technique. Highly sensitive $A\beta_{1-40}$ and $A\beta_{1-42}$ ELISA test kits were purchased from The Genetics Company™, Switzerland (SOP MET058). CSF was prepared as described above. For the brain homogenates frozen hemispheres were homogenized in TRIS buffered saline (TBS)-buffer (5 ml) containing protease inhibitor cocktail. 1.25 ml of this initial brain TBS homogenate was stored at −80° C., 1.25 ml have been further investigated. The remaining brain homogenate (2.5 ml) was centrifuged and the resulting supernatant (=TBS fraction) was aliquoted and kept at −20° C. until ELISA determination. The pellet was suspended in Triton X-100 (2.5 ml), centrifuged and the supernatant (=Triton X-100 fraction) was aliquoted and kept at −20° C. These steps were repeated with SDS (2.5 ml). The pellet out of the SDS fraction was suspended in 70% formic acid (0.5 ml) prior to subsequent centrifugation. The obtained supernatant was neutralized with 1 M TRIS (9.5 ml) aliquoted and kept at −20° C. (=FA fraction). Samples of the four brain homogenate fraction (TBS, Triton X-100, SDS, and FA) were used for $A\beta_{1-40}$ and $A\beta_{1-42}$ determination with ELISA technique. ELISA test kits were purchased from The Genetics Company™, Switzerland (SOP MET062). It could be assumed that TBS and Triton X-100 solubilize monomeric to oligomeric structures. Polymers like protofibrils and water insoluble fibrils could be dissolved in SDS and FA. In this regard the investigation of all four fractions also provides insight in A polymerization status.

viii) Evaluation of Brain Morphology

Brain tissues of all Tg animals investigated were handled in exactly the same way to avoid bias due to variation of this procedure. From brain halves of 24 Tg mice (8 of each group) 20 cryo-sections per layer (altogether 5 layers), each 10 μm thick (Leica CM 3050S) were sagittally cut and 5 (one from each layer) were processed and evaluated for quantification of plaque load. The five sagittal layers corresponded with the FIGS. 104 to 105, 107 to 108, 111 to 112, 115 to 116 and 118 to 119 according to the morphology atlas "The Mouse Brain" from Paxinos and Franklin (2nd edition). The first layer was specified by the requirement to include the whole hippocampus with it's regions CA1, CA2, CA3, GDlb and GDmb. Immunoreactivity was quantitatively evaluated in the hippocampus and in the cortex using the monoclonal human Aβ-specific antibody 6E10 (Signet) as well as ThioflavinS staining. Remaining brain hemispheres or tissue not used were saved and stored at JSW CNS until the end of the project.

B) Evaluation i) Behavior

In the Morris Water Maze trials length of swimming path, escape latencies, swimming speed and in the probe trial crossings over the former platform position and the time spent in each quadrant of the pool were measured for each Tg animal with a special computer software.

ii) Biochemical Evaluation

From all Tg mice CSF samples as well as samples from the brain preparations were analyzed with commercially available $A\beta_{1-40}$ and $A\beta_{1-42}$ ELISAs. Measurements of adequate standards were performed concurrently. Samples from brain preparations were analyzed in duplicates. Due to the small sample amount CSF samples were analyzed in a single measurement only.

iii) Histology i1) Measurement of Amyloid Depositions and Plaque Load

For 6E10 immunohistochemistry the following evaluation procedure was used:

aa) Contrasting the image for visualization of slice borders without applying the contrast on the image.

bb) Interactive drawing of the cortical outlines and the following measurement of the cortical area (=region area).

cc) Interactive drawing of the area of interest (AOI), in which stained objects are detected over a certain intensity based threshold level (the same for each image) and above a size of 8 μm$^2$.

dd) Measurement of the area of each object, the sum of stained area in the AOI as well as the number of objects after a smooth contrasting to enhance signal/noise ratio (the same for each image).

ee) Repetition of aa)-dd) for the hippocampus.

ff) Calculation of the mean plaque size (="sum area of plaques/number of plaques"), the relative plaque number and area (="number of plaques/region area" and "sum area of plaques/region area*100").

gg) Automated data export into an Excel spread sheet, including the parameters "image title, region area, number of plaques, sum of plaque area, relative plaque number, relative plaque area and mean plaque size. A field for remarks was used to record image quality and exclusion criteria, respectively. Exclusion criteria were missing parts of the slice, many wrinkles, dominant flaws or staining inconsistencies (e.g. due to bulges, which can impede the full reaction of the blocking reagent).

hh) Closing the image without saving (to keep raw data raw).

C) Results i) General Observations

In total 40 female hAPP Tg mice were enclosed to study. From these mice 12 animals died due to unknown reason before the treatment period was finished.

ii) Behavioral Results

Spatial learning in the MWM remained widely uninfluenced by XG-102 (SEQ ID NO: 11) treatment. 0.1 mg/kg treated mice showed a tendency to have worse learning performance between day 1 and day 4. A two-way ANOVA of the mean performance on day 1 and 4 revealed highly significant learning for all groups (p<0.001), but also a significant influence of factor treatment (p=0.045). However, Bonferroni's post tests did not reach significance.

iii) Biochemical Results aa) Aβ Levels in the Brain Homogenate Fractions

A treatment with the test compound XG-102 (SEQ ID NO: 11) did not affect brain homogenate $A\beta_{1-40}$ levels (see FIG. 11). Group differences in $A\beta_{1-42}$ levels appeared in Triton X-100 fraction, only. There, animals treated with the low dose of the test compound XG-102 (SEQ ID NO: 11) (0.1 mg/kg) featured a significant reduction compared to the vehicle group (p<0.05) as well as compared to the high dose group (p<0.01).

bb) CSF Aβ Levels

Figure 12:
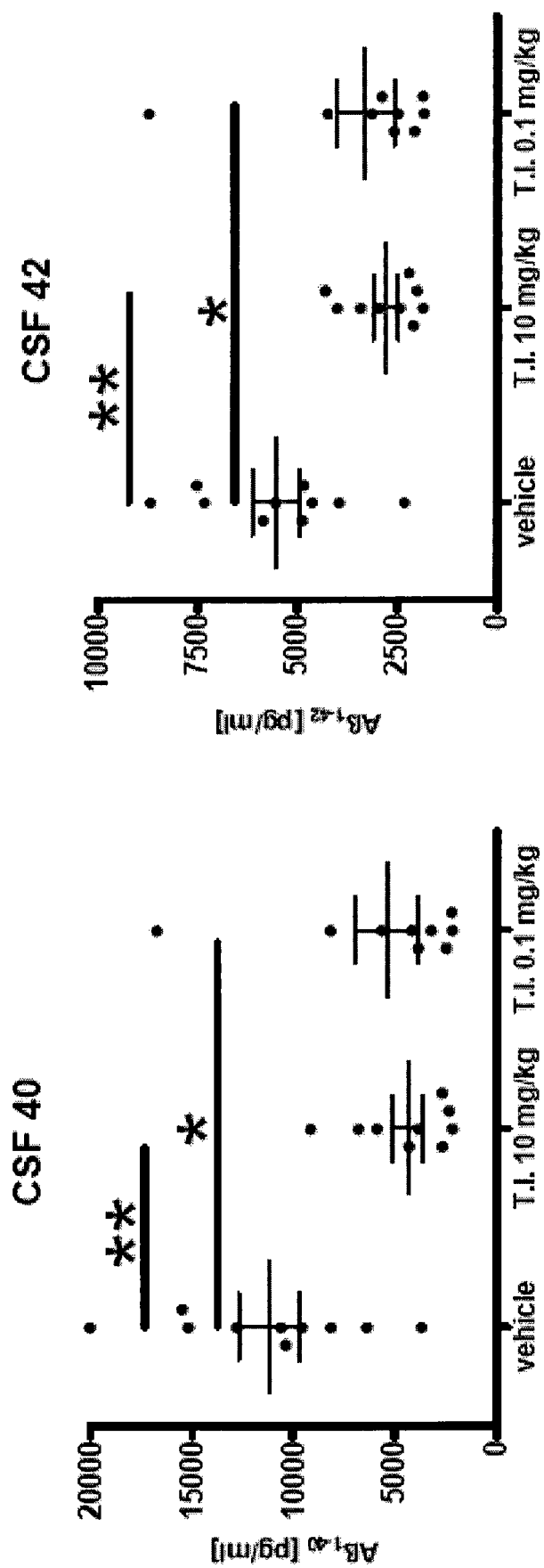
FIG. 12 depicts the effects of a treatment with XG-102 (SEQ ID NO: 11) on CSF $A\beta_{1-40}$ and $A\beta_{1-42}$ levels determined by ELISA. The Graphs represent the $A\beta_{1-40}$ (left) and $A\beta_{1-42}$ (right) levels determined by ELISA in CSF. Data are represented as scattered dot plot with individual values (black) and group mean±SEM. Significant differences are marked with asterisks (* p<0.05; ** p<0.01). Treatment with XG-102 (SEQ ID NO: 11) in both dosages led to a significant decrease of $A\beta_{1-40}$ and $A\beta_{1-42}$ in CSF.
Figure 13:
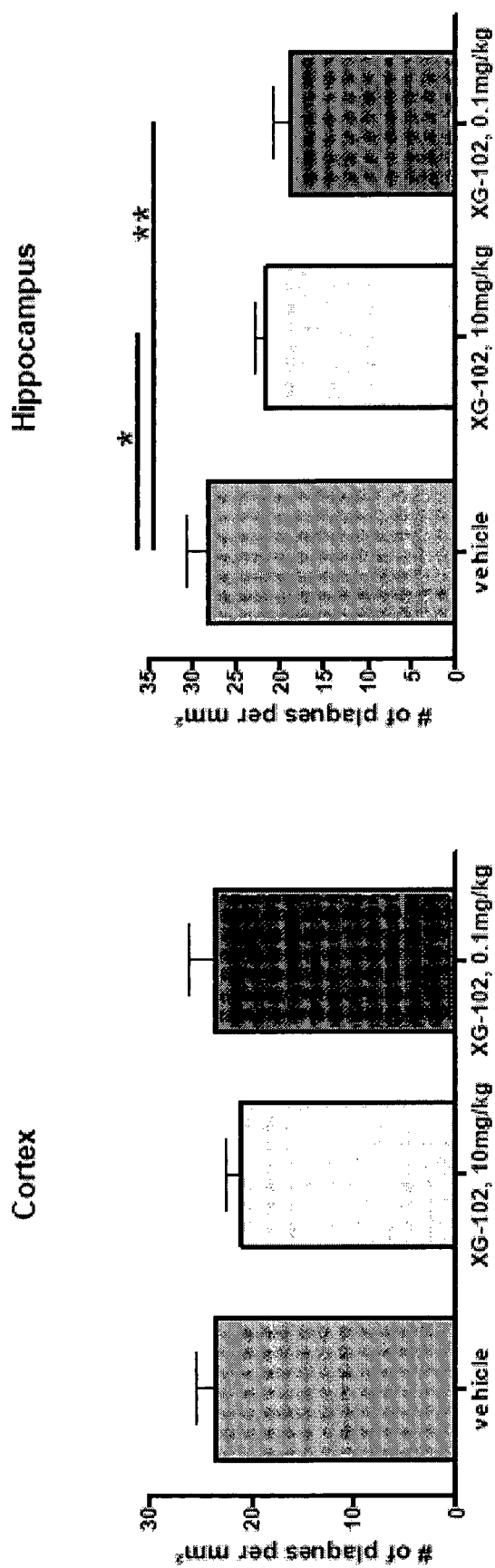
FIG. 13 shows the treatment effects on the ThioflavinS staining visualized number of plaques in the hAPP Tg mice: The graphs represent the number of ThioflavinS stained plaques per mm$^2$ in the cortex and the hippocampus. XG-102 (SEQ ID NO: 11) treatment reduced the number of plaques negatively dose-dependent in the hippocampus. Data are represented as means+SEM. N=8 per group. * . . . p<0.05; ** . . . p<0.01.
Figure 14:
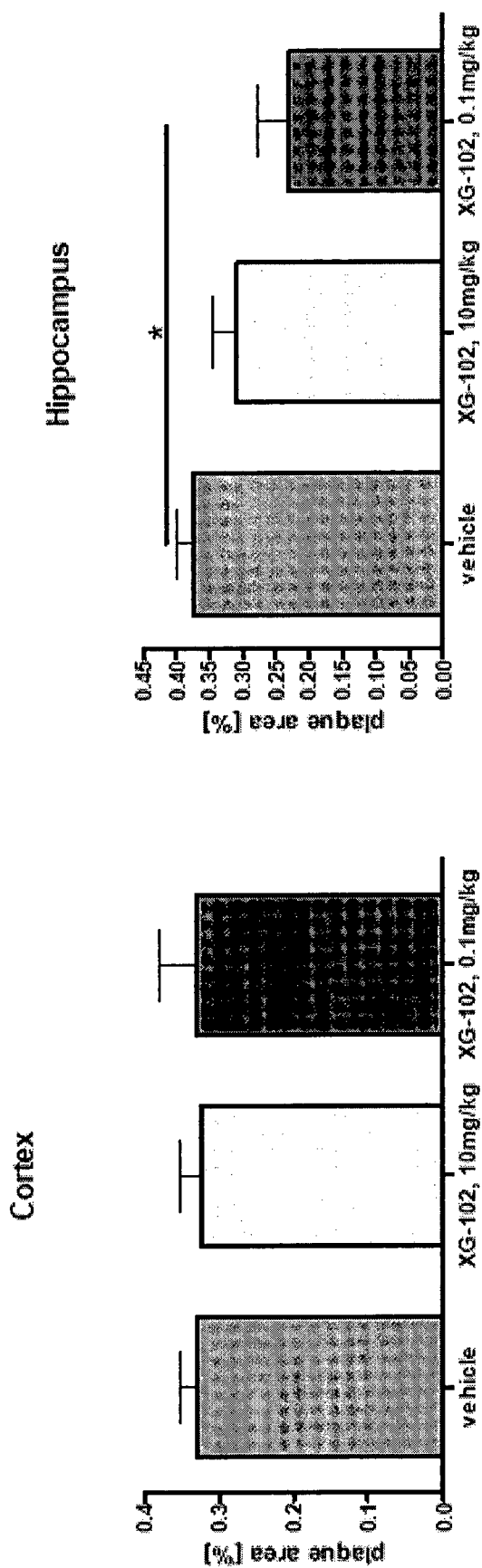
FIG. 14 depicts the treatment effects on the ThioflavinS visualized plaque area [%] in the hAPP Tg mice: The Graphs represent the plaque area [%] of ThioflavinS positive plaques in the cortex and the hippocampus. XG-102 (SEQ ID NO: 11) significantly reduced the area obtained by plaques in the hippocampus. Data are represented as means+ SEM. N=8 per group.

After treatment with the test substance XG-102 (SEQ ID NO: 2) $A\beta_{1-40}$ and $A\beta_{1-42}$ levels were significantly decreased in CSF compared to vehicle group. For both, $A\beta_{1-40}$ and $A\beta_{1-42}$ p-values were p<0.01 for the high dosage (10 mg/kg) and <0.05 for the lose dosage of XG-102 (SEQ ID NO: 2) (see FIG. 12).

iv) Results of Brain Histology and Immunohistochemistry aa) Amyloid Depositions and Plaque Load Plaque load was quantified with two different methods. On the one hand an IHC staining with 6E10 primary directed against AA1-17 of the human amyloid peptide was performed, on the other hand a ThioflavinS staining marking beta-sheet structures and cores of mature, neuritic plaques was carried out. First of all, measured region areas, cortex and hippocampus, were highly constant throughout all groups, indicating that problems in the cutting and IHC procedures can be excluded and to a certain degree also a treatment induced atrophy (changes of >5% would be detectable with this method). 6E10 and ThioflavinS quantifications revealed a selective reduction of beta-sheet structures in the center of the plaques after XG-102 (SEQ ID NO: 11) treatment, whereas human amyloid remained uninfluenced from treatment or slightly increased. In detail cortical 6E10 IR plaque load was increased versus vehicle in the 10 mg/kg XG-102 (SEQ ID NO: 11) treated mice, however, significance level was reached for the number of hippocampal plaques. FIGS. 13 and 14 show, in contrast to 6E10 IHC, that XG-102 (SEQ ID NO: 11) treatment led to a negatively dose dependent reduction of the number of hippocampal ThioflavinS positive plaques, as well as area percentage (number of plaques: p<0.05 for 10 mg/kg, p<0.01 for 0.1 mg/kg XG-102 (SEQ ID NO: 11)). 0.1 mg/kg XG-102 (SEQ ID NO: 11) treatment also reduced mean plaque size, however this effect did not reach significance level in the ANOVA (unpaired, two-tailed T-test: p=0.074) These effects were not given for cortical plaques, a circumstance which is most probably due to the later onset of plaque pathology in the hippocampus than in the cortex. Treatment start at five months of age exactly hits the time point of plaque deposition in the hippocampus, whereas cortical plaques start to become visible at the used magnification for quantification at the age of three months. Qualitatively the proportion of 6E10 to ThioflavinS stained plaques increase and the beta-sheet plaque cores, as seen in doubly labeled slices, become smaller in size. Summarized, these data support that XG-102 (SEQ ID NO: 11) treatment acts against beta-sheet formation in the early phase of plaque deposition and beta sheet formation in plaque cores, respectively.

D) Summary of Effects and Conclusions

Spatial navigation measured in the Morris water maze remained widely uninfluenced from treatment. 0.1 mg/kg XG-102 (SEQ ID NO: 11) treatment resulted in a slightly poorer learning performance between the first and the last training day.

Except a decrease in the Triton X-100 fraction in the 0.1 mg/kg XG-102 (SEQ ID NO: 11) group $A\beta_{1-40}$ and $A\beta_{1-42}$ brain levels stayed stable.

A decrease of Aβ levels was detectable in CSF for both dosages and fragments.

XG-102 (SEQ ID NO: 11) treatment led to a tendentious increase of human amyloid beta in the higher dosed group in the 6E10 quantifications, which is in compliance with data obtained in Aβ ELISA.

In contrast to that hippocampal beta-sheet load detected by ThioflavinS staining was dose dependently reduced after XG-102 (SEQ ID NO: 11) treatment, to a higher degree at lower dose 0.1 mg/kg XG-102 (SEQ ID NO: 11), whereas cortical plaque load remained unchanged. In accordance with the age-dependent onset of plaque deposition in the hippocampus at treatment start this hints at an early action on beta-sheet formation in the early phase of plaque deposition.

Example 15: Determining the Activity of all-D Retro-Inverso IB(s) Peptides and Variants Thereof in the Treatment of Diabetes Type 2

Example 15 is designed to determine the activity of IB(s) peptides and all-D retro-inverso IB(s) peptides and variants thereof in the treatment of Diabetes Type 2, particularly to determine the effect of chronic treatment with XG-102 (SEQ ID NO: 11) in the db/db mice model of type 2 diabetes by evaluating fasting blood glucose levels every third day (28 days)

a) Materials and Methods i) Animals

A total of twenty (20) male db/db mice (8 weeks old) were obtained from Charles River (Germany). Upon arrival, animals were group housed (n=6-7/group) and offered regular rodent chow (Altromin standard #1324 chow; C. Petersen, Ringsted, Denmark) and water ad libitum unless otherwise stated. The mice were housed under a 12:12 L/D cycle (lights on at 4:00 and lights off at 16:00) and in temperature and humidity controlled rooms.

ii) Groups and Randomization

On day −4, mice were randomized according to blood glucose level (fasted; blood glucose measured on Biosen S line analyzer (EKF diagnostic, Germany) to participate in one of the following drug treatment groups (n=6):

1) Vehicle control, S.C. (physiological saline)
2) XG-102 (SEQ ID NO: 11); 1 mg/kg; s.c.
3) XG-102 (SEQ ID NO: 11); 10 mg/kg; s.c All doses listed were calculated for the free-base. Drug purity: 95.28%, peptide content: 78.0%. All compounds were administered sub-cutaneously (s.c.) in a volume of 3 ml/kg. The formulation instructions for vehicle control and XG-102 (SEQ ID NO: 11) were as follows:

First, XG-102 (SEQ ID NO: 11) was dissolved in the vehicle. The formulations (concentrations of 0.33 and 3.3 mg/ml, corresponding to the doses of 1 and 10 mg/kg, respectively) were prepared according to the procedure detailed below. Concentrations were calculated and expressed taking into account test items purity and peptide content (multiplier coefficient was 1.346).

Preparation of a stock solution: the freeze-dried test compound XG-102 (SEQ ID NO: 11) is thawed for one hour minimum and prepared as a stock solution in the vehicle at 1 mM (corresponding to 3.823 mg/mL). Aliquots are prepared for each treatment day and stored at approximately −80° C. Dilutions of this stock solution to the required concentrations are performed on each treatment day;

Storage of the stock solution: at approximately −80° C.;

Storage of the diluted preparations: at room temperature for 24 hours maximum.

Prior to solubilisation, the powder was stored at −20° C. The stability of the stock solution is 3 months at approximately −80° C.; the stability of the diluted formulations for animal dosing is 24 hours at room temperature. Unused diluted material could be stored for up to 7 days if kept at 4-8° C.

c) Experimental Procedure

Following 8 days of acclimatization the mice were treated daily at 08.00 AM for 21 days by SC dosing 8 hours prior to lights out at 04.00 PM according to the outline groups. Then, on study day 21 dosing of the highest concentration of XG-102 (SEQ ID NO: 2) (10 mg/kg) was stopped, whereas daily dosing of vehicle control and XG-102 (SEQ ID NO: 2) (1 mg/kg) were continued until day study 28. From day 28 until termination at day 111 the vehicle and XG-102 (SEQ ID NO: 2) (10 mg/kg) treated mice were observed in a wash-out period (no dosing), whereas the mice treated with XG-102 (SEQ ID NO: 2) (1 mg/kg) was terminated after 28 days of treatment i) Blood Glucose Blood glucose was measured from 7 hour fasted animals 6 hours post dosing by collection of 10 µl blood samples from the tail-vein in hematocrit tubes and subsequent analysis on a Biosen s-line analyzer (EKE-diagnostic; Germany).

ii) Metabolic Cages

Groups 1+3: Mice were placed in metabolic cages for the recording of 24-hour food and water intake as well as 24-hour urine and faeces production. Mice were stratified into two sub-teams of n=6-7 and subsequently the metabolic characterisation were performed on study days 71-72.

iii) Adipokine Panel

Groups 1+3: On three occasions (study days 57, 66 and 108) blood was collected from the tail vein using EDTA coated hematocrit tubes (100 µl). Following centrifugation of blood the plasma was collected and stored at −20° C. until measurement. Then, the following panel of adipokines/cytokines was determined using Luminex based 7-plex: leptin, resistin, MCP-1, PAI-1, TNF, insulin and interleukin-6 (IL-6).

iv) Termination

Groups 1+3 (day 111): The following organs were excised and weighed: inguinal subcutaneous fat, epididymal fat, retroperitoneal fat, brain, liver, kidney, spleen and heart. All organs described above were samples in 4% PFA for possible future histo-pathological examination. Also, pancreas (en bloc) was sampled for possible stereological and imunohistochemical analysis, and eyes were sampled for possible later analysis of retinopathy. Group 2 (day 28): No tissues or plasma were collected.

c) Results i) General Observations

During the acute dosing period animals showed normal levels of alertness and activity and there were no signs of sedation in the drug treated animals. Food and water intake were within normal ranges among vehicle treated animals. However, after approximately two weeks dosing, nodular fibrosis was observed in the subcutaneous tissue as a reaction to the XG-102 (SEQ ID NO: 2) compound in the high dose, these progressed into open wounds all of the mice from group C. In group B mild nodular fibrosis was observed. As a consequence an alternation of injection sites were used. Following the end of dosing of the animals the animals healed and the nodular fibrosis was gradually disappearing. We observed no clinical effects in the vehicle treated animals.

ii) Blood Glucose

Figure 15:
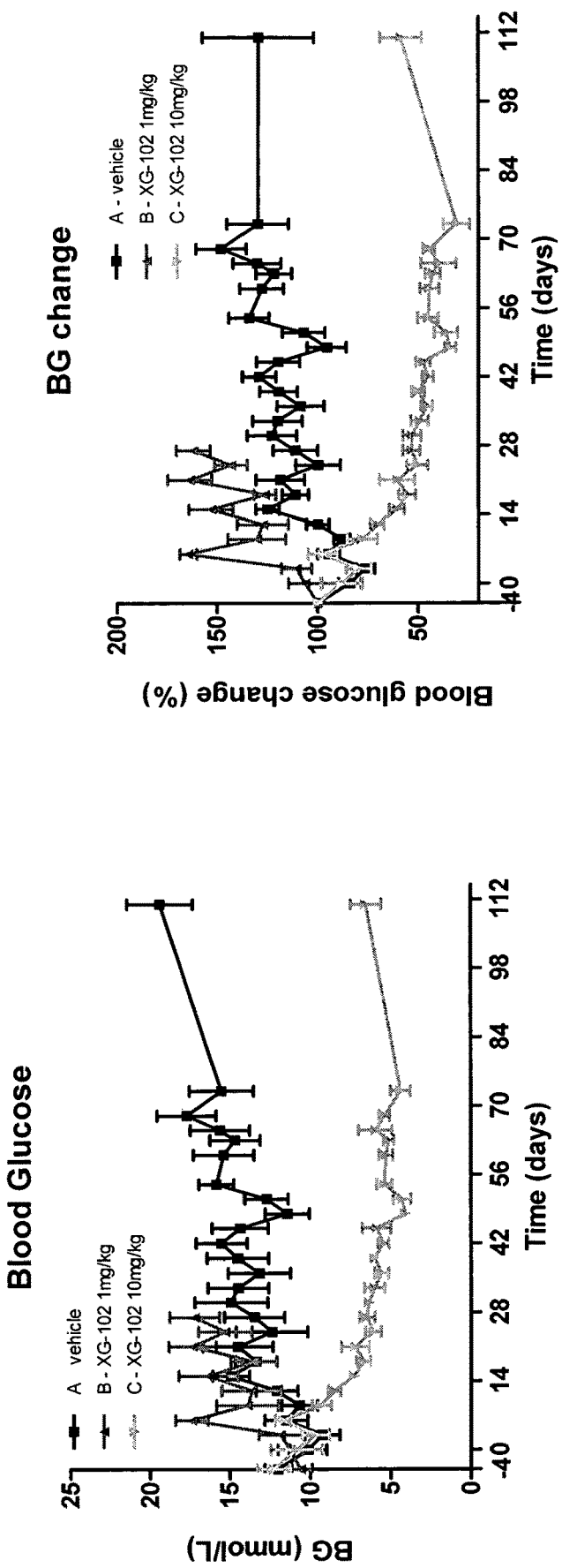
FIG. 15 describes the results of the administration of XG-102 (SEQ ID NO: 11) on fasting blood glucose levels (absolute and relative) in the animal model for diabetes type 2. Fasting blood glucose was measured every third day until day 68 and on a regular basis until termination at day 111 in groups A and C. We observed a clear and significant (p<0.001) decrease in the level of fasting blood glucose of the diabetic db/db mice treated with XG-102 (SEQ ID NO: 11) (10 mg/kg) as compared to vehicle control. The fasting blood glucose levels of the mice treated with XG-102 (SEQ ID NO: 11) (10 mg/kg) reached a low plateau of approximately 5 mmol/L. This effect was evident after 14 days of dosing and persisted throughout the study, thus during the entire wash-out period from day 21 to day 111. In contrast, we observed no effect of low dose of XG-102 (SEQ ID NO: 11) (1 mg/kg) during 28 days of dosing.

Fasting blood glucose levels (absolute and relative) are shown in FIG. 15. Fasting blood glucose was measured every third day until day 68 and on a regular basis until termination at day 111 in groups A and C. We observed a clear and significant ($p<0.001$) decrease in the level of fasting blood glucose of the diabetic db/db mice treated with XG-102 (SEQ ID NO: 2) (10 mg/kg) as compared to vehicle control. The fasting blood glucose levels of the mice treated with XG-102 (SEQ ID NO: 2) (10 mg/kg) reached a low plateau of approximately 5 mmol/L. This effect was evident after 14 days of dosing and persisted throughout the study, thus during the entire wash-out period from day 21 to day 111. In contrast, we observed no effect of low dose of XG-102 (SEQ ID NO: 2) (1 mg/kg) during 28 days of dosing.

iii) Body Weight

Figure 16:
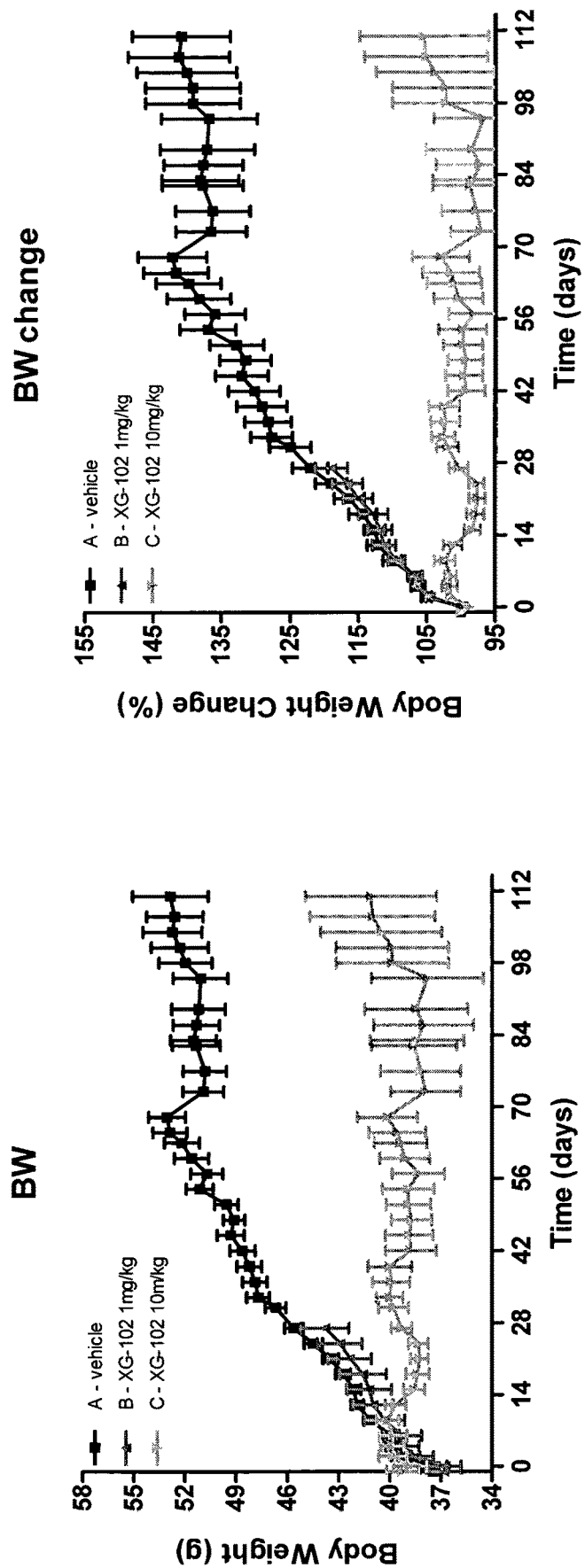
FIG. 16 describes the results of the administration of XG-102 (SEQ ID NO: 11), 10 mg/kg on body weight in the animal model for diabetes type 2. We observed a clear and significant (p<0.001) prevention of body weight increase in mice treated with XG-102 (SEQ ID NO: 11) (10 mg/kg) as compared to vehicle control. This effect was evident from day 28 of dosing and remained until the day of termination day 111. In contrast, we observed no effect of low dose of XG-102 (SEQ ID NO: 11) (1 mg/kg) on body weight during 28 days of dosing.

Body weight determinations (absolute and relative) are shown in FIG. 16. We observed a clear and significant ($p<0.001$) prevention of body weight increase in mice treated with XG-102 (SEQ ID NO: 2) (10 mg/kg) as compared to vehicle control. This effect was evident from day 28 of dosing and remained until the day of termination day 111. In contrast, we observed no effect of low dose of XG-102 (SEQ ID NO: 2) (1 mg/kg) on body weight during 28 days of dosing.

iv) Metabolic Cages

Figure 17:
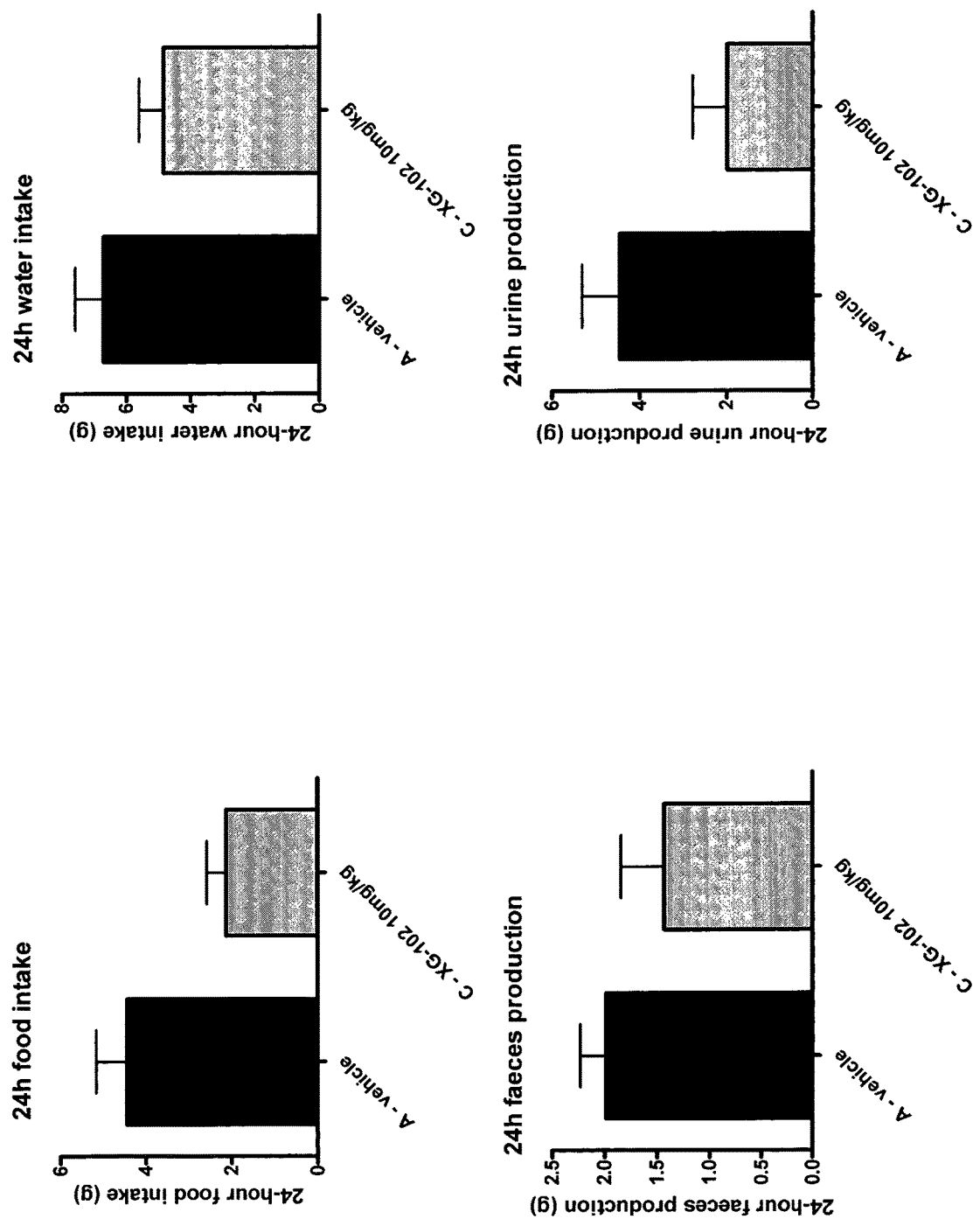
FIG. 17, 18 describe the effect of vehicle or XG-102 (SEQ ID NO: 11) (10 mg/kg) in the animal model for diabetes type 2 on 24 hour food and water intake, and urine and faeces production as measured in metabolic cages on study day 68 in FIGS. 17 (g) and 18 (normalized to g of body weight). We observed no significant effects of XG-102 (SEQ ID NO: 11) (10 mg/kg) on any of the measured parameters as compared to vehicle control though a trend towards a decrease in food intake and urine production was observed.
Figure 18:
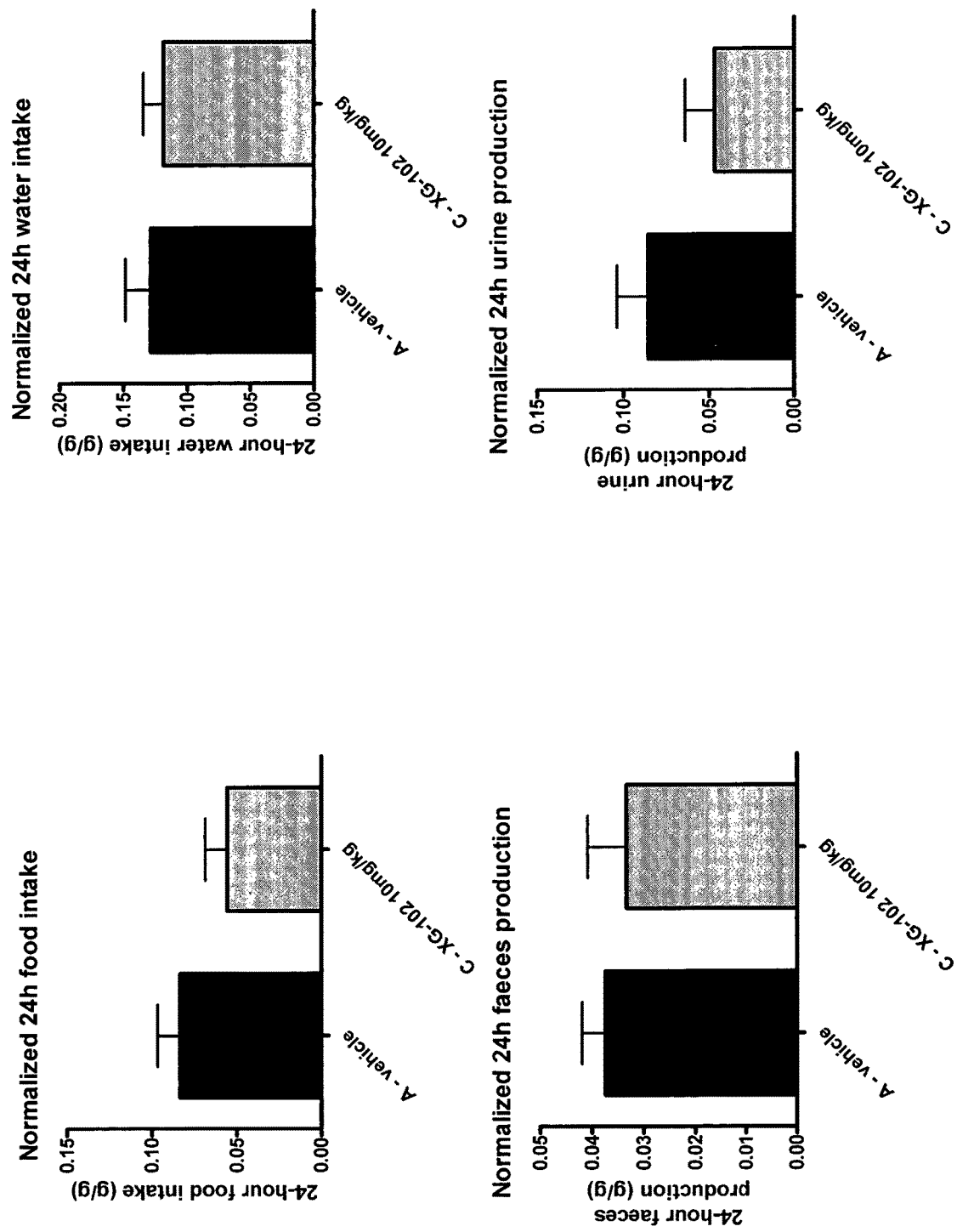

The effect of vehicle or XG-102 (SEQ ID NO: 2) (10 mg/kg) on 24 hour food and water intake, and urine and faeces production as measured in metabolic cages on study day 68 are shown in FIGS. 17 (g) and 18 (normalized to g of body weight). We observed no significant effects of XG-102 (SEQ ID NO: 2) (10 mg/kg) on any of the measured parameters as compared to vehicle control though a trend towards a decrease in food intake and urine production was observed.

v) Adipokines

Figure 19:
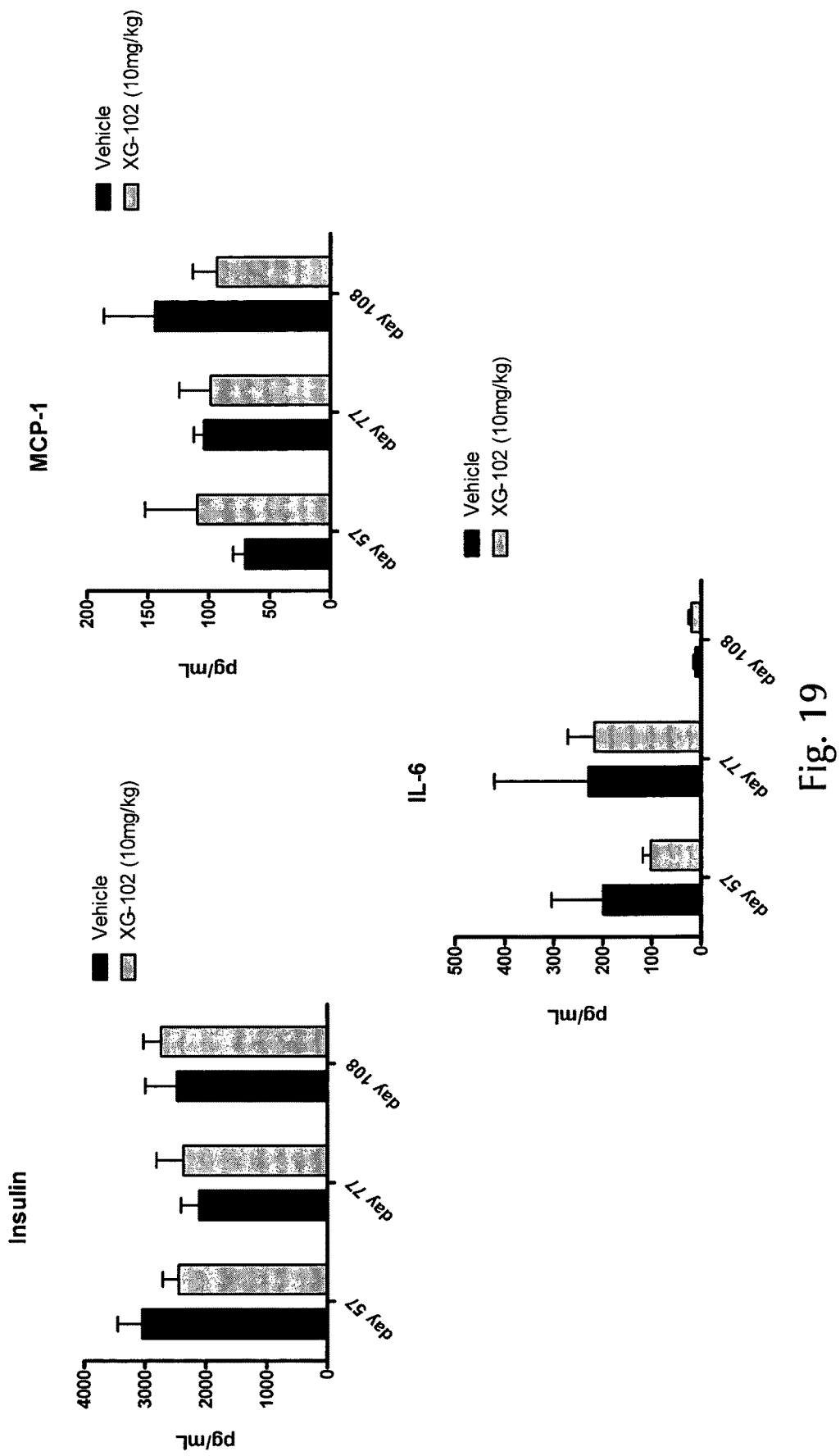
FIG. 19, 20 describe the effect of vehicle or XG-102 (SEQ ID NO: 11) (10 mg/kg) in the animal model for diabetes type 2 as measured on day 57, 77 and 108 on plasma levels of insulin, MCP-1 and IL-6 in FIG. 19; on plasma levels of tPAI-1, TNF and resistin in FIG. 20; We observed no significant effects of XG-102 (SEQ ID NO: 11) (10 mg/kg) on any of the measured parameters as compared to vehicle control except the levels of plasma resistin, which was significantly higher in XG-102 (SEQ ID NO: 11) treated animals at day 77 and 108.
Figure 20:
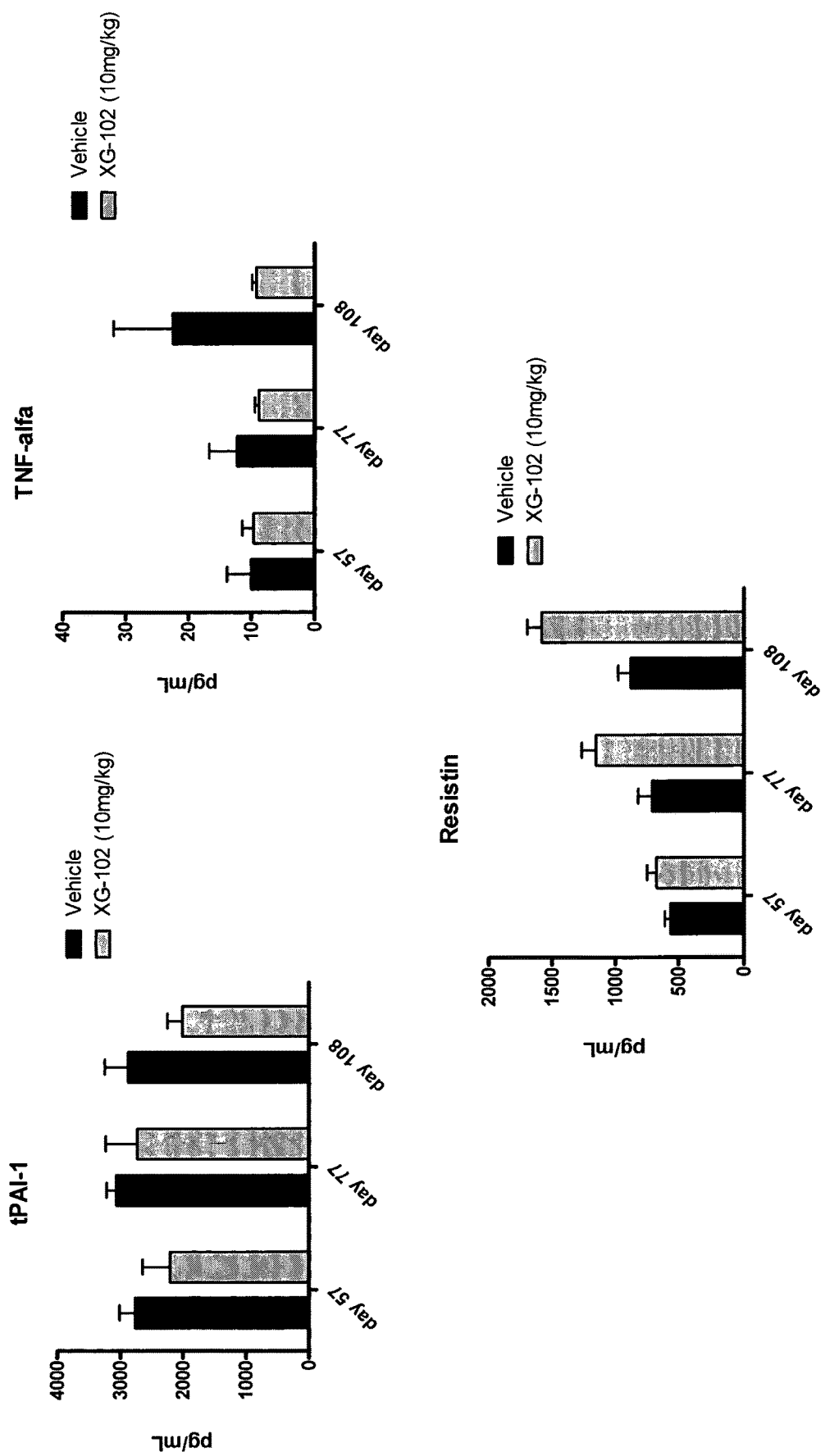

The effect of vehicle or XG-102 (SEQ ID NO: 2) (10 mg/kg) as measured on day 57, 77 and 108 on plasma levels of insulin, MCP-1 and IL-6 are shown in FIG. 19; on plasma levels of tPAI-1, TNF and resistin in FIG. 20; We observed no significant effects of XG-102 (SEQ ID NO: 2) (10 mg/kg) on any of the measured parameters as compared to vehicle control except the levels of plasma resistin, which was significantly higher in XG-102 (SEQ ID NO: 2) treated animals at day 77 and 108.

vi) Tissue Weight at Termination

Figure 21:
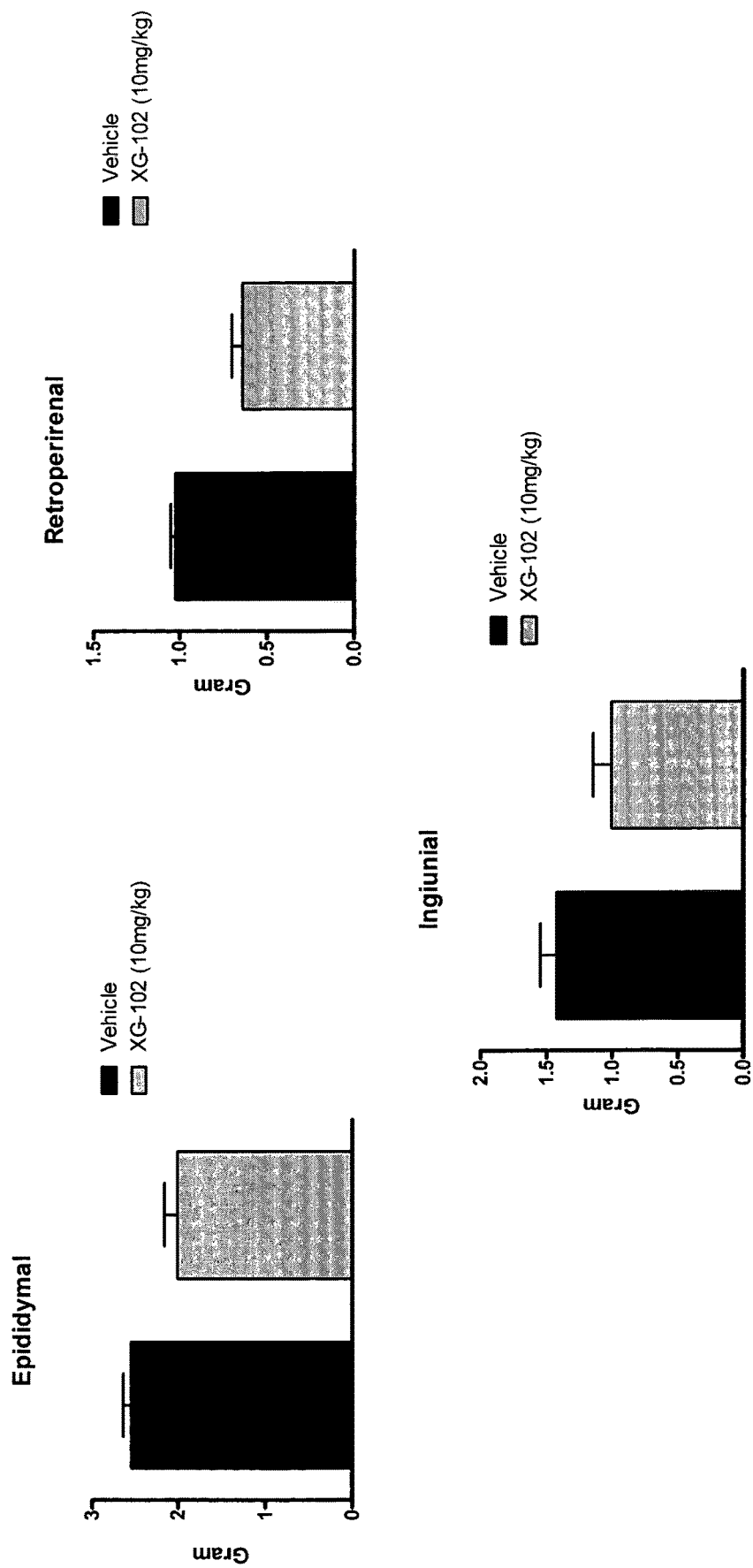
FIG. 21 shows the effect of vehicle or XG-102 (SEQ ID NO: 11) (10 mg/kg) in the animal model for diabetes type 2 on tissue weight of epididymal, inguinal subcutaneous, and retroperitoneal fat pads. We observed a significant decrease of epididymal (p<0.05) and retroperitoneal (p<0.01) fat mass in the mice treated with XG-102 as compared to vehicle control.
Figure 22:
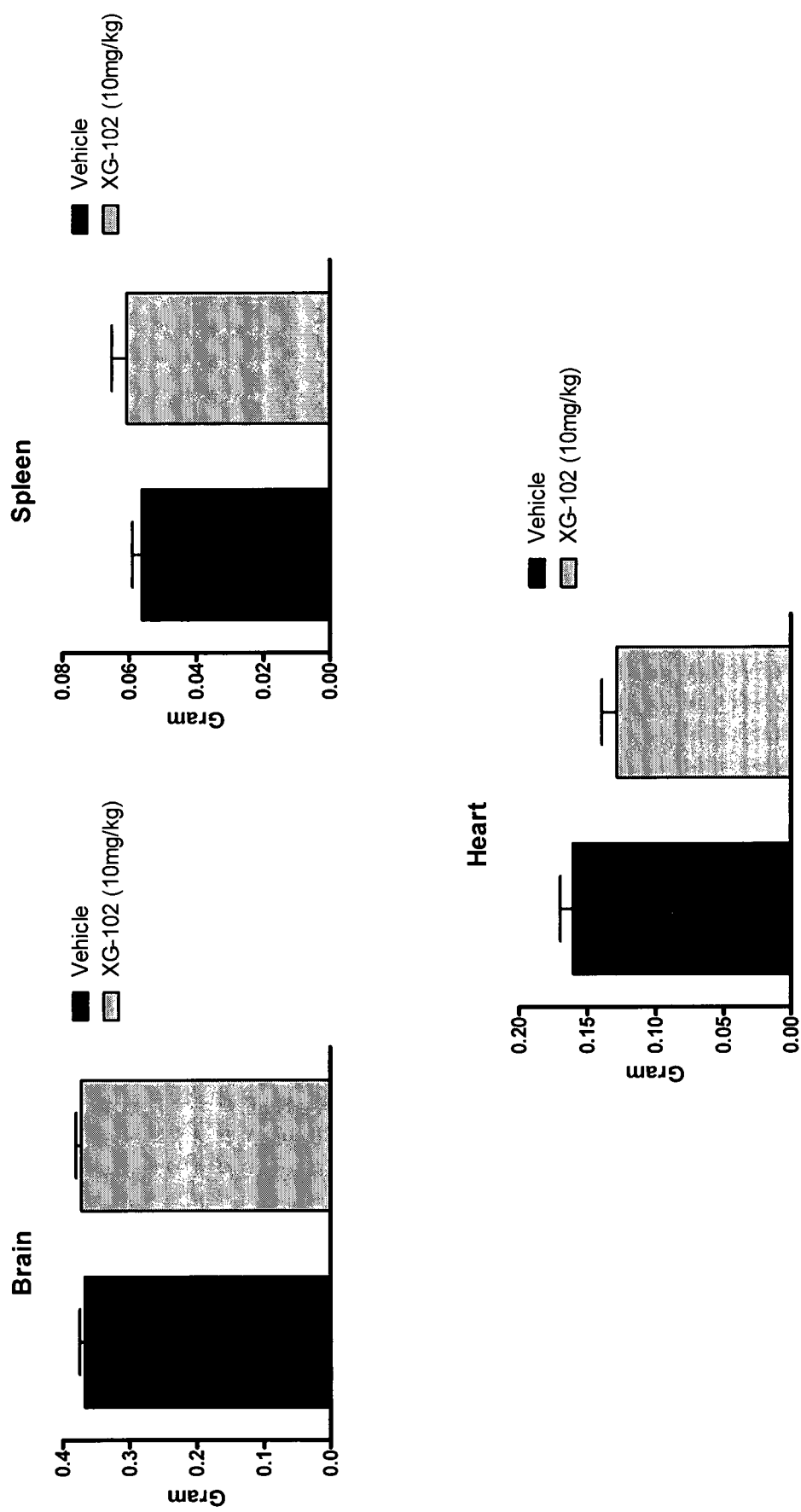
FIG. 22 depicts the effect of vehicle or XG-102 (SEQ ID NO: 11) (10 mg/kg) in the animal model for diabetes type 2 on tissue weight of brain, spleen and heart. We observed no significant effects of XG-102 (SEQ ID NO: 11) (10 mg/kg) on these parameters as compared to vehicle control.
Figure 23:
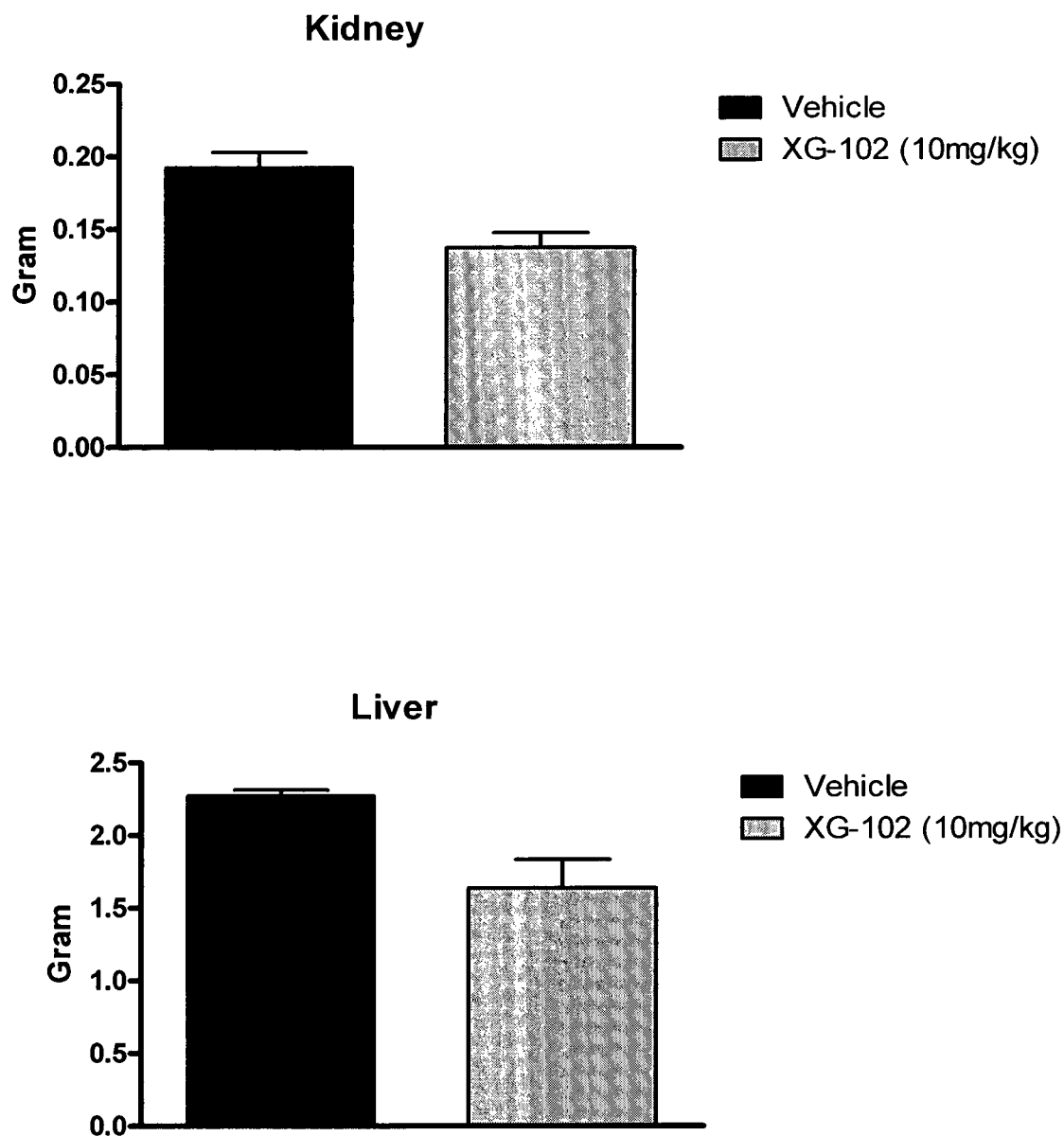
FIG. 23 describes the effect of vehicle or XG-102 (SEQ ID NO: 11) (10 mg/kg) in the animal model for diabetes type 2 on tissue weight of kidney and liver. We observed a significant decrease of kidney (p<0.05) and liver (p<0.01) mass in the mice treated with XG-102 (SEQ ID NO: 11) as compared to vehicle control.
Figure 25:
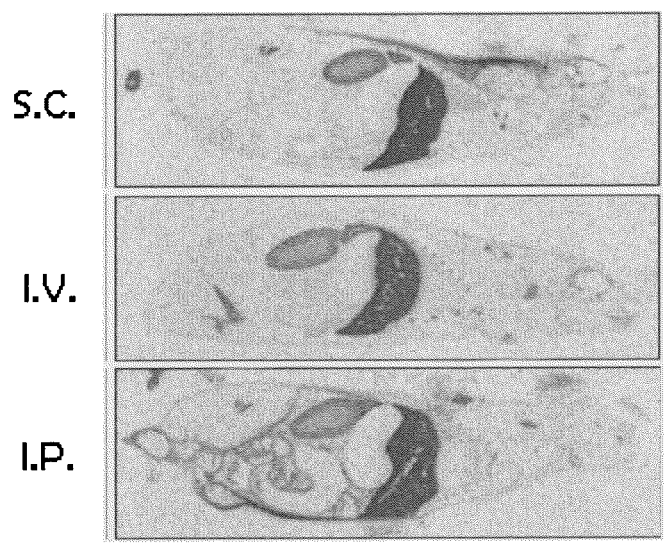
FIG. 25 Mice were treated via three different routes of administration (s.c., i.v., i.p.) with radiolabeled peptides with $C^{14}$ (1 mg/kg). Animals were sacrificed 72 hours after injection and processed for immunoradiography. Sagital sections were exposed and revealed the accumulation XG-102 peptides in the liver, spleen, and bone marrow predominantly (XG-102: SEQ ID NO: 11).
Figure 26:
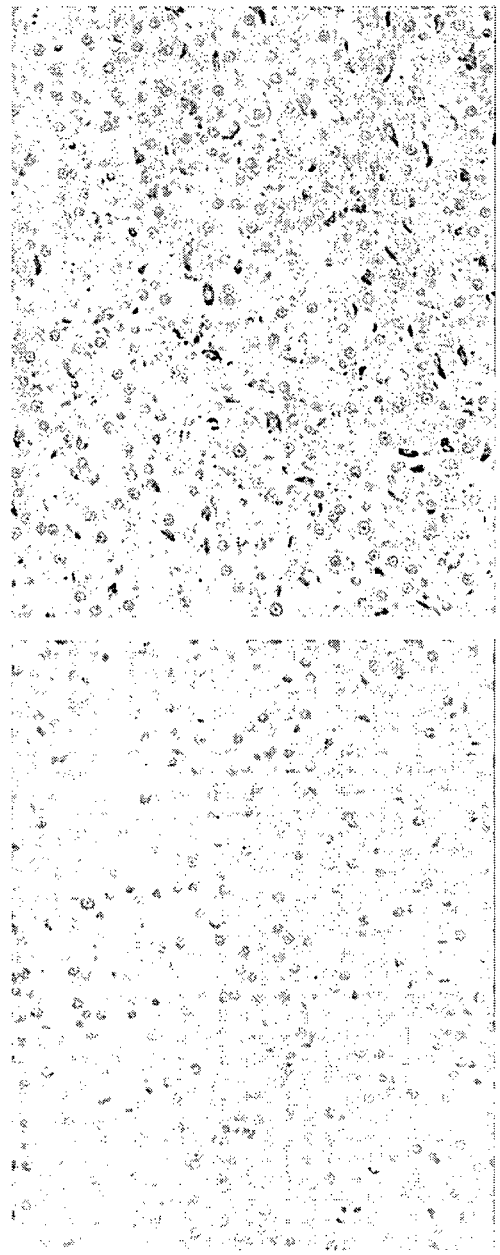
FIG. 26 shows an immunostaining against XG-102 (SEQ ID NO: 11) in the liver of rats injected with 1 mg/kg of XG-102 i.v. Animals were sacrificed 24 hours after injection. Revelation was done using DAB substrate. This figure shows again the pronounced accumulation of XG-102 in the liver, and especially, in the Kupffer cells (macrophages).
Figure 27:
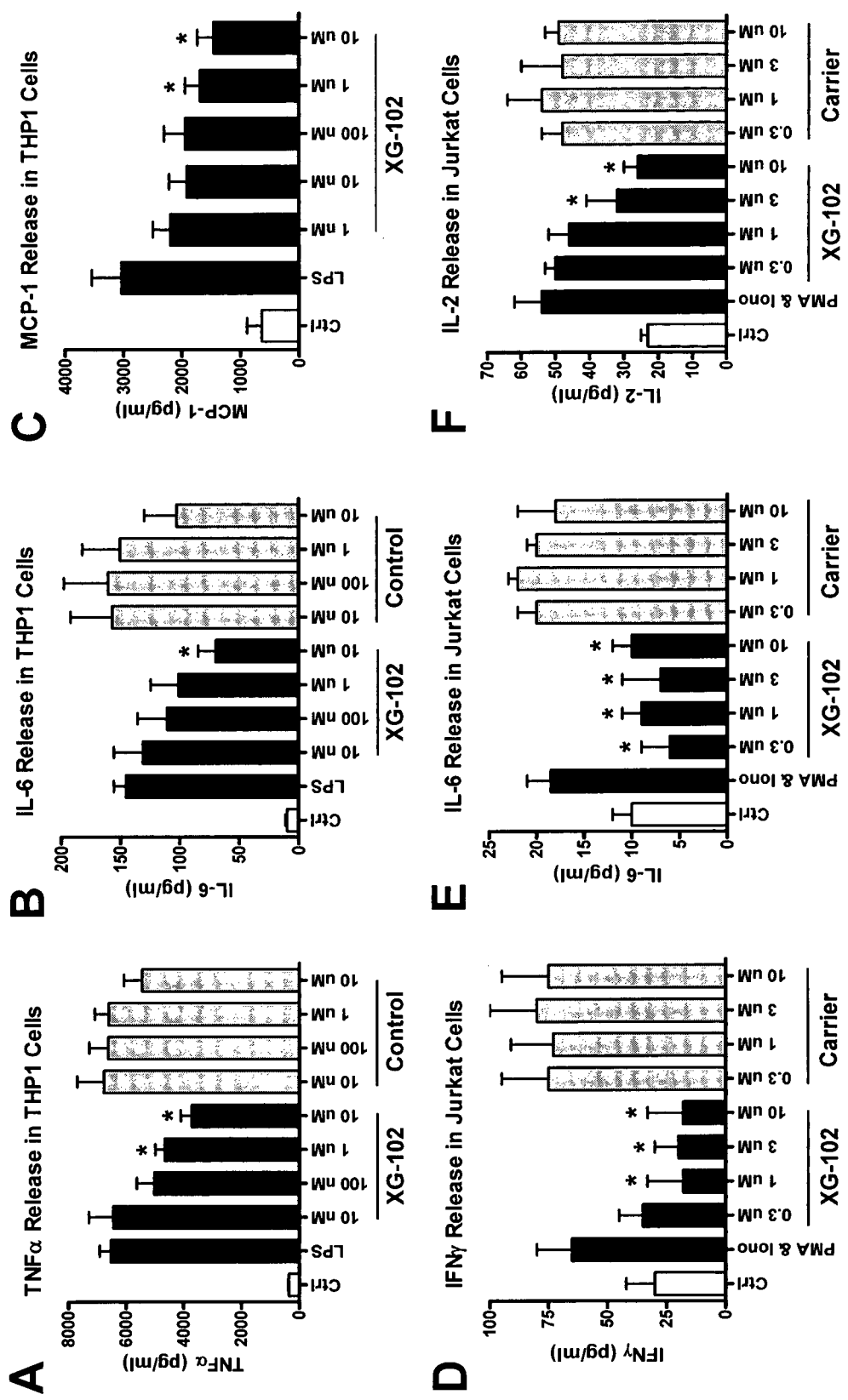
FIG. 27 shows the inhibition of Cytokine & Chemokine Release in two cell lines. XG-102 (SEQ ID NO:11) inhibits cytokine release in both myeloid and lymphoid cell lines, reducing LPS-induced TNFa, IL-6 and MCP-1 release in THP-1 cells (Panels A-C) and PMA & ionomycin-induced IFNg, IL-6 and IL-2 production in Jurkat cells (Panels D-F). The control (XG-101) is less effective due to its lesser stability.
Figure 28:
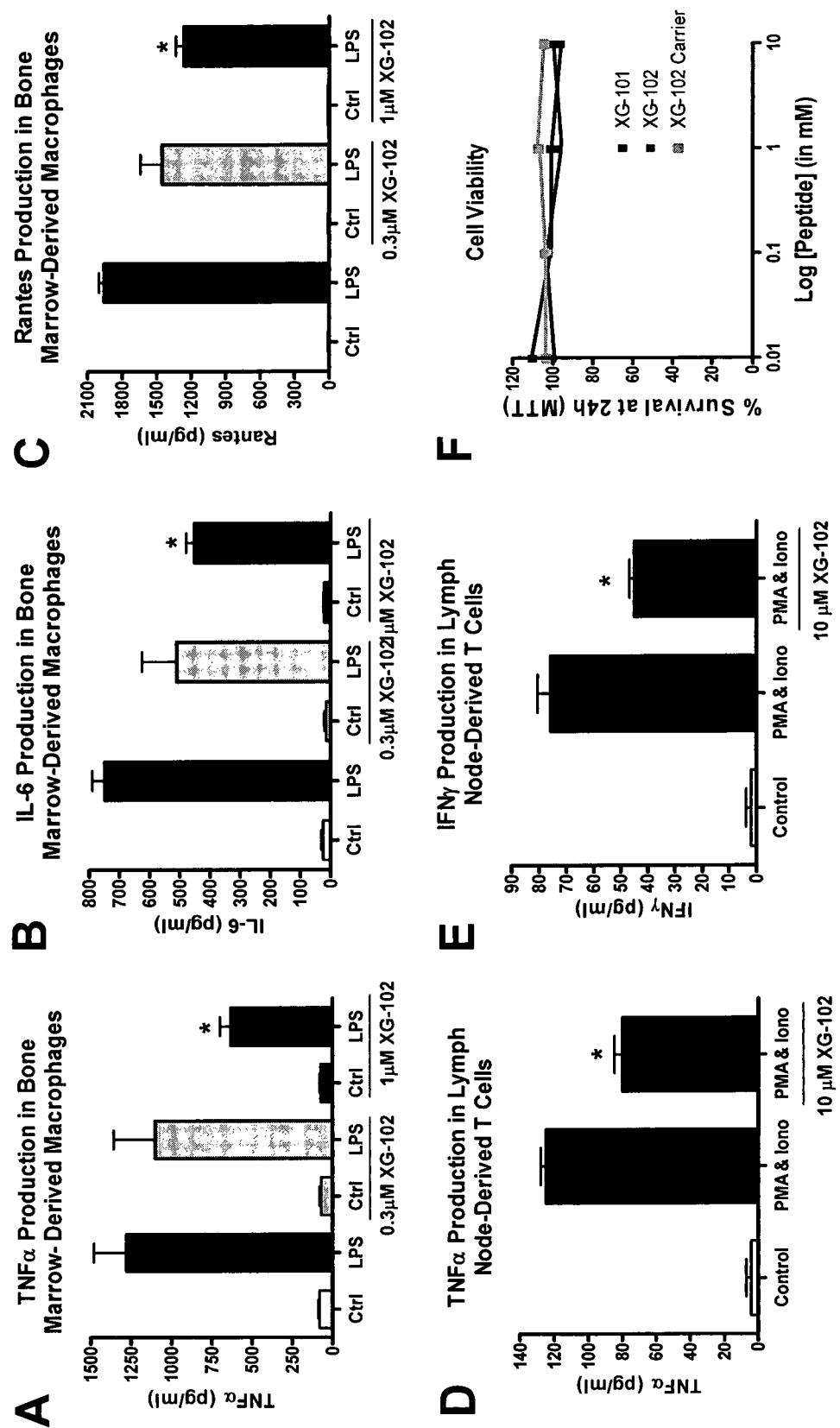
FIG. 28 shows the inhibition of cytokine release in primary cells. XG-102 (SEQ ID NO:11) also inhibits cytokine release in primary lymphoid and myeloid cells, reducing LPS-induced TNFa, IL-6 and Rantes release in murine macrophages (Panels A-C) and PMA & ionomycin-induced TNFa and IFNg production in murine T cells (Panels D-E). Effects occur at non-cytotoxic concentrations of XG-102 (Panel F)

The effect of vehicle or XG-102 (SEQ ID NO: 2) (10 mg/kg) on tissue weight of epididymal, inguinal subcutaneous, and retroperitoneal fat pads are shown in FIG. 21. We observed a significant decrease of epididymal (p<0.05) and retroperitoneal (p<0.01) fat mass in the mice treated with XG-102 as compared to vehicle control. The effect of vehicle or XG-102 (SEQ ID NO: 2) (10 mg/kg) on tissue weight of brain, spleen and heart is shown in FIG. 22. We observed no significant effects of XG-102 (SEQ ID NO: 2) (10 mg/kg) on these parameters as compared to vehicle control. Finally, the effect of vehicle or XG-102 (SEQ ID NO: 2) (10 mg/kg) on tissue weight of kidney and liver is shown in FIG. 23. We observed a significant decrease of kidney (p<0.05) and liver (p<0.01) mass in the mice treated with XG-102 (SEQ ID NO: 2) as compared to vehicle control.

Summarizing the results, administration of XG-102 (SEQ ID NO: 11), 10 mg/kg, appears to lead to a significant decrease in blood glucose levels and therefore, XG-102 (SEQ ID NO: 11) appears to be a promising new tool for treating diabetes and elevated blood glucose levels.

Example 16: Safety, Tolerability and Pharmacokinetics of a Single Intravenous Infusion of 10, 40 and 80 µg/kg XG-102 (SEQ ID No.: 11) Administered to Healthy Male Volunteers in a Randomized, Double Blind, Placebo Controlled, Dose Escalating Phase I Study The primary objective of the study was to assess the safety and tolerability of XG-102 following intravenous (iv) infusion of single escalating doses of XG-102 to healthy male volunteers. The secondary objective of the study was to assess the pharmacokinetics of XG-102 following iv infusion of single escalating doses of XG-102 to healthy male volunteers. Doses were administered as a 60 minute iv infusion. For control purposes, placebo iv infusion was administered to control subjects.

This was a single-centre, randomized, double blind, placebo controlled, ascending single dose, sequential group study. Three dose levels of XG-102 (10, 40 and 80 µg/kg) were studied in ascending order of dose, within each group subjects were randomized such that 6 subjects received XG-102, and 2 subjects received placebo. Screening was performed in the 3-week period prior to dosing. Dosing occurred on Day 0 for each subject. The Investigator checked on all subjects' well-being prior to their discharge from the CRU (at 24 hours after dosing). Subjects returned to the CRU 8±2 days and 28±5 days after dosing for post study assessments.

A total of 24 subjects (healthy male subjects in the age of 18 to 45), in 3 groups of 8. 24 subjects entered and completed the study. Data for all subjects were included in the safety analyses; data for all subjects who received XG-102 were included in the pharmacokinetic analyses.

Summary:
Pharmacokinetic results:
The pharmacokinetic parameters of XG-102Fehler! Verweisquelle konnte nicht gefunden werden. are presented in the following table:

| Parameter | 10 µg/kg (N = 6) | 40 µg/kg (N = 6) | 80 µg/kg (N = 6) |
|---|---|---|---|
| $AUC_{0-last}$ (ng · h/mL) | 24.7 (26.1) | 134 (15.2) | 431 (41.0) |
| $AUC_{0-\infty}$ (ng · h/mL) | 36.8 (23.4) | 146 (17.5) | 443 (41.0) |
| AUCextrap[a] (%) | 34.1 (18.6-49.7) | 6.7 (4.2-12.9) | 2.9 (1.9-3.4) |
| $C_{max}$ (ng/mL) | 31.3 (24.4) | 146 (16.7) | 362 (34.9) |
| $t_{max}$[a] (h) | 1.00 (1.00-1.05) | 1.00 (1.00-1.00) | 1.00 (1.00-1.00) |
| $AUC_{0-last}$ (norm) (ng · h/mL)/(µg/kg) | 3.10 (29.3) | 3.64 (13.8) | 5.91 (41.8) |
| $AUC_{0-\infty}$ (norm) (ng · h/mL)/(µg/kg) | 4.61 (24.8) | 3.96 (15.7) | 6.07 (41.8) |
| $C_{max}$ (norm) (ng/mL)/(µg/kg) | 3.93 (28.0) | 3.98 (15.9) | 4.97 (35.6) |
| MRT (h) | 1.00 (29.9) | 0.76 (11.0) | 1.02 (14.7) |
| $t_{1/2}$ (h) | 0.57 (44.6) | 0.36 (22.3) | 0.65 (38.8) |
| CL (mL/h) | 17537 (23.9) | 18399 (16.4) | 13217 (43.5) |
| CL (mL/h/kg) | 217 (24.8) | 253 (15.7) | 165 (41.8) |
| $V_{ss}$ (mL) | 17536 (36.8) | 14040 (15.7) | 13500 (30.5) |
| $V_{ss}$ (mL/kg) | 217 (27.5) | 193 (13.7) | 168 (29.8) |

Geometric mean (CV %) data are presented
N = Number of subjects studied
(norm) = Normalized for dose and body weight
[a]Median (min max)

The observed values of $t_{1/2}$ were short. Both peak exposure as measured by $C_{max}$ and cumulative exposure as measured by $AUC_{0\text{-}last}$ increased with dose. The increase with dose of $C_{max}$ appears to be more than linearly proportional on the basis of graphical examinations and of the geometric mean of its dose normalized values which after the highest 80 µg/kg dose are above the 90% confidence intervals for the other doses. The increase with dose of $AUC_{0\text{-}last}$ is clearly more than linearly proportional from 40 to 80 µg/kg as the 90% confidence intervals for its geometric mean dose normalized value does not overlap with those after the other tested doses; whereas when comparing values after 10 and 40 µg/kg the 90% confidence intervals overlap, but its geometric mean dose normalized value after the 10 µg/kg dose is lower than all values in the corresponding 90% confidence interval after the 40 µg/kg dose.

XG-102 was safe and well tolerated when administered as single iv doses of 10, 40 or 80 µg/kg to healthy male subjects. The incidence of adverse events in subjects who received XG-102 was similar to the incidence in subjects who received placebo. There were no clinically significant findings in clinical laboratory data, vital signs, ECGs, physical examinations or ocular examinations (fundus and IOP).

After the end of XG-102 intravenous infusion, its plasma concentrations quickly decreased, leading to values below the lower limit of quantification by at most 2 hours after the start of 10 µg/kg XG-102 iv infusions, 3 hours after the start of 40 µg/kg XG-102 iv infusions and by at most 7 hours after the start of 80 µg/kg XG-102 intravenous infusions. The measured tin and MRT values are short, with geometric mean values per dose level ranging from 0.36 to 0.65 hours and from 0.76 to 1.02 hours, respectively.

The $AUC_{0\text{-}last}$ of XG-102 increases in a more than linear proportion with dose in the tested dose range, with non-overlapping 90% confidence intervals for its geometric mean dose normalized values between the 40 µg/kg and the 80 µg/kg dose and only limited overlap between the 90% confidence intervals for its geometric mean dose normalized values between the 10 µg/kg and the 40 µg/kg.

The $C_{max}$ of XG-102 appears to increase in a more than linear proportion with dose from 40 to 80 µg/kg. The geometric mean dose normalized $C_{max}$ in the 80 µg/kg dose group is higher than and outside the 90% confidence intervals for the geometric mean dose normalized $C_{max}$ in the other dose groups, but the 90% confidence intervals for the geometric mean dose normalized $C_{max}$ overlap among all dose levels.

The intersubject variability of XG-102 pharmacokinetic parameters was moderate in subjects treated with 10 and 40 µg/kg doses (CV % of the geometric mean for most parameters approximately in the 15-30% range, exception was $t_{1/2}$ and total $V_{ss}$ at the 10 µg/kg dose group), but higher in the 80 µg/kg dose group, in the approximately 29-44% range, other than for MRT (14.7%). This higher variability may be either an effect of the low sample size or a consequence of the observed non-linearities which are clearer at this dose.

Example 17: Use of XG-102 (SEQ ID No.: 11) to Improve Porcine Islet Isolation Outcomes The object was to evaluate the ability of XG-102 to (a) block the massive activation of JNK that occurs during islet isolation leading to cell stress and death; (b) reduce islet death, resulting to improvements in islet viability post-isolation, using the porcine model.

Figure 33:
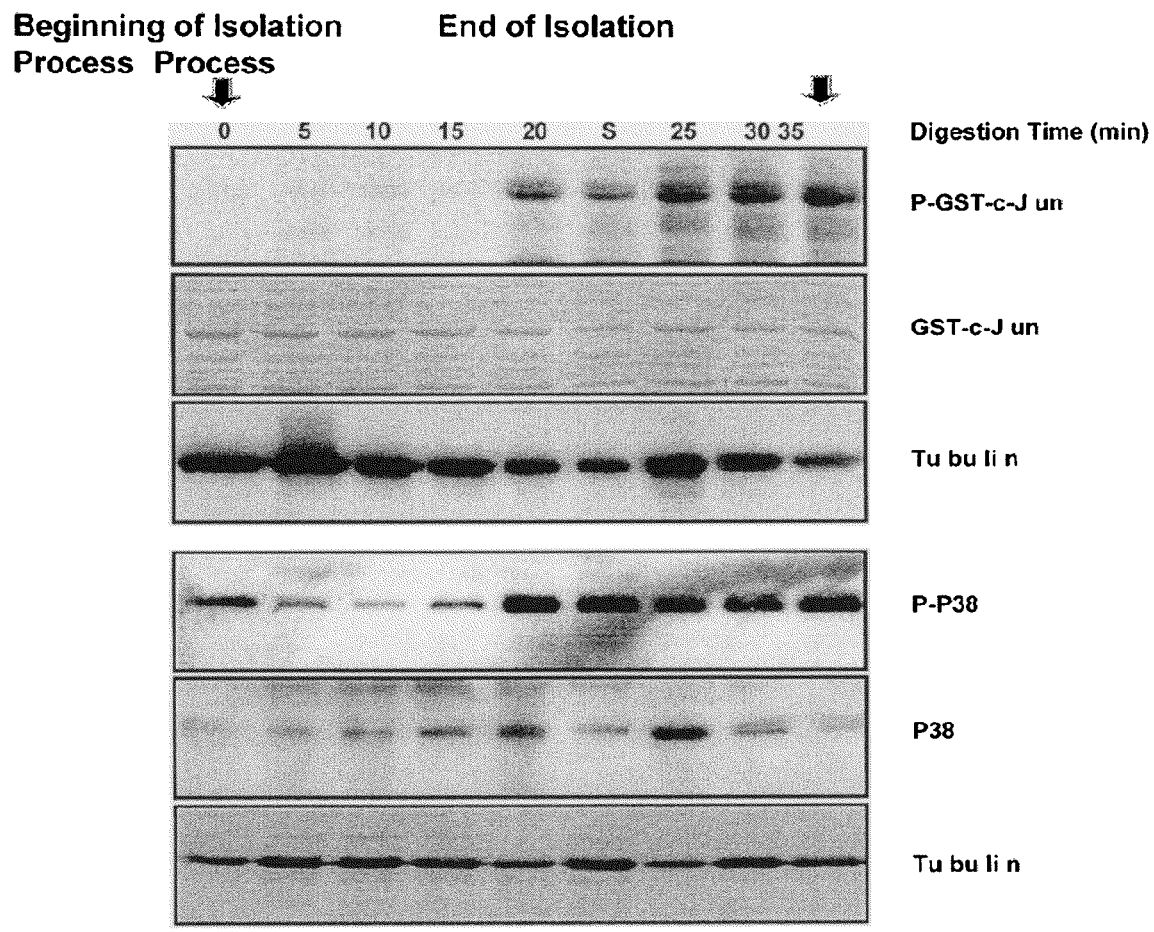
FIG. 33 Effect on islet Isolation on JNK/p38 activation. That experiment was designed to identify any effect evoked by the isolation process as such on JNK or p38. As control tubulin detection was used. Western blot staining as a function of the digestion time (min) is shown.
Figure 34:
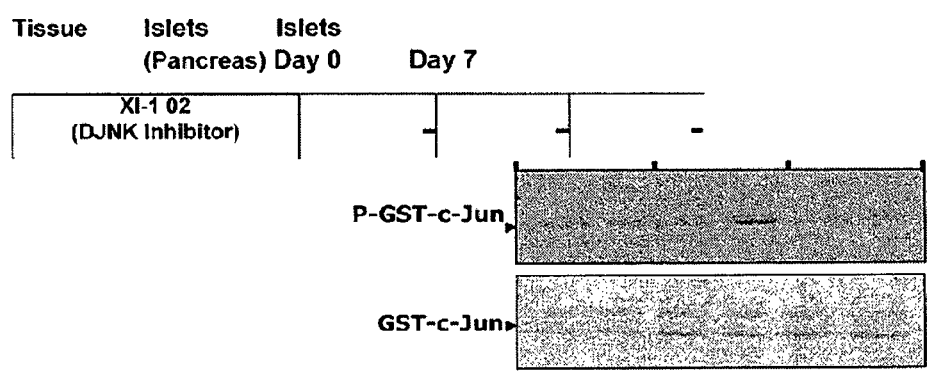
FIG. 34 By that figure the effect of XG-102 on JNK activation during isolation is shown.
Figure 35:
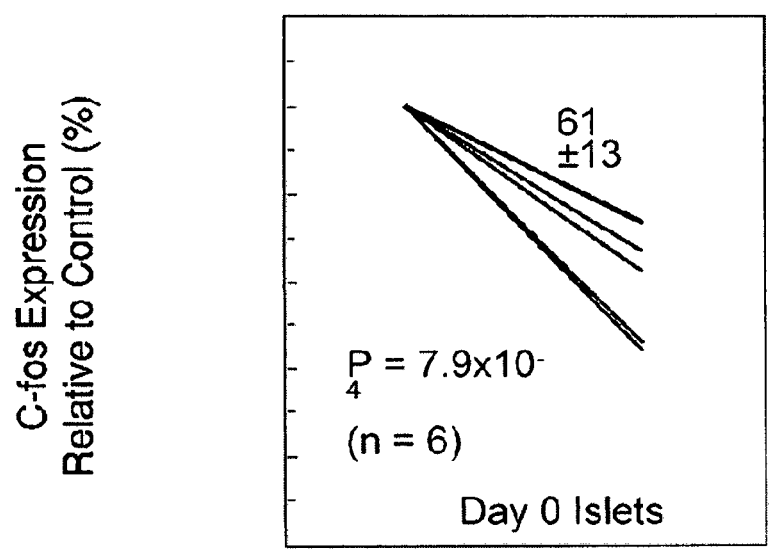
FIG. 35 Effect of XG-102 on JNK activation during isolation
Figure 36:
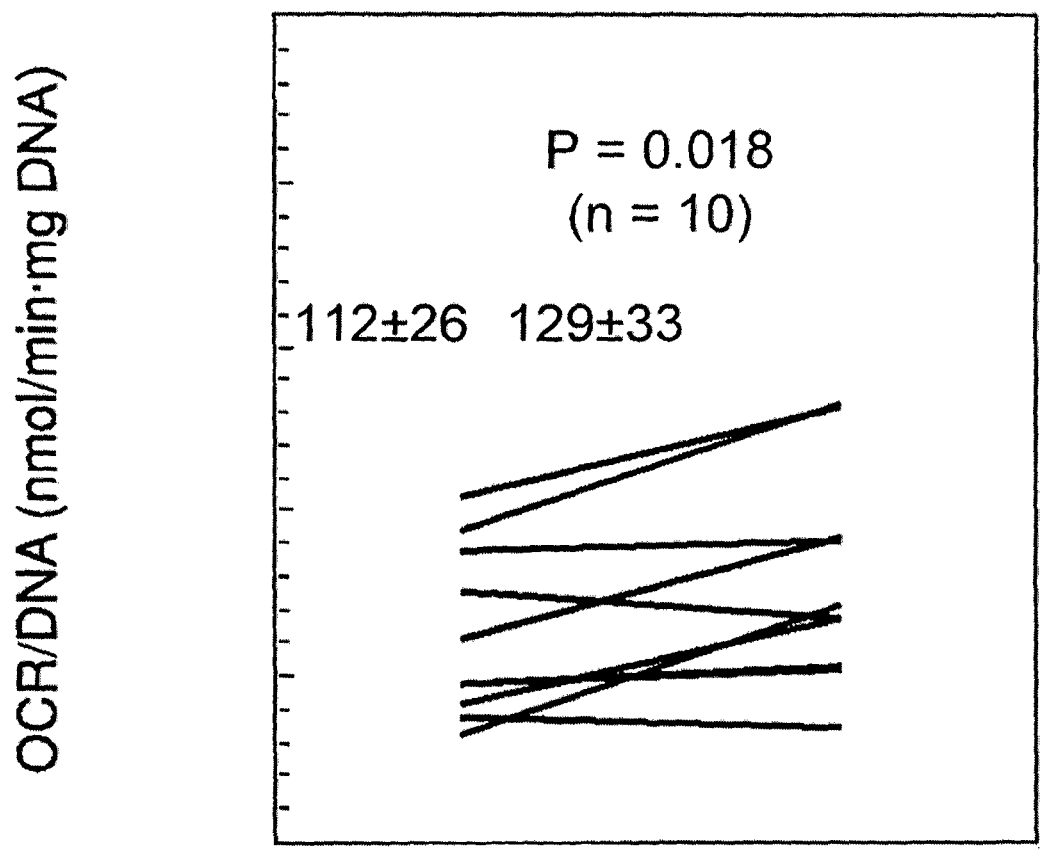
FIG. 36 Effect of XG-102 on OCR/DNA during isolation
Figure 37:
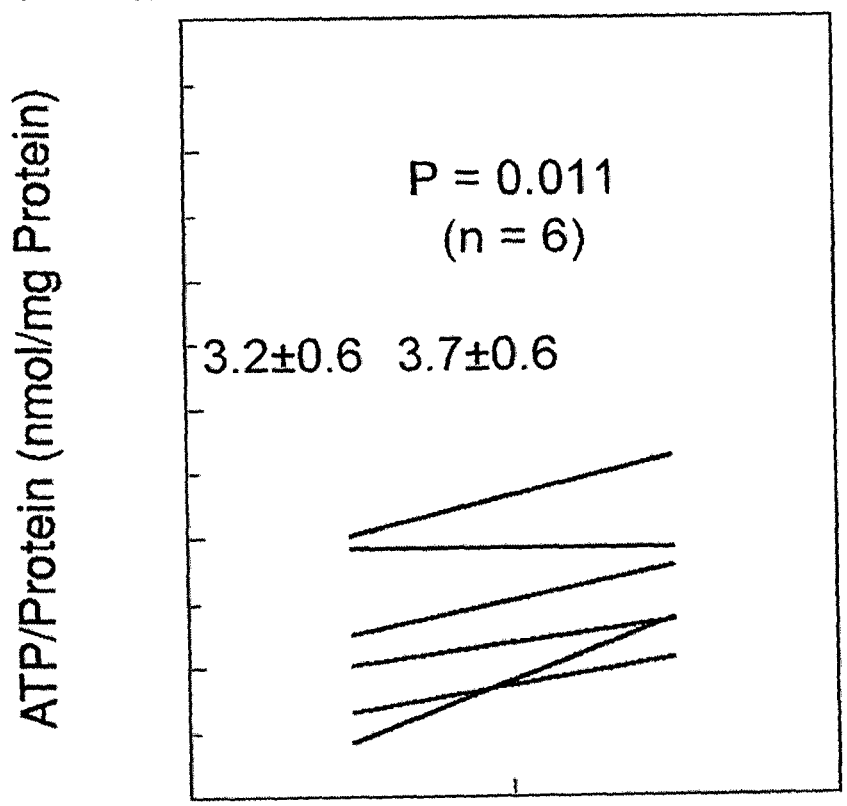
FIG. 37 Effect of XG-102 (DJNK inhibitor) on ATP/proteinJ by HPLC analysis

Porcine islet isolation results in a dramatic activation of JNK first observed in tissue samples ~20 min after the initiation of the islet isolation procedure (FIG. 33). Analysis of existing data demonstrates that the addition of the Xigen XG-102 JNK inhibitor at the pancreas level during procurement and transfer to the isolation lab and in islet isolation solutions (10 micromolar concentration) during isolation blocks the activation of JNK (FIG. 34), reduces the relative expression of the c-fos gene (FIG. 35), and has a statistically significant and important effect on the viability of freshly isolated islets as measured by OCR/DNA (FIG. 36) and ATP/protein [total cell protein] (FIG. 37). Comparisons were always made with paired untreated controls originating from the same pancreas donor. The data on islet viability presented in FIGS. 36 and 37 is consistent with a reduction in the activation of JNK typically observed during isolation (FIG. 33) and a reduction in resulting c-fos gene expression (FIG. 35). The differences in viability, JNK activation and c-fos expression became smaller after 7 days of culture.

Figure 38:
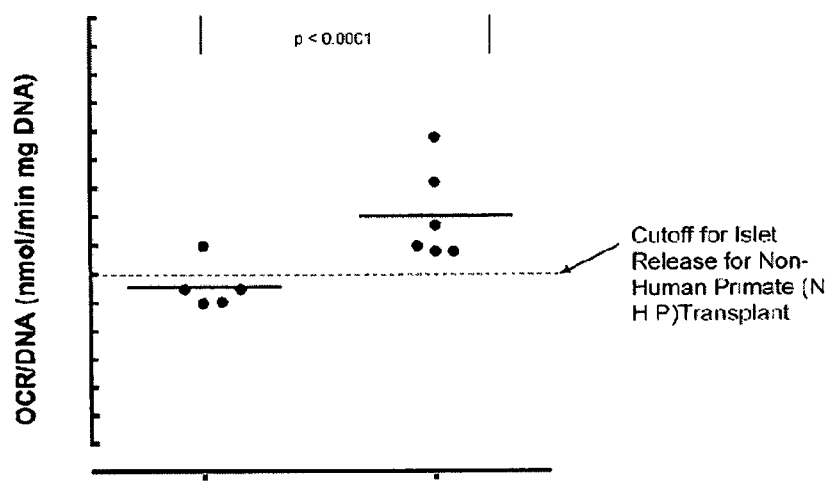
FIG. 38 shows that XG-103 increases significantly islet viability (OCR/DNA) as measured after 7 days of culturing FIG. 39 FIG. 41 (A): Fluorescein angiography evaluation (mean score) ten minutes after fluorescein injection. The mean score is presented for day 14 and day 21 for five groups (XG-102 300 microgramm/ml, XG-102 3 mg/ml, Kencort retard, 0.9% NaCl solution, untreated)
Figure 40:
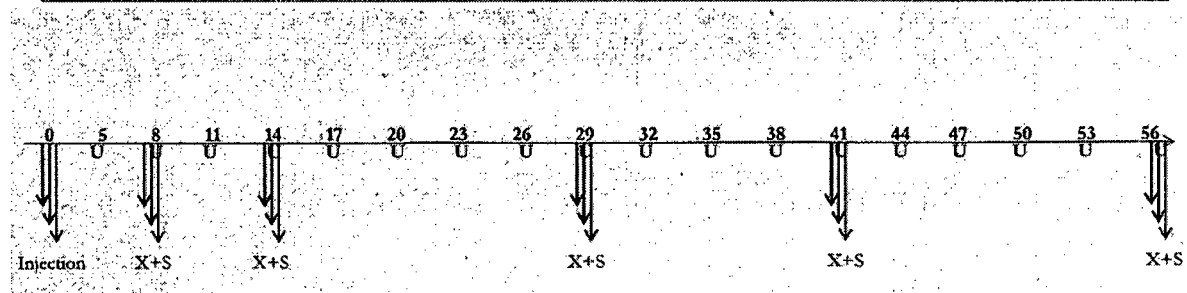
FIG. 40 The design of the experiment for assessing XG-102's effect on kidney tissue upon adriamycin-induced induction of nephropathy is shown. The rat groups and the and their treatment regimen is shown.
Figure 41:
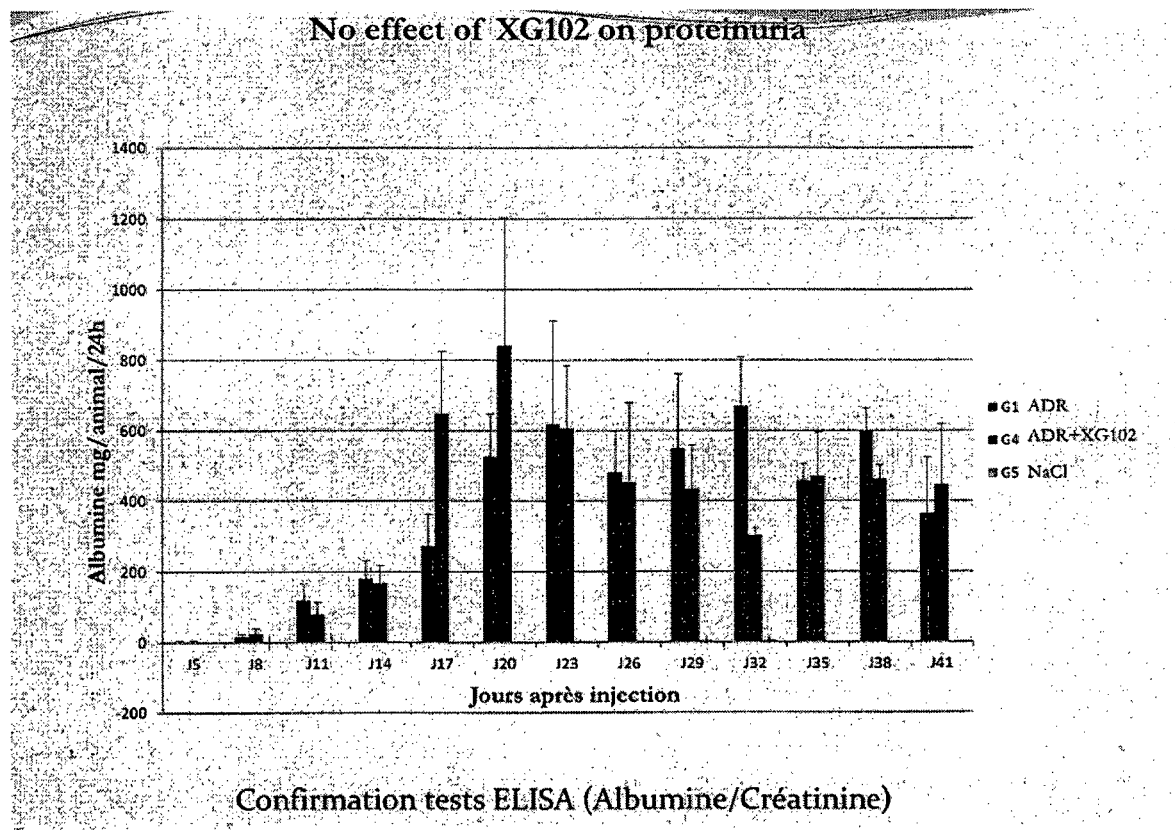
FIG. 41 (B) Proportion of fluorescein angiography evaluation (mean score) ten minutes after fluorescein injection, for five groups (XG-102 300 microgramm/ml, XG-102 3 mg/ml, Kencort retard, 0.9% NaCl solution, untreated) at day 14 and day 21.
Figure 42:
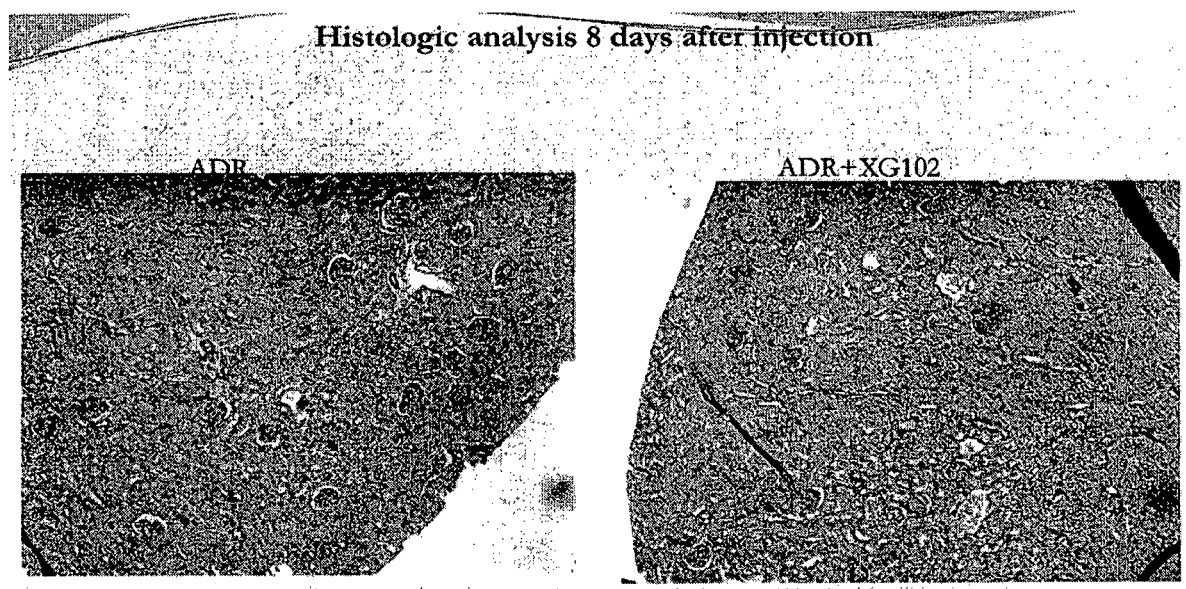
FIG. 42 Histological analysis 8 days after the onset of the experiment. Comparison of adriamycin treated rats of group 1 (left hand) and adriamycin and XG-102 treated rats of group 4 (right hand)
Figure 43:
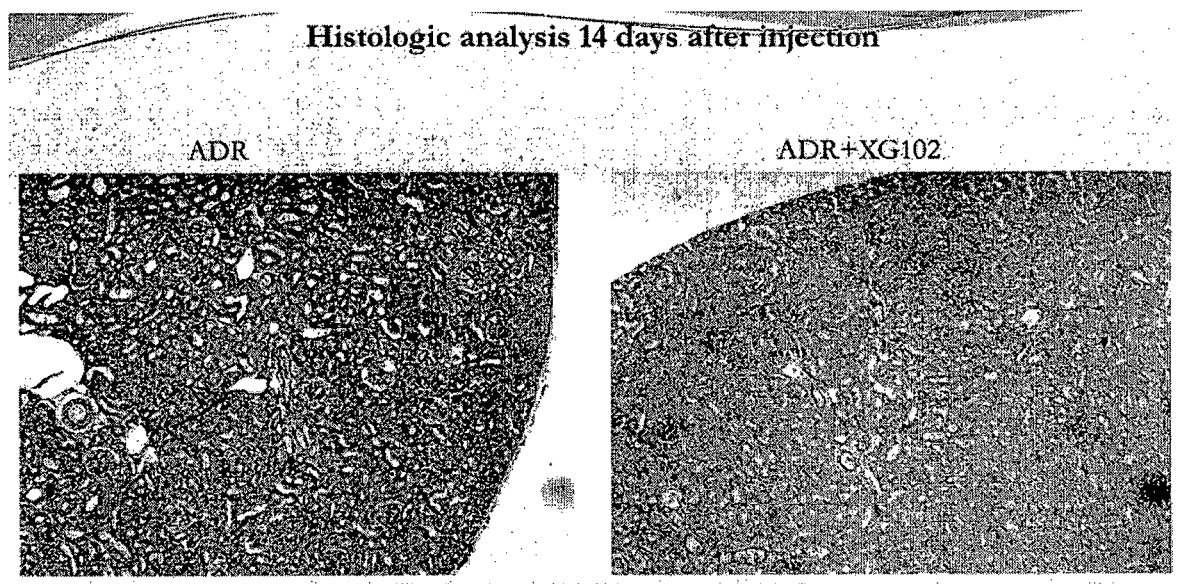
FIG. 43 Histological analysis 14 days after the onset of the experiment. Comparison of adriamycin treated rats of group 1 (left hand) and adriamycin and XG-102 treated rats of group 4 (right hand)
Figure 44:
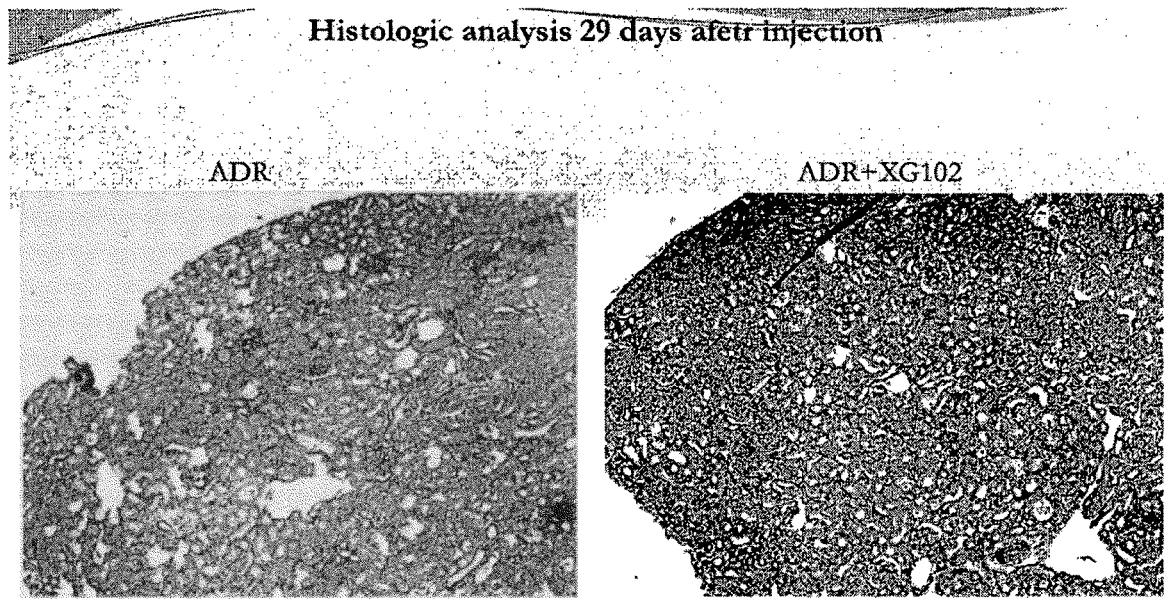
FIG. 44 Histological analysis 19 days after the onset of the experiment. Comparison of adriamycin treated rats of group 1 (left hand) and adriamycin and XG-102 treated rats of group 4 (right hand)
Figure 45:
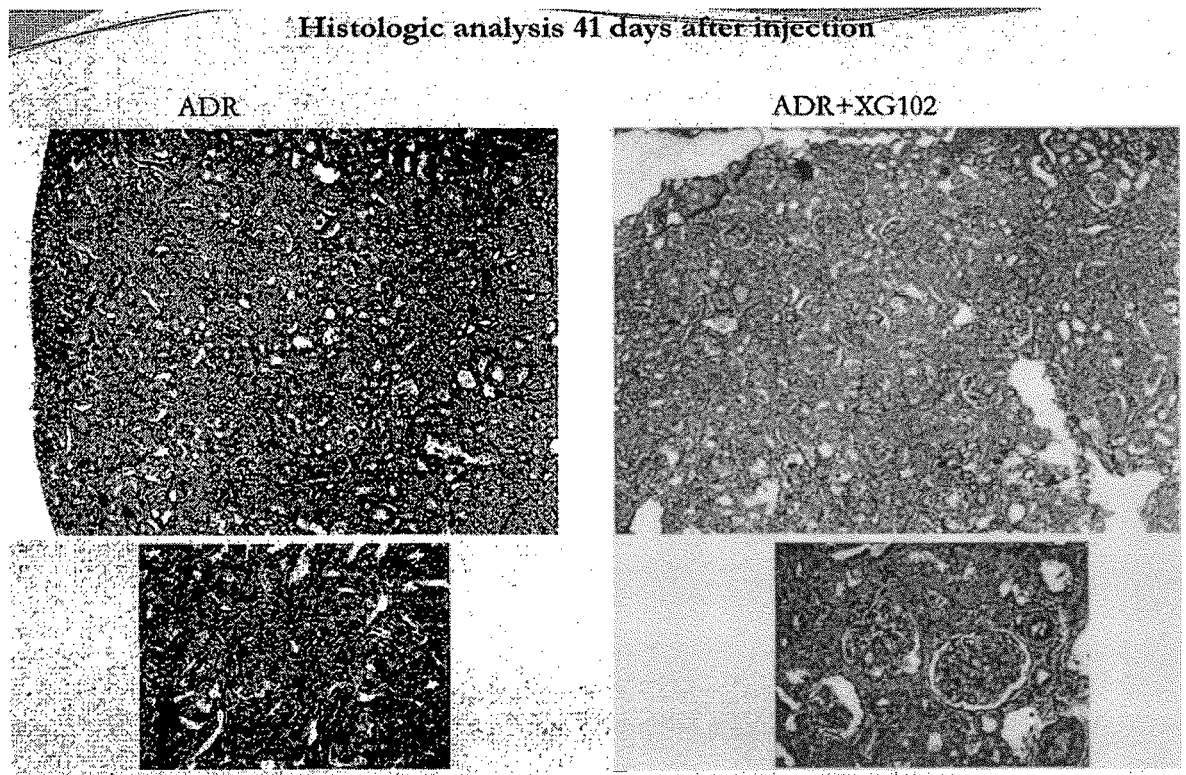
FIG. 45 Histological analysis 41 days after the onset of the experiment. Comparison of adriamycin treated rats of group 1 (left hand) and adriamycin and XG-102 treated rats of group 4 (right hand)

6/6 (100%) of the isolations resulted in OCR/DNA values above the cut-off and were successfully transplanted in NHPs (FIG. 38). This confirms that in this model even modest improvements in viability can have a profound impact on the transplantability of preparations. Based on the available data. XG-102 turned out to be an excellent agent to be used for clinical human or porcine islet isolations.

The porcine model is relevant for the following reasons: (1) The size of the porcine pancreas is closer to that of a human pancreas than a rat or canine pancreas; (2) Porcine islets are considered a viable option for future clinical islet xenotransplantation—therefore improvements in porcine islet isolation, which are critically needed can ultimately be clinically relevant.

Human pancreata for clinical islet allo-transplantation originating from brain-dead donors are typically not subjected to WIT but have 8-12 hrs of CIT (time needed for transportation from the procurement hospital to the isolation lab).

Human pancreata from non-heart beating donors are exposed to ~'15 min of WIT and are not currently utilized routinely) because of concerns about damage due to the WIT and they would also experience 8-12 hrs of CIT.

Organs removed from chronic pancreatitis patients for islet auto-transplantation may experience WIT and limited (1-2 hrs CIT). It is anticipated that improvements reported with the porcine model below would be even bigger in the clinical auto-transplant case because the pancreata from chronic pancreatitis patients are typically inflamed and already stressed. This is also expected to be true in the clinical allo-cases with prolonged cold ischemia time and it has been reported by other groups using different JNK inhibitors. JNK activation increases with CIT from the time of pancreas procurement; Blocking JNK activation with a JNK inhibitor improves islet yield, viability and transplant outcomes and that is most pronounced at the longest cold ischemia time tested.

Example 18: Efficacy of XG-102 (SEQ ID No. 11) in Reducing the Choroidal Neovascularization Using the Rat Argon Laser-Induced Choroidal Neovascularization Model The aim of this example was to determine whether two intravitreous administrations of XG-102 at two doses resulted in a decrease of choroidal neovascularization in a rat model of laser-induced choroidal neovascularization (ChNV). That model allows to make predictions on the potential use of a test compound for the treatment of age-related macular degeneration.

Forty (40) (+10 reserve) pigmented Brown Norway rats were divided into five (5) groups of eight (8) animals each. Choroidal neovascularization was induced using a 532 nm argon laser photocoagulator (six (6) 75 µm-sized spots at 150 mW for 100 ms) in the right eyes. Test, reference and control items were administered by intravitreous injection on Days 0 (just after induction) and 7. Angiography was performed 10 min after fluorescein (tracer) subcutaneous injection, on Days 14 and 21 after induction on treated and untreated animals.

After sacrifice on Day 23, the right treated eye from all animals was sampled and the choroid was flat mounted. On sponsor's request, no quantification of the volume of the ChNV was performed.

Experimental Set-Up:
XG-102: 3 000 µg/ml (equivalent to 15 µg/eye) and 300 µg/ml (equivalent to 1.5 µg/eye). Kenacort® Retard (4% triamcinolone acetonide) as control reference. Control Vehicle: Saline (0.9% NaCl).

Animals
Species: Rat. This is the species most commonly used in this experimental model
Strain: Brown Norway (pigmented).
Age: Approximately 8 weeks.
Weight: 175-200 g (on ordering).
Number/sex: 50 males (study 40; reserve 10).
Breeder: "HARLAN FRANCE"—FR-03800 GANNAT.

Study Design
Forty (40) (+ten (10) reserve) pigmented rats from the Brown Norway strain were divided into five (5) groups of eight (8) (+2 reserve) animals. Choroidal neovascularization was induced using a 532 nm argon laser photocoagulator (six (6) 75 µm-sized spots at 150 mW for 100 ms) in the right eyes.

Test item (two doses, groups 1-2), vehicle and reference (5 µl) were administered by intravitreous injection in right eyes at Day 0 (after induction of neovascularization under the same anesthesia) and Day 7. Fundus neovessels were evaluated on Days 14 and 21 using Heidelberg's Retinal Angiography (HRA) in right eyes for treated and untreated animals.

The table below summarizes the allocation of animals in treatment groups:

| Group No. | Treatment | Dose | Route of Administration | Number of animals |
|---|---|---|---|---|
| 1 | XG-102 | 3 000 µg/ml | IVT (5 µl in right eye at Day 0 and Day 7) | 14, 17, 38, 26, 28, 31, 23, S8 |
| 2 | | 300 µg/ml | | 24, 40, 19, 21, S5, 6, 39, 18 |
| 3 | Saline | — | | 37, 12, 22, S3, 4, 3, 33, 35 |
| 4 | Kenacort® Retard | 4% triamcinolone acetonide | | 10, 3, 15, S1, 32, 8, 16, 9 |
| 5 | Untreated | — | — | 29, 7, 20, 36, S9, 27, 1, 11 |

Selection of the Animals
Forty (40)+ten (10) reserve animals were involved in this study. Only animals with no visible sign of ocular defect were selected. Then, the allocation in the treatment groups was done by a random function in Excel® software. Fifty (50) animals were induced and followed. The random allocation in the treatment groups determined the eight animals and the reserve animals per group. These latter animals were included in the calculations of results only if one or two animals normally involved died, had impact on lens during administration procedure or a corneal opacity (due to repetitive anesthesia).

Induction of Neovascularization
On Day 0, animals were anesthetized by an intramuscular injection of a mix xylazine/ketamine. Pupils from the right eyes were dilated by instillation of one drop of 0.5% tropicamide. Then, six (6) choroidal burns (75 µm spot size) were done through a slit lamp, with a contact lens, around the optic disc, between the main vessel branches using an argon laser photocoagulator (532 nm; 150 mW; 100 ms). Production of a bubble at the time of laser treatment confirmed the rupture of Bruch's membrane.

Route and Method of Administration
Animals were anesthetized by intramuscular injection of a mix xylazine/ketamine. Test item, reference and vehicle (5 µl) were intravitreously injected in the right eyes dose regimen was on Day 0 and Day 7. The injection was performed under an operating microscope.

The intravitreal injections scheduled on Day 0 were done following the induction of neovascularization, under the same anesthesia.

The intravitreal injection was located in the supratemporal area at pars plana and performed using a 30G-needle mounted on a 10 µl Hamilton. The filled syringe was then mounted into the UltraMicroPump III to achieve accurate injection in microliter range.

Body Weights
The body weight of all animals was recorded before the start of study then once a week. The animal body weights, recorded before induction and treatment (baseline), then on Days 7, 14 and 21 were all within a normal range at the baseline: 180.6±12.3 g (mean±SD, n=40). At Day 21, no relevant difference between test item, vehicle and untreated groups was observed. The animals gained: +53 g (+29%) and +62 g (+34%) for XG-102 at 300 µg/ml and 3000 µg/ml, respectively, versus +56 g (+31%) and +59 g (+34%) for the vehicle group and untreated group, respectively.

Animals treated with Kenacort® retard gained +21 g (+12%) between the baseline and Day 21 after induction.

Fluorescein Angiography
Fluorescein angiography was performed on Days 14 and 21 using an HRA. After anesthesia by an intramuscular injection of a mix xylazine/ketamine and pupillary dilation, 250 µl/100 g (body weight) of a 10% sodium fluorescein was injected subcutaneously using a 26G insulin syringe, and fluorescein photos were recorded 10 minutes after dye injection.

This study was carried out on forty (40) Brown Norway rats. Argon laser was used to induce ChNV in the right eyes. The development of ChNV was evaluated by fluorescein angiography (FA). Treatments (test, reference and control items) were made by intravitreous administration on Days 0 and 7 after induction. Angiography was performed 10 min after fluorescein (tracer) injection, on Days 14 and 21 after induction. The grading was based on the highest intensity of fluorescein in each lesion and it was not determined by the size of the leakage area.

Results were expressed as the group mean score per time-point and by incidence of the number of spots at a given intensity score for each treatment and at each of both time-points. The Mann and Whitney test was used to determine if there was a statistically significant difference in the FA score between treated and control group. The statistical significance was attributed when $p<0.05$ was obtained with Mann and Whitney-U test.

FIG. 39 A shows the intensity of fluorescein leakage (mean score±SD). and FIG. 39 B illustrates the proportion of leaking spots in test item-treated eyes at both time-points. FIGS. 39 C and 39 D illustrate the percentage of leaking spots (score >0) and of maximum leaking spot (score of 3) respectively Evaluation by Fluorescein Angiography The leakage of fluorescein on the angiograms was evaluated by two examiners in a masked fashion and graded as follows: Score 0, no leakage; Score 1, slightly stained; Score 2, moderate stained; Score 3, strongly stained. If the two scores assigned to a particular lesion did not coincide, the higher score was used for analysis.

Evaluation with Isolectin $B_4$ of ChNV by Labelling on Flat Mount Preparation (Quantification in Option)

On Day 23, after euthanasia by an i.p. injection of Dolethal®, the treated right eyes were harvested and fixed 4% paraformaldehyde solution 1 hour at room temperature. After washing, retina, choroid and sclera were dissected. The retina was carefully peeled. The sclera-choroid was flat mounted and incubated after blocking with FITC-isolectin $B_4$[1] antibody.

Statistical Analyses

Group mean values and standard deviation were calculated for all parameters. To assess the statistical significance of differences between the various concentration of the test item and the vehicle, a Mann and Whitney U test was used.

Results (1) Reference Compound Kenacort Vs Vehicle and Untreated Groups

The following table summarizes the results of FA at 10 min on Days 14 and 21 (n=8 animals per group, right eyes)

At Day 14, 90% of the spots were leaking in the untreated right eyes indicating the formation of ChNV. The mean score was 2.1±1.0 (n=48). At Day 21, the untreated animals showed 96% of leaking spots and mean score at 2.1±0.9 (n=48) indicating the persistence of the ChNV.

At Day 14, 100% of the spots were leaking in vehicle treated eyes with a mean score of 2.9±0.5 (n=48) indicating the formation and the severity of the ChNV. By Day 21, no relevant change in the incidence of leaking spots with 94% of the spots that were leaking and a mean score of 2.2±1.0 (n=48), indicating the persistance of the ChNV.

Scoring of FA revealed that Kenacort® retard following two intravitreal administrations at Days 0 and 7 significantly reduced the fluorescein leakage by 97% ($p<0.001$, Mann & Whitney-U test) compared to the vehicle at Day 14 as shown by a mean score of 0.1±0.3 (n=46) vs 2.9±0.5 for vehicle group.

The incidence of the leaking spots were reduced in Kenacort® retard group with 13% of the leaking spots compared to the vehicle-treated animals which showed 100% of the leaking spots at Day 14.

By Day 21, animals treated twice with Kenacort® retard showed a relevant reduction by 86% of the vascular leakage compared to vehicle-treated animals ($p<0.001$, Mann & Whitney test) as shown by a mean score of 0.3±0.5 (n=45) vs 2.2±1.0, respectively.

The proportion of leaking spots compared to vehicle group at Day 21 was unchanged as shown by 31% of leaking spots for Kenacort® retard versus 94% for vehicle.

(2) XG-102-Treated Groups Vs Vehicle Group

The following table summarizes the results of FA at 10 min on Days 14 and 21 (n=8 animals per group, right eyes).

| | | | Mean score of fluorescein leakage | | Incidence | | | |
|---|---|---|---|---|---|---|---|---|
| | | | | % of reduction | (% spots with score x) | | | |
| Treatment | Dose | Time-point | Mean ± SD | vs Vehicle | Score 0 | Score 1 | Score 2 | Score 3 |
| Untreated | — | Day 14 | 2.1 ± 1.0 (n = 48) | — | 10 | 19 | 25 | 46 |
| | | Day 21 | 2.1 ± 0.9 (n = 48) | — | 4 | 21 | 38 | 38 |
| Vehicle (NaCl) IVT D 0, D 7 | 0.9% | Day 14 | 2.9 ± 0.5 (n = 48) | — | 0 | 4 | 6 | 90 |
| | | Day 21 | 2.2 ± 1.0 (n = 48) | — | 6 | 21 | 23 | 50 |
| Kenacort ® retard (triamcinolone acetonide) IVT D 0, D 7 | 4% | Day 14 | 0.1 ± 0.3 (n = 46) | 97% ($p < 0.001$) | 87 | 13 | 0 | 0 |
| | | Day 21 | 0.3 ± 0.5 (n = 45) | 86% ($p < 0.001$) | 69 | 31 | 0 | 0 |

Please note that numerical data may have been rounded for presentation, therefore, manual recalculation may result in slightly different values.

| Treatment | Dose | Time-point | Mean score of fluorescein leakage Mean ± SD | % of reduction vs Vehicle | Incidence (% spots with score x) Score 0 | Score 1 | Score 2 | Score 3 |
|---|---|---|---|---|---|---|---|---|
| XG-102 IVT D 0, D 7 | 300 µg/ml | Day 14 | 2.4 ± 0.9 (n = 44) | 17% (p < 0.05) | 1 | 9 | 18 | 66 |
|  |  | Day 21 | 2.4 ± 0.8 (n = 44) | −9% | 5 | 9 | 32 | 55 |
|  | 3000 µg/ml | Day 14 | 1.7 ± 0.7 (n = 43) | 41% (p < 0.001) | 0 | 44 | 44 | 12 |
|  |  | Day 21 | 2.3 ± 0.7 (n = 43) | −5% | 0 | 14 | 47 | 40 |
| Vehicle NaCl IVT D 0, D 7 | 0.9% | Day 14 | 2.9 ± 0.5 (n = 48) | — | 0 | 4 | 6 | 90 |
|  |  | Day 21 | 2.2 ± 1.0 (n = 48) | — | 6 | 21 | 23 | 50 |

Please note that numerical data may have been rounded for presentation, therefore, manual recalculation may result in slightly different values.

A summary of the results is provided in FIG. 39.

The general behaviour of animals was not altered following intravitreous administrations of XG-102 at both doses. No relevant complications were found during the clinical follow-up. The animal body weight increased during the study period: +53 g (+29%) and +62 g (+34%) for XG-102 at 300 µg/ml and 3000 µg/ml, respectively, versus +56 g (+31%) and +59 g (+34%) for the vehicle group and untreated group, respectively. Animals treated with Kenacort® showed a weight gain of 21 g (+12%).

In the vehicle group, the induced eyes showed consistent fluorescein leakage 14 and 21 Days after laser injury. The mean fluorescein leakage was 2.9±0.5 (n=48 impacts) at Day 14 with 100% of leaking spot indicating the formation and the severity of the ChNV. At Day 21, formation of the ChNV remained consistent with 94% of the leaking spots and a mean fluorescein leakage of 2.2±1.0 (n=48 impacts).

Two intravitreous administrations at Days 0 and 7 of Kenacort® (200 µg/administration) inhibited the incidence of ChNV formation at Days 14 and 21 after induction with a mean score of 0.1±0.3 (p<0.001) and 0.3±0.5 (p<0.001) for Kenacort® retard versus 2.9±0.5 and 2.2±1.0 for vehicle, on Days 14 and 21, respectively. On day 14, 13% of the lesions showed leakage in the reference-treated group while 100% showed leakage in vehicle group. By Day 21, the incidence of the leaking spots remained reduced with Kenacort® retard (31%) in comparison to vehicle (94%).

Animals treated with XG-102 at 300 µg/mL and 3000 µg/mL showed a significant reduction of the vascular leakage at Day 14 by 17% (p<0.05) with a mean score of 2.4±0.9 for low dose, and by 41% (p<0.001) with a mean score of 1.7±0.7 for high dose of XG-102, compared to vehicle. At Day 21, XG-102 at both doses did not show a relevant reduction of the vascular leakage compared to vehicle.

A reduction of the proportion of spots with a score 3 was recorded for 300 µg/ml and 3000 µg/ml XG-102 groups on Day 14 as shown by 66% and 12% of score 3 for low and high XG-102 concentration respectively, compared to 90% of spots scored by 3 for vehicle group.

Using anatomic and functional metrics of measuring ChNV and under the given experimental conditions, XG-102 intravitreously administered at 300 and 3000 µg/ml inhibited the vascular leakage 7 days (Day 14 of the study) after the last administration.

Example 19: Effects of XG-102 on Adriamycin-Induced Nephropathy

The object of that example was to study the effects of XG-102 on inflammatory kidney disease, nephropathy.

Adriamycin treatment induces glomerular disease in rat and mice mimicking human focal segmental and glomerular sclerosis (FSGS). In this model, tubular and interstitial inflammatory lesions occur during the disease course, partly due to heavy proteinuria. In the absence of therapy, kidney disease progresses to terminal renal failure within eight weeks. Podocyte injury is one of the initial steps in the sequences leading to glomerulosclerosis. The aim of the study was to investigate whether XG-102 could prevent the development of renal lesions and the renal failure.

XG-102 (control NaCl 0.9%) were administered to rats i.v. In total 50 rats were treated, whereby 3 groups (of 10 rats) received XG-102 (low dose (20 µg/kg), medium dose (200 µg/kg) and high dose (2000 µg/kg). All of these three groups (and the placebo group) were treated with 10 mg/kg Adriamycin on day 0. A fifth group of 10 animals did not receive any adriamycin and was treated by the NaCl control. Histological preparations were provided at day 8, 14, 29 and 41.

Figure 46:
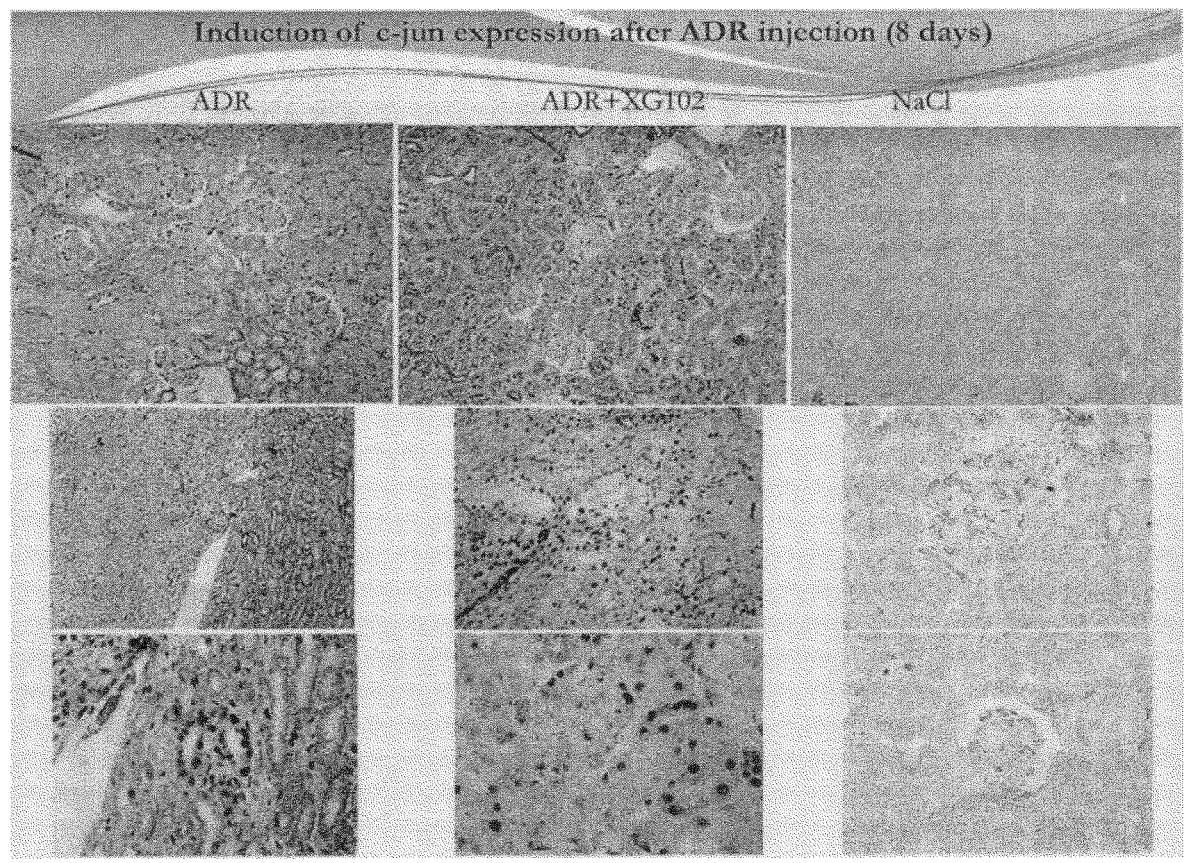
FIG. 46 Histological analysis (staining) of c-jun expression 8 days after onset of the experiment. Left hand Adriamycin treated histological preparation, in the middle: Adriamycin and XG-102 treated (resulting in a significant reduction of c-jun expression in the interstitium) and control on the right.
Figure 47:
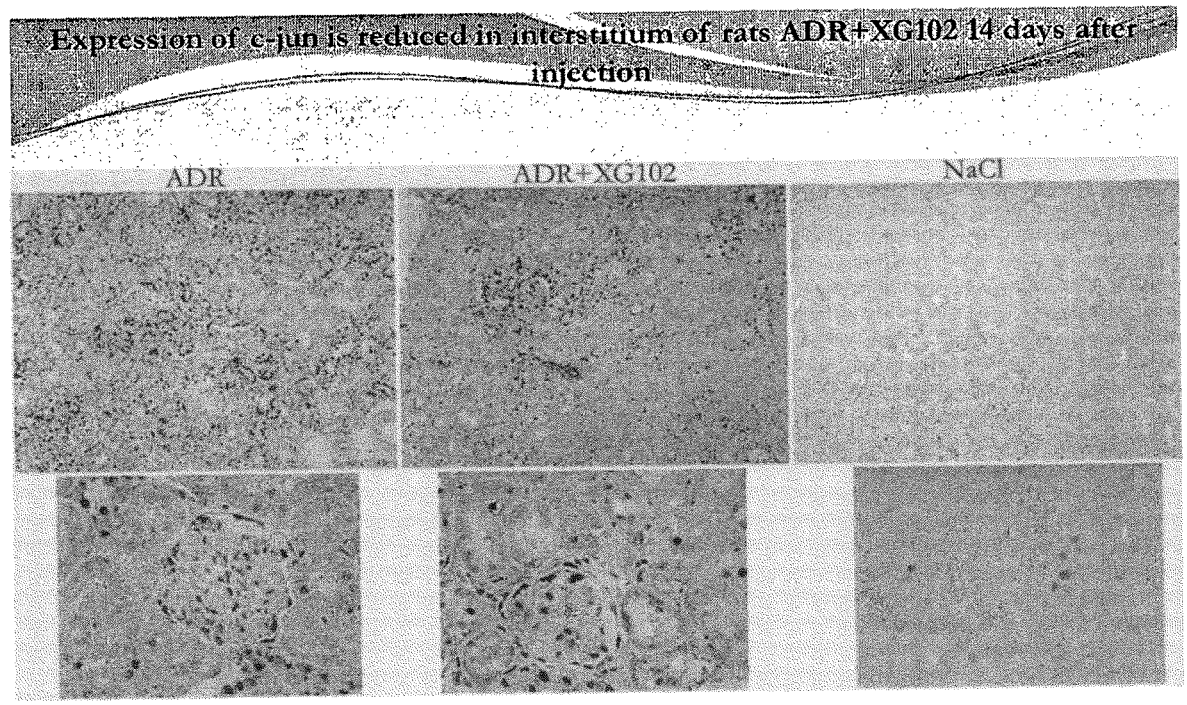
FIG. 47 Histological analysis (staining) of c-jun expression 14 days after onset of the experiment. Left hand Adriamycin treated histological preparation, in the middle: Adriamycin and XG-102 treated (resulting in a significant reduction of c-jun expression in the interstitium) and control on the right.

These histological preparations clearly indicated that XG-102 has—over the entire observation period—a significantly positive effect on adriamycin-induced nephropathy. The nephrological tissue is significantly rescued from cell loss, see FIGS. 42 to 45). The effect on c-jun expression without treatment by XG-102 or with treatment by XG-102 is provided in FIGS. 46 and 47, respectively.

In a further study 40 male Sprague-Dawley rats (Charles River) were used (divided into 4 groups of ten rats). Nephropathy has been induced by a single intravenous injection of Adriamycin 10 mg/kg on Day 0. XG-102 (SEQ ID NO: 11; 2 mg/kg; in NaCl 0.9%) was administered intravenously in the tail vein on Day 0. The administration volume has been 0.2 ml.

The table below summarizes the random allocation:

| Group N° | ADR (Day 0) | Treatment (Day 0) | Dose volume/ Route of administration | Dose concentration | Number of animals |
|---|---|---|---|---|---|
| 1 | 10 mg/kg | NaCl 0.9% | 0.2 ml, IV | 0 | 10 |
| 2 | 10 mg/kg | XG-102 2 mg/kg | 0.2 ml, IV | 1 mg/ml | 10 |
| 3 | NaCl 0.9% | NaCl 0.9% | 0.2 ml, IV | 0 | 10 |
| 4 | NaCl 0.9% | XG-102 2 mg/kg | 0.2 ml, IV | 1 mg/ml | 10 |

Each day, the general behavior and the appearance of all animals were observed. The health of the animals was monitored (moribund animals, abnormal important loss of weight, major intolerance of the substance, etc. . . . ). No rats were removed.

Blood was collected from the tail vein at Days 7, 14, 28, 42 and 56 from 4 rats per group. Serum creatinine concentrations, blood urea and protidemia were measured using appropriate kits from Advia Chemistry 1650 (Bayer Healthcare AG, Leverkusen, Germany). Two rats per group were sacrificed on Days 7, 14, 28, 42 and 56 after anesthesia. After animal sacrifice, both kidneys were collected. For histopathological examination fixed tissue specimens were dehydrated in graded alcohol solutions, cleared in toluene, and embedded in paraffin. Sections (4 µm) were stained with periodic acid-Schiff (PAS), and Masson's trichrome staining was performed to detect collagen deposition. Glomerular and tubulointerstitial sclerosis were quantified under microscope.

Results were expressed in the form of individual and summarized data tables using Microsoft Excel® Software. Numerical results were expressed as mean±standard error of the mean (SEM). Due to the small number of animal tested, no statistical analyses was performed.

Effect of XG-102 on Renal Function During the Progression of the Disease:

Urea and creatinine serum levels were measured to study the renal function during the kidney disease course. Because creatinine interferes with the calorimetric dosage, only urea that is a fine indicator of renal function was analyzed. Whereas urea serum levels were remarkably stable in untreated rats (below 5 mmol/l), ADR induced progressive increase of urea levels, which sharply raised from Day 28 up to 25 mmol/l at Day 41, then 48 mmol/l at Day 56 reflecting terminal renal failure (FIG. 38 B). On the other hand, XG-102-treated rats exhibited an urea serum level below 10 mmol/l throughout the course of the disease (FIG. 48 B). On the other hand, XG-102-treated rats exhibited an urea serum level below 10 mmol/l throughout the course of the disease (FIG. 48 B). The renal function of rats treated with XG-102 alone was similar to 0.9% NaCl-treated rats. These results suggest that XG-102 prevents the progression to renal disease and renal failure.

Figure 49:
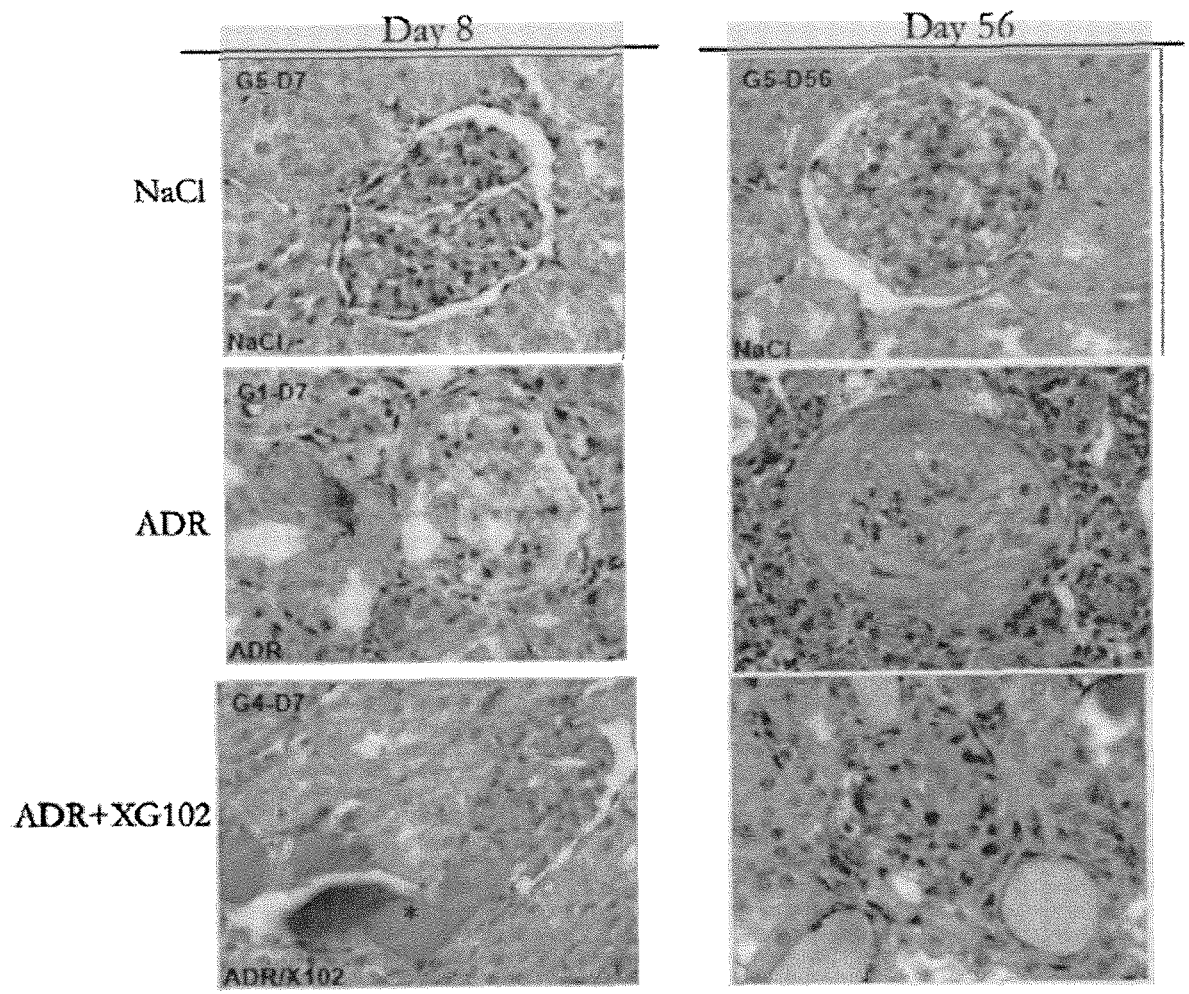
FIG. 49 shows kidney sections of the rats in the Adriamycin (ADR)-induced nephropathy model stained with periodic acid-Schiff (PAS) (original magnification ×40). For the sections shown in the left column, rats were sacrificed at Day 8 following ADR administration, whereas for the sections shown in the left column, rats were sacrificed at Day 56. ADR has been administered only to the groups "ADR" and "ADR+XG102", whereas the group "NaCl" received 0.9% NaCL only. The group "ADR+XG102" has been treated on Day 0 with XG-102, whereas the other groups ("ADR" and "NaCl") received vehicle (0.9% NaCl).
Figure 50:
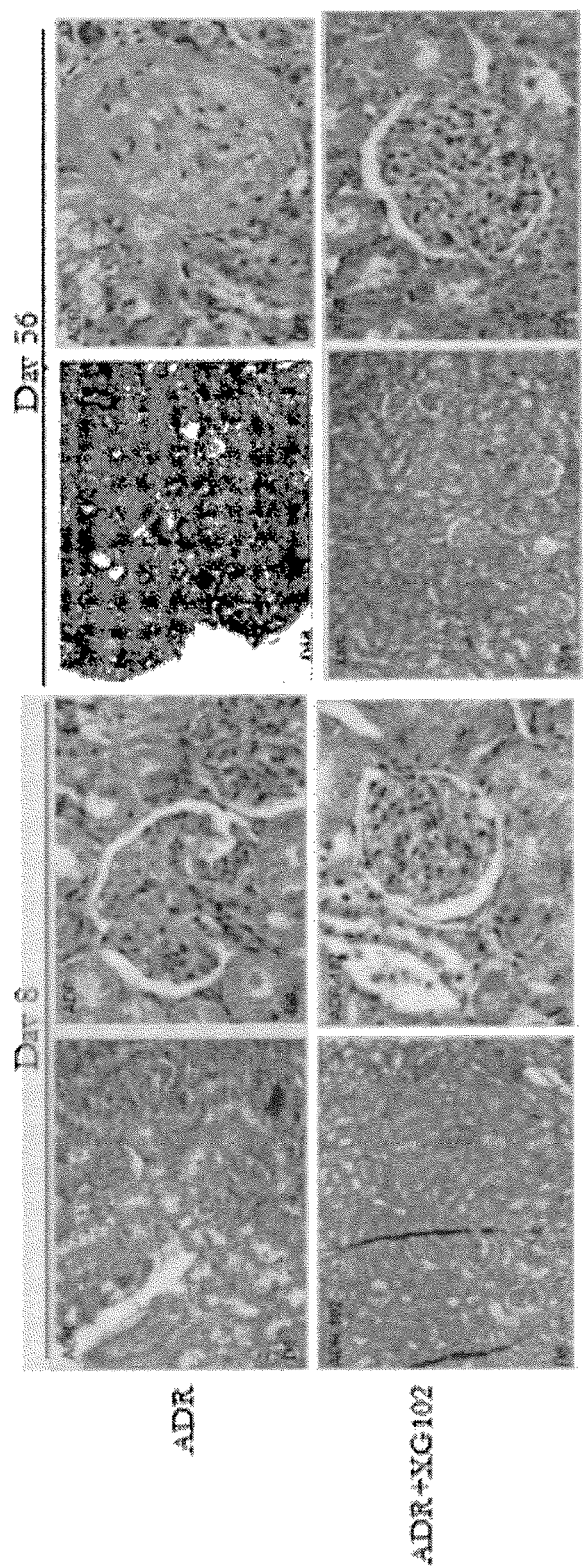
FIG. 50 shows the kidney fibrosis in ADR nephropathy evaluated with Masson's trichrome (blue) on Days 8 (left four panels) and 56 (right four panels) following ADR administration for the group "ADR" (upper panel), which has been treated with ADR and vehicle at Day 0 and for the group "ADR+XG102" (lower panel), which has been treated with ADR and XG-102 at Day 0. The original magnification ×10 is depicted in the left panels for the respective day and the original magnification ×40 is depicted in the right panels for the respective day.

Histopathological Findings (PAS and Masson Trichrome Staining):

ADR-induced structural changes were evaluated under light microscope. Saline-treated control rats showed morphologically normal glomeruli and tubules. On Day 8, light microscopic examination showed some areas with focal segmental glomerulosclerosis and proteinaceous casts in the ADR nephrosis group. In contrast, although some tubules were filled with proteins in XG-102-treated rats, glomeruli exhibited a normal architecture with absence or discrete mesangial hypercellularity, while the tubular structures and interstitium did not display pathological changes (FIG. 49). By Day 14, ADR treated rats exhibited progressive glomerulosclerosis, hyaline deposits, tubular dilation and cast formation. The degree of glomerulosclerosis was dramatically worsened in this group and became diffuse with obvious adhesion between the glomerular tufts and the Bowman's space in most glomeruli by Day 29 and 41, associated with severe tubular atrophy and interstitial fibrosis. At Day 56, diffuse glomerular sclerosis was observed in all glomeruli (FIG. 50). However, XG-102-treated rats had a relatively normal appearance at Day 8, and develop few focal and segmental glomerulosclerosis and tubulointerstitial fibrosis at Day 56 compared with ADR-treated rats. Altogether, these results strongly suggest that XG-102 prevents the development of glomerular and tubulointerstitial fibrosis and may explain the preservation of renal function in this group.

The study results provide evidence that XG-102 prevents the progression of glomerular and tubulointerstitial injuries induced by ADR. Moreover, this molecule preserves renal function.

Example 20: Effects of XG-102 on Puromycine Aminonucleoside (PAN)-Induced Nephropathy The aim of this study was to evaluate the effects of XG-102 on chronic puromycine aminonucleoside-induced nephropathy in rats during 56 days. Puromycin aminonucleoside (PAN) is a podocyte toxin inducing a loss and fusion of podocytes foot processes. PAN-induced nephropathy is a well-described model of human idiopathic nephritic syndrome and focal segmental glomerulosclerosis (Pippin J W, 2008). The glomerular morphologic changes seen in rats with PAN nephrosis closely resemble those in human minimal change disease (MCD) and focal segmental glomerulosclerosis (FSGS). Intraperitoneal administration of PAN in rats results in a rapid development of nephritic syndrome, characterized by proteinuria, hypoalbuminemia and hypercholesterolemia (acute phase). This is a well-established animal model of human MCD. The pathological lesions of focal segmental glomerulosclerosis have been observed in chronic PAN nephrosis induced by repeated intraperitoneal PAN injections (Nakajima, T., Kanozawa, K., & Mitarai, T. (2010). Effects of edaravone against glomerular injury in rats with chronic puromycin aminonucleoside nephrosis. *J Saitama medical university*, 37(1)). In accordance with the mechanism of injury, PAN causes direct DNA damage via the production of reactive oxygen species (ROS) and tissue damages, including glomerulosclerosis and interstitial fibrosis (Hewitson T D, 2012) in the chronic phase.

In this experiment 90 male Wistar rats (Charles River, France) were used (divided into 6 groups of 15 rats). To induce nephropathy puromycin aminonucleoside (PAN) was intraperitoneally administered at the dose of 130 mg/kg (5 ml/kg) at day 0 and at the dose of 60 mg/kg (5 ml/kg) at day 14 (Nakajima, T., Kanozawa, K., & Mitarai, T. (2010). Effects of edaravone against glomerular injury in rats with chronic puromycin aminonucleoside nephrosis. *J Saitama medical university*, 37(1)). Control rats (Group 1) received an equal amount of saline i.p at day 0 and at day 14. XG-102 or its vehicle (NaCl 0.9%) were administered into the tail vein (i.v.) once a week (Groups 1 to 5) starting from first PAN injection at day 0 for a total of 7 injections at day 0, 7, 14, 21, 28, 35 and 42. In a separate experimental group (Group 6), XG-102 was administered into the tail vein (i.v.) once a week starting from day 21 for a total of 4 injections at day 21, 28, 35 and 42 after PAN injection at day 0.

For XG-102 administration XG-102 powder has been dissolved in the vehicle NaCl 0.9% at the highest concentration to be tested. The highest concentration then represented the stock solution for the lower concentrations. Each stock solution has been filter (0.2 µm) sterilized. The lower concentration solutions to be administered were prepared by diluting the filtered stock solution in saline (0.9% NaCl) depending on the volume for i.v. injection.

The table below summarizes the experimental groups:

| Group | PAN (i.p.) | Treatment (i.v.) | Number of i.v. administrations | Number of animals/group |
|---|---|---|---|---|
| 1 | no | vehicle | 7 | 15 |
| 2 | yes | vehicle | 7 | 15 |
| 3 | yes | XG-102 (1 mg/kg) | 7 | 15 |
| 4 | yes | XG-102 (2 mg/kg) | 7 | 15 |
| 5 | yes | XG-102 (4 mg/kg) | 7 | 15 |
| 6 | yes | XG-102 (4 mg/kg) | 4 | 15 |

Figure 51:
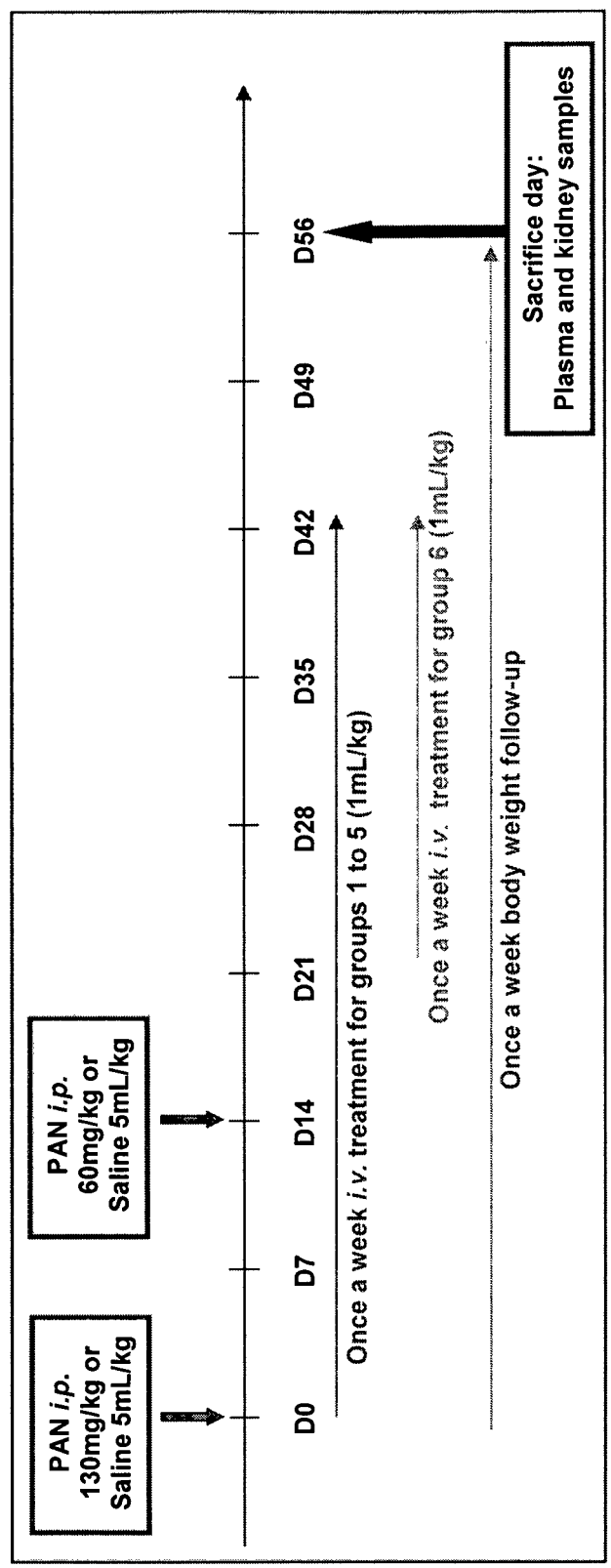
FIG. 51 The study design of the experiment investigating the effects of XG-102 on puromycine aminonucleoside (PAN)-induced nephropathy. On day 0 and day 14 PAN or its vehicle have been injected for induction of nephropathy. At day 0 and at day 14, PAN has been administered first, followed by XG-102 administration. From day 0 to day 42 XG-102 or its vehicle have been administered once a week by i.v. route as described above. On day 56 animals have been sacrificed and samples (blood and kidneys) have been collected.

The study design is shown in FIG. 51. Briefly, on day 0 and day 14 PAN or its vehicle (saline) have been injected for induction of nephropathy. At day 0 and at day 14, PAN has been administered first, followed by XG-102 administration. From day 0 to day 42 XG-102 or its vehicle (NaCl 0.9%) have been administered once a week by i.v. route as described above.

Animals were weighted once a week. All PAN-treated animals showed a decrease of body weight. However, all PAN-treated animals were homogeneous for body weight, i.e. no effects of XG-102 were observed compared to PAN/saline group (Group 2) on body weight.

On day 56 animals have been sacrificed and samples (blood and kidneys) have been collected. In particular, for blood and kidney sampling animals have been anesthetized by injection of pentobarbital (60 mg/kg; Ceva Sante Animale; Libourne, France). Blood samples have been collected from abdominal vein, transferred into tubes for coagulation (EDTA 3K; 30 minutes, 4° C.) then centrifuged (10 minutes, 3000 rpm, 4° C.) for plasma collection. Plasma has been stored at −20° C. until use for creatinine and urea assays. Kidneys have been removed, cleaned from all connective tissue and capsule and weighted on an electronic microbalance (Mettler, Toledo). Kidney samples have been fixed in formalin solution 10% (Sigma Aldrich, France) for 24-72 h, in particular 48 h, then embedded in paraffin. Three sections (3 to 5 µm) were made per block. The slides were stained by hematoxylin/eosin (HE), PAS-methenamine silver and Sirius Red for histological evaluation of morphological alterations, glomerulosclerosis and interstitial fibrosis quantification, respectively. All the slides were digitalized at ×20 using Nanozoomer 2.0 HT from Hamamatsu (Japan). Histological preparation and imaging has been performed by Histalim (Montpellier, France). Plasma creatinine and urea have been quantified using an ABX Pentra 400 Clinical Chemistry analyzer (HORIBA) by the Phenotypage platform of Genotoul (Rangueil Hospital, Toulouse, France).

Results are expressed by semi-quantitative scoring following to expert histopathologist evaluation. For the histological examination of glomerulosclerosis glomerular changes have been evaluated using a semi quantitative scoring system as described by Nakajima, T., Kanozawa, K., & Mitarai, T. (2010). Effects of edaravone against glomerular injury in rats with chronic puromycin aminonucleoside nephrosis. *J Saitama medical university*, 37(1), which is hereby incorporated by reference. In brief, the degree of glomerular injury was assessed in 25 glomeruli per kidney section (2 sections per animal) for a total of 50 glomeruli per animal. Degree of injury in individual glomeruli was graded using a scale from 0 to 4, based on the percentage of glomerular involvement.
Score 0: normal,
Score 1: lesions in up to 25% of the glomerulus,
Score 2: lesions between 25-50% of the glomerulus,
Score 3: lesions between 50-75% of the glomerulus, and
Score 4: lesions between 75-100% of the glomerulus All data have been calculated as mean values±standard error of the mean (s.e.m.). Statistical analysis has been performed using GraphPad Prism, version 4 (GraphPad Software Inc., LaJolla, USA). The comparison of all the groups using two-way ANOVA followed by Bonferroni's post-test for body weight results. Comparison between group 1 (Saline/saline) and group 2 (PAN/saline) was performed using unpaired Student t-test. The effects of vehicle and XG-102 were compared using one way ANOVA followed by Newman-Keuls test. A $P<0.05$ value was accepted as statistical significance. Comparison between group 2 (PAN/vehicle) and group 6 (PAN/XG-102 4 mg/kg-4 iv) was performed using unpaired Student t-test.

Figure 52:
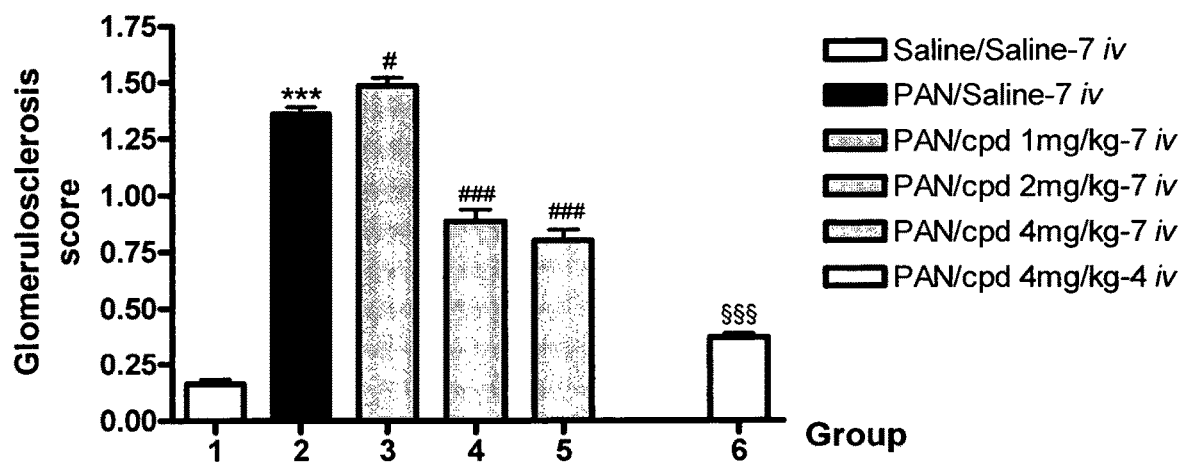
FIG. 52 shows the effects of XG-102 on the glomerulosclerosis injury in puromycine aminonucleoside (PAN)-induced nephropathy. XG-102 has been administered to Groups 3 to 6 (labelled as "cpd" in the legend). The Group 2 and the Group 6 are different in term of number of iv injections as stated in the study plan of Example 20. Note that the score for Group 2 is very similar to the one reported by Najakima et al. (2010) using the same experimental protocol. ***$P<0.001$ versus Group 1 using unpaired Student t-test; # $P<0.05$; ### $P<0.001$ versus Group 2 using one-way ANOVA followed by followed by Newman-Keuls test; § § § $P<0.001$ versus Group 2 using unpaired Student t-test.

The results of the glomerulosclerosis injury are shown in FIG. 52. One of the main objectives of this study was to evaluate the glomerulosclerosis injury in a well-established model of focal segmental glomerulosceloris (FSGS) induced by repeated puromycin aminonucleoside injections in rats. The results showed that 7 iv injections of XG-102 significantly reduced PAN-induced glomerulosclerosis in a dose dependent manner. However, the dose of 1 mg/kg had no effect on this pathological feature. 4 iv injections of XG-102 at the dose of 4 mg/kg, starting from day 21 resulted in a strong effect of XG-102 in reducing glomerulosclerosis induced by PAN (FIG. 52).

Figure 53:
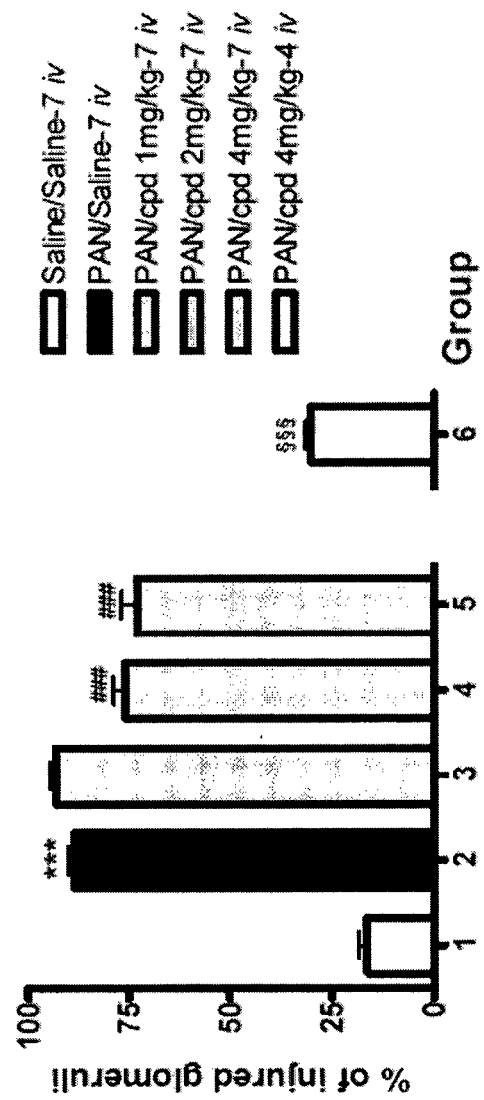
FIG. 53 shows the effects of XG-102 on the glomerular damage in puromycine aminonucleoside (PAN)-induced nephropathy. XG-102 has been administered to Groups 3 to 6 (labelled as "cpd" in the legend). The Group 2 and the Group 6 are different in term of number of iv injections as stated in the study plan of Example 20. ***$P<0.001$ versus Group 1 using unpaired Student t-test; ### $P<0.001$ versus Group 2 using one-way ANOVA followed by followed by Newman-Keuls test; § § § $P<0.001$ versus Group 2 using unpaired Student t-test.

The results of the glomerular damage are shown in FIG. 53. One of the main objective of this study was to evaluate the effect of XG-102 on the glomerular damage induced by repeated PAN injections in rats. The results showed that XG-102 has (i) a preventive effect in that 7 iv injections at the dose of 2 and 4 mg/kg significantly reduced PAN-induced glomerulosclerosis in term of severity of lesions (glomerular injury score) but also significantly decreased glomerular damage incidence (percentage of injured glomeruli) and that (ii) XG-102 has a curative effect in that 4 iv injections of XG-102 at the dose of 4 mg/kg, starting from day 21 post-PAN administration lead to a strong effect on glomerulosclerosis in term of both severity of lesions (glomerular injury score) and of glomerular damage incidence (percentage of injured glomeruli).

Example 21: Effects of Chronic Administration of XG-102 in a Rat Model of Diabetic Nephropathy The aim of this study has been to evaluate the effects of chronic administration of the JNK inhibitor peptide, XG-102 (1, 2, 4 mg/kg, weekly intravenous administration for 9 weeks), in a rat model of diabetic nephropathy. Losartan has been used as a positive control.

Seventy-four male Sprague-Dawley rats (200-250 g; including 4 spare animals) from Charles River (Margate, Kent) were used. Rats were housed in pairs in polypropylene cages with free access to a high fat diet (D12492 60% of kcal derived from fat) and tap water at all times. The diet has been purchased from Research Diets, New Jersey, USA. All animals have been maintained at 21±4° C. and 55±20% humidity on a normal light (lights on: 07:00-19:00).

Figure 54:
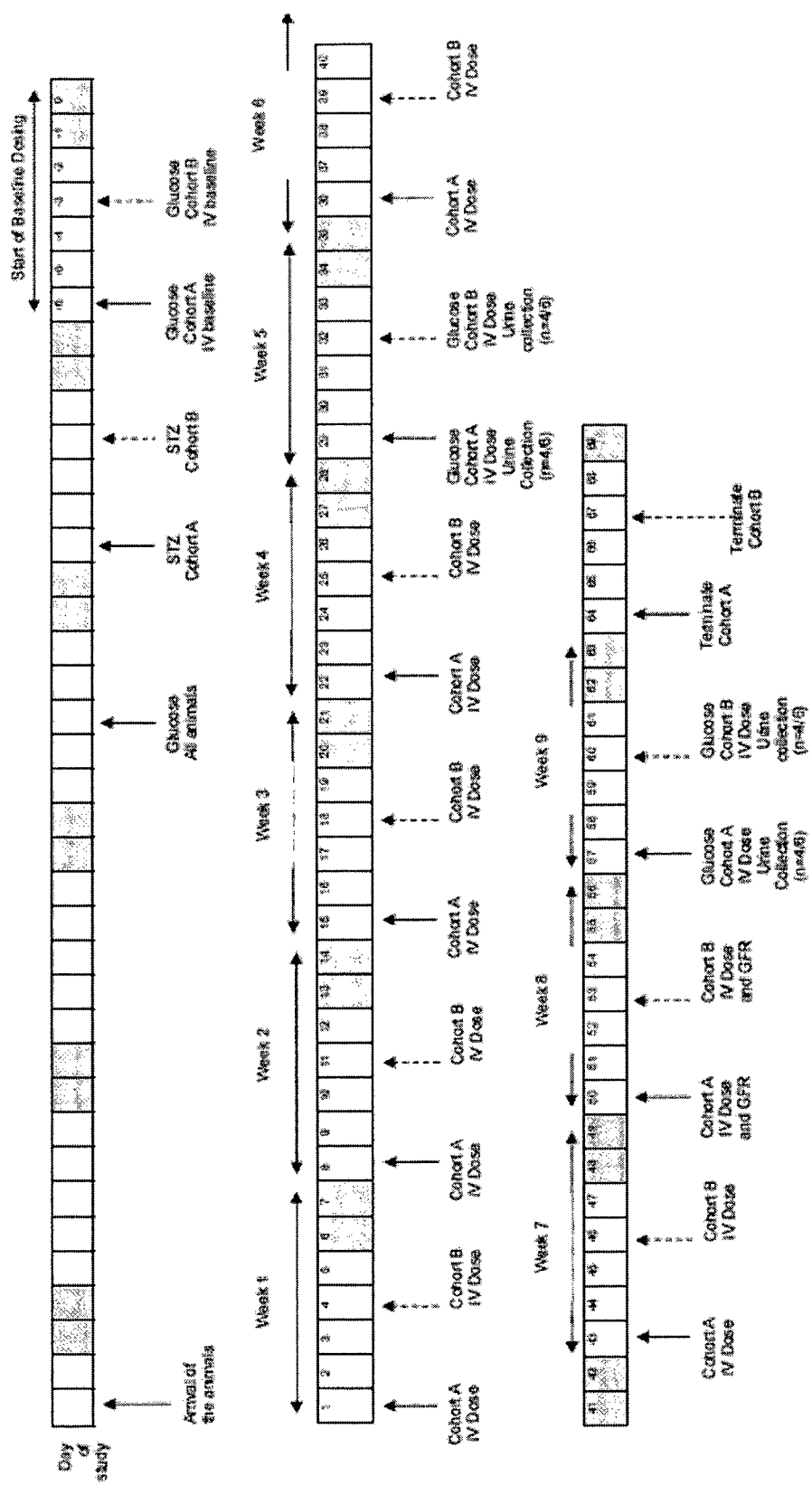
FIG. 54 shows the study schedule of Example 21 investigating the effects of chronic administration of XG-102 in a rat model of diabetic nephropathy. Animals were placed on high fat diet immediately after arrival. Animals in groups E and F are dosed daily each day from baseline phase onwards.

The study schedule is shown in FIG. 54. Animals have been housed in pairs throughout the study. For a 3-week period, during which time they have been weighed weekly (food and water will be weighed twice during the third week only (i.e. the week prior to STZ dosing on a Monday and a Thursday). During the third week of habituation, a blood sample has been taken from the lateral tail vein in the freely fed state using a hand-held glucose meter (One Touch Ultra 2). Blood sampling began at approximately 09:00.

Due to the size of the study, the animals have been run as two separate cohorts (each n=4 or 6 as far as possible due to paired housing) 72 hours out of phase (see FIG. 54). About 40 animals have been assigned to Cohort A and the remaining 30 to Cohort B, balanced as far as possible for body weight, plasma glucose and food and water intake. For induction of diabetes streptozotocin (STZ) has been used. Since the diabetic phenotype of animals dosed with STZ is highly dependent on the batch of STZ, a pilot study has been undertaken in order to confirm the optimal STZ dose (35 or 45 mg/kg ip). STZ or vehicle has been given after the animals have been maintained on the diet for approximately 3 weeks as detailed in FIG. 54. The spare animals will be dosed with STZ (one pair per cohort).

| Group | Dose (ip) | Cohort A | Cohort B |
|---|---|---|---|
| A | vehicle 0.05M citric acid pH 4.5 ip | 4 | 6 |
| B-G | STZ (selected from pilot) ip | 36 | 24 |

Each pair of animals has been administered the same treatment (i.e. both vehicle-treated or both will be STZ-treated). For the 7-day period post STZ dose, animals have been weighed daily and food and water intake determined twice weekly. For the remaining study duration, animals have been weighed and water and food intake assessed twice weekly (always on the day of intravenous dosing and typically on water refill day(s)). Subsequently, based on body weight and available food and water intake post STZ, animals have been allocated in groups B-F as detailed below in light of differences in dosing regimen.

| Group | Dose | Cohort A | Cohort B |
|---|---|---|---|
| B-E | IV dosing | 24 | 16 |
| F-G | PO dosing | 12 | 8 |

One week after STZ (or vehicle) treatment a blood sample has been taken from the lateral tail vein using a glucometer (One Touch Ultra2) in the freely fed state (blood samples taken beginning at approx. 09:00). Subsequently, animals in groups A-E have been dosed with vehicle by the intravenous route and animals in Groups F-G have been dosed with 1% methyl cellulose by the oral route. Animals in groups F-G continued to be dosed once daily beginning at approximately 09:00 each day. Animals have been weighed prior to dosing (this weight was recorded). Food and water have been recorded on the same days as the intravenous groups (A-E) only.

This baseline phase lasted for one week. Towards the end of the week animals have been allocated to drug treatments on the basis of blood glucose, and available body weight and food and water intake data. The allocation has been as detailed in the table below:

| Group | Group | STZ | Cohort A | Cohort B | Total N |
|---|---|---|---|---|---|
| A | Vehicle (saline) - NON-STZ | NO | 4 | 6 | 9-10 |
| B | Vehicle (saline iv weekly) | STZ | 6 | 4 | 9-10 |
| C | XG-102 (1 mg/kg iv weekly) | STZ | 6 | 4 | 9-10 |
| D | XG-102 (2 mg/kg iv weekly) | STZ | 6 | 4 | 9-10 |
| E | XG-102 (4 mg/kg iv weekly) | STZ | 6 | 4 | 9-10 |
| F | Vehicle (methyl cellulose po daily) | STZ | 6 | 4 | 9-10 |
| G | Losartan (25 mg/kg po daily) | STZ | 6 | 4 | 9-10 |

Dosing has been for 9 weeks in duration (9 administrations in total, see FIG. 54). Animals in groups F and G have been weighed and dosed daily at approximately 09:00. Animals in groups A-E have been dosed once weekly by the intravenous route (as detailed on FIG. 54). In all groups, food and water intake have been determined twice weekly (on the day of iv dosing and on water refill days. Blood glucose has been determined monthly. Samples were collected as detailed previously by glucometer (One Touch Ultra2). Blood samples have been taken in the freely fed state (beginning at approx. 09:00). Animals have been dosed immediately afterwards by the respective route to a timed schedule. Subsequent to dosing, each animal has been placed in a metabolism cage with free access to food and water for a 24 h period. To reduce evaporation, the glass urine collectors have been placed in a polystyrene container (Sca-online, UK) which was filled with ice. Due to the anticipated increase in daily urine volume with STZ, urine has been collected (and stored refrigerated) at intervals (e.g. 8 hourly) to ensure that twenty four hours total urine volume for each metabolic cage can be recorded. The aliquots at each time point have been pooled so that a single 24 h sample per animal is collected. Ten aliquots of 300 µl of pooled 24 h urine have been taken and frozen at −80° C. Creatinine, glucose, urea, total protein and electrolytes (Na, K, CI and Ca) have been determined on urine samples using a COBAS C111 and associated reagents (n=2 for all urine analyses). For urine collection sessions, the rats have been weighed at the time of placement in the cage and upon removal. Food consumed and water drunk has also been calculated. Blood glucose and urine parameters (creatinine, glucose, urea, total protein and electrolytes) have been determined again after a further month of dosing as previously described (see FIG. 54).

During week 8 of treatment (see FIG. 54) the glomerular filtration rate (GFR) of the animals has been assessed using the FITC-inulin method. This was performed based on the method of Stridh, S., Sallstrom, J. et al (2009): "C-Peptide Normalizes Glomerular Filtration Rate in Hyperfiltrating Conscious Diabetic Rats" *Oxygen Transport to tissue XXX. Advances in experimental medical and biology.* 645:219-25, which is hereby incorporated by reference. Specifically, FITC-inulin (1.5%) has been dissolved in saline and filtered through a 0.45 µm syringe filter. In order to remove residual free FITC, the solution has been dialysed in 2000 ml of saline at 4° C. overnight using a 1000 Da cut-off dialysis membrane (Spectra Por 6 from Fisher UK) and protected from light. The dialysed inulin has been filtered through a 0.22 µm syringe filter before use. Each animal has been dosed with 1 ml (15 mg) of FITC-inulin via the tail vein (i.e. intravenously). At 2, 5, 9, 15, 24, 35, 55, 80 minutes post dose a blood sample (80 µl) has been taken into a lithium-heparin collection tube (Sarstedt CB300LH). Each blood sample underwent centrifugation in a cooled centrifuge and the plasma sample dispensed into a clean aliquot vial for subsequent determination of fluorescence at 496 nm excitation and 520 nm emission.

At termination, animals and food and water have been weighed. Animals have then been killed and a terminal blood sample (approx. 4.5 mL in an EDTA-coated tube) has been taken via cardiac puncture). The blood sample has been spun in a cooled centrifuge and aliquots (5 aliquots of 0.5 mL) stored frozen (−80° C.). At necropsy, the left and right kidneys have been removed and weighed. Each kidney was cut sagittally into two halves and placed into a pot of 10% neutral buffered formalin to fix for approximately 5 days. The kidneys have then been wax embedded and one half from each kidney placed into each cassette to produce one wax block for subsequent processing (i.e. one block with one half right kidney and one half left kidney) The remaining kidney halves have been disposed of. For the wax blocks, all tissues have been prepared using a Tissue Tek VIP processor (using graded alcohols to dehydrate and xylene as a clearant). The blocks have then been impregnated with paraffin histo-wax prior to embedding in fresh histo-wax. Kidney tissues were sectioned at approximately 4-5 µm and stained using methods for Haematoxylin and Eosin (H&E) and periodic acid Schiff (PAS). Subsequently, slides will be sent for assessment by a pathologist (e.g. to Harlan Laboratories Ltd. UK). The pathologist evaluated all slides stained by H&E and PAS for glomerular sclerosis, tubule atrophy and interstitial expansion semi-quantitatively using a "+, ++, +++" system (or similar).

XG-102 has been dosed in the volume 1 ml/kg in commercially available sterile saline. To this end, XG-102 has been formulated prior to the first dosing by the addition of sterile saline, whereby the highest dose has been formulated (4 mg/ml) and the lower doses were prepared by dilution of this 4 mg/ml stock. Aliquots were then prepared for each dosing session and stored frozen (−80° C., stability 3 months at −80° C.) until use. On the morning of dosing each aliquot has been removed from the freezer and allowed to thaw at room temperature prior to dosing (e.g. 30 minutes). The thawed solution has been mixed by inversion prior to dosing. All dosing was completed as soon as possible after thawing but in all cases within 8 hours since the test item is stable in saline at room temperature at concentrations of 10 µg/ml-50 mg/ml for 8 hours. Sterile polypropylene plastics (including pipette tips) have been used. The stock solution will be filter sterilised (0.2 µm) prior to use and prior to dilution to lower doses. Losartan potassium has been purchased from a Chemical supplier (e.g. Tocris UK) and prepared for dosing each morning in a vehicle of 1% methyl cellulose at a volume of 5 ml/kg. Dosing factors have been applied where appropriate.

At the end of the study, body weights and weight of food and water bottles have been analysed. Results have been expressed as body weights, change in body weight per week for the first 4 weeks and per 4 weeks thereafter, and over the entire drug administration period, % reduction in body weight at the end of the study and drug treatment compared to the control group, food and water intakes, cumulative food intake and average food and water intakes per week for the first 4 weeks and per 4 weeks thereafter and over the duration of the feeding study. The effects of different treatments on body weight and food, cumulative food and water intake have been analysed by two-way analysis of covariance with treatment and cohort as factors and baseline (Day 1 body weight or the average food or water consumption from days −6 to 0) as the covariate, followed by appropriate multiple comparisons tests (two-tailed) to compare each group to the appropriate STZ vehicle group. Blood glucose has been analysed by general linear model with treatment and cohort as factors and baseline body weight, bleeding order and pre-study plasma level as covariates. Appropriate transformations and/or robust regression techniques may have been used to reduce the influence of outliers. Suitable multiple comparison tests (two-tailed) have been used to compare each group to the appropriate STZ vehicle group. Urine creatinine, glucose, urea, total protein and electrolytes have been expressed as treatment group means±SEM. Analysis has been by general linear model with treatment and cohort as factors. Appropriate transformations and/or robust regression techniques may have been used to reduce the influence of outliers. Suitable multiple comparison tests (two-tailed) have been used to compare each group to the appropriate STZ vehicle group. Kidney weights have been analysed by general linear model with treatment and cohort as factors and Day 1 body weight as a covariate. To determine effects in addition to effects caused by changes in body weight, analysis has been by general linear model with treatment and cohort as factors and terminal body weight as a covariate. A log transformation and/or robust regression techniques has been used if appropriate. Appropriate multiple comparison techniques has been used to compare each group to the appropriate STZ vehicle group. For the pathology assessment, each treatment has been compared to the appropriate STZ vehicle group by exact Wilcoxon rank sum tests.

GFR has been calculated as Dose of FITC inulin/$AUC_{0-\infty}$. The AUC (of FITC inulin concentration) has been calculated by the log-linear trapezoidal rule (Stridh) with extrapolation of the 2 to 5 min line to 0 min and linear regression of log-transformed data during a terminal phase from 24 to 80 min. Calculated GFR values were analysed by two-way analysis of variance with treatment and cohort as factors. A log transformation and/or robust regression techniques has been used if appropriate.

In all analyses except GFR, animals dosed iv have been analysed separately from animals dosed po, as dosing by different routes during the baseline week may affect the baseline values used as covariates. The non-STZ group has been excluded from all analyses described above. Separate analyses have been performed for comparisons to the non-STZ group, including all groups in the analysis, but using baseline covariates before treatment with STZ, rather than those during the week before dosing. In all analyses, a p value of less than 0.05 will be considered to be statistically significant.

Figure 55:
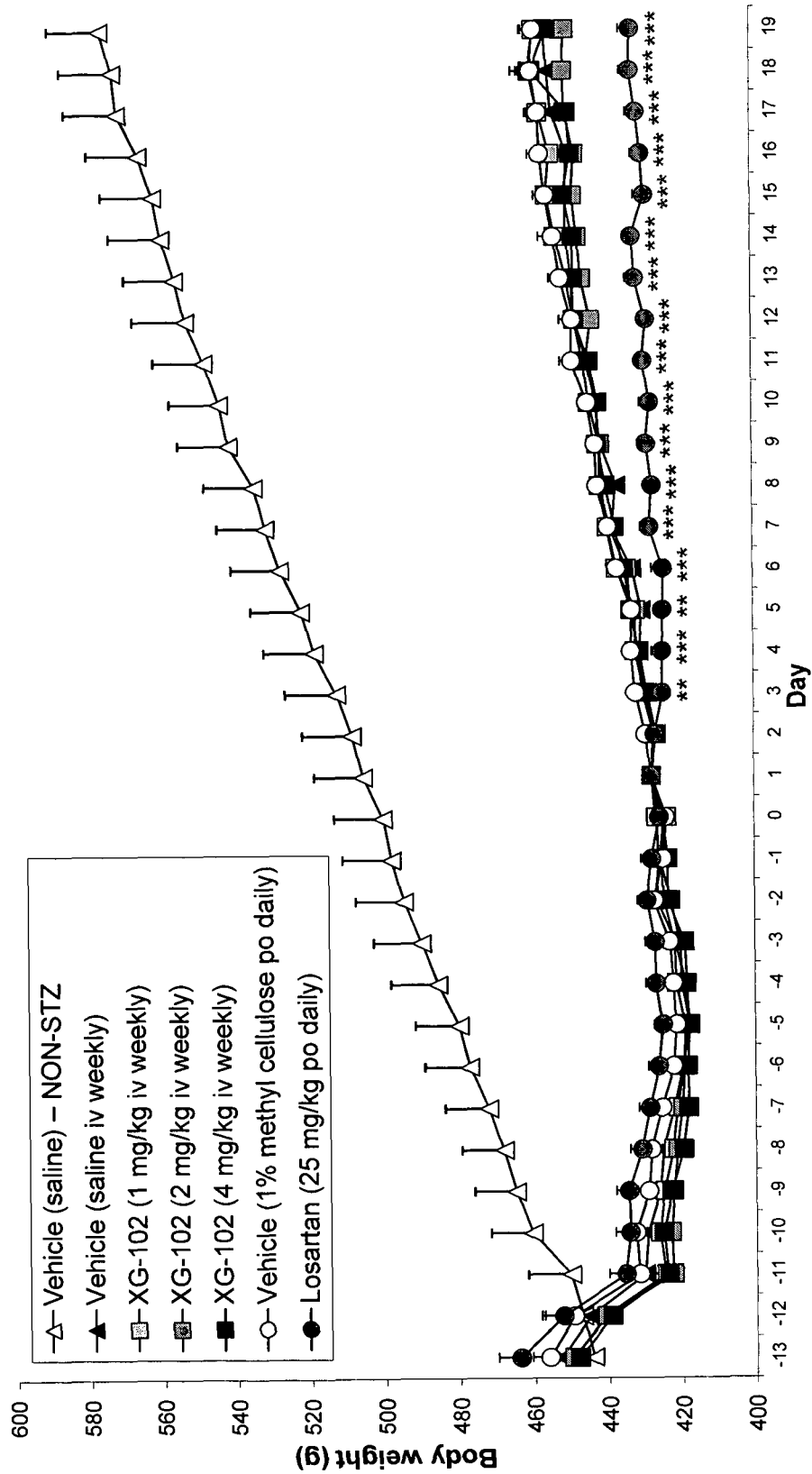
FIG. 55 shows the effects of chronic administration of XG-102 in a rat model of diabetic nephropathy on the body weight of the rats. Only non-STZ treated rats showed an increase in body weight. Rats treated with XG-102 showed no differences in body weight compared to vehicle-treated rats in the STZ model. The body weight of rats treated with the positive reference (Losartan), however, was significantly lower.

The effects of chronic administration of XG-102 in this rat model of diabetic nephropathy on the body weight of the rats are shown in FIG. 55. Only non-STZ treated rats showed an increase in body weight. Rats treated with XG-102 showed no differences in body weight compared to vehicle-treated rats in the STZ model. The body weight of rats treated with the positive reference Losartan, however, has been significantly lower. These results indicate that XG-102 is well-tolerated, whereas the positive reference Losartan resulted in a significant decrease of the body weight.

Example 22: Evaluation of the Dose-Response to XG-102 in Islet Isolation/Transplantation This study is based on the previous study on islet isolation (cf. Example 17) and on the publication by Noguchi et al. (Noguchi, H., S. Matsumoto, et al. (2009). "Ductal injection of JNK inhibitors before pancreas preservation prevents islet apoptosis and improves islet graft function." *Hum Gene Ther* 20(1): 73-85). These studies have shown, in a porcine islet isolation model that islets undergo a dramatic activation of JNK starting as early as 20 minutes after the initiation of the islet isolation procedure. This activation is the result of the method that combines warm ischemia, enzymatic digestion and mechanic stress on an already fragile tissue. The study of Example 17 it has shown that intravascular addition of XG-102 (10 µM) to the preservation solution flushed into the porcine pancreas at the time of procurement has a significant impact on islet cell viability and functionality, assessed by oxygen consumption rate (OCR), and ATP concentration, and correlates with a decrease in JNK activation and c-fos gene expression. Noguchi et al have used a different inhibitor and added it at the same molar concentration into the pancreatic duct immediately after procurement. Porcine and human pancreases were used. They showed a similar effect on islet viability assessed by ATP concentration, but also an impact in vivo on diabetes reversal after transplantation under the kidney capsule of diabetic mice. The purpose of the present set of experiments has been to determine the dose-response curve of XG-102 and the optimal concentration at which to utilize it in islet isolation. In order to answer this question, a rodent model has been utilized. While differences between human and rodent pancreas and islets are acknowledged, this model was selected because of its straightforwardness and high cost-efficiency. The purpose of these experiments being solely the determination of the optimal dose of XG-102 required, the rat model appears as valid. Since the major purpose is JNK inhibition in human pancreases for the improvement of clinical allogeneic islet transplantation outcome, intraductal injection of the inhibitor has been done in these experiments. This is in effect the most likely way that the compound will be used in the clinical setting.

To assess the JNK activation in rat islets after isolation, islets of Langerhans have been isolated from Lewis rats by a classic enzymatic method using collagenase. Isolation has been carried out either immediately after animal sacrifice or after a 15-minute period of warm ischemia. JNK activation has been assessed by western blot at the end of the isolation process. JNK activation has been assessed on unprocessed rat pancreases as negative controls. Experiments have been done on 3 rats for each condition of ischemia plus 1 for the negative control, and repeated 3 times. This represents a total of 21 Lewis rats. The results shown in FIG. 56 show that XG-102 dose-dependently decreased JNK (FIG. 56 A) and PAF2 (FIG. 56 B) phosphorylation induced by 15-min ischemia.

To study the effects of XG-102 on islet viability, the best model in terms of duration of ischemia (no warm ischemia vs 15-minute warm ischemia), i.e. the model most likely to show differences after JNK inhibition, has been selected based on the results of the previous experiments. Isolation has been carried out using XG-102 at a set concentration or vehicle, diluted in the collagenase solution and injected into the pancreatic duct prior to enzymatic digestion of the pancreas. XG-102 at the same molar concentration or vehicle has been used throughout the isolation procedure in the various washing or purification solutions utilized, and in the culture medium. Isolated islets have been cultured overnight in RPMI-based culture medium. For each set of experiments, the following XG-102 concentrations have been utilized: 1 µM, 3 µM, 10 µM, 50 µM and 100 µM. Three animals have been utilized in each group for each concentration, and experiments have been repeated 2-3 times depending on results. This represents a total of 60-90 Lewis rats. Islet yields have been determined. The following assessments of islet viability has been performed: JNK activation, OCR, ATP concentration, caspase release, etc.

To study the effect of XG-102 on islet function in vivo supplementary isolations have been done in order to assess the effect of JNK inhibition on in vivo islet function. In vivo experiments have been done only with islets isolated using the most effective XG-102 molar concentration in the in vitro experiments detailed above or with vehicle. Islet isolation has been performed as above. For each isolation, 1000 and 2000 IEQ have been transplanted under the kidney capsule of streptozotocin-induced diabetic immunodeficient mice. Proportion of animals reversing diabetes and time necessary for reversal of diabetes have been compared between animals transplanted with XG-102-treated or control islets. Transplants have been repeated 3 times. Number of animals required is approximately 30 Lewis rats and 24 NOD-scid mice.

Figure 57:
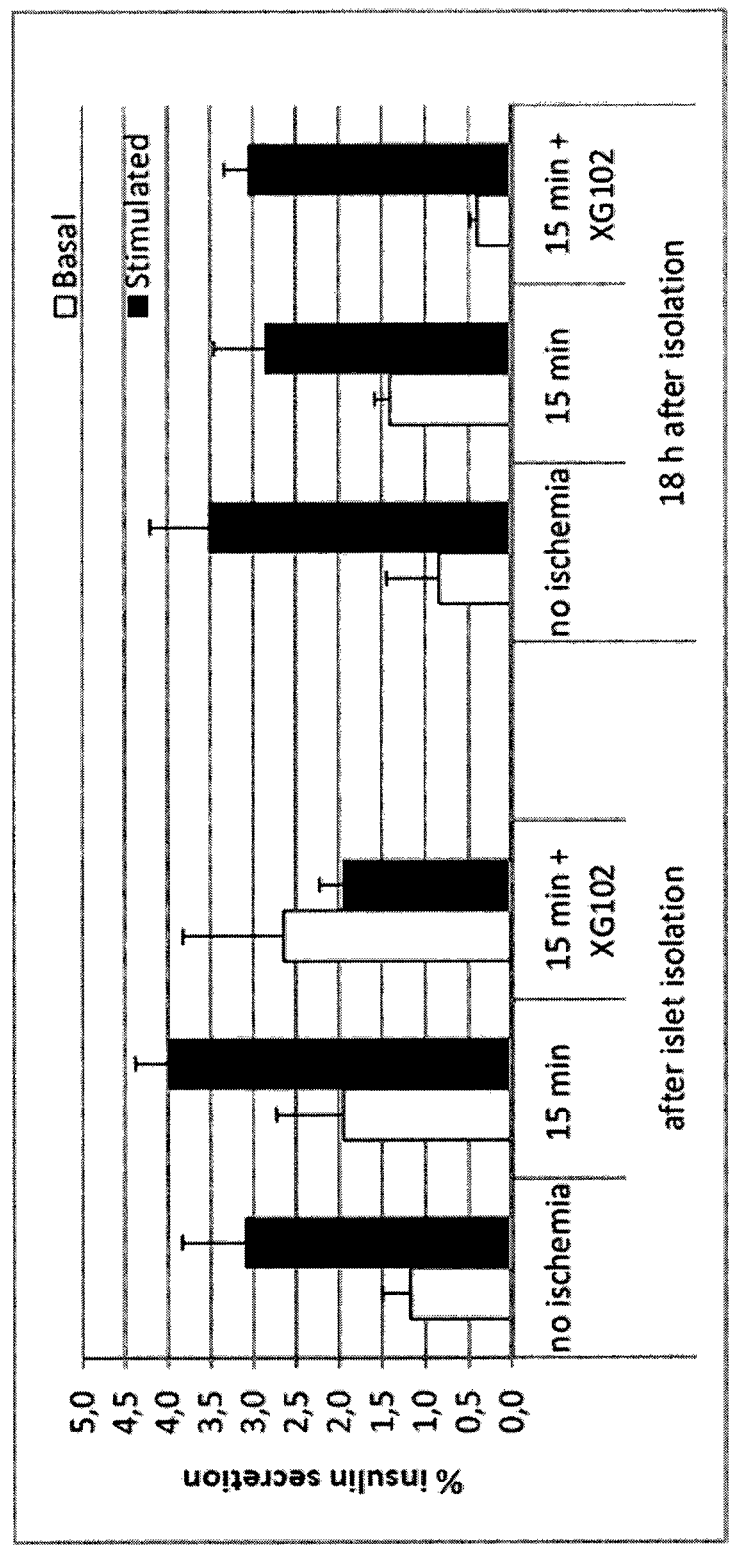
FIG. 57 shows the effects of XG-102 on function and viability of rat pancreatic islets, whereby the islets have been isolated islets from 15 min ischemia rat and from no ischemia rat. A static insulin secretion test (basal or stimulated using glucose) has been performed directly after islet isolation and 18 h after culture at 37° C. Isolation affected islet function, whereby basal insulin secretion was higher in islets used directly after isolation compared to islets incubated during 18 h whatever the conditions. However after culture, ischemia and inhibitor XG-102 had no impact on islet function in this experiment.

As shown in FIG. 57, to study the effects of XG-102 on function and viability of rat pancreatic islets have been isolated islets from 15 min ischemia rat and from no ischemia rat. A static insulin secretion test (basal or stimulated using glucose) has been performed directly after islet isolation and 18 h after culture at 37° C. It can be observed that isolation affects islet function. Indeed basal insulin secretion was higher in islets used directly after isolation compared to islets incubated during 18 h whatever the conditions. These high basal levels reflect a distress of islet. However after culture, ischemia and inhibitor XG-102 had no impact on islet function in this experiment.

Figure 58:
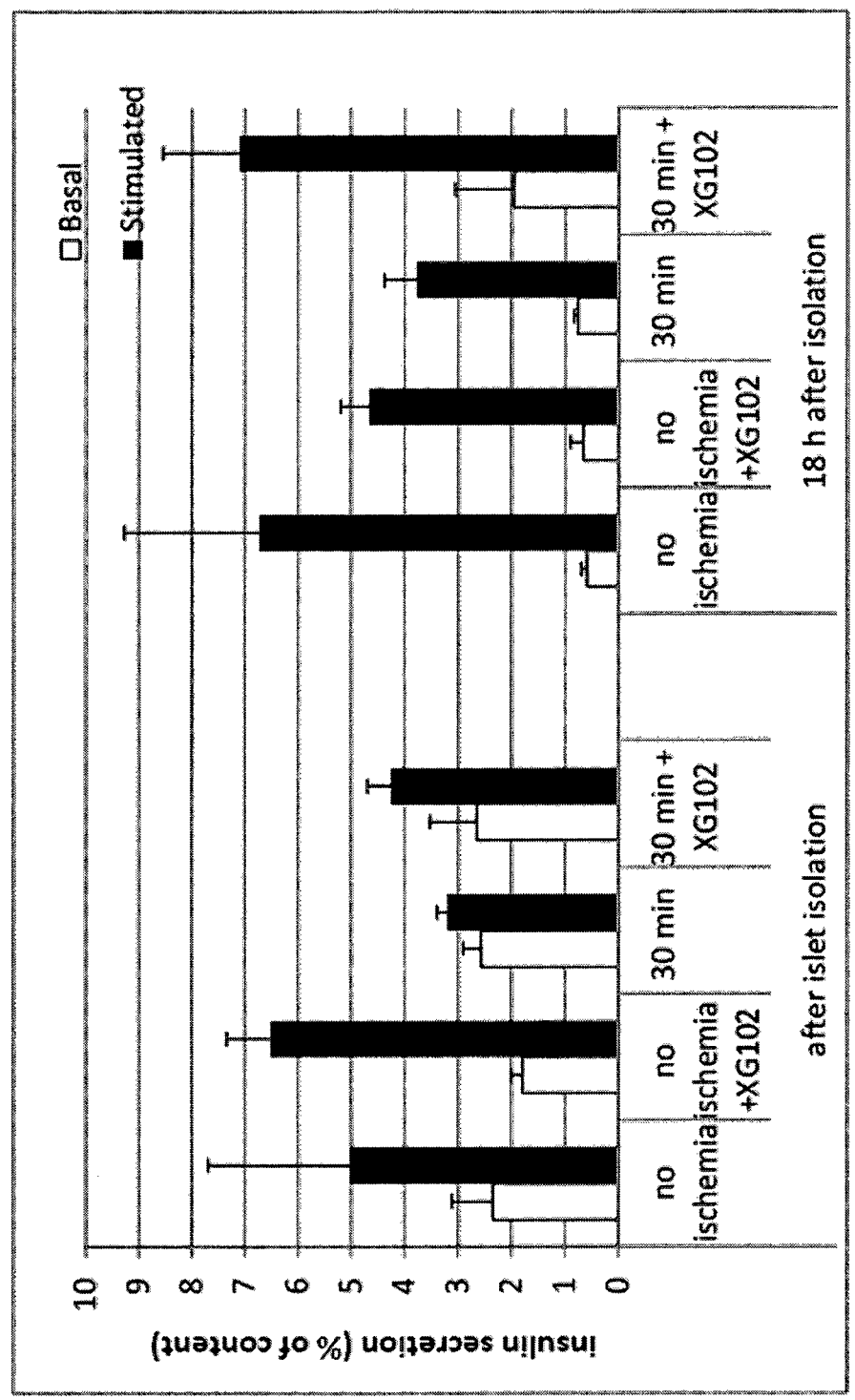
FIG. 58 shows another experiment wherein ischemia was pushed until 30 min and XG-102 was used at 100 microM. Still, a high basal secretion is observed when insulin secretion test was performed directly after isolation. Moreover, 30 min ischemia had a negative impact on islet function. These preliminary results suggested that 30 min ischemia seems to be a better model than 15 min to induce JNK activation. When islets from ischemic rats were isolated and incubated with XG-102, glucose-induced insulin secretion was higher as compared to ischemic rats.

Because in the previous experiment it has been shown that islet from 15 min ischemia rats secreted same amount of insulin than islet from control rats in response to glucose, a new experiment has been performed, wherein ischemia was pushed until 30 min and JNK inhibitor XG-102 was used at 100 microM (FIG. 58). In this experiment a high basal secretion when insulin secretion test was performed directly after isolation is still observed. Moreover, 30 min ischemia had a negative impact on islet function. These preliminary results suggested that 30 min ischemia seems to be a better model than 15 min to induce JNK activation. When islets from ischemic rats were isolated and incubated with XG-102, glucose-induced insulin secretion was higher as compared to ischemic rats (FIG. 58), suggesting a positive effect of XG-102 on the islet function.

Example 23: Efficacy of XG-102 (SEQ ID No. 11) in a Rat Laser-Induced Choroidal Neovascularization (CNV) Model Following Subconjunctival Injections The objectives of this study were to determine the efficacy of XG-102, a JNK-inhibitor, when administered by subconjunctival injections to rats in a model of laser-induced choroidal neovascularization (CNV). As outlined in the context of Example 18, this model allows predictions about a potential use of a compound for the treatment of age-related macular degeneration (AMD). In contrast to the study described in Example 18, the subconjunctival route of administration has been selected for the present study, because it is another preferred route for the administration in humans.

The following experimental groups have been assigned:

| Group No. | Test Material | Dose Level (µg/eye) | Dose Volume (µL/eye) | Dose Concentration | Number of Animals Males |
|---|---|---|---|---|---|
| 1 | Vehicle Control | 0 | 5 | 0 mg/mL | 8 |
| 2 | XG-102 | 0.15 | 5 | 0.03 mg/mL | 8 |
| 3 | XG-102 | 1.5 | 5 | 0.3 mg/mL | 8 |
| 4 | XG-102 | 15 | 5 | 3 mg/mL | 8 |
| 5 | Reference Item 2 | 200 | 5 | 4% | 8 |

The vehicle control, 0.9% NaCl, has been administered as received. Triamcinolone acetonide 4% serves as "Reference Item 2" and has also been administered as received. For XG-102 preparation, a stock solution equal to the highest dose level has been prepared in vehicle, 0.9% Sodium Chloride for Injection, and sterile filtered through a 0.22 um polyvinylidene difluoride (PVDF) filter. The lower dose levels have been prepared by directly diluting the stock solution. Dose formulations have been prepared once at appropriate concentrations to meet dosage level requirements. All dilutions have been prepared by directly diluting the stock solution with vehicle. Two dosing aliquots (Days 1 and 8) have been prepared and stored in a freezer set to maintain −20° C. Aliquot(s) of each dose level have been thawed at ambient temperature on each day of dosing and the solution maintained at room temperature for no longer than 6 hours.

44 male Brown Norway rats (Charles River; age 10 weeks) have been used. A minimum acclimation period of 14 days has been allowed between animal receipt and the start of treatment in order to accustom the animals to the laboratory environment. Animals have been assigned to groups by a stratified randomization scheme designed to achieve similar group mean body weights. Animals in poor health or at extremes of body weight range were not assigned to groups. Before the initiation of dosing, any assigned animals considered unsuitable for use in the study has been replaced by alternate animals obtained from the same shipment and maintained under the same environmental conditions. After initiation of dosing, study animals have been replaced during the replacement period with alternate animals in the event of accidental injury, non-test article-related health issues, or similar circumstances. The alternate animals have been used as replacements on the study within 3 days. On arrival, animals have been individually housed until randomization. Following randomization, animals have been group housed (up to 3 animals of the same dosing group together) in stainless steel perforated floor cages equipped with an automatic watering valve. Animals have been separated during designated procedures/activities. PMI Nutrition International Certified Rodent Chow No. 5CR4 (14% protein) has been provided ad libitum throughout the study, except during designated procedures. Municipal tap water after treatment by reverse osmosis and ultraviolet irradiation has been freely available to each animal via an automatic watering system (except during designated procedures). Animals have been socially housed for psychological/environmental enrichment and provided with items such as a hiding tube and a chewing object, except during study procedures/activities.

On day 1 of the study Laser-Induced Choroidal Neovascularization (CNV) Procedure has been performed. Prior to the CNV procedure, mydriatic drops (1% tropicamide) were applied to both eyes. Further applications have been performed as considered appropriate by the veterinary ophthalmologist. The animals have been anesthetized an isoflurane/oxygen mix prior to and during the procedure. Under anesthesia, a 4-spot pattern have been made between the major retinal vessels around the optic disc of each eye using an 810 nm diode laser at an initial power setting of 300 mW (laser power may be increased for bubble formation), an initial spot size of 80 µm and a duration of 0.1 seconds. Laser parameters have been adjusted as required to ensure rupture of Bruch's membrane (correlated with bubble formation). In the event that rupture of Bruch's membrane is not confirmed for a particular spot, this has been documented. In this case or in the case of hemorrhage, an additional spot may be added if considered appropriate by the veterinary ophthalmologist. Any notable events, such as retinal hemorrhage were documented for each laser spot. If hemorrhage is too severe, the animal has been excluded from the study and replaced. Hydration of the eyes has been maintained with a saline solution and/or carboxymethylcellulose sodium 1.0% during the procedure, as necessary.

Vehicle control, test item or reference item will be administered by subconjunctival injection to the left and right eyes of each animal on Days 1 and 8 as indicated in the Experimental Design above. The animals have been anesthetized (isoflurane) for the dose administration, which has been performed by a board-certified veterinary ophthalmologist. Topical antibiotics (gentamicin ophthalmic solution) have been applied to both eyes twice on the day before treatment, following the injection and at least once on the day following the injection. Prior to dosing, mydriatic drops (1% tropicamide and/or 2.5% phenylephrine) have been applied to each eye (further applications may be performed as considered appropriate by the veterinary ophthalmologist). During dosing, animals are maintained under anesthesia with isoflurane/oxygen gas. The conjunctivae has been flushed with 0.9% Sodium Chloride for Injection USP. A 29-gauge, ½-inch needle attached to a 0.5 cc Terumo insulin syringe has been used for each subconjunctival injection (one syringe/group/treatment). XG-102, vehicle control or reference item has been administered into the eyes of each animal at a dose volume of 50 µL/eye on Days 1 and 8. Both eyes have been examined immediately following each treatment to document any abnormalities caused by the administration procedure.

The in-life procedures, observations, and measurements listed below have been performed. More frequent observations may be undertaken if considered appropriate. Twice daily, once in the morning and once in the afternoon, throughout the study Mortality/Moribundity Checks have been performed, whereby the animals were observed for general health/mortality and moribundity. Animals have not been removed from cage during observation, unless necessary for identification or confirmation of possible findings. Once daily, beginning Week −1, Cageside Observations have been performed, whereby animals have not been removed from cage during observation, unless necessary for identification or confirmation of possible findings. Weekly, beginning Week −1, Detailed Clinical Observations have been performed, whereby the animals were removed from the cage for examination. Weekly, starting Week −2, Body Weights have been recorded for health monitoring purposes only whereby animals were individually weighed. Weekly, starting during the last week of the pre-treatment period, Food consumption has been quantitatively measured except on the day of scheduled euthanasia for health monitoring purposes only. Once prestudy for screening purposes, Ophthalmic Examinations have been performed, whereby all animals were subjected to funduscopic (indirect ophthalmoscopy) and biomicroscopic (slit lamp) examinations. The mydriatic used was 1% tropicamide. Once prestudy and at the end of Weeks 1, 2 and 3, Fluorescein Angiography has been performed, whereby mydriatic drops (1% tropicamide) have been applied to each eye at least 10 minutes prior to the test (further applications may be administered if considered necessary). Hydration of the eyes has been maintained by frequent irrigation with saline solution. The animals have been maintained under isoflurane/oxygen mix and/or with a sedative cocktail (ketamine 75 mg/kg; xylazine 7.5 g/kg), as necessary. Single and/or ART fundus images in infrared and/or red free modes have been obtained to serve as reference images for the angiographies. 0.2 ml of 10% Sodium Fluorescein Injection USP has been administered via rapid tail vein injection (via an abbocath), followed by a 0.5 ml saline flush. Still images have been recorded from both eyes at least 2 minutes following the fluorescein injection and no later than 5 minutes following the fluorescein injection. For evaluation the individual laser spots on the still images have been evaluated for leakage semiquantitatively on a scale of 0-4 by 2 independent readers, who will subsequently determine a consensus score.

In the fluorescein angiogram scoring procedure, firstly Angiography images (JPEG or BMP) have been exported from the HRA2 and copied on a CD or other appropriate medium and reviewed on a suitable computer. In the Grading Procedure the Images have been selected at an appropriate focus level for grading. (More than 1 image/eye may be needed in order to grade all laser spots.) The angiograms have been graded independently by 2 scientific personnel and the grade for each of the laser spots has been recorded. Following completion of the grading by each person, the grades have been compared and any discrepancy has been reviewed by both parties, and a grade agreed upon and documented. The grading scale will be from 0-4 as indicated below:

0=no leakage (only laser scar or very diffuse small hyperfluorescent area visible).
1=minimal leakage (small areas of diffuse or solid hyperfluorescence generally remaining within the laser-induced defect region).
2=slight leakage (semisolid hyperfluorescence generally remaining within the boundary of the laser-induced defect region).
3=moderate leakage (semisolid to solid hyper-fluorescence generally remaining within the boundary of the laser-induced defect region).
4=Substantial leakage (solid hyper-fluorescent region extending beyond the boundary of the laser-induced defect region).

If an animal dies or is euthanized during the study, a necropsy has not been conducted and the carcass discarded. Animals surviving until scheduled euthanasia have a terminal body weight recorded. The animals will undergo exsanguination from the abdominal aorta after isoflurane anesthesia. When possible, the animals have been euthanized rotating across dose groups such that similar numbers of animals from each group, including controls, have been necropsied throughout the day(s). Representative samples of the tissues identified in the Tissue Collection and Preservation table below have been collected from all animals and preserved in 10% neutral buffered formalin, unless otherwise indicated:

The following critical computerized systems have been used in the study:

| System Name | Description of Data Collected and/or Analyzed |
| --- | --- |
| Provantis | Dose administration, bodyweight, food consumption, clinical observations, incidence of clinical observations, clinical biochemistry, hematology, coagulation, urinalysis, ophthalmology and gross pathology |
| Dispense | Test Item receipt and/or accountability of Test Item and/or vehicle and/or Reference Item(s) |
| SRS (PCS-MTL in-house application built with SAS) and SAS system for Windows | Statistical analyses of numerical in-life and terminal data |
| Heidelberg HRA 2/Heidelberg Spectralis with EyeExplorer | Fluorescein angiography |

Means and standard deviations have been calculated for body weight, food consumption and fluorescein angiography. Other data have been reported on an individual basis.

Example 24: Inhibitory Effects of the JNK Inhibitor XG-102 on the Inflammatory Response in a Rat Periodontitis Model The aim of this study is to investigate the influence of XG-102 (SEQ ID NO: 11) on inflammation induced in a periodontitis model in the rat.

30 rats are used in this study (divided into 4 groups of ten rats). Experimental periodontitis is induced by a ligature placed around the $1^{st}$ molar (one molar per animal) on Day 0. One dose of 2 or 4 mg/kg is administered intragingivally (IGV).

The table below summarizes the random allocation:

| Group N° | Ligature (Day 0) | Treatment | Route of administration | Number of animals |
| --- | --- | --- | --- | --- |
| 1 | — | — | IGV | 10 |
| 2 | Yes | NaCl 0.9% | IGV | 10 |
| 3 | Yes | XG-102 2 or 4 mg/kg | IGV | 10 |

Each day, the general behavior and the appearance of all animals is observed. If animal health is not compatible with the continuation of the study (moribund animals, abnormal

| Tissue | Weight | Collect | Microscopic Evaluation | Comment |
| --- | --- | --- | --- | --- |
| Animal identification | — | X | — | — |
| Eye | — | X | — | Bilateral; fixed 24 to 48 hrs in Davidson's fixative and transferred in ethanol 70% for at least 18 hrs, stored in 70% ethanol until processing. (euthanized animals only) |
| Nerve, optic | — | X | — | Bilateral; fixed 24 to 48 hrs in Davidson's fixative and transferred in ethanol 70% for at least 18 hrs, stored in 70% ethanol until processing (euthanized animals only) |

X = procedure to be conducted;
— = not applicable.

important loss of weight, major intolerance of the substance, etc. . . . ), animals are ethically sacrificed under the responsibility of the Study Director. Periodontitis inflammation aspect are analyzed by macroscopic observation of gingival tissue. Plaque index and gingival inflammation index are measured as periodontal clinical indices.

Approximately on day 17 the animals are sacrificed and samples are collected. For the evaluation of inflammatory cells, quantification of inflammatory cells is performed by histomorphometric measurements. For the evaluation of inflammatory protein levels, the level of inflammatory proteins (p-JNK, TNF, IL-1, IL-10, MMP-8, MMP-9) are measured from gingival tissue homogenates. For the evaluation of tissue destruction, bone tissue destruction is evaluated on 3 animals per group by radiological analysis (micro-CT). Periodontal complex destruction is evaluated by histological analysis. For the evaluation of bone microarchitecture, bone trabecular measurements (thickness, separation) are evaluated by radiological analysis (micro-CT). For the identification of oral bacteria, bacterial population in dental pockets are identified by DNA probes (real time PCR) on 9 periodontopathogens. For the collagen framework, measurements of total collagen amount are performed using Polarized-light microscopy. The collagen I/collagen III ratio is evaluated by histomorphometrical analysis.

Example 25: Effects of XG-102 (SEQ ID No. 11) in a Diabetic Retinopathy Prevention Study in the Streptozotocin Treated Rat (IVT)

The objective of this study was to determine the ability of XG-102 to prevent diabetic retinopathy when administered by intravitreal injections to streptozotocin (STZ)-treated (hyperglycemic) rats.

The study design was as follows:

| Group No./ Identification | STZ (mg/kg) Day −7 | XG-102 Dose Level (µg/eye) Days 1, 8, 15 | Dose Volume (µL) | Dose Concentration (mg/mL) | Number of Animals Males |
|---|---|---|---|---|---|
| 1/Not induced, Vehicle | 0 | 0 | 5 | 0 | 3 |
| 2/XG-102 - 0.2 µg/eye | 55 | 0.2 | 5 | 0.04 | 8 |
| 3/XG-102 - 2 µg/eye | 55 | 2 | 5 | 0.4 | 8 |
| 4/Vehicle | 55 | 0 | 5 | 0 | 5 |

All animals from Groups 2, 3, 4 received a 55 mg/kg intravenous (IV) dose of STZ on Day −7.

Sterile vials containing 0.0412 g of inducing agent (STZ) were pre-weighed, sealed and transferred to the dosing room for administration to Groups 2 to 4 animals and Spares on Day −7. A duplicate set of empty, appropriately labeled sterile vials were provided. The reconstituted STZ solution was filtered into these vials for dosing. The Reference Item, 0.9% NaCl, was administered as received. XG-102 was prepared using the correction factor 1.383. A stock solution equal to the highest dose level was prepared in vehicle, 0.9% Sodium Chloride for Injection, and sterile filtered through a 0.22 µm polyvinylidene difluoride (PVDF) filter. The lower dose levels were prepared by directly diluting the stock solution. Dose formulations were prepared once at appropriate concentrations to meet dosage level requirements. All dilutions were prepared by directly diluting the stock solution with vehicle. Three dosing aliquots (Days 1, 8 and 15) were prepared and stored in a freezer set to maintain −20° C. Aliquot(s) of each dose level were thawed at ambient temperature on each day of dosing and the solution maintained at room temperature for no longer than 6 hours.

60 male Brown Norway rats were received from Charles River Labs, Inc., Portage, Ill. The animals were approximately 8 weeks old and weighed between 166 and 228 g. The Brown Norway rat was chosen as the animal model for this study as it is an accepted species for use in the STZ-induced diabetic retinopathy model. The total number of animals used in this study was considered to be the minimum required to properly characterize the effects of the Test Items. This study has been designed such that it did not require an unnecessary number of animals to accomplish its objectives. A minimum acclimation period of 20 days was allowed between animal receipt and the start of treatment in order to accustom the animals to the laboratory environment. Animals were assigned to groups by a stratified randomization scheme designed to achieve similar group mean body weights. Animals in poor health or at extremes of body weight range were not assigned to groups. Before the initiation of dosing, any assigned animals considered unsuitable for use in the study were replaced by alternate animals obtained from the same shipment and maintained under the same environmental conditions. The alternate animals were used as replacements on the study within 3 days of initiation. On arrival, animals were individually housed until randomization. Following randomization, animals were group housed (up to 3 animals of the same dosing group together) in stainless steel perforated floor cages equipped with an automatic watering valve. The room in which the animals were kept was documented in the study records. Animals were separated during designated procedures/activities. Temperatures of 19° C. to 25° C. with a relative humidity of 30% to 70% were maintained. A 12-hour light/12-hour dark cycle was maintained, except when interrupted for designated procedures. PMI Nutrition International Certified Rodent Chow No. 5CR4 (14% protein) was provided ad libitum throughout the study, except during designated procedures. Municipal tap water after treatment by reverse osmosis and ultraviolet irradiation was freely available to each animal via an automatic watering system (except during designated procedures). Animals were socially housed for psychological/environmental enrichment and were provided with items such as a hiding device and a chewing object, except when interrupted by study procedures/activities.

For administration of Inducing Agent (Groups 2 to 4, Day −7), one vial of STZ per animal (including spares) was reconstituted within 3 minutes of injection with 1.5 mL of Sterile Water for Injection, USP, to provide a concentration of 27.5 mg/mL. The vial was inverted or swirled to dissolve STZ. The resultant solution was filtered via a 0.22 µm Millex-GV filter into a empty sterile appropriately labeled vial. The STZ (55 mg/kg) was administered by intravenous injection on Day −7, within 3 minutes of formulation via a syringe. The dose volume was 2 mL/kg and the actual dose administration was based on the most recent practical body weight of each animal. The animals were restrained during the injection.

Test items or reference item were administered by intravitreal injection to the left and right eyes of each animal on Days 1, 8 and 15 as indicated in the Experimental Design table. The animals were anesthetized (isoflurane) for the dose administration, which was performed by a board-certified veterinary ophthalmologist. Topical antibiotics (gentamicin ophthalmic solution) were applied to both eyes twice on the day before treatment, following the injection and at least once on the day following the injection. Prior to dosing, mydriatic drops (1% tropicamide and/or 2.5% phenylephrine) were applied to each eye (further applications were performed when considered appropriate by the veterinary ophthalmologist). During dosing, animals were maintained under anesthesia with isoflurane/oxygen gas. The conjunctivae were flushed with 0.9% Sodium Chloride for Injection USP. A 10 µl Hamilton syringe with 32-gauge, ½-inch needle was used for each intravitreal injection (one syringe/group/treatment). The dose volume was 5 µL/eye. Both eyes were examined by slit-lamp biomicroscopy and/or indirect ophthalmoscopy immediately following each treatment to document any abnormalities (especially to the lens, vitreous and retina) caused by the administration procedure. Corneal opacities were considered secondary to experimental procedures involving anesthesia. Some of these opacities were associated also with corneal vascularization. Other ocular findings were noted, but were generally of low incidence or sporadic across groups, and/or did not persist. These findings included, but were not limited to: multifocal/diffuse corneal opacities, vitreous air bubbles, focal/diffuse/multifocal vitreous opacities, and focal retina opacities.

Streptozotocin was administered by intravenous injection to induce diabetic retinopathy in the rat. The intravitreal injection route was selected for the Test Items because this is the intended route of administration in humans. The dose levels were selected based on information obtained with previous proof of concept studies as well as MTD and toxicity studies using the IVT route of administration.

The in-life procedures, observations, and measurements listed below were performed for study animals. Throughout the study, animals were observed for general health/mortality and moribundity twice daily, once in the morning and once in the afternoon. Animals were not removed from cage during observation, unless necessary for identification or confirmation of possible findings. The animals were removed from the cage, and a detailed clinical observation was performed weekly, beginning during Week −1. Animals were weighed individually twice weekly, starting during Week −1. Food consumption was quantitatively measured weekly starting during the last week of the pretreatment period. All animals were subjected to funduscopic (indirect ophthalmoscopy) and biomicroscopic (slit lamp) examinations once pre-treatment and again on Day 22. The mydriatic used was 1% tropicamide. Intraocular pressure was measured following each ophthalmology examination, once prestudy and on Day 22, using a TonoVet™ rebound tonometer. The pre-treatment tonometry readings were performed at the same times as anticipated for the final measurements to reduce diurnal variability.

Electroretinogram evaluations were performed once pre-treatment and on Days 6, 13, and 20, prior to fluorescein angiography Animals were dark-adapted overnight prior to ERG recording and then anesthetized with an intramuscular injection of 75 mg/kg ketamine and 7.5 mg/kg xylazine. Tropicamide (1%) was applied to each eye prior to the test (further applications were administered if considered necessary). The eyelids were retracted by means of a lid speculum, and a contact lens or gold loop electrode was placed on the surface of each eye. A needle electrode was placed cutaneously under each eye (reference) and on the head, posterior to the brow or at the base of the tail (ground). Carboxymethylcellulose (1%) drops were applied to the interior surface of the contact lens electrodes prior to placing them on the eyes. Each ERG occasion consisted of the following series of scotopic single flash stimuli:

1) −30 dB single flash, a-wave amplitude and latency, average of 5 single flashes, 10 seconds between flashes.

2) −10 dB single flash, a- and b-wave amplitudes and latency, average of 5 single flashes, 15 seconds between flashes.

3) 0 dB, average of 2 single flashes, a- and b-wave amplitude and latency, approximately 120 seconds between flashes (a longer time period is acceptable).

Following evaluation of the scotopic response, the animals were adapted to background light at approximately 25 to 30 cd/m2 for a period of approximately 5 minutes (a longer time period was acceptable), followed by an average of 20 sweeps of photopic white flicker at 1 Hz (a- and b-wave amplitudes and latency), then 20 sweeps of photopic flicker at 29 Hz (b-wave amplitude and latency). Waveforms were analyzed for a- and b-wave amplitudes and latency, and oscillatory potentials (OP) 1 through 4 from the 0 dB scotopic stimulus were filtered and analyzed for amplitude and latency.

Fluorescein angiography evaluations were performed once pretreatment and on Days 7, 14, and 21, following electroretinography. An isoflurane/oxygen mix was used prior to and during the procedure as the anesthesia. The mydriatic agent, 1% tropicamide, was used as necessary. Hydration of the eyes was maintained by irrigation with saline solution, as needed. 0.2 mL of 10% Sodium Fluorescein Injection U.S.P. was administered via rapid tail vein injection, followed by a 0.5 mL saline flush. Still images of the fundus were recorded from both eyes between 10-15 minutes following the fluorescein injection. Images were taken from the right eye first, followed by the left. A topical bland ophthalmic ointment was administered to the eyes following the angiographies. Images were evaluated qualitatively for vascular integrity/diffuse leakage.

Blood Glucose Level Determination were once pre-STZ treatment, Day −6 (the day following STZ administration) and three times per week thereafter (all animals). Additional blood glucose measurements may have been performed as required to monitor animal health status. Levels were determined by glucometer using blood drops taken from the tail vein. Values were measured in mmol/L and converted into mg/dL by multiplying by 18 for reporting purposes. Urine Glucose Level Determination was weekly, beginning Week −1, following overnight collection. Animals had access to food and water during the collection period. Urine glucose was measured by the Clinical Laboratory department using the P800 analyzer. from the abdominal aorta after isoflurane anesthesia. When possible, the animals were euthanized rotating across dose groups such that similar numbers of animals from each group, including controls were necropsied at similar times throughout the day.

Main study animals were subjected to a complete necropsy examination, which included evaluation of the carcass and musculoskeletal system; all external surfaces and orifices; cranial cavity and external surfaces of the brain; and thoracic, abdominal, and pelvic cavities with their associated organs and tissues. Necropsy procedures were performed by qualified personnel with appropriate training and experience in animal anatomy and gross pathology. A veterinary pathologist, or other suitably qualified person, was available.

Representative samples of the tissues identified below were collected from all animals and preserved in 10% neutral buffered formalin, unless otherwise indicated.

Tissue Collection and Preservation

| Tissue | Weight | Collect | Microscopic Evaluation | Comment |
|---|---|---|---|---|
| Animal identification | — | X | — | — |
| Eye | — | X | — | Bilateral; fixed in Davidson's fixative (euthanized animals only). |
| Gross lesions/ masses | — | X | — | — |
| Nerve, optic | — | X | — | Bilateral; fixed in Davidson's fixative (euthanized animals only) |

X = procedure to be conducted;
— = not applicable.

The following parameters and end points were evaluated in this study: mortality, clinical signs, body weights, body weight changes, food consumption, ophthalmology, intraocular pressure, electroretinography (ERG), fluorescein angiography, blood and urine glucose determination, gross necropsy examinations.

Consistent with the diabetic retinopathy rat model, there were hyperglycemia-related deaths, clinical signs of deteriorating condition, and decreases in body weights, body weight gains, increased food consumption, and severe increases blood and urine glucose levels. Multiple ocular changes noted in the STZ-induced groups were secondary to the nature of the hyperglycemic state, notably the anterior cortical cataracts. There were no XG-102-related deaths during the study. There were no XG-102-related clinical signs or effects on body weights, body weight gains or food consumption. Fluorescein angiography imagery did not reveal any vascular leakage and there were no apparent XG-102-related macroscopic findings at necropsy.

On Days 6, 13 and 20, some amplitudes of scotopic and photopic ERG assessments for animals given ≤2 µg/eye XG-102 were mildly increased or comparable to the STZ-treated control animals, but these responses generally remained within the control variability. Latencies for XG-102 groups were comparable and remained within the control and/or pretreatment variation. There were some sporadic differences in oscillatory potential amplitudes when comparing animals given ≤2 µg/eye XG-102 with STZ-treated controls.

The following Table includes a summary of amplitudes for all ERG stimuli by occasion (pretreatment, and Days 6, 13 and 20, respectively). The values represent the group mean and standard deviation (below):

| | Amplitude (µV) | | | |
|---|---|---|---|---|
| Group | Pre | 6 | 13 | 20 |
| Oscillatory Potential #1 Scotopic Single Flash 0 dB - B-Wave | | | | |
| Non-induced | 54 | 50 | 34 | 41 |
| Vehicle | 9 | 11 | 12 | 7 |
| XG-102 | 46 | 49 | 37 | 36 |
| 0.2 µg/eye | 10 | 12 | 17 | 18 |
| XG-102 | 58 | 40 | 33 | 26 |
| 2 µg/eye | 14 | 11 | 15 | 7 |
| Vehicle | 53 | 40 | 14 | 35 |
| | 21 | 4 | 11 | 12 |
| Oscillatory Potential #2 Scotopic Single Flash 0 dB - B-Wave | | | | |
| Non-induced | 180 | 129 | 107 | 84 |
| Vehicle | 14 | 32 | 40 | 8 |
| XG-102 | 167 | 98 | 63 | 70 |
| 0.2 µg/eye | 34 | 28 | 25 | 33 |
| XG-102 | 226 | 93 | 92 | 49 |
| 2 µg/eye | 49 | 17 | 31 | 14 |
| Vehicle | 180 | 98 | 124 | 58 |
| | 88 | 27 | 39 | 12 |
| Oscillatory Potential #3 Scotopic Single Flash 0 dB - B-Wave | | | | |
| Non-induced | 376 | 273 | 214 | 195 |
| Vehicle | 26 | 68 | 80 | 18 |
| XG-102 | 326 | 219 | 165 | 164 |
| 0.2 µg/eye | 64 | 82 | 58 | 63 |
| XG-102 | 428 | 239 | 219 | 137 |
| 2 µg/eye | 77 | 33 | 55 | 35 |
| Vehicle | 348 | 251 | 239 | 164 |
| | 149 | 58 | 54 | 37 |
| Oscillatory Potential #4 Scotopic Single Flash 0 dB - B-Wave | | | | |
| Non-induced | 219 | 162 | 136 | 142 |
| Vehicle | 26 | 39 | 24 | 14 |
| XG-102 | 172 | 147 | 129 | 116 |
| 0.2 µg/eye | 33 | 64 | 45 | 38 |
| XG-102 | 219 | 182 | 160 | 130 |
| 2 µg/eye | 32 | 27 | 49 | 50 |
| Vehicle | 162 | 178 | 143 | 136 |
| | 52 | 31 | 45 | 35 |
| Scotopic Single Flash −30 dB - B-Wave | | | | |
| Non-induced | 434 | 311 | 308 | 170 |
| Vehicle | 35 | 113 | 47 | 60 |
| XG-102 | 360 | 269 | 270 | 240 |
| 0.2 µg/eye | 90 | 120 | 143 | 136 |
| XG-102 | 417 | 270 | 292 | 166 |
| 2 µg/eye | 68 | 140 | 142 | 108 |
| Vehicle | 369 | 224 | 197 | 136 |
| | 85 | 77 | 71 | 47 |
| Scotopic Single Flash −10 dB - A-Wave | | | | |
| Non-induced | −217 | −152 | −124 | −109 |
| Vehicle | 23 | 39 | 31 | 30 |
| XG-102 | −191 | −151 | −128 | −129 |
| 0.2 µg/eye | 39 | 64 | 59 | 56 |
| XG-102 | −254 | −124 | −152 | −84 |
| 2 µg/eye | 48 | 46 | 75 | 40 |
| Vehicle | −206 | −104 | −111 | −96 |
| | 57 | 26 | 38 | 30 |
| Scotopic Single Flash 0 dB - A-Wave | | | | |
| Non-induced | −355 | −244 | −188 | −188 |
| Vehicle | 37 | 57 | 96 | 77 |
| XG-102 | −303 | −209 | −203 | −198 |
| 0.2 µg/eye | 70 | 73 | 78 | 74 |
| XG-102 | −394 | −205 | −261 | −147 |
| 2 µg/eye | 75 | 74 | 142 | 61 |
| Vehicle | −323 | −177 | −208 | −142 |
| | 110 | 38 | 67 | 43 |
| Scotopic Single Flash 0 dB - B-Wave | | | | |
| Non-induced | 899 | 415 | 640 | 180 |
| Vehicle | 99 | 161 | 201 | 80 |
| XG-102 | 739 | 421 | 442 | 433 |
| 0.2 µg/eye | 169 | 176 | 209 | 224 |
| XG-102 | 944 | 383 | 524 | 278 |
| 2 µg/eye | 176 | 177 | 132 | 202 |
| Vehicle | 755 | 283 | 468 | 255 |
| | 250 | 103 | 194 | 83 |
| Photopic 1 Hz Flicker A-Wave | | | | |
| Non-induced | −3 | −2 | −7 | −5 |
| Vehicle | 1 | 2 | 4 | 4 |
| XG-102 | −2 | −3 | −4 | −2 |

103
-continued

| Group | Amplitude (μV) | | | |
|---|---|---|---|---|
| | Pre | 6 | 13 | 20 |
| 0.2 μg/eye | 2 | 2 | 4 | 3 |
| XG-102 | −3 | −3 | −6 | −2 |
| 2 μg/eye | 2 | 3 | 6 | 3 |
| Vehicle | −4 | −2 | −2 | −6 |
| | 2 | 2 | 2 | 5 |
| Photopic 1 Hz Flicker B-Wave | | | | |
| Non-induced | 133 | 72 | 95 | 40 |
| Vehicle | 15 | 21 | 36 | 8 |
| XG-102 | 112 | 63 | 71 | 70 |
| 0.2 μg/eye | 29 | 25 | 34 | 32 |
| XG-102 | 146 | 69 | 91 | 45 |
| 2 μg/eye | 31 | 28 | 27 | 28 |
| Vehicle | 100 | 61 | 100 | 32 |
| | 14 | 20 | 39 | 16 |
| Photopic 29 Hz Flicker - B-Wave | | | | |
| Non-induced | 22 | 13 | 16 | 12 |
| Vehicle | 4 | 3 | 4 | 5 |
| XG-102 | 18 | 9 | 14 | 10 |
| 0.2 μg/eye | 6 | 4 | 6 | 4 |
| XG-102 | 27 | 11 | 17 | 9 |
| 2 μg/eye | 6 | 4 | 7 | 4 |
| Vehicle | 19 | 11 | 19 | 13 |
| | 9 | 3 | 7 | 7 |

As can be retrieved from these data, there is a tendency for XG-102 to reverse the decrease of the wave amplitude.

Example 26: Effects of XG-102 (SEQ ID No. 11) in a Diabetic Retinopathy Prevention Study in the Streptozotocin Treated Albino Rat (Subconjunctival)

The objective of this study was determine the ability of XG-102 to prevent diabetic retinopathy when administered by weekly subconjunctival injection to streptozotocin (STZ)-treated (hyperglycemic) rats for 3 weeks.

The experimental design is shown in the following:

| Group No./ Identification | STZ (mg/kg) Day −7 | Test Item Dose Level (μg/eye/week) | Dose Volume (μL) | Dose Concentration (mg/mL) | No. of Animals Males |
|---|---|---|---|---|---|
| 1/Not induced, Vehicle | 0 | — | 50 | 0 | 8 |
| 2/Induced, Vehicle | 55 | — | 50 | 0 | 10 |
| 3/XG-102 - low dose | 55 | 2 | 50 | 0.04 | 8 |
| 4/XG-102 - mid dose | 55 | 20 | 50 | 0.4 | 8 |
| 5/XG-102 - high dose | 55 | 200 | 50 | 4 | 8 |

All animals from Groups 2 to 5 will receive a 55 mg/kg intravenous (IV) dose of STZ on Day −7.

Naïve Long Evans rats were used (42 male animals; 10 weeks of age, at time of dosing; Charles River, St. Constant, QC). The Long Evans rat was chosen as the animal model for this study as it is an accepted species for use in the STZ-induced diabetic retinopathy model. The total number of animals to be used in this study is considered to be the minimum required to properly characterize the effects of the test item and has been designed such that it does not require an unnecessary number of animals to accomplish its objectives. At this time, studies in laboratory animals provide the best available basis for extrapolation to humans. Acceptable models which do not use live animals currently do not exist. Projected release of alternates will be Day 4. Animals will be housed in stainless-steel cages. PMI Nutrition International Certified Rodent Chow No. 5CR4 (14% protein) was provided daily in amounts appropriate for the size and age of the animals. Municipal tap water, processed through a reverse osmosis filter and passed through UV light treatment, was freely available to each animal. Animals were socially housed (up to 3 animals/cage) for psychological/environmental enrichment and were provided with items such as a hiding tube and a chewing object, except during study procedures/activities. Only animals that are determined to be suitable for use on study were assigned. On arrival, animals were individually housed until randomization. Following randomization, animals will be socialized.

Sterile vials containing 0.0412 g of inducing agent (STZ) will be pre-weighed, sealed and transferred to the dosing room for administration to Groups 2 to 5 animals and selected spares on Day −7. A duplicate set of empty, appropriately labeled sterile vials will be provided. The reconstituted STZ solution will be filtered into these vials for dosing. The Test Item, XG-102, was prepared using the provided correction factor. A stock solution equal to the highest dose level was prepared in vehicle, 0.9% Sodium Chloride for Injection, and sterile filtered through a 0.22 μm polyvinylidene difluoride (PVDF) filter. The lower dose levels were prepared by directly diluting this stock solution with saline. Dosing aliquots were prepared and stored in a freezer set to maintain −20° C. Aliquot(s) of each dose level were thawed at ambient temperature on each day of dosing and the solutions maintained at room temperature for no longer than 6 hours. The vehicle, 0.9% Sodium Chloride for Injection, was administered as received. One vial of STZ per animal (including spares) was reconstituted within 3 minutes of injection with 1.5 mL of Sterile Water for Injection, USP, to provide a concentration of 27.5 mg/mL. The vial was inverted or swirled to dissolve the STZ. The reconstituted STZ solution was filtered via a 0.22 μm Millex-GV filter into empty sterile vials for dosing. STZ was administered by intravenous injection on Day −7, within 3 minutes of formulation via a syringe. The dose volume was 2 mL/kg and the actual dose administration was based on the most recent practical body weight of each animal. The animals will be restrained during the injection. STZ-treated animals were considered diabetic if the blood glucose level is ≥250 mg/dl. Test item or vehicle were administered by subconjunctival injection to the left and right eyes of each animal on Days 1, 8 and 15 and again on Day 24 (Rep 1), Day 23 (Rep 2 and 3), Day 22 (Rep 4) and Day 34 (Rep 1) Day 33 (Rep 2 and 3) and Day 32 (Rep 4). The animals were anesthetized (isoflurane) for the dose administration, which was performed by a board-certified veterinary ophthalmologist.

Topical antibiotics (0.3% tobramycin ointment) was applied to both eyes twice on the day before treatment, following the injection and at least once on the day following the injection. Prior to dosing, mydriatic drops (1% tropicamide and/or 2.5% phenylephrine) were applied to each eye (further applications may be performed as considered appropriate by the veterinary ophthalmologist). During dosing, animals were maintained under anesthesia with isoflurane/oxygen gas. The conjunctivae were flushed with 0.9% Sodium Chloride for Injection USP. A 29-gauge, ½-inch needle attached to a 0.5 cc Terumo insulin syringe was used for each subconjunctival injection (one syringe/group/treatment). Test items or reference item were administered into the eyes of each animal at a dose volume of 50 µL/eye. Both eyes were examined immediately following each treatment to document any abnormalities caused by the administration procedure. Streptozotocin is being administered IV to induce diabetic retinopathy in the rat. The subconjunctival route has been selected for the Test Item because this is the intended route of administration in humans. The dose levels were selected based on information obtained with previous proof of concept studies as well as MTD and toxicity studies using the subconjunctival route of administration. Morbidity/mortality checks were performed at least twice daily (AM and PM). Cage side observations were performed once daily. Detailed clinical examinations were performed weekly. Quantitative food consumption were performed weekly. Body weights were recorded twice weekly. Ophthalmic examinations were performed once prestudy and again on Day 37 (Rep 1), Day 36 (Rep 2 and 3) and Day 35 (Rep 4). All animals were subjected to funduscopic (indirect ophthalmoscopy) and biomicroscopic (slit lamp) examinations. The mydriatic used will be 1% tropicamide. Intraocular pressure was measured once prestudy and on Day 37 (Rep 1), Day 36 (Rep 2 and 3) and Day 35 (Rep 4). The pre-treatment tonometry readings were performed at the same times as anticipated for the final measurements to reduce diurnal variability. Intraocular pressure was measured following the ophthalmology examinations, using a TonoVet™ rebound tonometer.

Electroretinogram evaluations were performed once pretreatment and on Days 7, 14, 21, and Day 36 (Rep 1), Day 35 (Rep 2 and 3) and Day 34 (Rep 4). Animals were dark-adapted overnight prior to ERG recording and then anesthetized with an intramuscular injection of 75 mg/kg ketamine and 7.5 mg/kg xylazine. Tropicamide (1%) was applied to each eye prior to the test (further applications may be administered if considered necessary). The eyelids were retracted by means of a lid speculum, and a contact lens or gold loop electrode was placed on the surface of each eye. A needle electrode was placed cutaneously under each eye (reference) and on the head posterior to the brow or at the base of the tail (ground). Carboxymethylcellulose (1%) drops were applied to the interior surface of the contact lens electrodes prior to placing them on the eyes.
1) −30 dB single flash, average of 5 single flashes, 10 second between flashes
2) −10 dB single flash, average of 5 single flashes, 15 seconds between flashes.
3) 0 dB, average of 2 single flashes, approximately 120 seconds between flashes (a longer time period is acceptable).

Following evaluation of the scotopic response, the animals were adapted to background light at approximately 25 to 30 cd/m$^2$ for a period of approximately 5 minutes (a longer time period is acceptable), followed by an average of 20 sweeps of photopic white flicker at 1 Hz, then 20 sweeps of photopic flicker at 29 Hz. Waveforms were analyzed for a- and b-wave amplitudes and latency and oscillatory potentials 1 through 4 from the 0 dB scotopic stimulus will be filtered and analyzed for amplitude and latency.

Indocyanin Green angiography evaluations were performed once pretreatment (Day −2 or −1) and on Days 8, 15, 22, and Day 35 (Rep 1), Day 34 (Rep 2 and 3) and Day 33 (Rep 4). An isoflurane/oxygen mix was used prior to and during the procedure as the anesthesia. The mydriatic agent used was 1% tropicamide as necessary. Hydration of the eyes was maintained by irrigation with saline solution, as needed. 0.2 mL of 0.5% Indocyanin Green was administered via rapid tail vein injection, followed by a 0.5 mL saline flush. Still images of the fundus were recorded from both eyes between 10-15 minutes following the ICG injection. Images were taken from the right eye first, followed by the left. A topical bland ophthalmic ointment was administered to the eyes following the angiographies. Images were evaluated qualitatively for vascular integrity/diffuse leakage.

Blood glucose level were measured once pre-STZ treatment, on Day −6 (the day following STZ administration) and again on Day −1. Additional blood glucose measurements may be performed as required to monitor animal health status. Levels were determined by glucometer using blood drops taken in the tail vein. Values were measured in mmol/L and converted into mg/dL by multiplying by 18 for reporting purposes.

Main study animals surviving until scheduled euthanasia were euthanized by exsanguination from the abdominal aorta after isoflurane anesthesia. When possible, the animals were euthanized rotating across dose groups such that similar numbers of animals from each group, including controls were necropsied at similar times throughout the day. Representative samples of the tissues (eye, nerve optic) were collected from all animals and preserved in 10% neutral buffered formalin, unless otherwise indicated. Eyes and optic nerves collected bilaterally and fixed in Davidson's fixative 24 to 48 hours and then stored in 70% ethanol (euthanized animals only).

Example 27: A Randomized, Double-Blind, Parallel Group, Controlled, Multicentre Trial to Assess the Efficacy and Safety of a Single Sub-Conjunctival Injection of XG-102, Compared to Dexamethasone Eye Drops in Post-Surgery Intraocular Inflammation (Clinical Phase II)

Despite technical advances in ocular surgery, the physical trauma of this procedure continues to induce post-operative ocular inflammation warranting treatment. In ocular tissue, arachidonic acid is metabolized by cyclooxygenase (COX) to prostaglandins (PG) which are the most important lipid-derived mediators of inflammation1. Surgical trauma causes a trigger of the arachidonic acid cascade which in turn generates PGs by activation of COX-1 and COX-2. Phospholipids in the cell membrane are the substrate for phospholipase A to generate arachidonic acid from which a family of chemically distinct PGs and leukotriens are produced2. The 'golden standard' for the treatment of ocular inflammation are topical corticosteroids and/or Non-Steroidal Anti-inflammatory Drugs (NSAIDs). Side effects reported with (short-term) corticosteroid use include cataract formation, increased Intra Ocular Pressure (IOP), increased susceptibility to viral infections and retardation of the corneal epithelial and stromal wound healing3, 4. In addition, prolonged treatment with corticosteroids have been known to induce systemic side effects such as glucose impairment, hypertension, development of glaucoma, visual acuity defects, loss of visual field, and posterior subcapsular cataract formation5. The Investigational Medicinal Product (IMP) under investigation—XG-102—is a protease-resistant peptide that selectively inhibits c-Jun N-terminal Kinase (JNK) activity in a non-Adenosine Triphosphate (ATP) competitive manner. XG-102 is a 31 D-amino acids JNK inhibitor peptide with all amino acids except glycine (which is achiral) in the D-configuration. This choice was made to increase the resistance of the compound to proteases, which usually degrade peptides soon after their administration. Since JNK activation leads to the phosphorylation and activation of the activator protein-1 (AP-1) transcription factor family and other cellular factors implicated in autoimmune and inflammatory diseases, compounds that inhibit the JNK pathway may have an indicated therapeutic value. Ocular MTD (Maximum Tolerated Dose) studies in rats and rabbits as well as ocular local tolerance in rabbits showed that XG-102 was well-tolerated after sub-conjunctival, intravitreal (IVT) and intravenous (iv) administrations. Ocular MTD studies in rats and rabbits after sub-conjunctival administration showed that the No Observed Adverse Effect Level (NOAEL) was around 20 µg in rats and 600 µg in rabbits. Ocular pharmacokinetics after single and repeated (daily for 7 days) sub-conjunctival administration have been studied in rabbits and showed that XG-102 was still present in choroid, bulbar conjunctiva and iris-ciliary body 7 days after administration with a tmax between 1 and 4 hours depending on the ocular structure, whereas no XG-102 was detectable at any time in plasma. Given the deleterious side effects of the current 'golden standard' to treat (post-operative) intraocular inflammation, it is clinically justified to find other treatment alternatives which on the one hand are efficacious in reducing the inflammation while on the other hand, do not have the (deleterious) side effects associated with corticosteroid use. XG-102 has shown promising results both in the pre-clinical studies and phase I/Ib studies performed to date.

The previous trial was an open label, single-center, dose escalation/dose finding study which was designed to assess the safety and tolerability of a single sub-conjunctival injection of XG-102, administered in addition to the 'usual' post-op anti-inflammatory therapy in patients with post-surgery or post-traumatic intraocular inflammation. The XG-102 doses which were investigated were 45, 90, 450 and 900 µg. In total, 20 patients (5 patients in each dose group) were enrolled in this study. The conclusion of the previous study was that XG-102, administered as a sub-conjunctival injection in patients with recent post-surgery or trauma intraocular inflammation was safe and well tolerated. Following the successful completion of the previous study, it was decided to continue with the development of XG-102 in intraocular inflammation and to perform the present study where the objective was to evaluate the efficacy and safety, compared to dexamethasone eye drops, of a single sub-conjunctival dose of XG-102 administered immediately post-op in the evolution of post-op intraocular inflammation, as assessed by chamber cell grade. This is the first study investigating the efficacy of XG-102 when administered as a stand-alone therapy in the evolution of post-operative intraocular inflammation.

The objectives of the SDD-1002-035 study were to evaluate the efficacy and safety of a single sub-conjunctival injection of XG-102 90 or 900 µg administered within maximally 3 hours after the end of the surgical procedure compared to dexamethasone eye drops administered 4 times/day for 21 days in post-operative intraocular inflammation.

The primary objective of the SDD-1002-035 study was to evaluate if a single sub-conjunctival injection of 900 µg XG-102 is non-inferior to treatment with dexamethasone eye drops administered 4 times/day for 21 days in the evolution of post-operative intraocular inflammation. In accordance with this trial's primary objective, the primary outcome was evaluated by the mean anterior chamber cells grade at day 28 post-administration of the sub-conjunctival injection of study treatment comparing XG-102 900 µg with dexamethasone eye drops.

The secondary objectives were to evaluate the effect of a single sub-conjunctival injection of either 90 µg or 900 µg XG-102 compared to dexamethasone eye drops (4 times/day, administered for 21 days) on:

Efficacy Outcome Parameters
a) Anterior chamber cells grade at day 28 (XG-102 90 µg vs dexamethasone)
b) Anterior chamber cells grade at day 7 and day 14 (XG-102 900 µg vs dexamethasone)
c) Anterior chamber cells grade at day 7 and day 14 (XG-102 90 µg vs dexamethasone)
d) Anterior chamber flare grade at day 7, 14 and day 28 (XG-102 900 µg vs dexamethasone)
e) Anterior chamber flare grade at day 7, 14 and day 28 (XG-102 90 µg vs dexamethasone)
f) Rescue medication use
g) Evolution of the intraocular inflammation over time
Safety and Tolerability Outcome Parameters:
a) Visual acuity by ETDRS method
b) Slit Lamp examination findings
c) The results of the ophthalmic fundus examination
d) Intra Ocular Pressure (IOP) measurements
e) Vital signs (blood pressure (BP), pulse rate (PR) and rhythm)
f) The results of the hematology and chemistry laboratory tests
g) The occurrence of Adverse Events
h) Presence (or not) of XG-102 in plasma 1 hour after the administration of study treatment in a subset of patients (approximately 30)

The present trial was a randomized (1:1:1), controlled, double-blind, multicenter non-inferiority clinical trial with three parallel groups of equal size. Randomization, which was blocked by center, was performed using a web-based, secure, randomization system. Eligible patients were male or female (post-menopausal, or sterile by tubal ligation or hysterectomy), who were >18 years of age and who had undergone one of the following ocular surgeries: (a) anterior and posterior segment combined surgery which may include surgery for: cataract and retinal detachment, cataract and epimacular membrane and/or cataract and macular hole or (b) glaucoma surgery or (c) complex posterior segment surgery or (d) complicated intraocular surgery which may include cataract surgery associated with diabetic retinopathy and/or complicated retinal detachment ocular surgery. Patients were not eligible to participate if any of the following exclusion criteria was present at the moment of randomization:

1. Administration of any investigational drug within 12 weeks prior to the administration of study treatment.
2. Presence of a contraindication to prescribe dexamethasone eye drops.
3. Existence of a persistent fungal or bacterial eye infection, refractory to anti-infective treatment.
4. History of intraocular hypertension known to be provoked by corticosteroid use.

5. Presence of a corneal ulcer, corneal perforation or lesion associated with an incomplete re-epithelialization.
6. Existence of any surgical or medical condition which, in the judgment of the Investigator, might interfere with this study.
7. A history of any serious adverse reaction or hypersensitivity to protein-type drugs or to vaccines.
8. Currently treated for seasonal allergic reactions (example: hay fever, asthma).
9. Females of childbearing potential.
10. Males not willing to use an effective method of contraception (e.g. combined contraceptive pill or barrier methods) with non-menopausal female partners up to day 28 (i.e. the date when the last visit is performed) in the study.
11. Patients not willing to comply with the provisions of this protocol.

The study protocol planned that 138 patients would be randomized and administered the sub-conjunctival injection of study treatment. It was also stated in the study protocol that randomized patients for whom the sub-conjunctival injection of study treatment was not administered would be replaced. Patients were randomly allocated to either XG-102 90 or 900 µg which was administered as a single, sub-conjunctival injection of 250 µl within maximally 3 hours after the end of the eye surgery or to dexamethasone eye drops, which were instilled 4 times per day for 21 days. The first study treatment eye drop was instilled within maximally 15 minutes after the sub-conjunctival injection of study treatment. In order to maintain the blinding, patients randomized to the XG-102 group received eye drops containing a NaCl 0.9% solution and patients randomized to the dexamethasone group were administered a sub-conjunctival injection containing NaCl 0.9%. Patients were followed for, in total, 28 (±5) days after administration of the sub-conjunctival injection of study treatment. They returned to the out-patient clinic to perform the visits/investigations as required by the study protocol. The below table shows planned visit schedule in addition to the procedures/investigations carried out at each visit. The study protocol planned that the data safety and monitoring board (DSMB) would be responsible to oversee patient safety. This was to be achieved by reviewing Serious Adverse Events (SAE) as they occurred in addition to reviewing the cumulative patient data during the study. Details concerning the timing of the data reviews were detailed in the DSMB charter.

| Assessment | Screening visit: prior to eye surgery | Visit 1 21 hrs (±3 hrs) after sub-conj. inj | Visit 2 7 days (±1 day) after sub-conj. inj | Visit 3 14 days (±2) after sub-conj. inj | Visit 4 28 days (±5) after sub-conj. inj |
|---|---|---|---|---|---|
| Written informed consent | x[a] | | | | |
| Demographic data, ophthalmolog, MH | x[b] | | | | |
| Body height, body weight | x[b] | | | | |
| Concomitant treatments | x[b] | x | x | x | x |
| Seated vital signs | x[b] | x | | | x |
| Ophthalmic fundus | x[b] | x | x | x | x |
| Intra Ocular Pressure | x[b] | x | x | x | x |
| Slit Lamp examination ± Laser Flare Meter | x[b] | x | x | x | x |
| Visual acuity examination (by ETDRS method) | x[b] | x | x | x | x |
| Blood sampling | x[b,c] | x | | | x |
| Final Inclusion/exclusion criteria review | x[b] | | | | |
| Randomization | x[d] | | | | |
| Preparation of study treatment syringe | x[e] | | | | |
| Admin. study treatment | x[f] | | | | |
| Blood sampling for XG-102 quantification | x[g] | | | | |
| Adverse Event reporting | x[h] | x | x | x | x |

[a]Informed consent was obtained prior to he surgical procedure being performed and prior to any study related procedure being performed.
[b]Was done prior to ocular eye surgery being performed.
[c]The following blood samples were performed prior to the surgical procedure being performed. Chemistry blood samples to be performed were: Aspartate Transaminase (AST), Alanine Transaminase (ALT), C-Reactive Protein (CRP), creatine kinase (CK), glucose, creatinine and gamma-glutamyl transferase. Hematology: hemoglobin (Hb), hematocrit (HCT) and full white cell count.
[d]Prior to performing the surgical procedure, the patient eligibility was determined. Eligible patients were randomized using the web-based system before the surgical procedure was started.
[e]The study treatment vial was removed from the freezer at least one hour prior to the sub-conjunctival injection. The vial was placed in a secure location at ambient temperature to defrost before preparation of the study treatment syringe. The study treatment eye drops were retrieved from the pharmacy at the same time as the study treatment vials.
[f]The administration of study treatment (sub-conjunctival injection and eye drops) was done within maximally 3 hours after the end of the surgical procedure. The sub-conjunctival injection was administered first, followed by the eye drops 5 to 15 minutes later.
[g]Was done 1 hour after administration of study treatment in approximately 30 patients recruited from the Hotel-Dieu Hospital.
[h]Observation for the occurrence of Adverse Events started as soon as the administration of study treatment was started.

Patients were randomized to one of the three study groups:
1. A single sub-conjunctival injection of XG-102 90 µg+placebo eye drops 4 times/day for 21 days or
2. A single sub-conjunctival injection of XG-102 900 µg+placebo eye drops 4 times/day for 21 days or
3. A single sub-conjunctival injection of NaCl 0.9%+ dexamethasone eye drops 4 times/day for 21 days.

Randomization, which was blocked by center, was done centrally using a web-based (i.e. e-SOCDAT™) randomization system.

The Test product XG-102 was used at doses 90 and 900 µg (single administration of 250 µl). Mode of administration was a single sub-conjunctival injection. Duration of treatment was one single administration (sub-conjunctival injection). (Manufacturing batch number XG-102 90 µg: PF.243.CR and Manufacturing batch number XG-102 900 µg: PF.245.CR)

The Reference product Dexamethasone (Dexafree®) was used at a dose of 1 mg/ml. Mode of administration was eye drop (4 times/day, 21 days). Duration of treatment was 21 days—4 times/day. (Batch number: X750 and Z472)

The Placebo NaCl was used at a dose of 0.9%. Mode of administration was a single sub-conjunctival injection (250 µL) or eye drop (4 times/day, 21 days). Duration of treatment was one single administration (sub-conjunctival injection) and for the eye drops, 21 days—4 times/day. Manufacturing batch number: Y479 (eye drops) and 1139512112 (sub-conjunctival injection.

Based on preclinical pharmacology and toxicology studies in addition to the safety and preliminary efficacy data obtained from the previous study, two doses—90 and 900 µg XG-102—were selected for this trial. In the SDD-1002-023 study, the safety profile of the 90 and 900 µg doses were similar. In addition, the reduction of the intraocular inflammation, in combination with corticosteroid eye drops, behaved in the same manner in both dose groups. Taking into account the precautionary measures taken for this study (role of the DSMB, and possibility to introduce open label anti-inflammatory treatment in the case of persistent inflammation), the XG-102 doses selected for this study were on the one hand, considered not to compromise patient safety while on the other hand, were sufficiently high to provide meaningful data for the objectives of the study. The sub-conjunctival route of administration is one of the intended routes of administration for patients with the diagnosis under investigation as both safety and efficacy has been shown in animals and in humans using this route of administration. The dexamethasone dose (i.e. 1 mg/ml/0.4 ml eye drops) in addition to the frequency (i.e. 4 drops per day) and duration (i.e. 21 days) for use chosen for this study is the standard dose/duration of use for dexamethasone eye drops as used in clinical practice for post-operative ocular inflammation.

The study protocol stipulated that the sub-conjunctival injection of study treatment was to be administered within maximally 3 hours at the end of the eye surgery and that this was to be followed within maximally 15 minutes by the instillation of the first study treatment eye drop. The administration of the study treatments at the end of the ocular surgery followed the standard routine for the administration of anti-inflammatory treatments following the eye surgery procedures which were part of the study inclusion.

Neither the Investigator, the patient, the operational team at the CC (Coordinating Center) nor the Sponsor personnel (other than pharmacovigilance staff) had access to the randomization plan. The study treatment vials containing the XG-102 solution or placebo (i.e. NaCl 0.9% solution) were identical in appearance and consistency. The eye drop solutions in single dose containers containing either dexamethasone solution or NaCl 0.9% were identical in appearance and consistency. The packaging and labeling of study treatment was performed according to GMP (Good Manufacturing Practice) and GCP (Good Clinical Practice). In addition, the content of the labels affixed on the study treatment packs was in accordance with local regulations for clinical trials. For each patient two identically numbered study treatment packs were supplied. One study treatment 'pack' contained 1 vial of XG-102 solution (90 or 900 µg) or 1 vial of placebo (NaCl 0.9%)—depending on the treatment group to which the patient was randomized—and the second 'pack' contained the eye drop solution in single dose containers containing either dexamethasone or placebo (NaCl 0.9%) with sufficient supplies to enable treatment for 4 times/day for 21 days. Once allocated to a patient, a study treatment pack number was not allocated to another patient. The patient's study identification number (i.e. patient identification number) was written on the label by hand by the person who handed out the study treatment. The size and shape of the outer study treatment boxes were identical for the XG-102 and placebo solutions. In an emergency situation where knowledge of a patient's study treatment allocation would have been necessary to determine the further medical management of the patient concerned, or if knowledge of a patient's treatment allocation was required for regulatory reporting purposes, the blinded Investigator or the Sponsor delegated pharmacovigilance officer, respectively had the user access rights to the study treatment code for the patient concerned via the secure, web-based trial-specific treatment allocation system within e-SOCDATTM. If the treatment code was accessed for any one patient, all information (i.e. the name of the person who accessed the treatment code, the reason, date and time and patient for whom the code was accessed) concerning study treatment code access, would be tracked and stored in the web-based system if the study treatment code was accessed.

The primary objective was evaluated by the mean anterior chamber cells grade at day 28 post-administration of the sub-conjunctival administration of study treatment. The criteria for evaluation of the primary objective was
a. Anterior chamber cells grade at day 28 (XG-102 900 µg vs dexamethasone).

The criteria for evaluation of the secondary objectives were
a. Anterior chamber cells grade at day 28 (XG-102 90 µg vs dexamethasone
b. Anterior chamber cells grade at day 7 and day 14 (XG-102 900 µg vs dexamethasone)
c. Anterior chamber cells grade at day 7 and day 14 (XG-102 90 µg vs dexamethasone)
d. Anterior chamber flare grade at day 7, 14 and day 28 (XG-102 900 µg vs dexamethasone)
e. Anterior chamber flare grade at day 7, 14 and day 28 (XG-102 90 µg vs dexamethasone)
f. Rescue medication use
g. Evolution of the intraocular inflammation over time as assessed by Cleared ocular inflammation.

The flow chart depicting the timing and frequency of the visits in addition to the procedures to be performed at each visit may be found in the table above. The ophthalmology examinations were performed at baseline (i.e. either on the day of surgery, but before the surgery was performed). Thereafter, patients were seen at 21 (±3) hours after the sub-conjunctival injection was administered, and then at 7 (±1), 14 (±2) and 28 (±5) days. In order to reduce operator variability, the sites were instructed that, where possible, the same operator should perform all ophthalmology examinations for the same patient throughout the trial. The ophthalmology measurements were performed in accordance with the study-specific instructions. The latter were reviewed and discussed with the site teams during the initiation visit and during each monitoring visit. For the determination of the cell/flare count and cell/flare grade, the SUN Working Group's consensus was used by the sites using the SUN Working group definitions ("Standardization of Uveitis Nomenclature for Reporting Clinical Data. Results of the First International Workshop.," American Journal of Ophthalmology, vol 140, no. 3, pp. 509-516, 2005).

The criteria for evaluation of safety were:
a. Visual acuity by ETDRS method
b. Slit Lamp examination findings
c. The results of the ophthalmic fundus examination
d. Intra Ocular Pressure (IOP) measurements
e. Vital signs (blood pressure (BP), pulse rate (PR) and rhythm)

f. The results of the hematology and chemistry laboratory tests
g. The occurrence of Adverse Events
h. Presence (or not) of XG-102 in plasma 1 hour after the administration of study treatment in a subset of patients (approximately 30).

The definitions for an adverse event were:

An Adverse Event (AE) is defined as 'any untoward medical occurrence in a patient administered a medicinal product and which does not necessarily have a causal relationship with this treatment'. An AE is therefore any unfavorable and unintended sign, symptom or disease temporally associated with the use of a medicinal product, whether or not considered related to the medicinal product.

An AE was considered to be serious if the event:
resulted in death
was life-threatening
required in-subject hospitalization or prolongation of existing hospitalization
resulted in persistent or significant disability/incapacity
resulted in a congenital anomaly/birth defect in an offspring conceived during the treatment period
was medically significant and jeopardizes the patient or requires intervention to prevent one of the above outcomes The term "life-threatening" in the definition of "serious" referred to an event in which the subject was at risk of death at the time of the event; it did not refer to an event which hypothetically might have caused death, were it more severe. A Suspected Unexpected Serious Adverse Reaction (SUSAR) was defined as a suspected adverse reaction related to the treatment that is both unexpected (i.e. not consistent with the expected outcomes of the study treatment being administered) and serious.

The quantification (plasma) of XG-102 in plasma was evaluated in a subset of 32 patients located in one site. A venous blood sample (2 ml) was obtained using a Li-Heparin tube 60 minutes after sub-conjunctival administration of study treatment. The exact time when the sample was performed was entered in the space provided on the e-CRF. The blood sample was centrifuged for 10 minutes at 2,500 RPM at room temperature. After centrifugation, using a pipette, the plasma was transferred to two 1.5 ml cryotubes. The cryotubes were then placed in a freezer at −80° C. and were then subsequently sent in dry ice with a temperature data logger to the central laboratory responsible for the analysis. Upon receipt at the central laboratory, the samples were stored at −80° C. until analyzed.

Statistical methods: The primary objective was a non in-inferiority comparison between XG-102 900 µg and dexamethasone eye drops on anterior chamber cell grade at day 28 following the sub-conjunctival injection of study treatment. The primary outcome was analyzed for the Per-Protocol (PP) population and repeated for sensitivity reasons on the Full Analysis Set (FAS). Non-inferiority of XG-102 900 µg to dexamethasone could be declared if the upper bound of the 95% CI around the estimated difference lay below 0.5 anterior chamber cell grade. The first secondary end-point-anterior chamber cell grade at day 28 comparing XG-102 90 µg and dexamethasone was analyzed in the same manner as for the primary outcome. All other secondary outcomes were evaluated by superiority testing on the FAS using a two-sided alpha value of 0.005. The safety analyses were performed on the FAS group by treatment received.

Figure 59:
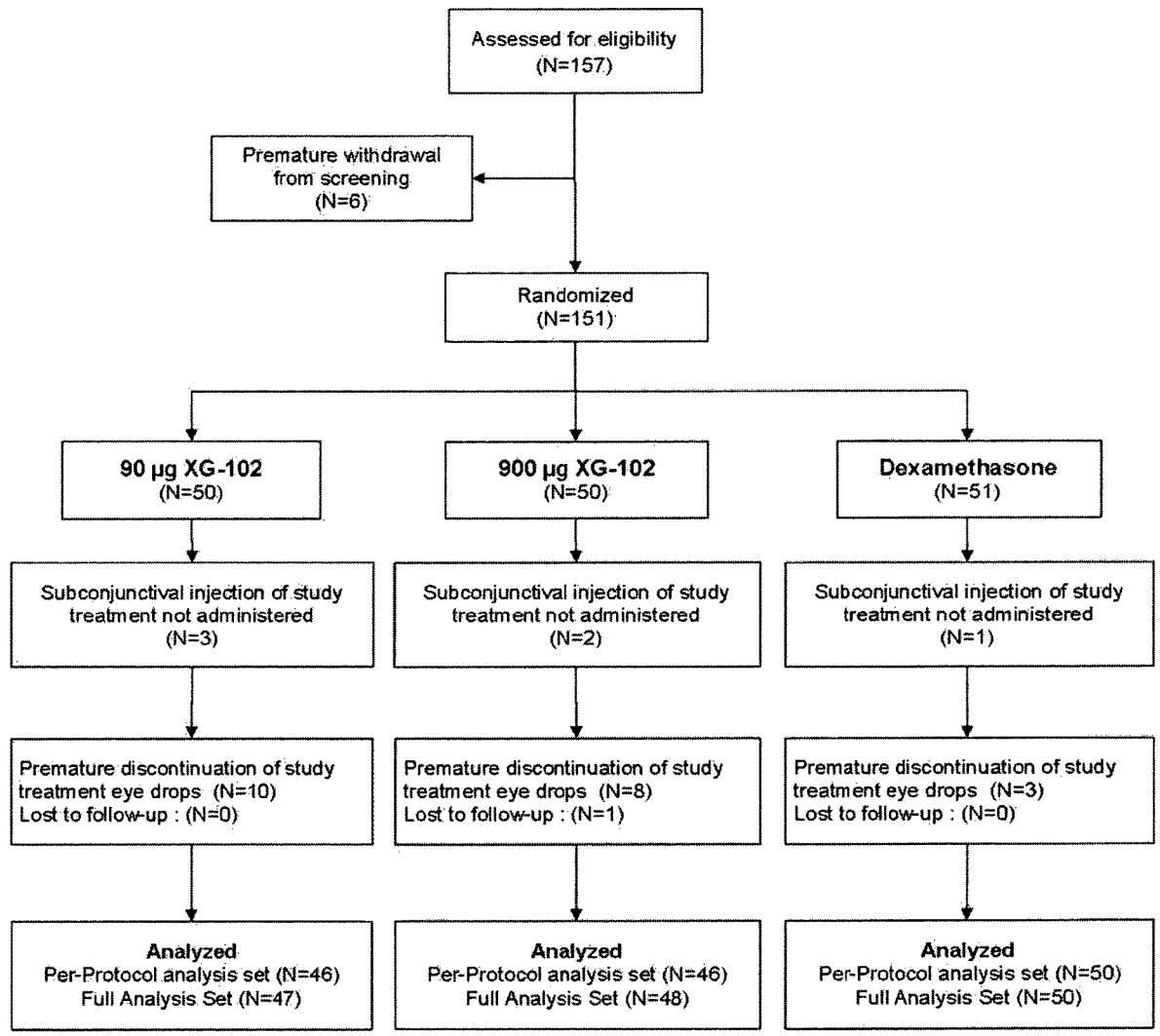
FIG. 59 The disposition of patients included in the study of Example 27, i.e. the randomized, double-blind, parallel group, controlled, multicentre trial to assess the efficacy and safety of a single sub-conjunctival injection of XG-102, compared to dexamethasone eye drops in post-surgery intraocular inflammation (Clinical Phase II).

The disposition of patients included in the present study is shown in FIG. 59. The first patient provided informed consent on Jul. 18, 2012. The last patient was randomized on Sep. 2, 2013 with the last patient, last visit being performed on Oct. 3, 2013. In total, 157 patients provided informed consent and 151 of these were randomized. Of the 151 randomized patients, 6 were not administered the sub-conjunctival injection of study treatment. As per the requirements in the study protocol, these randomized patients were replaced. In total, 145 patients were administered the sub-conjunctival injection of study treatment (i.e. XG-102 or placebo) and 144 patients completed the study as planned by the study protocol. In total, 1 patient withdrew from follow-up. The following Table displays the completeness of follow-up for the three study groups:

|  | 90 µg XG-102 (N = 47) # patients (%) | 900 µg XG-102 (N = 48) # patients (%) | Dexamethasone (N = 50) # patients (%) |
| --- | --- | --- | --- |
| Randomized | 50 | 50 | 51 |
| Randomized but not administered study tx | 3 | 2 | 1 |
| Randomized and administered study tx | 47 (100.0%) | 48 (100.0%) | 50 (100.0%) |
| Premature withdrawal of study tx eye drops | 10 (21.3%) | 8 (16.7%) | 3 (6.0%) |
| Premature withdrawal from follow-up | 0 (0.0%) | 1 (2.1%) | 0 (0.0%) |
| Visit 4 performed as planned by the protocol | 47 (100.0%) | 47 (97.9%) | 50 (100.0%) |
| Lost to follow-up | 0 (0.0%) | 1 (2.1%) | 0 (0.0%) |

Data are number of patients (%).
N = Number of patients in each group,
# = number,
µg = microgram,
% = percentage,
tx = treatment.

The Full Analysis Set (FAS) comprised all randomized patients for whom the sub-conjunctival injection of study treatment was started/administered. The FAS set was analyzed according to the intention-to-treat principle, i.e. patients were evaluated in the treatment group to which they were randomized irrespective of the treatment received. In addition, data was removed from the FAS analysis sets for visits which were performed outside the allowed time windows.

The PP analysis set was a subset of the FAS. Patients were excluded from the PP analysis data set in case because of either major violations after randomization and/or introduction of open label anti-inflammatory treatment during follow-up. In addition, data was removed from the PP analysis sets for visits which were performed outside the allowed time windows.

The safety set included all randomized patients for whom the sub-conjunctival injection of study treatment was started/administered. Patients were analyzed as treated, i.e. according to the treatment which they received. The safety set was the primary analysis set for the safety analysis.

The baseline characteristics and comorbidities were balanced between the three treatment groups both for FAS and PP populations. The table below shows some of the main baseline co-morbidities by treatment group for the PP analysis population. The percentage of patients with retinal detachment was higher in patients allocated to the XG-102 90 µg (52%) compared to the XG-102 900 µg (41%) and the dexamethasone groups (40%) while the percentage of patients with diabetes was higher in patients randomized to XG-102 900 µg group (33%) compared to XG-102 90 µg group (22%) and dexamethasone group (26%).

|  | 90 µg XG-102 (N = 46) # patients (%) | 900 µg XG-102 (N = 46) # patients (%) | Dexamethasone (N = 50) # patients (%) |
| --- | --- | --- | --- |
| Retinal detachment | 24 (52.2%) | 19 (41.3%) | 20 (40.0%) |
| Glaucoma | 6 (13.0%) | 6 (13.0%) | 6 (12.0%) |
| Diabetic retinopathy | 5 (10.9%) | 6 (13.0%) | 4 (8.0%) |
| Hypertension | 16 (34.8%) | 25 (54.3%) | 24 (48.0%) |
| Diabetes | 10 (21.7%) | 15 (32.6%) | 13 (26.0%) |
| Hypercholesterolemia | 17 (37.0%) | 20 (43.5%) | 21 (42.0%) |

Data are number of patients (%).
N = Number of patients in each group,
# = number,
µg = microgram,
% = percentage.

The following table shows, by treatment group, the indication for ocular surgery at baseline in addition to the type of surgery performed for the PP analysis population. The percentage of patients who underwent complex posterior segment surgery was higher in patients allocated to the XG-102 90 µg (50%) compared to those allocated to the XG-102 900 µg (46%) and the dexamethasone groups (42%). The percentage of patients in each treatment group for whom gas (SF6 or C2F6) was instilled during the surgery performed at baseline was 43% (XG-102 90 µg), 37% (XG-102 900 µg) and 38% (dexamethasone) respectively.

|  | 90 µg XG-102 (N = 46) # patients (%) | 900 µg XG-102 (N = 46) # patients (%) | Dexamethasone (N = 50) # patients (%) |
| --- | --- | --- | --- |
| Type of ocular surgery |  |  |  |
| Anterior and posterior segment combined surgery | 18 (39.1%) | 22 (47.8%) | 26 (52.0%) |
| Glaucoma surgery | 5 (10.9%) | 3 (6.5%) | 3 (6.0%) |
| Complex posterior segment surgery | 23 (50.0%) | 21 (45.7%) | 21 (42.0%) |
| Eye concerned |  |  |  |
| Left | 17 (37.0%) | 23 (50.0%) | 25 (50.0%) |
| Right | 29 (63.0%) | 23 (50.0%) | 25 (50.0%) |
| Indication of ocular surgery |  |  |  |
| Cataract | 19 (28.8%) | 22 (31.4%) | 25 (31.6%) |
| Epimacular membrane | 8 (12.1%) | 8 (11.4%) | 10 (12.7%) |
| Epiretinal membrane | 4 (6.1%) | 6 (8.6%) | 10 (12.7%) |
| Foveoschisis | 0 (0.0%) | 0 (0.0%) | 1 (1.3%) |
| Intravitreous hemorrhage | 5 (7.6%) | 4 (5.7%) | 3 (3.8%) |
| Macular hole | 2 (3.0%) | 6 (8.6%) | 2 (2.5%) |
| Neovascular glaucoma | 1 (1.5%) | 0 (0.0%) | 0 (0.0%) |
| Relief of intraocular pressure | 5 (7.6%) | 3 (4.3%) | 3 (3.8%) |
| Retinal detachment | 22 (33.3%) | 19 (27.1%) | 20 (25.3%) |
| Subluxation of intraocular lens | 0 (0.0%) | 1 (1.4%) | 0 (0.0%) |
| Subluxation of lens | 0 (0.0%) | 0 (0.0%) | 1 (1.3%) |
| Vitreomacular traction | 0 (0.0%) | 1 (1.4%) | 4 (5.1%) |
| Type of gas | 20 (43.5%) | 17 (37.0%) | 19 (38.0%) |
| SF6 | 11 (55.0%) | 11 (64.7%) | 12 (63.2%) |
| C2F6 | 9 (45.0%) | 6 (35.3%) | 7 (36.8%) |

Figure 60:
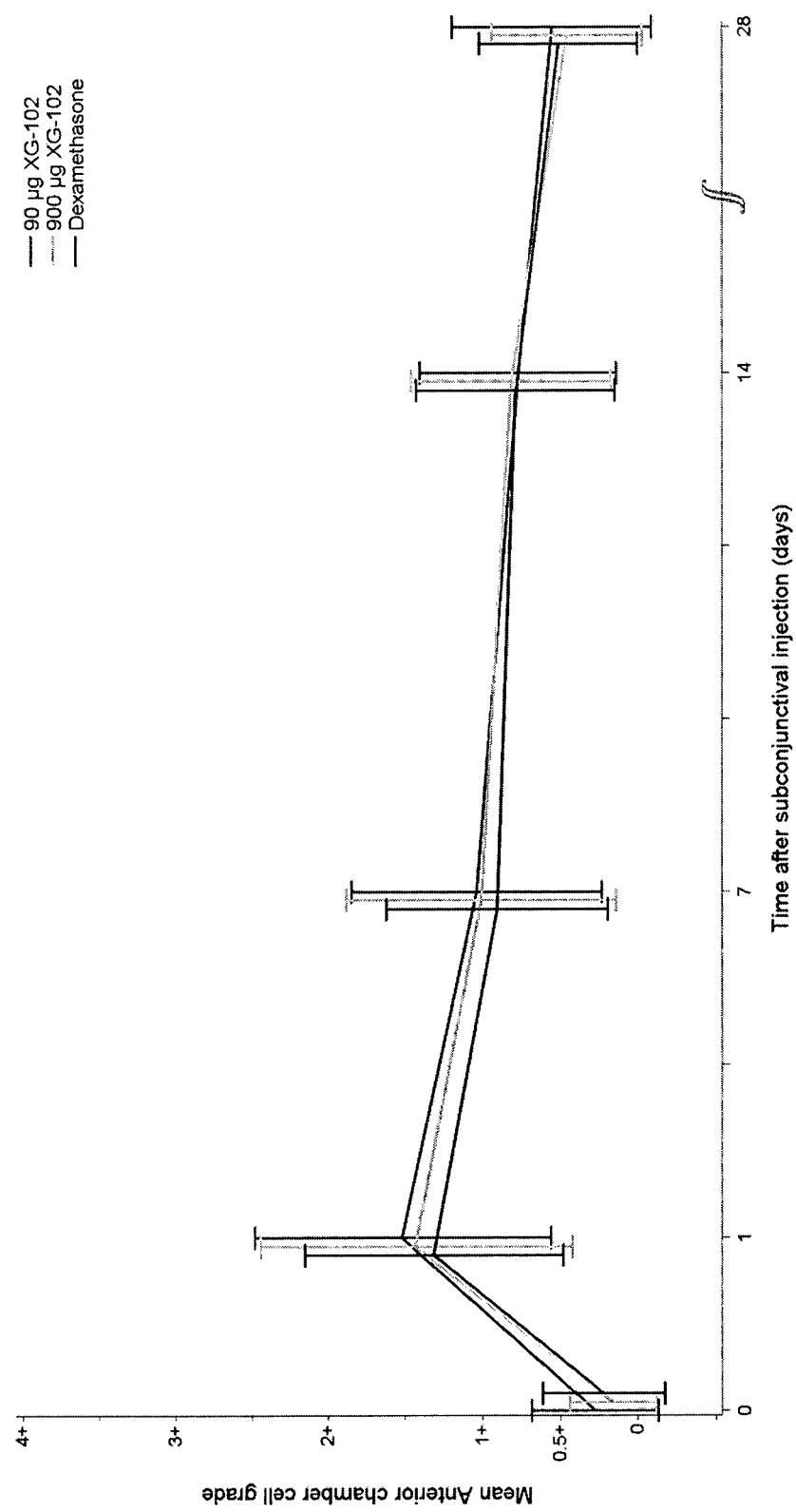
FIG. 60 shows for the study of Example 27 the mean anterior chamber cell grade up to 28 days after the administration of the sub-conjunctival injection of study treatment for the PP analysis population for the three treatment groups XG-102 90 µg, XG-102 900 µg and the dexamethasone. The vertical lines represents the standard deviations (SD).

Data are number of patients (%).
N = Number of patients in each group,
# = number,
µg = microgram,
% = percentage,
SD = Standard deviation.
Nr. available = Number of patients for whom data are available Anterior Chamber Cell Grade at Day 28—XG-102 900 µg Vs Dexamethasone:

The primary endpoint was analyzed as the mean difference in the anterior chamber cells grade at day 28, comparing the XG-102 900 µg dose with the dexamethasone group, using an adjusted repeated measures model. Only data collected for the day 7, 14 and 28 visits were used in the repeated model. The primary analysis was performed on the PP analysis data set and a sensitivity analysis was performed on the FAS data set. For the first secondary outcome,—i.e. Anterior chamber cells grade at day 28 (XG-102 90 µg vs dexamethasone)—non-inferiority was determined in the same manner as for the primary endpoint, using the same non-inferiority margin of 0.5 anterior chamber cell grade. The mean anterior chamber cell grade up to 28 days after the administration of the sub-conjunctival injection of study treatment for the PP analysis population is shown in FIG. 60 for the three treatment groups—i.e. XG-102 90 µg, XG-102 900 µg and the dexamethasone—while the statistical model results are shown in the following table:

| Dose group | Model adjusted mean [95% CI] | Dose group comparison | Estimated difference [95% CI] | Pvalue (non-inferiority) | Pvalue (superiority) |
| --- | --- | --- | --- | --- | --- |
| Visit 2 (7 days +/− 2 days after administration of study tx) | | | | | |
| XG-102 90 µg | 1.05 [0.84-1.26] | XG-102 90 µg versus Dexamethasone | 0.142 [−0.142-0.425] |  | 0.327 |
| XG-102 900 µg | 0.96 [0.76-1.16] | XG-102 900 µg versus Dexamethasone | 0.056 [−0.222-0.333] |  | 0.694 |
| Dexamethasone | 0.91 [0.72-1.10] | XG-102 900 µg versus XG-102 90 µg | −0.086 [−0.377-0.205] |  | 0.561 |

-continued

| Dose group | Model adjusted mean [95% CI] | Dose group comparison | Estimated difference [95% CI] | Pvalue (non-inferiority) | Pvalue (superiority) |
|---|---|---|---|---|---|
| Visit 3 (14 days +/− 3 days after administration of study tx) | | | | | |
| XG-102 90 μg | 0.80 [0.58-1.01] | XG-102 90 μg versus Dexamethasone | 0.009 [−0.278-0.296] | | 0.948 |
| XG-102 900 μg | 0.77 [0.56-0.98] | XG-102 900 μg versus Dexamethasone | −0.017 [−0.300-0.266] | | 0.906 |
| Dexamethasone | 0.79 [0.60-0.98] | XG-102 900 μg versus XG-102 90 μg | −0.026 [−0.323-0.271] | | 0.862 |
| Visit 4 (28 days +/− 8 days after administration of study tx) | | | | | |
| XG-102 90 μg | 0.58 [0.36-0.81] | XG-102 90 μg versus Dexamethasone | 0.086 [−0.214-0.385] | 0.003 | 0.573 |
| XG-102 900 μg | 0.44 [0.23-0.66] | XG-102 900 μg versus Dexamethasone* | −0.054 [−0.350-0.242] | <0.001* | 0.720 |
| Dexamethasone | 0.50 [0.30-0.70] | XG-102 900 μg versus XG-102 90 μg | −0.140 [−0.453-0.174] | | 0.381 |

CI = Confidence Interval,
μg = microgram,
% = percentage,
tx = treatment.
*Primary comparison'

Figure 61:
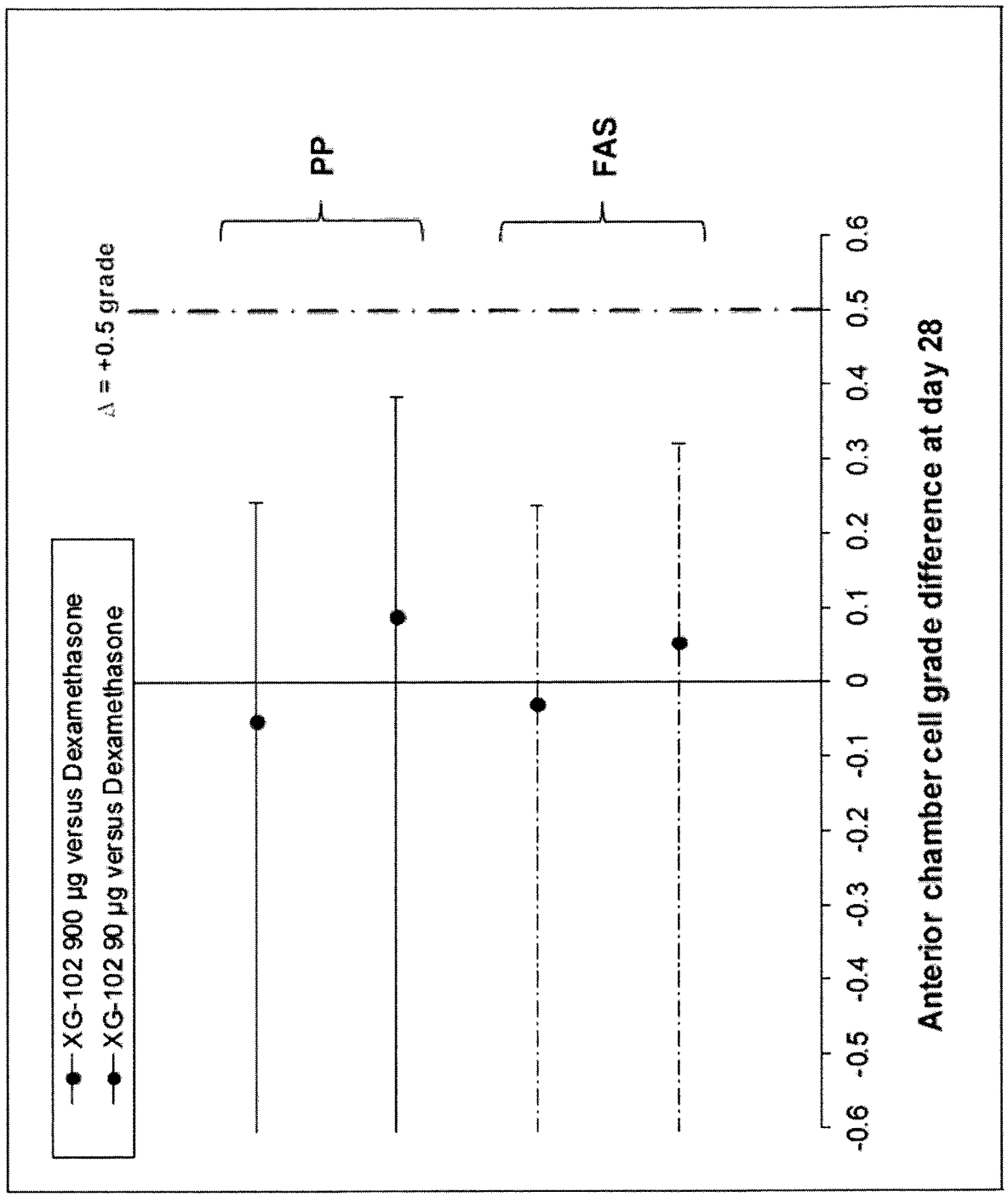
FIG. 61 shows for the study of Example 27 the results of the primary outcome in addition to the first secondary outcome for both the PP and FAS data sets regarding anterior chamber cell grade at day 28: Confidence Intervals and the Non-inferiority margin.

The results of the primary outcome in addition to the first secondary outcome are shown in FIG. 61 for both the PP and FAS data sets. XG-102 900 μg was non-inferior to dexamethasone eye drops in the evolution of post-operative intraocular inflammation as assessed by anterior chamber cell grade at day 28 (difference of −0.054 anterior cell grade, 95% Confidence Interval (CI) −0.350-0.242, p<0.001). The same analysis was repeated on the FAS and XG-102 900 μg was found to be non-inferior to dexamethasone eye drops (difference −0.032 cell grade, 95% CI—0.301-0.238, p<0.001). Given that the upper boundary crossed zero for the FAS and PP analysis sets, XG-102 900 μg was not superior to dexamethasone eye drops (p=0.818 for the FAS and p=0.720 for the PP analysis set) for anterior chamber cell grade at day 28.

Anterior Chamber Cell Grade at Day 28—XG-102 90 μg Vs Dexamethasone:

Concerning the secondary endpoint comparing XG-102 90 μg with dexamethasone eye drops, XG-102 90 μg was non-inferior to dexamethasone in the evolution of post-operative intraocular inflammation (difference 0.086 anterior cell grade, 95% CI—0.214-0.385, p=0.003). The same analysis was repeated on the FAS and XG-102 90 μg was found to be non-inferior to dexamethasone eye drops (difference of 0.053 anterior cell grade 95% CI—0.215-0.321 p<0.001).

Anterior Chamber Cell Grade at Day 7 and 14 for XG-102 90 μg Vs Dexamethasone and XG-102 900 μg Vs Dexamethasone:

The statistical analyses for the anterior chamber cell grade at day 7 and 14 for XG-102 90 μg vs dexamethasone and XG-102 900 μg vs dexamethasone were performed on the FAS data set. There were no statistically significant differences in anterior chamber cell grade between XG-102 90 μg and dexamethasone and between XG-102 900 μg and dexamethasone at either day 7 or day 14.

Figure 62:
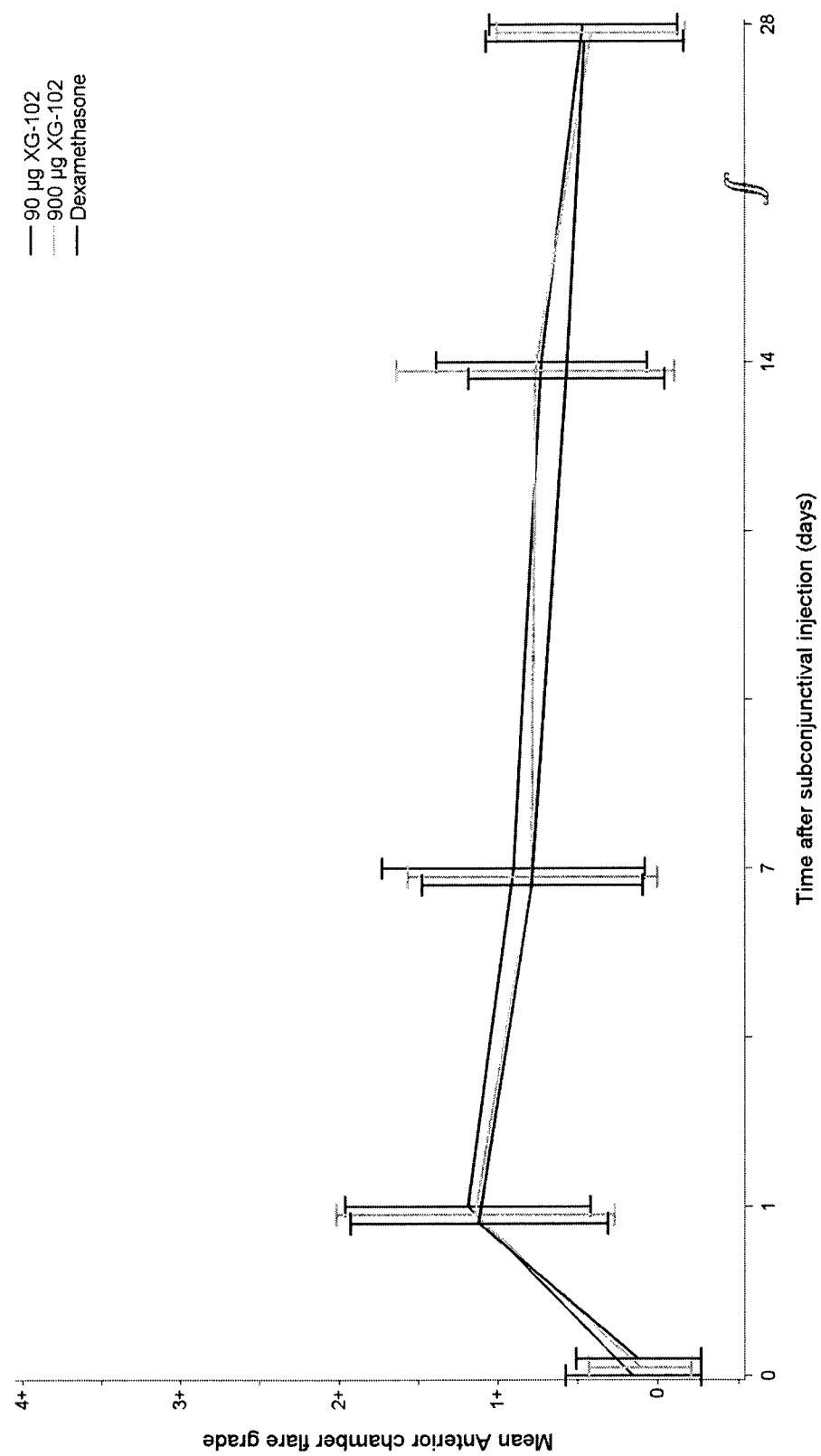
FIG. 62 shows for the study of Example 27 the anterior chamber flare grade (for the FAS) obtained up to day 28 after the administration of the sub-conjunctival injection of study treatment for the three treatment groups XG-102 90 µg, XG-102 900 µg and the dexamethasone. The vertical lines represents the standard deviations (SD).

Anterior Chamber Flare Grade at Day 7, 14 and Day 28 for XG-102 90 μg Vs Dexamethasone and XG-102 900 μg Vs Dexamethasone:

The anterior chamber flare grade (for the FAS) obtained up to day 28 is shown in FIG. 62 and the model results is shown in the table below. There was no statistically significant difference in the anterior chamber flare grade between XG-102 90 μg and dexamethasone and between XG-102 900 μg and dexamethasone at either day 7 or day 14 or at day 28.

| Dose group | Model adjusted mean [95% CI] | Dose group comparison | Estimated difference [95% CI] | Pvalue |
|---|---|---|---|---|
| Visit 2 (7 days +/− 2 days after administration of study tx) | | | | |
| XG-102 90 ug | 0.93 [0.73-1.14] | XG-102 90 ug versus Dexamethasone | 0.133 [−0.154-0.420] | 0.363 |
| XG-102 900 ug | 0.80 [0.60-1.00] | XG-102 900 ug versus Dexamethasone | −0.003 [−0.284-0.278] | 0.983 |
| Dexamethasone | 0.80 [0.60-1.00] | XG-102 900 ug versus XG-102 90 ug | −0.136 [−0.424-0.152] | 0.353 |
| Visit 3 (14 days +/− 3 days after administration of study tx) | | | | |
| XG-102 90 ug | 0.72 [0.52-0.92] | XG-102 90 ug versus Dexamethasone | 0.142 [−0.140-0.424] | 0.322 |
| XG-102 900 ug | 0.80 [0.59-1.00] | XG-102 900 ug versus Dexamethasone | 0.220 [−0.061-0.502] | 0.125 |
| Dexamethasone | 0.58 [0.38-0.77] | XG-102 900 ug versus XG-102 90 ug | 0.078 [−0.210-0.366] | 0.595 |

-continued

| Dose group | Model adjusted mean [95% CI] | Dose group comparison | Estimated difference [95% CI] | Pvalue |
|---|---|---|---|---|
| Visit 4 (28 days +/− 8 days after administration of study tx) | | | | |
| XG-102 90 ug | 0.48 [0.28-0.69] | XG-102 90 ug versus Dexamethasone | 0.027 [−0.255-0.309] | 0.851 |
| XG-102 900 ug | 0.44 [0.23-0.64] | XG-102 900 ug versus Dexamethasone | −0.017 [−0.301-0.267] | 0.906 |
| Dexamethasone | 0.46 [0.26-0.65] | XG-102 900 ug versus XG-102 90 ug | −0.044 [−0.333-0.245] | 0.764 |

CI = Confidence Interval,
µg = microgram,
% = percentage,
tx = treatment.

Cleared Ocular Inflammation:

The evaluation of ocular inflammation over time was assessed by cleared ocular inflammation. The latter was defined as the proportion of subjects that had a summed ocular inflammation score of grade 0 defined as anterior cell grade=0 and anterior chamber flare grade=0. This outcome was evaluated at day 7, 14 and day 28 comparing XG-102 900 µg with dexamethasone and XG-102 90 µg with dexamethasone. The summary statistic results for the FAS and PP populations is shown in the table below. Concerning the analysis performed on the FAS, compared to the usual care group, for patients allocated to the XG-102 900 µg group the odds of having cleared inflammation at day 7 post-surgery was 0.76 (95% CI 0.25-2.28), at day 14 post-surgery, 1.25 (95% CI 0.47-3.32) and at day 28 post-surgery, 1.13 (95% CI 0.49-2.60). Concerning patients allocated to the XG-102 90 µg group, compared to the usual care group, the odds of having cleared inflammation at day 7 post-surgery was 0.52 (95% CI 0.15-1.83), at day 14 post-surgery, 0.85 (95% CI 0.30-2.40) and at day 28 post-surgery, 1.24 (95% CI 0.54-2.87). Concerning the analysis performed on the PP analysis set, compared to the usual care group, for patients allocated to the XG-102 900 µg group the odds of having cleared inflammation at day 7 post-surgery was 0.84 (95% CI 0.28-2.46), at day 14 post-surgery, 1.12 (95% CI 0.41-3.05) and at day 28 post-surgery, 1.26 (95% CI 0.52-3.04). Concerning patients allocated to the XG-102 90 µg group, compared to the usual care group, the odds of having cleared inflammation at day 7 post-surgery was 0.56 (95% CI 0.16-1.97), at day 14 post-surgery, 0.97 (95% CI 0.34-2.77) and at day 28 post-surgery, 1.45 (95% CI 0.58-3.61).

| | Full analysis population | | | Per-protocol analysis population | | |
|---|---|---|---|---|---|---|
| | 90 µg XG-102 (N = 47) # patients (%) | 900 µg XG-102 (N = 48) # patients (%) | Dexamethasone (N = 50) # patients (%) | 90 µg XG-102 (N = 46) # patients (%) | 900 µg XG-102 (N = 46) # patients (%) | Dexamethasone (N = 50) # patients (%) |
| Visit 1 (21 hours after administration of study tx) | | | | | | |
| Nr. available (%) | 47 (100.0%) | 48 (100.0%) | 49 (98.0%) | 46 (100.0%) | 46 (100.0%) | 49 (98.0%) |
| Yes | 2 (4.3%) | 2 (4.2%) | 4 (8.2%) | 2 (4.3%) | 2 (4.3%) | 4 (8.2%) |
| Visit 2 (7 days +/− 2 days after administration of study tx) | | | | | | |
| Nr. available (%) | 42 (89.4%) | 47 (97.9%) | 48 (96.0%) | 39 (84.8%) | 44 (95.7%) | 48 (96.0%) |
| Yes | 5 (11.9%) | 7 (14.9%) | 9 (18.8%) | 5 (12.8%) | 7 (15.9%) | 9 (18.8%) |
| Visit 3 (14 days +/− 3 days after administration of study tx) | | | | | | |
| Nr. available (%) | 45 (95.7%) | 43 (89.6%) | 49 (98.0%) | 37 (80.4%) | 40 (87.0%) | 47 (94.0%) |
| Yes | 8 (17.8%) | 10 (23.3%) | 10 (20.4%) | 8 (21.6%) | 9 (22.5%) | 10 (21.3%) |
| Visit 4 (28 days +/− 8 days after administration of study tx) | | | | | | |
| Nr. available (%) | 45 (95.7%) | 43 (89.6%) | 48 (96.0%) | 33 (71.7%) | 34 (73.9%) | 43 (86.0%) |
| Yes | 18 (40.0%) | 17 (39.5%) | 17 (35.4%) | 14 (42.4%) | 15 (44.1%) | 15 (34.9%) |

Data are number of patients (%).
N = Number of patients in each group,
# = number,
µg = microgram,
% = percentage.
Tx = treatment.
**Cleared ocular inflammation is defined as 0 cell (i.e. cell grade as 0) and no flare (i.e. flare grade as 0)

Figure 63:
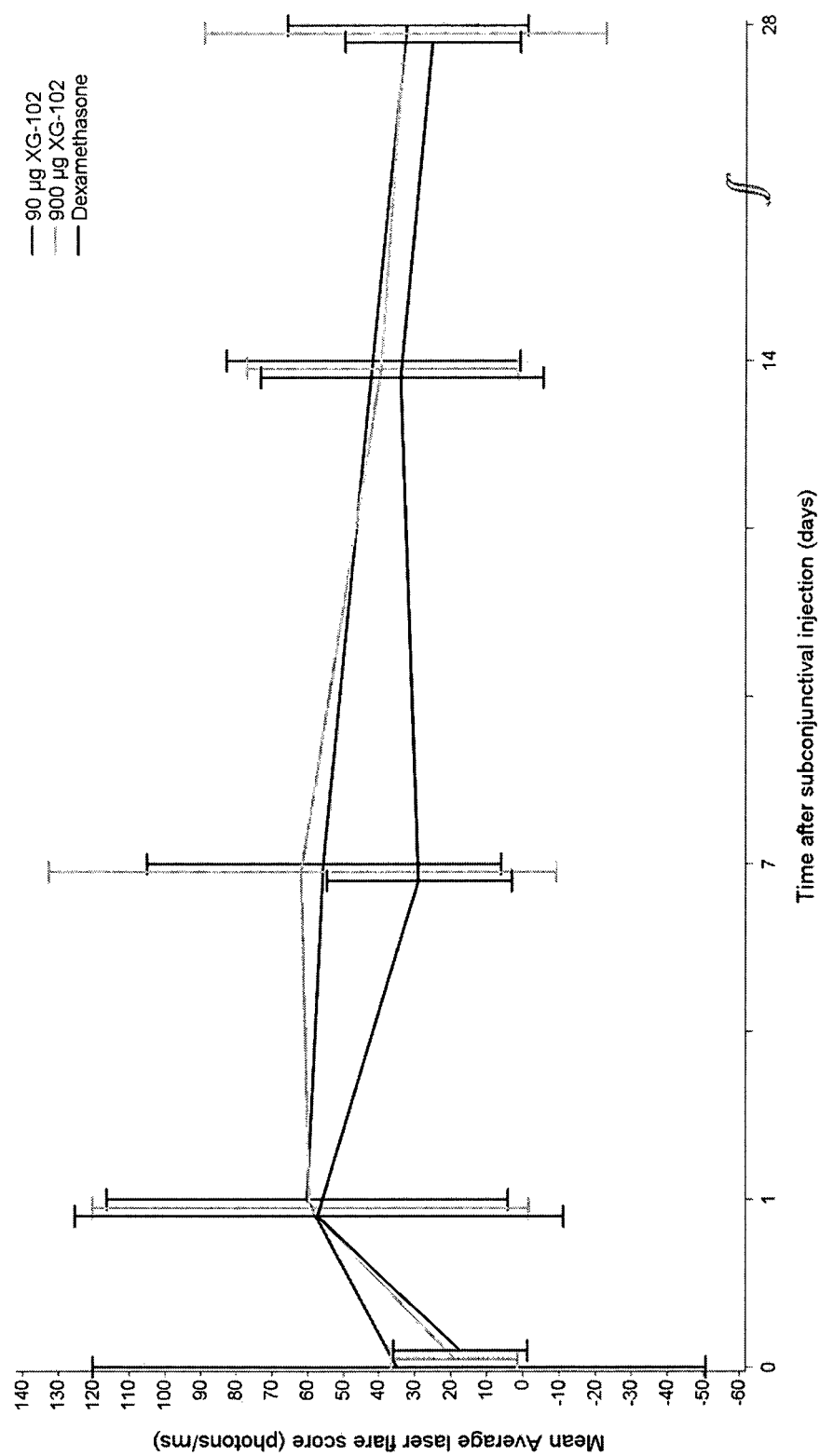
FIG. 63 shows for the study of Example 27 the LFM (Laser Flare Meter) measurements which were obtained at the defined time points throughout the study up to day 28 for the FAS. The vertical lines represents the standard deviations (SD).

Laser Flare Meter (LFM):

The LFM measurements which were obtained at the defined time points throughout the study are depicted as the LFM measurements over time and up to day 28 for the FAS in FIG. 63. Rescue medication was defined in the study protocol as any open-label anti-inflammatory ocular treatment which was prescribed for patients during follow-up because of persistent eye inflammation as judged by the Investigator. The study protocol stipulated that the study treatment eye drops were to be stopped at the introduction of open-label anti-inflammatory ocular treatment. The percentage of patients for whom rescue medication was introduced in the XG-102 90 µg group was statistically different when compared to the dexamethasone group (21.3% vs 4.0% for the XG-102 90 µg and dexamethasone groups respectively (p=0.013)) while the difference between XG-102 900 µg and dexamethasone (14.6% and 4.0% respectively for the two groups) was not statistically significant (p=0.88)

Pharmacokinetics in Plasma:

Blood sampling for quantification of XG-102 was taken 60 minutes after the sub-conjunctival administration of XG-102 in a subset of 32 patients recruited in the hospital Hotel Dieu (Paris). The analytical report of quantification of XG-102 in plasma shows that XG-102 was not detected in the plasma samples for any patient—see the following table:

|  | 90 µg XG-102 (N = 11) # patients (%) | 900 µg XG-102 (N = 9) # patients (%) | Dexamethasone (N = 12) # patients (%) |
| --- | --- | --- | --- |
| # patients with sample | 11 (100.0%) | 9 (100.0%) | 12 (100.0%) |
| <LLOQ* | 11 (100.0%) | 9 (100.0%) | 12 (100.0%) |

Data are number of patients (%).
N = Number of patients for whom an XG-102 quantification sample was obtained,
# = number,
µg = microgram,
% = percentage.
LLOQ = Less than the Limit of Quantification
*Values which were below the LLOQ (i.e. <10 ng/mL) were considered as 'not detectable'

In summary, XG-102 900 µg was non-inferior to dexamethasone eye drops in the evolution of post-operative intraocular inflammation (difference of −0.054 anterior cell grade, 95% CI—0.350-0.242, p<0.001). The same analysis was repeated on the FAS and XG-102 900 µg was found to be non-inferior to dexamethasone eye drops (difference −0.032 cell grade, 95% CI—0.301-0.238, p<0.001). Given that the upper boundary crossed zero for the FAS and PP analysis sets, XG-102 900 µg was not superior to dexamethasone eye drops (p=0.818 for the FAS and p=0.720 for the PP analysis set) for the anterior chamber cell grade at day 28.

Concerning the secondary endpoint comparing XG-102 90 µg with dexamethasone eye drops, XG-102 90 µg was non-inferior to dexamethasone eye in the evolution of post-operative intraocular inflammation (difference 0.086 anterior cell grade, 95% CI—0.214-0.385, p=0.003). The same analysis was repeated on the FAS and XG-102 90 µg was found to be non-inferior to dexamethasone eye drops (difference of 0.053 anterior cell grade 95% CI—0.215-0.321 p<0.001).

There were no statistically significant differences in anterior chamber cell grade between XG-102 90 µg and dexamethasone and between XG-102 900 µg and dexamethasone at either day 7 or day 14. There was no statistically significant difference in the anterior chamber flare grade between XG-102 90 µg and dexamethasone and between XG-102 900 µg and dexamethasone at either day 7 or day 14 or at day 28.

The evaluation of ocular inflammation over time was assessed by cleared ocular inflammation. The latter was defined as the proportion of subjects that had a summed ocular inflammation score of grade 0 defined as anterior cell grade=0 and anterior chamber flare grade=0. This outcome was evaluated at day 7, 14 and day 28 comparing XG-102 900 µg with dexamethasone and XG-102 90 µg with dexamethasone. Concerning the analysis performed on the FAS, compared to the usual care group, for patients allocated to the XG-102 900 µg group the odds of having cleared inflammation at day 7 post-surgery was 0.76 (95% CI 0.25-2.28), at day 14 post-surgery, 1.25 (95% CI 0.47-3.32) and at day 28 post-surgery, 1.13 (95% CI 0.49-2.60). Concerning patients allocated to the XG-102 90 µg group, compared to the usual care group, the odds of having cleared inflammation at day 7 post-surgery was 0.52 (95% CI 0.15-1.83), at day 14 post-surgery, 0.85 (95% CI 0.30-2.40) and at day 28 post-surgery, 1.24 (95% CI 0.54-2.87).

Safety Evaluation
Extent of Exposure:

The present study was a double-blind study. All patients who were randomized and for whom the sub-conjunctival injection was started are included in the safety analysis by dose group. Only treatment emergent AEs have been analyzed, i.e. AEs that occurred after the start of the sub-conjunctival injection of study treatment. If the study treatment eye drops were stopped prematurely (i.e. before day 21), the patients concerned continued follow-up until day 28, in accordance with the study protocol. The sub-conjunctival injection of study treatment was administered for 145 patients in total of which 47 patients were administered XG-102 90 µg, 48 patients were administered XG-102 900 µg and 50 patients allocated to the dexamethasone group were administered to NaCL 0.9%. For all patients in whom the sub-conjunctival injection of study treatment was started, the total amount (i.e. 250 µL) of study treatment was administered.

The exposure by patient for the study treatment eye drops is shown in the table below. Concerning the study treatment eye drops, the overall compliance with the instillation of the study treatment eye drops as required by the study protocol was >90% in the three study groups. Patients allocated to the XG-102 treatment groups had a slightly higher compliance with the instillation of the study treatment eye drops (95% and 94% for the XG-102 90 µg and XG-102 900 µg groups respectively) compared to patients allocated to the dexamethasone group where the compliance was 91%. Fifty patients received dexamethasone eye drops for an average of 20 days (6-21 days, min-max) with a maximal cumulated dose of 81 drops (81×0.05 mg=4.05 mg).

|  | 90 µg XG-102 (N = 47) mean (min-max) | 900 µg XG-102 (N = 48) mean (min-max) | Dexamethasone (N = 50) mean (min-max) |
| --- | --- | --- | --- |
| Days under treatment eye drops | 18 (1-21) | 19 (1-21) | 20 (6-21) |
| Compliance with study treatment eye drops* | 95.3% (75.3%-100%) | 93.8% (33.3%-100%) | 90.6% (33.3%-100%) | footnote:
For patients who stopped the study treatment eye drops prematurely, compliance was calculated as used/planned
*100 where planned = 4 * (days from start and up to withdrawal). For patients who used the study treatment eye drops as planned by the protocol, compliance was calculated as ((81 − unused eye drops bottles)/81) * 100

Adverse Events
Summary of Adverse Events by Dose Group:

The overview of reported adverse events (serious and non-serious) is displayed in FIG. 64 by dose group. There was not a statistically significant difference between the XG-102 90 µg and dexamethasone groups and between the XG-102 900 µg and dexamethasone groups with respect to the number of patients for whom an AE was reported. For patients allocated to XG-102 90 µg, a total of 78 AEs were reported for 31/47 (66%) patients allocated to this group and for patients allocated to XG-102 900 µg, a total of 69 AEs were reported for 32/48 (67%) patients. For patients allocated to the dexamethasone group, a total of 55 AEs were reported for 29/50 (58%) patients. The percentage of patients who experienced an AE within 24 hours after administration of study treatment was similar between the three study treatment groups (i.e. 34%, 27% and 30% for the XG-102 90 µg, the XG-102 900 µg and dexamethasone groups' respectively).

The distribution of the reported AEs by severity and dose group is shown in table below. The majority (approximately 70%) of reported AEs were considered by the Investigator as being 'mild' for the three dose groups.

| Dose group | Severity | | |
|---|---|---|---|
| | Mild | Moderate | Severe |
| XG-102 90 µg | 55 (70.5%) | 6 (7.7%) | 17 (21.7%) |
| XG-102 900 µg | 49 (71.0%) | 12 (17.4%) | 8 (11.6%) |
| Dexamethasone | 42 (76.4%) | 9 (16.4%) | 4 (7.3%) |

Data are number of events (% or reported events)

The summary overview of AEs which led to an interruption of the study treatment eye drops is shown by dose group in the following table:

| Dose group | Adverse events which led to an interruption of study treatment |
|---|---|
| XG-102 90 µg | 11 (14.1%) |
| XG-102 900 µg | 8 (11.6%) |
| Dexamethasone | 3 (5.5%) |

Data are number of events (% of reported events)

For patients allocated to the XG-102 90 µg dose group, 11 events (14% of all reported AEs in this dose group) resulted in the premature withdrawal of study treatment while in the XG-102 900 µg and dexamethasone dose groups, the study treatment eye drops were interrupted for 8 events (12% of all reported AEs in this dose group) and 3 events (6% of all reported AEs in this dose group) respectively.

Investigators assessed (in a blinded manner) the relationship of each reported AE to any of the study treatments. An event was considered to be related to study treatment if the Investigator ticked either 'possible' or 'probable' as the reply to this question. In addition, the Investigator had to specify to which of the study treatments (i.e. XG-102 or dexamethasone) the event was considered related to—see the table below. AEs were considered by the Investigators (blinded assessment) to be possibly or probably related to study medication for 18 events reported for patients in the XG-102 90 µg, for 13 events reported for patients in the XG-102 900 µg, and for 15 events reported for patients in dexamethasone group (see table below). None of the reported SAEs were considered by the Investigator to be either possibly or probably related to either of the study treatments.

| Relationship to study treatment as assessed by the Investigator | 90 µg XG-102 (N = 47) Total # events | 900 µg XG-102 (N = 48) Total # events | Dexamethasone (N = 50) Total # events |
|---|---|---|---|
| Possibly or Probably related | 18 | 13 | 15 |
| AEs considered by the Investigator to be related to: | | | |
| XG-102 | 16 (20.5%) | 12 (17.4%) | 13 (23.64%) |
| Dexamethasone | 2 (2.6%) | 1 (1.5%) | 2 (3.6%) |

Data are number of events.
N = Number of patients in each group,
# = number,
µg = microgram,
% = percentage.

Display of Adverse Events:

A reported event was considered to be related to study treatment if the Investigator had ticked either 'Possible' or 'Probable' as the reply to the question 'Related to study treatment' on the e-CRF. The summary of the AEs (sorted by MedDRA SOC and PT term) which were reported for at least 2% of patients randomized to either of the three study groups may be found in FIG. 65.

Analysis of Adverse Events

Overall, there was not a statistically significant difference between either of the XG-102 dose groups and the dexamethasone dose group with respect to the number of patients for whom an AE was reported. For patients allocated to XG-102 90 µg, a total of 78 AEs were reported for 31/47 (66%) patients allocated to this group and for patients allocated to XG-102 900 µg, a total of 69 AEs were reported for 32/48 (67%). For patients allocated to the dexamethasone group, a total of 55 AEs were reported for 29/50 (58%). The percentage of patients who experienced an AE within 24 hours after administration of study treatment was similar between the three study treatment groups (i.e. 34%, 27% and 30% for the XG-102 90 µg, the XG-102 900 µg and dexamethasone groups' respectively).

The most frequently reported AEs were in the SOC 'EYE DISORDERS. Within this SOC, 49 events were reported for 26 (55%) patients allocated to XG-102 90 µg, 43 events were reported for 24 (50%) patients allocated to XG-102 900 µg and 30 events were reported for 16 (32%) of patients allocated to dexamethasone. There was a statistically significant difference between the XG-102 90 µg and dexamethasone group with respect to the number of patients for whom an event was reported in this SOC (p=0.025). Events suggestive of inflammation (such as 'eye inflammation', 'Corneal oedema', 'Eyelid oedema') were more frequently reported for patients allocated to XG-102 90 µg compared to patients allocated to either the XG-102 900 µg or dexamethasone dose groups. Eye pain was more frequently reported for patients allocated to the XG-102 900 µg group and when compared to the dexamethasone group, the difference in the number of patients for whom this event was reported was statistically significant (p=0.029). Within the SOC 'investigations', 'Intraocular pressure increased' was reported more frequently for patients allocated to XG-102 90 µg (23%) when compared to 10% and 14% for the XG-102 900 µg and dexamethasone groups respectively. The difference in number of patients for whom this event was reported (between XG-102 90 µg and dexamethasone) was not statistically significant. The study treatment eye drops were interrupted because of an AE for 11 patients allocated to XG-102 90 µg, for 8 patients allocated to XG-102 900 µg and for 3 patients allocated to dexamethasone. FIG. 65 displays a summary of the AEs (sorted by MedDRA SOC and Preferred Term (PT)) which occurred for at least 2% of patients, irrespective of the randomized group.

Serious Adverse Events

The serious adverse events concerned are listed in FIG. 66. In total, 9 SAEs were reported for 9 patients—i.e. for 4 patients randomized to the XG-102 90 µg dose group, for 3 patients randomized to the XG-102 900 µg dose group and for 2 patients randomized to the dexamethasone dose group. In total, one SAE (for a patient randomized to the XG-102 90 µg dose group) was reported within the first 24 hours after administration of the sub-conjunctival injection of study treatment. None of the reported SAEs were considered by the Investigator as being related to study treatment. The 'reason for seriousness' for all reported SAEs was 'hospitalization'. The overview of the reported SAEs is shown in FIG. 66.

Clinical Laboratory Evaluation

The hematology and chemistry assays which were performed for the study are shown in the following table. All laboratory tests were performed locally.

| | |
|---|---|
| Hematology: | Hemoglobin, hematocrit, White blood cell count (WBC), neutrophils, basophils, eosinophils, monocytes and lymphocytes |
| Chemistry: | Creatinine, Aspartate Transaminase (AST), Alanine Transaminase (ALT), gamma-glutamyltransferase (gamma-GT), glucose, CK, CRP |

Safety Conclusions

Overall, XG-102 90 µg and XG-102 900 µg was well tolerated in patients who underwent complex ocular surgery. The study treatment eye drops were stopped prematurely for 11 patients randomized to XG-102 90 µg, for 8 patients randomized to XG-102 900 µg and for 3 patients randomized to dexamethasone. The reason for the premature withdrawal of study treatment was primarily because of persistent eye inflammation which in the opinion of the Investigator necessitated intensification of anti-inflammatory treatment. For the patients concerned, treatment with open-label anti-inflammatory ocular treatment was initiated.

No fatal events were reported in this study. In total, 9 SAEs were reported for 9 patients and none of these events were considered as being related to the study treatment.

Concerning the overall number of reported AEs, there are not a statistically significant difference between either of the XG-102 dose groups and the dexamethasone group with respect to the number of patients for whom an AE was reported. For patients allocated to XG-102 90 µg, a total of 78 AEs were reported for 31/47 (66%) patients allocated to this group and for patients allocated to XG-102 900 µg, a total of 69 AEs were reported for 32/48 (67%) patients. For patients allocated to the dexamethasone group, a total of 55 AEs were reported for 29/50 (58%) patients. The percentage of patients who experienced an AE within 24 hours after administration of study treatment was similar between the three study treatment groups (i.e. 34%, 27% and 30% for the XG-102 90 µg, the XG-102 900 µg and dexamethasone groups, respectively). The number of patients who experienced an AE suggestive of eye inflammation was higher in patients allocated to the XG-102 90 µg group compared to the XG-102 900 µg and dexamethasone groups which suggests that XG-102 90 µg may be less efficacious in the treatment of eye inflammation secondary to complex ocular surgery. The number of patients who experienced an AE suggestive of eye pain was higher in patients allocated to the XG-102 900 µg group compared to the XG-102 90 µg and dexamethasone groups. For two patients in the XG-102 90 µg group, eye pain was reported less than 24 hours after the injection of the sub-conjunctival injection of study treatment—for one of these patients, analgesic treatment had not been prescribed post-operatively. For one of these patients, eye pain was again reported as an AE 35 days later which was at the same time when the patient was reported as having an elevated IOP.

For three patients in the XG-102 900 µg group (i.e. patients FR-02-0013, FR-03-003 and FR-05-0060), eye pain was reported less than 24 hours after the injection of the sub-conjunctival injection of study treatment and for one of these patients (i.e. patient FR-02-0013), eye pain was again reported as an AE five days later. For four patients in the same dose group (i.e. patients FR-04-0108, FR-05-0127, FR-05-0152 and FR-05-0155), eye pain was reported >24 hours after the sub-conjunctival injection of study treatment concomitantly. For three of these patients, eye pain was reported concomitantly with other AEs (i.e. patients FR-02-0113, FR-05-0127 and FR-05-0155). Eye pain was reported for one patient in the dexamethasone group (i.e. FR-03-0087) >24 hours after the sub-conjunctival injection of study treatment concomitantly. This event was reported concomitantly with another AE. Given that complex surgery was performed, eye pain could also be related to the presence of stitches following the surgery.

Summary

Compliance: For all patients in whom the sub-conjunctival injection of study treatment was started, the total amount (i.e. 250 µL) was administered. In the three study treatment groups, the overall compliance with the study treatment eye drops was >90%.

Safety: There was not a statistically significant difference between either of the XG-102 dose groups and the dexamethasone group with respect to the number of patients for whom an adverse event was reported. For patients allocated to XG-102 90 µg, a total of 78 adverse events were reported for 31/47 (66%) patients allocated to this group and for patients allocated to XG-102 900 µg, a total of 69 adverse events were reported for 32/48 (67%) patients. For patients allocated to the dexamethasone group, a total of 55 adverse events were reported for 29/50 (58%) patients. The percentage of patients who experienced an adverse event within 24 hours after administration of study treatment was similar between the three study treatment groups (i.e. 34%, 27% and 30% for the XG-102 90 µg, the XG-102 900 µg and dexamethasone groups' respectively). More patients allocated to the XG-102 90 µg group, compared to the XG-102 900 µg and dexamethasone groups, experienced an adverse event suggestive of eye inflammation which may suggest that XG-102 90 µg may be less efficacious (compared to the 900 µg and dexamethasone dose groups) in the treatment of eye inflammation secondary to complex ocular surgery. The number of patients who experienced an adverse event suggestive of eye pain was higher in patients allocated to the XG-102 900 µg group compared to the XG-102 90 µg and dexamethasone groups. The eye pain may be related to the presence of stitches following the surgery. 'Intraocular pressure increased' was reported more frequently for patients allocated to XG-102 90 µg (23%) when compared to 10% and 14% for the XG-102 900 µg and dexamethasone groups respectively. The difference in number of patients for whom this event was reported (between XG-102 90 µg and dexamethasone was not statistically significant).

The majority (approximately 70%) of all reported adverse events (AE) were considered by the Investigator as being mild. In total, AEs were considered by the Investigators (blinded assessment) to be possibly or probably related to study medication for 18 events reported for patients in the XG-102 90 µg, for 13 events reported for patients in the XG-102 900 µg, and for 15 events reported for patients in dexamethasone group. No fatal events were reported in this study. In total, 9 SAEs were reported for 9 patients and none of these events were considered as being related to the study treatment.

The quantification of XG-102 was performed in a sub-set of 32 patients. A blood sample was obtained 1 hour after the sub-conjunctival injection of study treatment. For all samples obtained (and irrespective of the assigned dose group) the XG-102 concentration was analyzed as being below the Lower Limit of Quantification (LLOQ) of <10 ng/ml.

According to our definitions of non-inferiority, both XG-102 900 µg and XG-102 90 µg administered as a single sub-conjunctival injection was non-inferior to treatment with dexamethasone eye drops instilled 4 times/day for 21 days in the treatment of post-operative intraocular inflammation as assessed by anterior chamber cell grade, in patients who underwent complex ocular surgery.

Overall, XG-102 90 µg and XG-102 900 µg was well tolerated. None of the reported adverse events were suggestive of an intolerable or irreversible side effect of XG-102. The increased number of events suggestive of eye inflammation reported in the XG-102 90 µg suggests that this dose is less effective in the treatment of post-operative intraocular inflammation in patients following complex intraocular surgery. This is also probably enforced by the percentage of patients for whom rescue medication was introduced due to persistent eye inflammation in the XG-102 90 µg group. The plasma quantification of XG-102 which was assessed 1 hour after administration of the sub conjunctival injection of study treatment demonstrated that there was no systemic passage of XG-102.

Example 28: Effects of XG-102 on In Vivo Hepatocarcinoma in p-38 (Mapk14) Deficient Mice Mapk14, which is also known as p-38, is a well-known negative regulator of cell proliferation and tumorigenesis. In this study, Mapk14$^{f/f}$ and Mapk14$^{\Delta li*}$ mice as well as Mapk14$^{f/f}$Jun$^{f/f}$ and Mapk14$^{\Delta li*}$Jun$^{\Delta li*}$ mice have been used. "Mapk14$^{\Delta li*}$", and "Mapk14$^{\Delta li*}$Jun$^{\Delta li*}$" respectively, means herein polyIC-treated Mx-cre/Mapk14$^{f/f}$ mice, and Mx-cre deleted Mapk14$^{f/f}$Jun$^{f/f}$ mice respectively, thus resulting in Mapk14 "deletion", and Jun deletion respectively, by the Mx-cre process, i.e. "Mapk14$^{-/-}$" mice, and "Mapk14$^{-/-}$Jun$^{-/-}$" mice respectively.

XG-102 has been administered intraperitoneal twice weekly at a dose of 20 mg/kg to study its effects on the diethylnitrosamine (DEN)-induced hyperproliferation of hepatocytes and liver tumor cells (cf. Hui L. et al., p38a suppresses normal and cancer cell proliferation by antagonizing the JNK-c-Jun pathway. Nature Genetics, 2007; 39: 741-749). PBS has been used as control. Specifically, the Mapk14$^{f/f}$ and Mapk14$^{\Delta li*}$ mice were injected with either PBS or XG-102 (20 mg per kg body weight) before DEN treatment. The proliferation of hepatocytes in the mice was then analyzed by Ki67 staining 48 h after DEN treatment and quantified.

Figure 67:
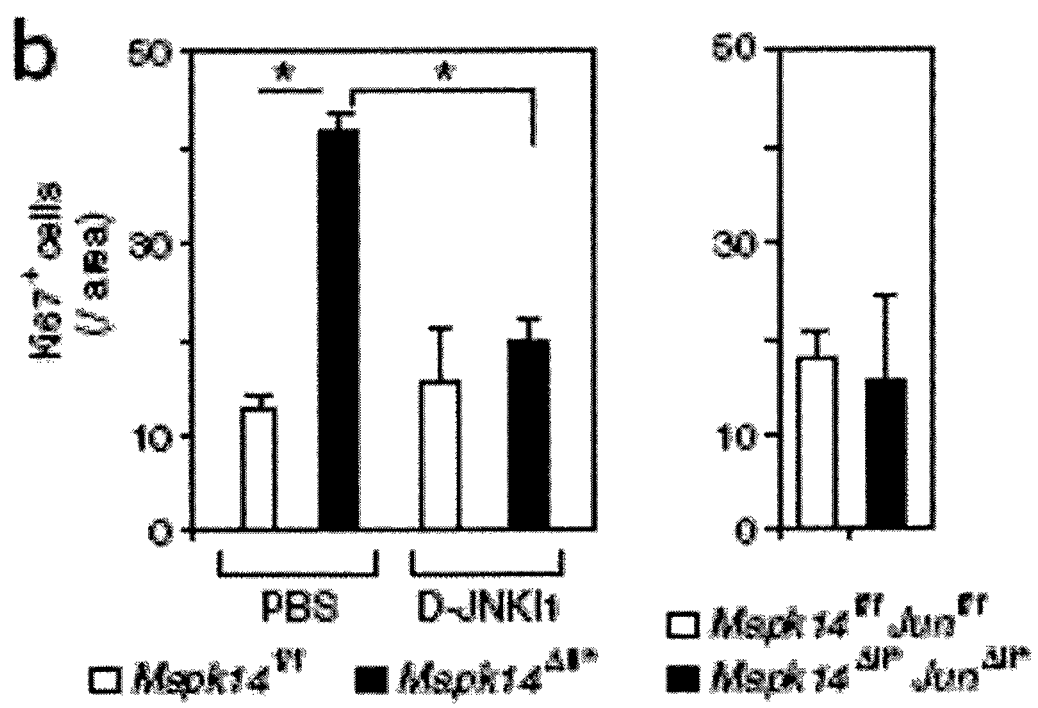
FIG. 67 shows for Example 28 the proliferation of hepatocytes in XG-102 (in the figure referred to as "D-JNKI1") or PBS treated Mapk14$^{f/f}$ and Mapk14$^{\Delta li*}$ mice (left panel) and in XG-102 (i.e. "D-JNKI1") treated Mapk14$^{f/f}$ Jun$^{f/f}$ and Mapk14$^{\Delta li*}$ Jun$^{\Delta li*}$ mice (right panel). Mice were injected with either XG-102 (20 mg per kg body weight) or PBS, if applicable, before DEN treatment. The proliferation of hepatocytes was analyzed by Ki67 staining 48 h after DEN treatment. Quantification of Ki67-positive cells is shown.

FIG. 67 shows in the left panel the proliferation of hepatocytes (quantification of Ki67-positive cells) in XG-102 (in the figure referred to as "D-JNKI1") or PBS treated Mapk14$^{f/f}$ and Mapk14$^{\Delta li*}$ mice. In PBS conditions (control), Mapk14$^{-/-}$ cells (Mapk14$^{\Delta li*}$) are proliferating more intensively than Mapk14$^{+/+}$ cells (Mapk14$^{f/f}$), since the negative regulation of Mapk14 (p38) on cell proliferation and tumorigenesis is not present. Administration of XG-102 reverts this "non-activity" of Mapk14 (in Mapk14$^{-/-}$ cells) by the activity of XG-102 (DJNKI1).

In the right panel of FIG. 67 the proliferation of hepatocytes (quantification of Ki67-positive cells) in XG-102 (in the figure referred to as "D-JNKI1") treated Mapk14$^{f/f}$Jun$^{f/f}$ (meaning Mapk14$^{+/+}$Jun$^{+/+}$) and Mapk14$^{\Delta li*}$Jun$^{\Delta li*}$ mice (meaning Mapk14$^{-/-}$Jun$^{-/-}$) is shown. The results are equivalent and mimic those of Mapk14$^{f/f}$ in PBS condition and Mapk14$^{\Delta li*}$ in XG-102 (DJNKI1) condition. Thus, XG-102 activity is "equivalent" to deleting the Jun gene in the cell line.

Taken together, these results are confirming that XG-102 has an activity on the growth of cancer cell lines (reverting the overgrowth induced by Mapk14 deletion) and this is probably mediated by Jun.

Example 29: Effects of XG-102 on In Vivo Human Liver Cancer Cells (Implanted)

To study the effect of XG-102 on in vivo human liver cancer cells, 3×10$^6$ Huh7 human liver cancer cells were injected subcutaneously to both flank area of nude mice at 4 weeks of age. Nude mice treated with XG-102 intraperitoneally twice a week at 5 mg/kg after Huh7 injection. Tumor volumes were measured twice a week. Mice were killed 4 week after xenograft.

Figure 68:
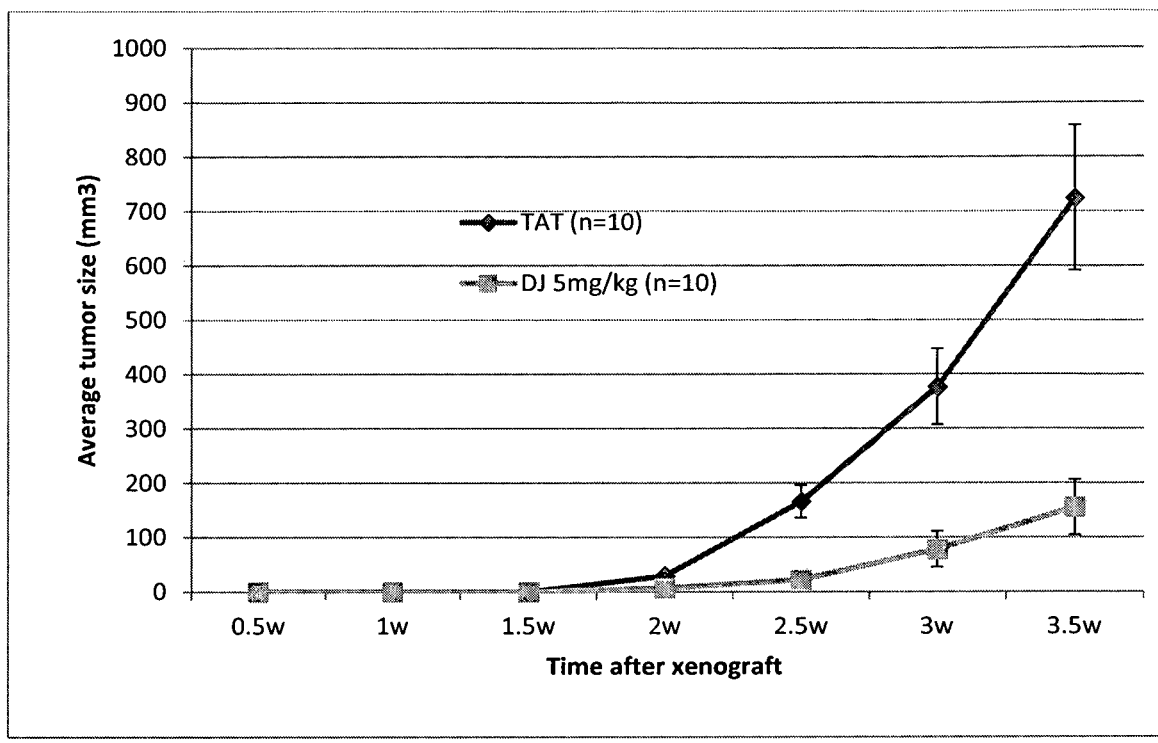
FIG. 68 $3\times10^6$ Huh7 human liver cancer cells were injected subcutaneously to both flank area of nude mice at 4 weeks of age (Example 29). Nude mice treated with XG-102 intraperitoneally twice a week at 5 mg/kg after Huh7 injection. Tumor volumes were measured twice a week. Mice were killed 4 week after xenograft. Dotted cycles indicate the xenografted tumors.

As shown in FIG. 68, XG-102 administered intraperitoneally twice weekly after subcutaneous injection of human hepatocellular carnimoma in nude mice markedly reduced tumor growth at a dose of 5 mg/kg.

Example 30: Antitumor Activity of 1 mg/kg XG-102 in Swiss Nude Mice Bearing Orthotopic HEP G2 Human Liver Carcinoma The objective of this study was to determine the antitumor activity of 1 mg/kg XG-102 in the model of SWISS Nude mice bearing the orthotopic Hep G2 human hepatocarcinoma tumor.

20 healthy female SWISS Nude mice were obtained from Charles River (L'Arbresles, France). Animal experiments were performed according to the European ethical guidelines of animal experimentation and the English guidelines for welfare of animals in experimental neoplasia. The animals were maintained in rooms under controlled conditions of temperature (23±2° C.), humidity (45±5%), photoperiod (12 h light/12 h dark) and air exchange. Animals were maintained in SPF conditions and room temperature and humidity was continuously monitored. The air handling system was programmed for 14 air changes per hour, with no recirculation. Fresh outside air pass through a series of filters, before being diffused evenly into each room. A high pressure (20±4 Pa) was maintained in the experimentation room to prevent contamination or the spread of pathogens within a mouse colony. All personnel working under SPF conditions followed specific guidelines regarding hygiene and clothing when they entered the animal husbandry area. Animals were housed in polycarbonate cages (UAR, Epinay sur Orge, France) that are equipped to provide food and water. The standard area cages used were 800 cm2 with a maximum of 10 mice per cage according to internal standard operating procedures. Bedding for animals was sterile wood shavings (SERLAB, Cergy-Pontoise, France), replaced once a week. Animal food was purchased from SERLAB (Cergy-Pontoise, France). The type of sterile controlled granules was DIETEX. The food was provided ad libitum, being placed in the metal lid on top of the cage. Water was also provided ad libitum from water bottles equipped with rubber stoppers and sipper tubes. Water bottles was cleaned, filled with water, sterilized by filtration and replaced twice a week.

For XG-102 administration a stock solution was prepared at 10 mM (corresponding to 38.22 mg/ml) in sterile water (WFI, Aguettant). Aliquots were prepared for each treatment day and stored at approximately −80° C. Dilutions with WFI of this stock solution to 0.2 mg/ml was performed on each treatment day and stored at 2-4° C. for maximum 24 hours. The stability of the stock solution is more than 100 days at approximately −80° C.; the stability of the diluted formulations for animal dosing is 24 hours at 2-4° C. Diluted formulations were maintained on ice until use and unused diluted material was discarded. The treatment dose of XG-102 was injected at 1 mg/kg/inj. Injections were performed at days D10, D14, D18, D22, D41, D45, D49 and D53 ([Q4D×4]×2). XG-102 substances were injected intravenously (IV) at 5 ml/kg via the caudal vein of mice. The injection volumes were adapted according to the most recent individual body weight of mice.

The tumor cell line and culture media were purchased and provided by Oncodesign:

| Cell line | Type | Specie | Origin | Reference |
|---|---|---|---|---|
| Hep G2 | Human hepatocarcinoma | human | ATCC* | 4 |

*American Type Culture Collection, Manassas, Virginia, USA.

The Hep G2 cell line was established from the tumor tissue of a 15-year old Argentine boy with a hepatocellular carcinoma in 1975 (ADEN D. P. et al., Nature, 282: 615-616, 1979). Tumor cells grew as adherent monolayers at 37° C. in a humidified atmosphere (5% $CO_2$, 95% air). The culture medium was RPMI 1640 containing 2 mM L-glutamine (Ref BE12-702F, Lonza, Verviers, Belgium) and supplemented with 10% FBS (Ref DE14-801E, Lonza). For experimental use, the cells were detached from the culture flask by a 5-minute treatment with trypsin-versene (Ref 02-007E, Cambrex), diluted in Hanks' medium without calcium or magnesium (Ref BE10-543F, Cambrex) and neutralized by addition of complete culture medium. Cells were counted in a hemocytometer and their viability was assessed by 0.25% trypan blue exclusion. *Mycoplasma* detection was performed using the MycoAlert® *Mycoplasma* Detection Kit (Ref LT07-318, Lonza) in accordance with the manufacturer instructions. The MycoAlert® Assay is a selective biochemical test that exploits the activity of mycoplasmal enzymes. The viable *mycoplasma* are lysed and the enzymes react with the MycoAlert® substrate catalyzing the conversion of ADP to ATP. By measuring the level of ATP in a sample both before and after the addition of the MycoAlert® substrate a ratio can be obtained which is indicative of the presence or absence of *mycoplasma*. The *mycoplasma* test was assayed in duplicate from the culture supernatants of the cell lines and compared to negative and positive controls (MycoAlert® Assay Control Set Ref LT07-518, Lonza) (Internal Standard Operating Procedure No TEC-007/002, data not shown but archived).

Experimental Design:

Twenty four hours before tumor induction, 20 female SWISS Nude mice were irradiated with a γ-source (2.5 Gy, Co60, INRA, Dijon, France). At D0, Hep G2 tumors were induced orthotopically on 20 female SWISS Nude. Under anesthesia, the animal abdomen was opened through a median incision under aseptic conditions. Ten millions ($10^7$) Hep G2 tumor cells suspended in 50 µl of RPMI 1640 culture medium were injected in the subcapsular area of the liver. The abdominal cavity was subsequently closed in 2 layers with 5-0 sutures.

At D10, mice were randomized before treatment start according to their body weight to form 2 groups of 10 mice. The body weight of each group was not statistically different from the others (analysis of variance). Mice from group 1 received one IV injection of vehicle at 5 ml/kg/inj. at D10, D14, D18, D22, D41, D45, D49 and D53 ([Q4D×4]×2) and mice from group 2 received one IV injection of XG-102 at 1 mg/kg/inj. at D10, D14, D18, D22, D41, D45, D49 and D53 ([Q4D×4]×2):

| Group | No. | Treatment | Dose | Route | Treatment |
|---|---|---|---|---|---|
| 1 | 8 | vehicle | — | IV | [Q4Dx4]x2 |
| 2 | 7 | XG-102 | 1 | IV | [Q4Dx4]x2 |

Surviving mice were sacrificed at D185.

Mice were monitored every day throughout the study for behaviour and survival. The body weight was monitored twice a week for all mice throughout the study. Isoflurane® Forene (Centravet, Bondoufle, France) was used to anaesthetize the animals before cell injection, IV treatments and sacrifice. During the course of the experiment, animals were killed under anaesthesia with Isoflurane® by cervical dislocation if any of the following occurred:

Signs of suffering (cachexia, weakening, difficulty to move or to eat),

Compound toxicity (hunching, convulsions),

20% weight loss for 3 consecutive days or 25% body weight loss on any day.

An autopsy was performed in each case. When mice looked moribund, they were sacrificed and necropsied. Livers were collected and weighed.

For the body weight analysis body weight curves of mice were drawn. Mean body weight change (MBWC): Average weight change of treated animals in grams (weight at day X minus weight at D10) was calculated.

Efficacy parameters were expressed as a percent (T/C %). T will be the median survival times of animals treated with drugs and C is the median survival times of control animals treated with vehicle. Survival systems indicated a degree of success when T/C percents exceed 125. T/C % was expressed as follows: T/C %=[T/C]×100. Survival curves of mice were drawn. Mean survival time was calculated for each group of treatment as the mean of the days of death. Median survival time was calculated for each group of treatment as the median of the days of death. The log-Rank (Kaplan-Meier) test was used to compare the survival curves. Statistical analysis of the body weight and MBWC was performed using the Bonferroni/Dunn test (ANOVA comparison) using StatView® software (Abacus Concept, Berkeley, USA). A p value <0.05 is considered significant. All groups were compared with themselves.

Figure 69:
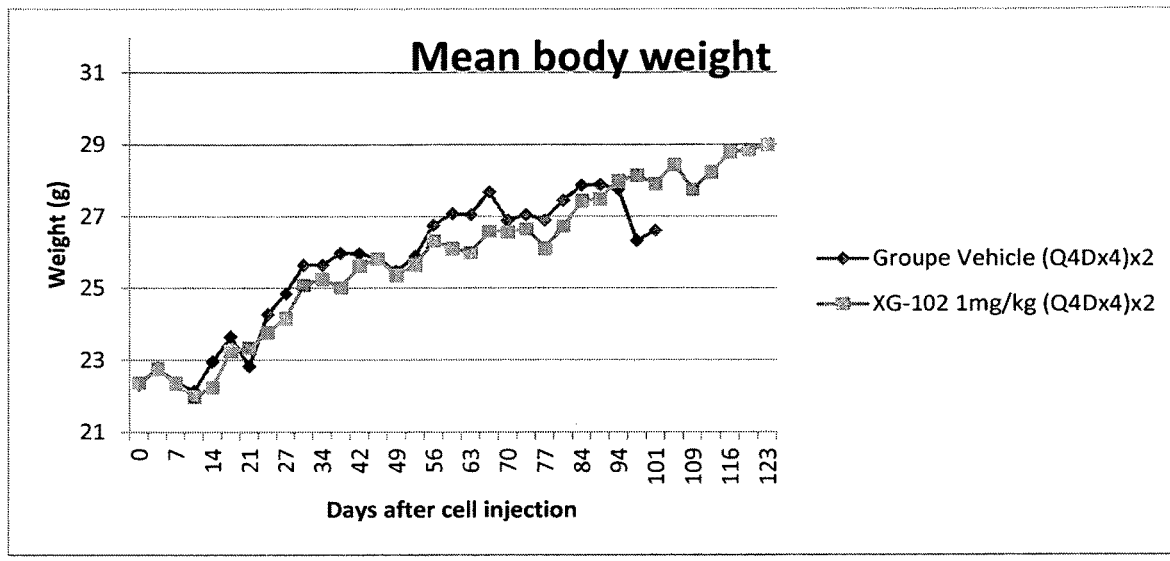
FIG. 69 shows for Example 30 the mean body weight and mean body weight change curves of mice bearing orthotopically injected HEP G2 tumor are shown. Mice were IV treated with XG-102 at 1 mg/kg/inj following the Q4Dx4 treatment schedule repeated two times, at D10 and D41. Accordingly, in FIG. 70 the respective statistical data are presented.

In FIG. 69 the mean body weight and mean body weight change curves of mice bearing orthotopically injected HEP G2 tumor are shown. Mice were IV treated with XG-102 at 1 mg/kg/inj following the Q4D×4 treatment schedule repeated two times, at D10 and D41. As shown in FIG. 69, no apparent differences occurred for the body weight, indicating that XG-102 was well-tolerated. Accordingly, in FIG. 70 the respective statistical data are presented.

Figure 71:
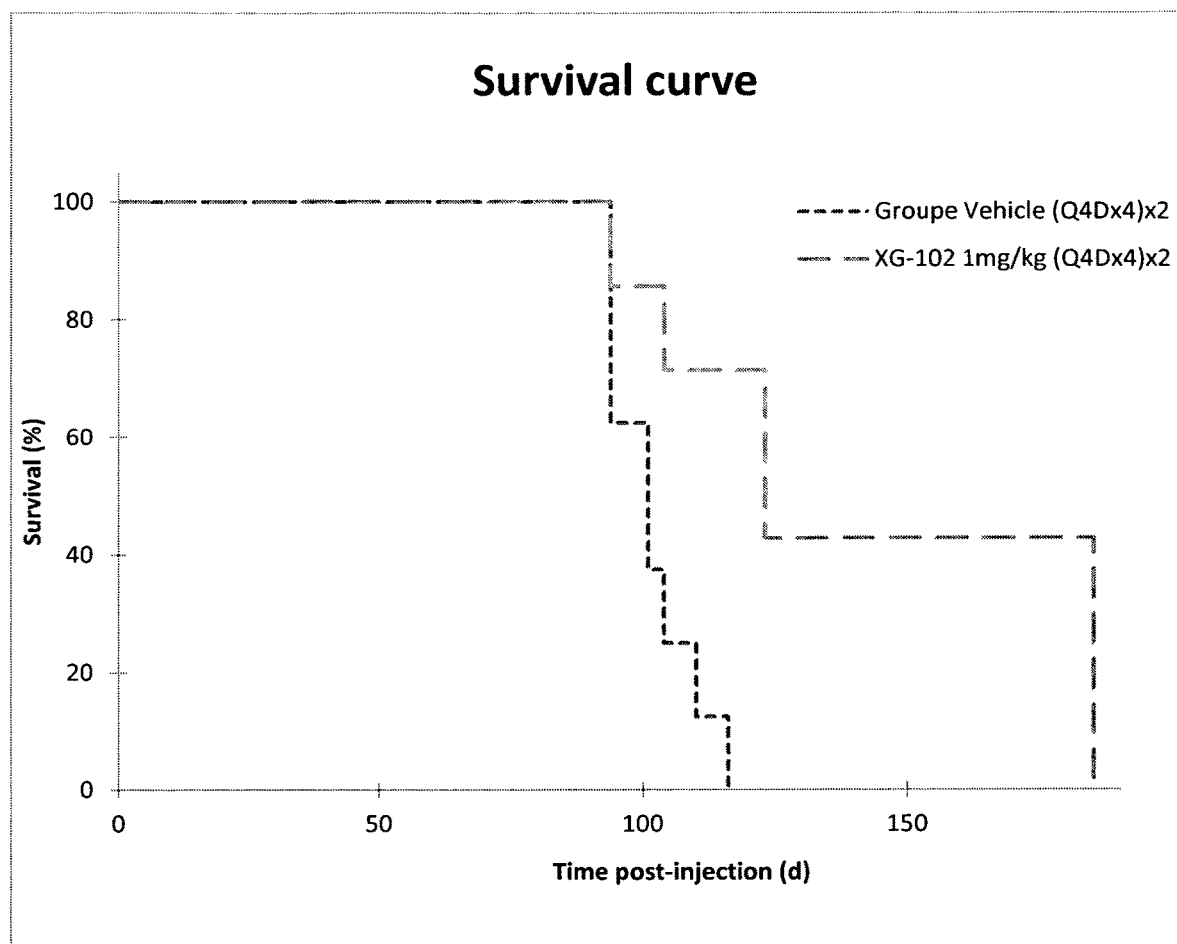
FIG. 71 shows for Example 30 the mice long survival curves, whereby proportion of surviving mice per group until sacrifice day (D185) is depicted. Mice were treated with XG-102 at the indicated doses following the Q4Dx4 treatment schedule repeated two times, at D10 and D41.

FIG. 71 shows the mice long survival curves, whereby proportion of surviving mice per group until sacrifice day (D185) is depicted. Mice were treated with XG-102 at the indicated doses following the Q4D×4 treatment schedule repeated two times, at D10 and D41. These data clearly show a prolonged survival for mice treated with XG-102. Accordingly, the statistical data are presented below (survival analysis of mice xenografted with HepG2 tumor and treated with XG-102):

| Treatment (D 10 &D 41, Q4Dx4) | Median survival time ± SD (day) | Mean survival time (day) | T/C (%) |
|---|---|---|---|
| Vehicle | 102 ± 8 | 102 | — |
| XG-102 1 mg/kg | 111 ± 14 | 123 | 120 |

| Group | Chi | df | p | significance |
|---|---|---|---|---|
| XG-102 1 mg/kg | 5.1550 | 1 | 0.0232 | S |

Mice survival time was expressed as median survival time as T/C (%) values (the ratio between the median of the days of death of treated group and the tumor bearing untreated control group). Statistical analysis was performed with the Log-Rank test, taking vehicle treated group as reference.

Taken together, these data indicate that administration of XG-102 prolongs the survival time of mice xenografted with HepG2 tumor.

Example 31: Antitumor Activity of XG-102 (Dose/Response) in Swiss Nude Mice Bearing Orthotopic HEP G2 Human Liver Carcinoma The objective of this study was to determine the antitumor activity of XG-102 (dose/response) in the model of SWISS Nude mice bearing the orthotopic Hep G2 human hepatocarcinoma tumor.

32 healthy female SWISS Nude mice were obtained from Charles River (L'Arbresles, France). Animal experiments were performed according to the European ethical guidelines of animal experimentation and the English guidelines for welfare of animals in experimental neoplasia. The animals were maintained in rooms under controlled conditions of temperature (23±2° C.), humidity (45±5%), photoperiod (12 h light/12 h dark) and air exchange. Animals were maintained in SPF conditions and room temperature and humidity was continuously monitored. The air handling system was programmed for 14 air changes per hour, with no recirculation. Fresh outside air pass through a series of filters, before being diffused evenly into each room. A high pressure (20±4 Pa) was maintained in the experimentation room to prevent contamination or the spread of pathogens within a mouse colony. All personnel working under SPF conditions followed specific guidelines regarding hygiene and clothing when they entered the animal husbandry area. Animals were housed in polycarbonate cages (UAR, Epinay sur Orge, France) that are equipped to provide food and water. The standard area cages used were 800 cm2 with a maximum of 10 mice per cage according to internal standard operating procedures. Bedding for animals was sterile wood shavings (SERLAB, Cergy-Pontoise, France), replaced once a week. Animal food was purchased from SERLAB (Cergy-Pontoise, France). The type of sterile controlled granules was DIETEX. The food was provided ad libitum, being placed in the metal lid on top of the cage. Water was also provided ad libitum from water bottles equipped with rubber stoppers and sipper tubes. Water bottles was cleaned, filled with water, sterilized by filtration and replaced twice a week.

For XG-102 administration XG-102 was prepared at the concentration of 1 mg/ml with sterile water (WFI, Aguettant, France). Lt was then diluted at the concentrations of 0.2 and 0.02 mg/ml with sterile water. All these steps were performed within one hour prior to injection to mice. XG-102 was injected at 0.1, 1 and 5 mg/kg/inj. Four injections were performed, each separated by four days (Q4Dx4). XG-102 substances were injected intravenously (IV) at 5 ml/kg via the caudal vein of mice. The injection volumes were adapted according to the most recent individual body weight of mice.

The tumor cell line and culture media were purchased and provided by Oncodesign:

| Cell line | Type | Specie | Origin | Reference |
|---|---|---|---|---|
| Hep G2 | Human hepatocarcinoma | human | ATCC* | 4 |

*American Type Culture Collection, Manassas, Virginia, USA.

The Hep G2 cell line was established from the tumor tissue of a 15-year old Argentine boy with a hepatocellular carcinoma in 1975 (ADEN D. P. et al., Nature, 282: 615-616, 1979). Tumor cells grew as adherent monolayers at 37° C. in a humidified atmosphere (5% CO2, 95% air). The culture medium was RPMI 1640 containing 2 mM L-glutamine (Ref BE12-702F, Lonza, Verviers, Belgium) and supplemented with 10% FBS (Ref DE14-801E, Lonza). For experimental use, the cells were detached from the culture flask by a 5-minute treatment with trypsin-versene (Ref 02-007E, Cambrex), diluted in Hanks' medium without calcium or magnesium (Ref BE10-543F, Cambrex) and neutralized by addition of complete culture medium. Cells were counted in a hemocytometer and their viability was assessed by 0.25% trypan blue exclusion. *Mycoplasma* detection was performed using the MycoAlert® *Mycoplasma* Detection Kit (Ref LT07-318, Lonza) in accordance with the manufacturer instructions. The MycoAlert® Assay is a selective biochemical test that exploits the activity of mycoplasmal enzymes. The viable *mycoplasma* are lysed and the enzymes react with the MycoAlert® substrate catalyzing the conversion of ADP to ATP. By measuring the level of ATP in a sample both before and after the addition of the MycoAlert® substrate a ratio can be obtained which is indicative of the presence or absence of *mycoplasma*. The *mycoplasma* test was assayed in duplicate from the culture supernatants of the cell lines and compared to negative and positive controls (MycoAlert® Assay Control Set Ref LT07-518, Lonza) (Internal Standard Operating Procedure No TEC-007/002).

Experimental Design:

Twenty four hours before tumor induction, 32 female SWISS Nude mice were irradiated with a γ-source (2.5 Gy, $Co^{60}$, INRA, Dijon, France). At D0, Hep G2 tumors were induced orthotopically on 32 female SWISS Nude. Under anesthesia, the animal abdomen was opened through a median incision under aseptic conditions. Ten millions ($10^7$) Hep G2 tumor cells suspended in 50 µl of RPMI 1640 culture medium were injected in the subcapsular area of the liver. The abdominal cavity was subsequently closed in 2 layers with 5-0 sutures.

At D10, mice were randomized before treatment start according to their body weight to form 4 groups of 8 mice. The body weight of each group was not statistically different from the others (analysis of variance). Mice from group 1 received one IV injection of vehicle at 5 ml/kg/inj. once every four days repeated four times (Q4Dx4), mice from group 2 received one IV injection of XG-102 at 0.1 mg/kg/inj. once every four days repeated four times (Q4Dx4), mice from group 3 received one IV injection of XG-102 at 1 mg/kg/inj. once every four days repeated four times (Q4Dx4), and mice from group 4 received one IV injection of XG-102 at 5 mg/kg/inj. once every four days repeated four times (Q4Dx4):

| Group | No. | Treatment | Dose | Route | Treatment |
|---|---|---|---|---|---|
| 1 | 8 | vehicle | — | IV | Q4Dx4 |
| 2 | 8 | XG-102 | 0.1 | IV | Q4Dx4 |
| 3 | 8 | XG-102 | 1 | IV | Q4Dx4 |
| 4 | 8 | XG-102 | 5 | IV | Q4Dx4 |

Surviving mice were sacrificed at D171.

Mice were monitored every day throughout the study for behaviour and survival. The body weight was monitored twice a week for all mice throughout the study. Isoflurane® Forene (Centravet, Bondoufle, France) was used to anaesthetize the animals before cell injection, IV treatments and sacrifice. During the course of the experiment, animals were killed under anaesthesia with Isoflurane® by cervical dislocation if any of the following occurred:

Signs of suffering (cachexia, weakening, difficulty to move or to eat),
Compound toxicity (hunching, convulsions),
20% weight loss for 3 consecutive days or 25% body weight loss on any day.

An autopsy was performed in each case.

At D67, 3 mice randomly selected per group during randomization were sacrificed for observation of macroscopic development. The remaining mice in each group were kept for survival monitoring. Final sacrifice was performed at D171. Primary tumors and livers were collected and weighed from sacrificed animals. Each liver was fixed in 10% neutral buffered fonnalin. Forty eight (48) hours after collection, they were embedded in paraffin (Histosec®) and used for anapathological analysis. For the estimation of metastatic invasion in mouse liver by histological analysis, paraffin-embedded sections (5 µm) were deparaffinized in xylene and rehydrated by serial incubations in 100%, 95%, and 70% ethanol. All sections were stained with haematoxylin and eosin (HE) (Ref. S3309, Dakocytomation, Trappes, France) for histological analyses. The coverslip was mounted with aqueous mountant (Aquatex, Ref 1.08562, Merck) and sections were viewed under a light microscope (DMRB Leica). Histological sections were analyzed by a pathologist expert to determine the metastatic invasion in liver.

For the body weight analysis body weight curves of mice were drawn. Mean body weight change (MBWC): Average weight change of treated animals in grams (weight at day X minus weight at D10) was calculated.

Efficacy parameters were expressed as a percent (T/C %). T will be the median survival times of animals treated with drugs and C is the median survival times of control animals treated with vehicle. Survival systems indicated a degree of success when T/C percents exceed 125. T/C % was expressed as follows: T/C %=[T/C]×100. Survival curves of mice were drawn. Mean survival time was calculated for each group of treatment as the mean of the days of death. Median survival time was calculated for each group of treatment as the median of the days of death. The log-Rank (Kaplan-Meier) test was used to compare the survival curves. Statistical analysis of the body weight and MBWC was performed using the Bonferroni/Dunn test (ANOVA comparison) using StatView® software (Abacus Concept, Berkeley, USA). A p value <0.05 is considered significant. All groups were compared with themselves.

FIG. 72 shows the statistical data regarding the mean body weight and mean body weight change curves of mice bearing orthotopically injected HEP G2 tumor. Mice were IV treated with XG-102 following the Q4Dx4 treatment schedule repeated two times, at D10 and D41. As shown in FIG. 72, no apparent differences occurred for the body weight, indicating that XG-102 was well-tolerated.

Figure 73:
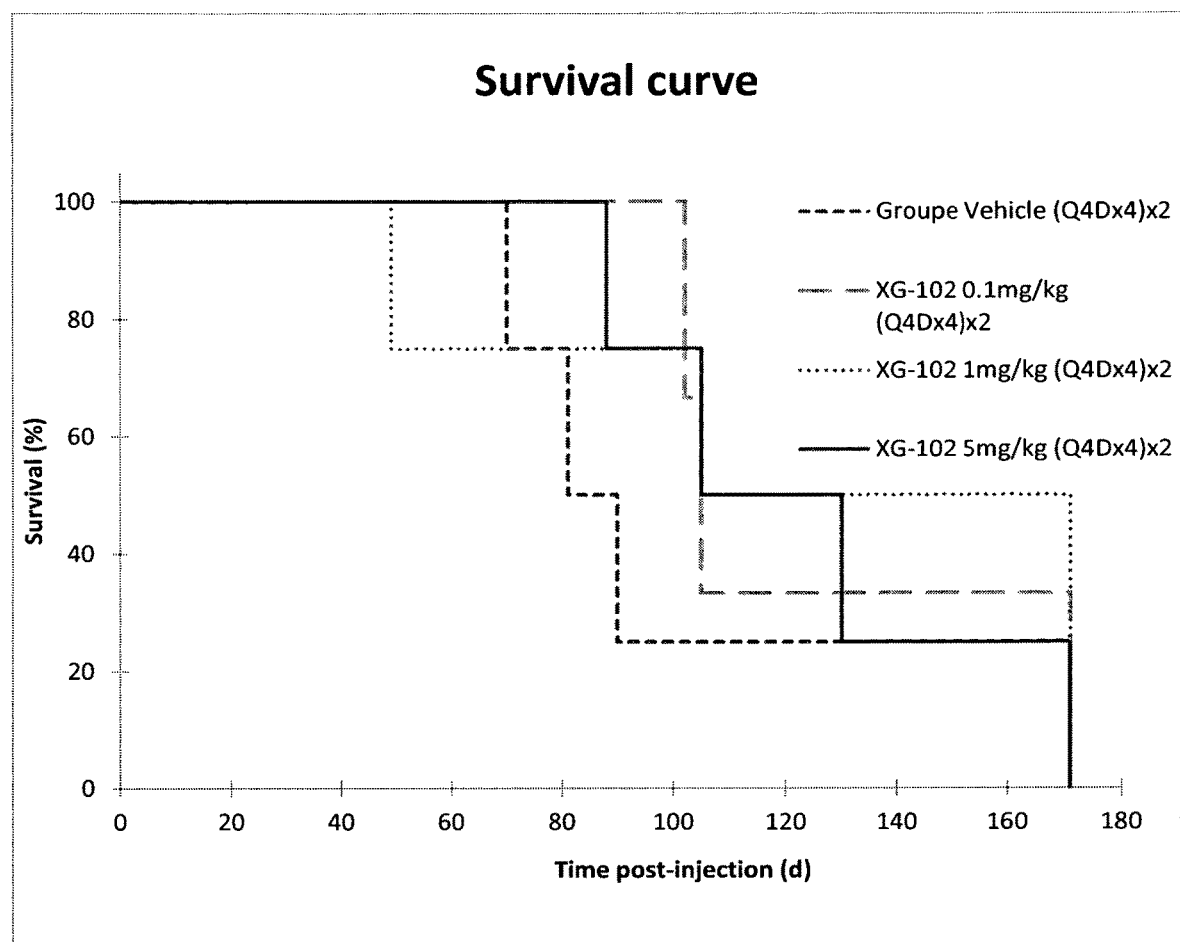
FIG. 73 shows for Example 31 the mice long survival curves, whereby proportion of surviving mice per group until sacrifice day (D171) is depicted. Mice sacrificed at D67 for autopsy were excluded from calculation. Mice were treated with XG-102 at the indicated doses following the Q4Dx4 treatment schedule repeated two timed, at D10 and D41.

FIG. 73 shows the mice long survival curves, whereby proportion of surviving mice per group until sacrifice day (D171) is depicted. Mice sacrificed at D67 for autopsy were excluded from calculation. Mice were treated with XG-102 at the indicated doses following the Q4Dx4 treatment schedule repeated two timed, at D10 and D41. These data clearly show a prolonged survival for mice treated with XG-102 in a dose-dependent manner. Accordingly, the statistical data are presented below (survival analysis of mice xenografted with HepG2 tumor and treated with XG-102):

| Treatment (D 10 &D 41, Q4Dx4) | Median survival time (day) | T/C (%) | Statistical analysis |
|---|---|---|---|
| Vehicle | 86 | — | — |
| XG-102 0.1 mg/kg | 105 | 123 | NS |
| XG-102 1 mg/kg | 138 | 161 | NS |
| XG-102 5 mg/kg | 118 | 137 | NS |

Mice sacrificed as D67 for autopsy were excluded from calculation. Mice survival time was expressed as median survival time as T/C (%) values (the ratio between the median of the days of death of treated group and the tumor bearing untreated control group). A T/C % value >125% is indicative of anti-tumor effectiveness.

The following table shows the tumor development of HepG2 cancer cells into liver. Detection of tumor masses on liver was performed by microscopic observation after HE staining on mice sacrificed at D171:

| Group | Animal ID | Observation |
|---|---|---|
| Vehicle | 933 | Tumor on liver |
| XG-102 0.1 mg/kg | 8665 | Tumor (1.3 cm) on liver |
|  | 2925 | No tumor detected |
| XG-102 1 mg/kg | 8631 | No tumor detected |
|  | 8641 | No tumor detected |
|  | 2929 | Tumor (1.9 cm) on liver |
| XG-102 5 mg/kg | 2931 | No tumor detected |
|  | 2765 | No tumor detected |
|  | 2767 | No tumor detected |

In FIG. 74 the tumor invasion observed by microscopic evaluation of mice sacrificed at D67 or between D67 and final sacrifice are shown as histogram representations. The level of tumor take was classified in 4 different categories specified in the figure legend.

Example 32: Antitumor Activity of XG-102 in Balb/c Nude Mice Bearing Subcutaneous PC-3 Human Prostate Tumors The objective of this study was to determine the antitumor activity of XG-102 (dose/response) in the model of Balb/c Nude mice bearing the subcutaneous PC-3 human prostate tumors.

15 healthy male Balb/c Nude mice were obtained from Charles River (L'Arbresles, France). Animal experiments were performed according to the European ethical guidelines of animal experimentation and the English guidelines for welfare of animals in experimental neoplasia. The animals were maintained in rooms under controlled conditions of temperature (23±2° C.), humidity (45±5%), photoperiod (12 h light/12 h dark) and air exchange. Animals were maintained in SPF conditions and room temperature and humidity was continuously monitored. The air handling system was programmed for 14 air changes per hour, with no recirculation. Fresh outside air pass through a series of filters, before being diffused evenly into each room. A high pressure (20±4 Pa) was maintained in the experimentation room to prevent contamination or the spread of pathogens within a mouse colony. All personnel working under SPF conditions followed specific guidelines regarding hygiene and clothing when they entered the animal husbandry area. Animals were housed in polycarbonate cages (UAR, Epinay sur Orge, France) that are equipped to provide food and water. The standard area cages used were 800 cm2 with a maximum of 10 mice per cage according to internal standard operating procedures. Bedding for animals was sterile wood shavings (SERLAB, Cergy-Pontoise, France), replaced once a week. Animal food was purchased from SERLAB (Cergy-Pontoise, France). The type of sterile controlled granules was DIETEX. The food was provided ad libitum, being placed in the metal lid on top of the cage. Water was also provided ad libitum from water bottles equipped with rubber stoppers and sipper tubes. Water bottles was cleaned, filled with water, sterilized by filtration and replaced twice a week.

For XG-102 administration XG-102 was prepared at the concentration of 0.2 mg/ml with sterile water (WFI, Aguettant, France). It was then diluted to the concentration of 0.02 mg/ml with sterile water. All these steps were performed within one hour prior to injection to mice. XG-102 was injected at 0.1 and 1 mg/kg/inj. Four injections were performed, each separated by four days (Q4D×4). XG-102 substances were injected intravenously (IV) at 5 ml/kg via the caudal vein of mice. In case of necrosis of the tail during the injection period, the intraperitoneal (IP) route was used. The injection volumes were adapted according to the most recent individual body weight of mice.

The tumor cell line and culture media were purchased and provided by Oncodesign:

| Cell line | Origin | Source | Reference |
|---|---|---|---|
| PC-3 | Human prostatic adenocarcinoma | ATCC* | BISSERY M. C. et al., Bull. Cancer 1991, 78: 587-602. |

*American Type Culture Collection, Manassas, Virginia, USA.

The PC-3 was initiated from a bone metastasis of a grade IV prostatic adenocarcinoma from a 62-year old male Caucasian (VOLENEC F. J. et al., J Surg Oncol 1980; 13(1): 39-44). Tumor cells grew as adherent monolayers at 37° C. in a humidified atmosphere (5% $CO_2$, 95% air). The culture medium was RPMI 1640 containing 2 mM L-glutamine (Ref BE12-702F, Lonza, Verviers, Belgium) and supplemented with 10% FBS (Ref DE14-801E, Lonza). For experimental use, the cells were detached from the culture flask by a 5-minute treatment with trypsin-versene (Ref 02-007E, Cambrex), diluted in Hanks' medium without calcium or magnesium (Ref BE10-543F, Cambrex) and neutralized by addition of complete culture medium. Cells were counted in a hemocytometer and their viability was assessed by 0.25% trypan blue exclusion. *Mycoplasma* detection was performed using the MycoAlert® *Mycoplasma* Detection Kit (Ref LT07-318, Lonza) in accordance with the manufacturer instructions. The MycoAlert® Assay is a selective biochemical test that exploits the activity of mycoplasmal enzymes. The viable *mycoplasma* are lysed and the enzymes react with the MycoAlert® substrate catalyzing the conversion of ADP to ATP. By measuring the level of ATP in a sample both before and after the addition of the MycoAlert® substrate a ratio can be obtained which is indicative of the presence or absence of *mycoplasma*. The *mycoplasma* test was assayed in duplicate from the culture supernatants of the cell lines and compared to negative and positive controls (MycoAlert® Assay Control Set Ref LT07-518, Lonza) (Internal Standard Operating Procedure No TEC-007/002).

Experimental Design:

Forty-eight hours before tumor induction, 15 male Balb/c Nude mice were irradiated with a γ-source (2.5 Gy, $Co^{60}$, INRA, Dijon, France). At D0, twenty millions ($2 \times 10^7$) PC-3 cells suspended in 200 µl of RPMI medium were subcutaneously injected in the right flank of the 60 male Balb/c Nude mice.

When the mean tumor volume reached 80±38 $mm^3$, mice were randomized before treatment start according to their tumor volume to form 3 groups of 5 mice. The tumor volume of each group was not statistically different from the others (analysis of variance).

The treatment schedule of the test substance was as follows: Mice from group 1 received one IV injection of vehicle at 5 ml/kg/inj. once every four days repeated four times (Q4D×4), Mice from group 2 received one IV injection of XG-102 at 0.1 mg/kg/inj. once every four days repeated four times (Q4D×4), and Mice from group 3 received one IV injection of XG-102 at 1 mg/kg/inj. once every four days repeated four times (Q4D×4):

| Group | No. | Treatment | Dose | Route | Treatment |
|---|---|---|---|---|---|
| 1 | 5 | vehicle | — | IV | Q4Dx4 |
| 2 | 5 | XG-102 | 0.1 | IV | Q4Dx4 |
| 3 | 5 | XG-102 | 1 | IV | Q4Dx4 |

Mice were sacrificed when tumors reached a maximum volume of 2000 $mm^3$.

Mice were monitored every day throughout the study for behaviour and survival. The body weight and tumor volume was monitored twice a week for all mice throughout the study. Isoflurane® Forene (Centravet, Bondoufle, France) was used to anaesthetize the animals before cell injection, IV treatments and sacrifice. During the course of the experiment, animals were killed under anaesthesia with Isoflurane® by cervical dislocation if any of the following occurred:

Signs of suffering (cachexia, weakening, difficulty to move or to eat),
Compound toxicity (hunching, convulsions),
20% weight loss for 3 consecutive days or 25% body weight loss on any day,
Tumor volume of more than 2000 $mm^3$.

An autopsy was performed in each case.

For the body weight analysis body weight curves of mice were drawn. Curves were stopped when more than 40% of dead mice were recorded in at least one group. Mean body weight change (MBWC): Average weight change of treated animals in grams (weight at day X minus weight at D33) was calculated.

The tumor volume was calculated with the following formula where length corresponds to the largest tumor diameter and width to the smallest tumor diameter: TV= (length×$width^2$)/2. Tumor growth curves were drawn using the mean tumor volumes (MTV)+/−SD. Curves were stopped when more than 40% of mice were dead. Individual tumor volume curves were also drawn. Relative tumor volume curve using the relative tumor volumes (RTV) at different time points calculated as shown below were drawn. Curves were stopped when more than 40% of mice were dead. The RTV was calculated following the formula:

RTV=(Tumor volume at $DX$)/(Tumor volume at $D33$)×100

Tumor doubling time (DT) defined as the period required to reach a MTV of 200% during the exponential tumor growth phase was calculated using Vivo Manager® software. Time to reach V was calculated. Volume V was defined as a target volume deduced from experimental data and chosen in the exponential phase of tumor growth. Volume V was chosen as close as possible for all mice of each group, the time to reach this Volume V was deduced from experimental data. Tumor growth inhibition (T/C %) defined as the ratio of the median tumor volumes of treated groups versus vehicle treated group was calculated. The effective criteria for the T/C % ratio according to NCI standards, is ~42% (BISSERY M. C. et al., Bull. Cancer 1991, 78: 587-602). All statistical analyses were performed using Vivo Manager® software. Statistical analysis of the toxicity and the efficiency of the treatment (BWC, MBWC, TV, RTV, TTRV and DT) was performed using the Bonferroni/Dunn test (ANOVA comparison). All groups were compared with each other.

Figure 75:
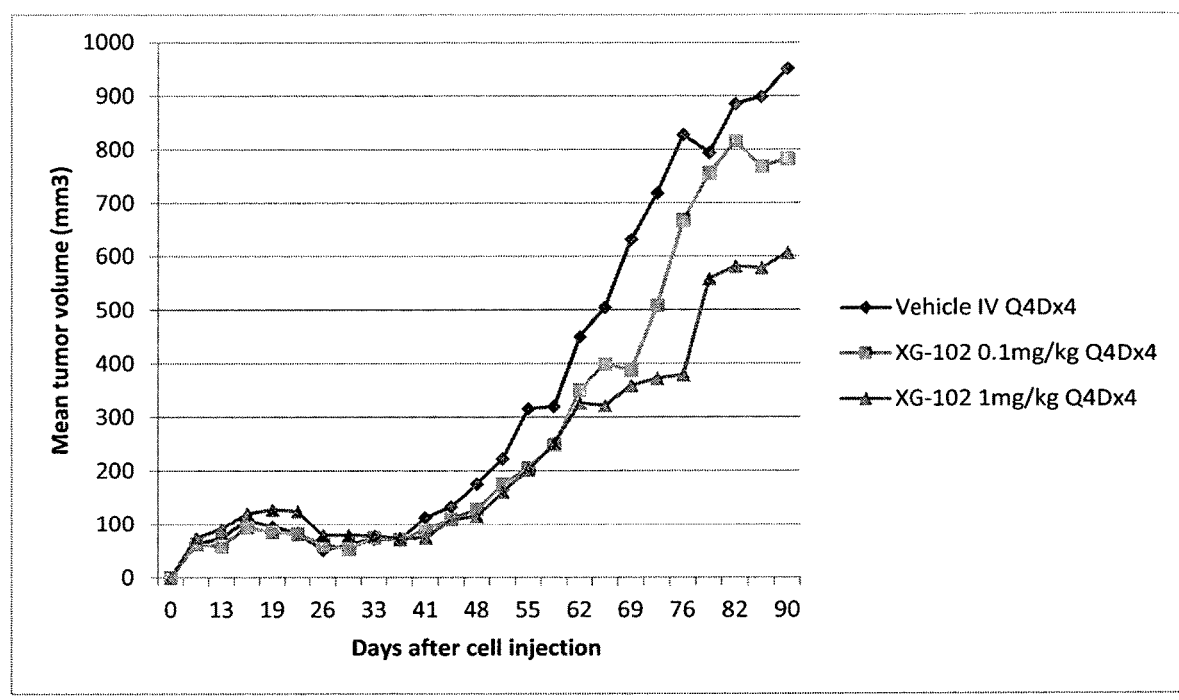
FIG. 75 shows for Example 32 the mean tumor volume of PC-3 tumor bearing mice during the antitumor activity experiment. At D33, 3 groups of 5 animals were treated with vehicle and XG-102 (0.1 and 1 mg/kg/inj, Q4Dx4).

In FIG. 75 shows the mean tumor volume of PC-3 tumor bearing mice during the antitumor activity experiment. At D33, 3 groups of 5 animals were treated with vehicle and XG-102 (0.1 and 1 mg/kg/inj, Q4D×4). These data indicate a reduction of tumor volume over time for XG-102 treatment in a dose-dependent manner, whereby the effects were more prominent for 1 mg/kg XG-102.

Example 33: Effects of XG-102 on Tumor Growth in SCID Mice Bearing Orthotopic HCT 116 Human Colon Tumors The objective of this study was to determine the effect of XG-102 on the growth of HCT 116 human colon tumor orthotopically xenografted in SCID mice.

80 healthy female SCID mice were obtained from Charles River (L'Arbresles, France). Animal experiments were performed according to the European ethical guidelines of animal experimentation and the English guidelines for welfare of animals in experimental neoplasia. The animals were maintained in rooms under controlled conditions of temperature (23±2° C.), humidity (45±5%), photoperiod (12 h light/12 h dark) and air exchange. Animals were maintained in SPF conditions and room temperature and humidity was continuously monitored. The air handling system was programmed for 14 air changes per hour, with no recirculation. Fresh outside air pass through a series of filters, before being diffused evenly into each room. A high pressure (20±4 Pa) was maintained in the experimentation room to prevent contamination or the spread of pathogens within a mouse colony. All personnel working under SPF conditions followed specific guidelines regarding hygiene and clothing when they entered the animal husbandry area. Animals were housed in polycarbonate cages (UAR, Epinay sur Orge, France) that are equipped to provide food and water. The standard area cages used were 800 cm2 with a maximum of 10 mice per cage according to internal standard operating procedures. Bedding for animals was sterile corn cob bedding (LAB COB 12, SERLAB, CergyMPontoise, France), replaced once a week. Animal food was purchased from DIETEX. The type of sterile controlled granules was DIETEX. The food was provided ad libitum, being placed in the metal lid on top of the cage. Water was also provided ad libitum from water bottles equipped with rubber stoppers and sipper tubes. Water bottles was cleaned, filled with water, sterilized by filtration and replaced twice a week.

For XG-102 administration the required amount of XG-102 was dissolved in the vehicle. The formulation was prepared according to the procedure detailed below. Concentrations were calculated and expressed taking into account test item purity and peptide content (multiplier coefficient was 74.6%). After thawing of XG-102, a stock solution was prepared at 10 mM (corresponding to 38.22 mg/ml) in sterile water (WFI, Batch 500 111 00 J, Aguettant, France) and allowed to equilibrate to room temperature for 20 minutes minimum. Aliquots were prepared for each treatment day and stored at approximately −80° C. Dilutions of this stock solution to the required concentrations were performed on each treatment day and stored at 2-4° C. for maximum 24 hours. The period of stability of the stock solution is more than 100 days at approximately −80° C. The period of stability of the diluted formulations for animal dosing is 24 hours at 2-4° C. Diluted solutions were maintained on ice until use. Unused material was discarded. XG-102 was injected once daily at 0.1 and 1 mg/kg/inj. for a total of fourteen consecutive administrations (Q1D×14). The routes of substance administrations were: injected subcutaneously (SC) at 5 ml/kg/inj., administered per os (PO) to mice by oral gavage via a canula at 5 ml/kg/adm. The injection and administration volumes were adapted, according to the daily individual body weight of mice.

The tumor cell line and culture media were purchased and provided by Oncodesign:

| Cell line | Origin | Source | Reference |
|---|---|---|---|
| HTC116 | Human colon adenocarcinoma | ATCC* | BRATTAIN M. G. et al. Cancer Res. 1981, 41: 1751M1756. |

*American Type Culture Collection, Manassas, Virginia, USA.

The HCT 116 variant cell line was isolated from a primary cell culture of a single colonic carcinoma of a male patient (BRATTAIN M. G. et al., Cancer Res. 1981, 41: 1751 M1756).

Tumor cells grew as adherent monolayers at 37° C. in a humidified atmosphere (5% CO2, 95% air). The culture medium was RPMI 1640 containing 2 mM L-glutamine (Ref BE12-702F, Lonza, Verviers, Belgium) and supplemented with 10% FBS (Ref DE14-801E, Lonza). For experimental use, the cells were detached from the culture flask by a 5-minute treatment with trypsin-versene (Ref 02-007E, Cambrex), diluted in Hanks' medium without calcium or magnesium (Ref BE10-543F, Cambrex) and neutralized by addition of complete culture medium. Cells were counted in a hemocytometer and their viability was assessed by 0.25% trypan blue exclusion. *Mycoplasma* detection was performed using the MycoAlert® *Mycoplasma* Detection Kit (Ref LT07-318, Lonza) in accordance with the manufacturer instructions. The MycoAlert® Assay is a selective biochemical test that exploits the activity of mycoplasmal enzymes. The viable *mycoplasma* are lysed and the enzymes react with the MycoAlert® substrate catalyzing the conversion of ADP to ATP. By measuring the level of ATP in a sample both before and after the addition of the MycoAlert® substrate a ratio can be obtained which is indicative of the presence or absence of *mycoplasma*. The *mycoplasma* test was assayed in duplicate from the culture supernatants of the cell lines and compared to negative and positive controls (MycoAlert® Assay Control Set Ref LT07-518, Lonza) (Internal Standard Operating Procedure No TEC-007/002).
Experimental Design:

Twenty four to Forty-eight hours before tumor induction, 5 SCID mice were irradiated with a γ-source (1.8 Gy, $Co^{60}$, INRA, Dijon, France). Ten millions ($10^7$) HCT 116 cells suspended in 200 µl of RPMI medium were subcutaneously injected in the right flank of the 5 female SCJD mice. When tumors reached 1000-2000 $mm^3$, mice were sacrificed. Tumors were surgically excised from the animal to obtain fresh tumor fragments (20-30 mg) to be orthotopically implanted on the caecum of 75 mice at D0.

Twenty four to forty-eight hours before tumor implantation, 75 SCID mice were irradiated with a γ-source (1.8 Gy, $Co^{60}$, INRA, Dijon, France). The surgery was performed in the afternoon, with a minimum delay of two hours after the 7th XG-102 treatment. The abdomen from anaesthetized animal was opened through a median incision under aseptic conditions. The caecum was exteriorized and a small lesion was performed on caecum wall. The tumor fragment was placed on lesion and fixed with 6/0 sutures. The abdominal cavity was subsequently closed in 2 layers with 4/0 sutures.

At D-7, mice were randomized according to their body weight before treatment start to form 5 groups of 15 mice. The body weight of each group was not statistically different from the others (analysis of variance). The treatment began at D-7 according to following treatment schedule:

Mice from group 1 received one PO administration of XG-102 vehicle at 5 ml/kg/inj. once daily for a total of fourteen consecutive administrations (Q 1D×14), Mice from group 2 received one PO administration of XG-102 at 0.1 mg//kg/inj. once daily for a total of fourteen consecutive administrations (QI D×14), Mice from group 3 received one PO administration of XG-102 at 1 mg//kg/inj. Once daily for a total of fourteen consecutive administrations (Q1 D×14), Mice from group 4 received one SC injection of XG-102 at 0.1 mg//kg/inj. once daily for a total of fourteen successive administrations (Q1D×14), Mice from group 5 received one SC injection of XG-102 at 1 mg//kg/inj. once daily for a total of fourteen consecutive administrations (Q1D×14):

| Group | No. | Treatment | Route | Dose (mg/kg/inj.) | Treatment Schedule |
|---|---|---|---|---|---|
| 1 | 15 | vehicle | po | — | Q1Dx14 |
| 2 | 15 | XG-102 | po | 0.1 | Q1Dx14 |
| 3 | 15 | XG-102 | po | 1 | Q1Dx14 |
| 4 | 15 | XG-102 | sc | 0.1 | Q1Dx14 |
| 5 | 15 | XG-102 | sc | 1 | Q1Dx14 |

Mice were monitored every day throughout the study for behaviour and survival. The body weight and tumor volume was monitored twice a week for all mice throughout the study. Isoflurane® Forene (Centravet, Bondoufle, France) was used to anaesthetize the animals before cell injection, surgery (orthotopic tumor implantation) and sacrifice.

During SC tumor amplification, the tumor volume was monitored twice a week for all mice throughout the study.

Mice were sacrificed at D26. The liver and tumors were collected and weighed for all animals. Invasion of liver by tumor nodules was evaluated macroscopically. Livers and tumors were fixed in 10% neutral buffered formalin. Forty eight (48) hours after collection, they were embedded in paraffin (Histosec®) and used for histology analysis. Two slides were issued from two different parts into the core of each tumor. Each slide was identified by the mouse identification number. One slide was issued per liver, localized at its center. It was identified by the mouse identification number. For determination of proliferating index by Ki67 marker, paraffin-embedded sections (5 µm) were deparaffinized in xylene (Ref. 11699027, Labonord, Templemars, France) and rehydrated by serial incubations in 100%, 95%, and 70% ethanol (Ref. 13099500, Labonord). Endogenous peroxidase was inhibited by incubating tissues in hydrogen peroxide containing solution for 10 min at room temperature before addition of the first antibody. A biotin blocking system was used to reduce background. Sections were treated for 20 min with 3% bovine serum albumin (BSA) in PBS (1×) completed with 3% goat serum at room temperature to inhibit crossreactivity before addition of the first antibody. Tissue sections were incubated for 1 hour at room temperature with the mouse anti-human Ki-67 clone MIB-1 monoclonal antibody (Ref M7240, Dako cytomation; 1:100 dilution, 80 µg/ml). A non-relevant biotinylated mouse IgGl antibody (Ref X0931, Dako cytomation, 1:120 dilution, 100 µg/ml) was used as a negative control slide ensuring the specificity of reaction. The sections were further incubated with the secondary goat anti-mouse antibody (Ref. 89904, Sigma) coupled to biotin. Then, tissue sections were incubated for 30 min at room temperature with the avidin-biotin-peroxidase conjugate (Ref PK-6100, Vector Laboratories, 1:50 dilution). DAB peroxydase substrate (Ref SK-4100, Vector Laboratories) was used as a chromogen to visualize the reaction. Sections were counterstained with Mayer's haematoxylin for histological study. After each incubation, sections were washed two times with 1×PBS. The coverslip was mounted with aqueous mountant and sections were visualized under a light microscope (DMRB Leica).

For detection of metastasis in mouse liver by histological analysis, paraffin-embedded sections (5 µm) were deparaffinized in xylene and rehydrated by serial incubations in 100%, 95%, and 70% ethanol. All sections were stained with haematoxylin and eosin (HE) (Ref. 83309, Dakocytomation, Trappes, France) for histological analyses. The coverslip was mounted with aqueous mountant (Aquatex, Ref 1.08562, Merck) and sections were viewed under a light microscope (DMRB Leica). Histological sections were analyzed by an experienced pathologist to determine the metastatic invasion in liver.

For the body weight analysis body weight curves of mice were drawn. Curves were stopped when more than 40% of dead mice were recorded in at least one group. Mean body weight change (MBWC): Average weight change of treated animals in grams (weight at day X minus weight at D-7) was calculated.

Tumor weights were calculated. Tumor growth inhibition (T/C %) was defined as the ratio of the median tumor weight of treated groups versus vehicle treated group. The effective criteria for the T/C % ratio according to NCI standards is ≤42%. For semi-quantification of proliferating index (Ki-67 staining), the numeric images of stained tumor sections were blindly analyzed and classified as no staining (level 0 corresponding to none stained area), low staining (level 1 corresponding to less than 10% of stained area), moderate staining (level 2 corresponding to 10 to 30% of stained area) and strong staining (level 3 corresponding to more than 30% of stained area). Representative pictures were taken. For detection of metastasis in the liver mean liver weights were measured, and the number of metastasis per liver was estimated on entire liver macroscopically and on section by histological analysis. Results were reported in a table. Representative pictures were taken. All statistical analyses were performed using Vivo Manager® software, Statistical analysis of the toxicity and the efficiency of the treatment (MBWC, TV, Volume V and time to reach V, DT) were performed using the Bonferroni/Dunn test (ANOVA comparison). All groups were compared with each other.

Ten millions ($10^7$) HCT 116 cells were SC injected in 5 irradiated female SCID mice. No *mycoplasma* was detected in cells and their viability was 99% before injection. Thirty-nine days after, when mean tumor volume was 864±426 mm3, mice were sacrificed. Their tumor was isolated and cut into pieces of approximately 20~30 mg. These pieces were implanted at D0 onto the ceacum of 75 treated animals. From D0 to 09, surgery complications due to tumor implantation induced death of 33% of mice in vehicle treated group. In the treated groups, percentages of death were 40%, 34%, 47% and 40%, with no dose related effect. The fact that treatments with XG-102 did not significantly modify lethality compared to vehicle treated group suggest that treatments were tolerated by animals. Moreover, between the day of treatment start (D−7) and two days before surgery (D−2), the six daily treatments did not induce any significant body weight loss, indicating again that XG-102 was well tolerated. At D−2, MBWC was distributed between +5.2±4.6% for vehicle treated group to +7.1±4.6% in the group PO treated at 0.1 mg/kg/adm. In addition, after surgery, no MBWC difference was observed between the group treated with vehicle and those treated with XG-102 at different doses, even if a significant decrease caused by surgery was observed for all groups, when comparing MBWC before and after surgery.

Figure 76:
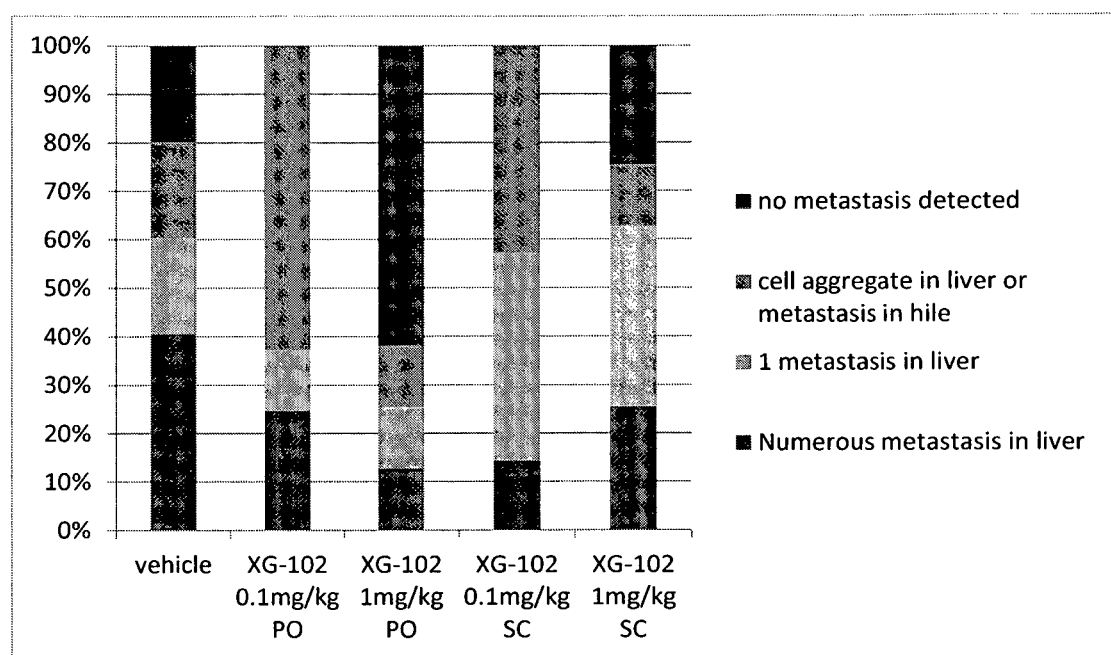
FIG. 76 shows for Example 33 a histogram representation of metastatic tumor invasion observed within liver or at its periphery (hilus) twenty-six days after HCT 116 tumor xenografting on mice caecum, in the different groups, PO or SC treated with vehicle or X0-102 at 0.1 and 1 mgl/kg/adm. following the Q1Dx14 treatment schedule. The classification of microscopic observations was performed as described within the legend.

The mean liver weights in mice sacrificed at D26 were distributed between 0.82±0.17 g in vehicle treated group and 0.91±0.17 g in the group PO treated at 0.1 mg/kg. They were not significantly different. In the vehicle treated group, 20% did not develop any metastasis in liver. As shown in FIG. 76, this control group was the one where the number of mice developing more than 1 metastasis in liver was the highest (40%). In the treated groups, this score was distributed between 12.5% for the group PO treated at 1 mg/kg to 25% for the groups PO treated at 0.1 mg/kg or SC treated at 1 mg/kg. Remarkably, the group PO treated at 1 mg/kg had the highest number of mice with no liver metastasis, suggesting that XG-102 might decrease metastatic power of HCT 116 orthotopic tumor.

Example 34: Evaluation of Efficacy of XG-102 in Reducing the Photoreceptors Light Damage in Rat (AMD Model)

The aim of this study was to investigate the dose effect of XG-102 on light-induced photoreceptor cell death.

50 male Rat (Sprague-Dawley (albinos rat); approximately 8 weeks; 200-250 g (on ordering)) have been used. Rats are most commonly used in this experimental model. Animals were examined before study, and particular attention was paid to the eyes. Animals were held in observation for 2 weeks following their arrival. Animals were observed daily for signs of illness. Only healthy animals with no ocular abnormalities were accepted for use in experiments. Animals were housed individually in standard cages (420× 270×190 mm)². All animals were housed under identical environmental conditions. The temperature was held at 22±2° C. and the relative humidity at 55±10%. Rooms were continuously ventilated (15 times per hour). A cycle of 12 hours light (200-300 lx) and 12 hours darkness was automatically controlled. These parameters were continuously controlled and recorded. Throughout the study, animals had free access to food and water. They were fed a standard dry pellet diet. Tap water was available ad libitum from plastic bottles.

Study Design:

Forty-eight (48) rats were randomly divided into six (6) groups of eight (8) animals each.

Test item (XG-102: 30 mg/ml, 3 mg/ml, and 0.3 mg/ml) and vehicle (0.9% NaCl) were administered by intravitreal injection in right eyes the day before induction. The reference (Phenyl-N-test-Butylnitrone (PBN) (50 mg/kg)) and vehicle were intraperitoneally injected 30 min before induction then, 3 times during 12 hours of light exposition, then once after induction. Animals were placed in constant light (7000 lux) for 24 h. Electroretinograms (ERG) were recorded before light treatment and on days 9, 16 and 23 after induction. Eyes were then taken for histology and outer nuclear layer (ONL) thickness assessment. The table below summarizes the allocation of animals in treatment groups:

| Group No. | Treatment | Dose | Route of administration (volume) | Time of administration | Animals Identification |
|---|---|---|---|---|---|
| 1 | XG-102 | 30 000 μg/mL 150 μg/eye | i.v.t. (5 μl) | Day before induction (D 0) | 13, 38, 9, 35, 2, 23, 25, 36 |
| 2 | | 3 000 μg/mL 15 μg/eye | | | 18, 28, 5, 27, 16, 12, 30, 1 |
| 3 | | 300 μg/mL 1.5 μg/eye | | | 3, 11, 8, 17, 31, 7, 22, 15 |
| 4 | Vehicle | — | | | 6, 29, 24, 21, 40, 32, 14, 37 |
| 5 | PBN | 50 mg/kg | i.p. (2.5 ml/kg) (5 times) | 30 min before induction, then 2 h, 4 h, 6 h (during light exposure - D 1) and 24 h (at the cessation of exposure - D 2) after induction | 4, 39, 19, 33, 10, 26, 34, 20 |
| 6 | Vehicle | — | | | 41, 42, 43, 44, 45, 46, 47, 48 |

Forty-eight (48) animals out of fifty (50) were used in this study. Only animals with no visible sign of ocular defect were selected. Then, the randomization in the treatment groups was done by a random function in Excel® software.

Route and Method of Administration

For the intravitreal injection animals were anesthetized by intramuscular injection of a mixture of xylazine/ketamine. Test item (5 μl) and vehicle (5 μl) were injected in the right eye. The injection was performed under an operating microscope in the supratemporal area at pars plana using a 33G-needle mounted on a 50 µl Hamilton. The filled syringe was mounted into the UltraMicroPump III to achieve accurate injection in microliter range. Reference and vehicle were injected intraperitoneally at a dose volume of 2.5 ml/kg using a 30G-needle mounted on a 1 ml-syringe.

Light Exposure: The rats that had been dark-adapted overnight were exposed for 24 hours to a continuous white fluorescent light (7000 lx) in clear plastic cages. Each cage contained one rat. After exposure, the rats returned to rearing cyclic light conditions.

The body weight of all animals was recorded before the start of the study then at the end of the study. Each day, the general behavior and the aspect of all animals were observed.

ERG was recorded before induction and 7, 14 and 21 days after cessation of exposure (Days 9, 16 and 23) on right eyes of dark-adapted and anesthezied animals. The latency times (for a- and b-wave) and the a-wave and b-wave amplitudes were measured for each ERG; the latency times were expressed as millisecond and the a-wave and b-wave as a percentage of the baseline value obtained before light exposure. 15 min before measurement 10 µl Mydriaticum® (0.5% tropicamide) were instilled for pupillary dilatation.
ERG parameters:
  Color: white maximum.
  Maximum intensity: 2.6 cd·s/m² (0 dB); Duration 0.24 ms; number of flash: 1.
  Filter: 50 Hz.
  Impedance Threshold: 90 kΩ.

Measurement of the ONL Thickness: After ERG testing, animal was euthanized by an overdose of pentobarbital and the right eyes were enucleated, fixed and embedded in paraffin. Sections (5 µm thick) were performed along the vertical meridian and stained with Trichrome-Masson. The vertical meridian included the optic nerve. ONL Thickness was done every 500 µm (seven points) between 500 and 3500 µm from the optic nerve in the inferior retina using a standard microscope (Leica).

Results were expressed in the form of individual and summarized data tables using Microsoft Excel® Software. Group mean values and standard deviation were calculated. A statistical Mann and Whitney test was used to evaluate the differences between pair-wise groups. For comparison between time-point into each vehicle groups, a Friedman test was used.

Results

General behavior and appearance were normal in all animals.

The animal body weights all were within a normal range at baseline: 379±13 g (mean±SD; n=48). On sacrifice day (Day 23) no visible differences between test articles, and vehicle were observed. The mean body weights, recorded for each group just before the start of the study (baseline) and on the day of euthanasia were within a normal range with a body weight gain about 31±5% (mean±SD; n=48).

Electroretinograms

Figure 77:
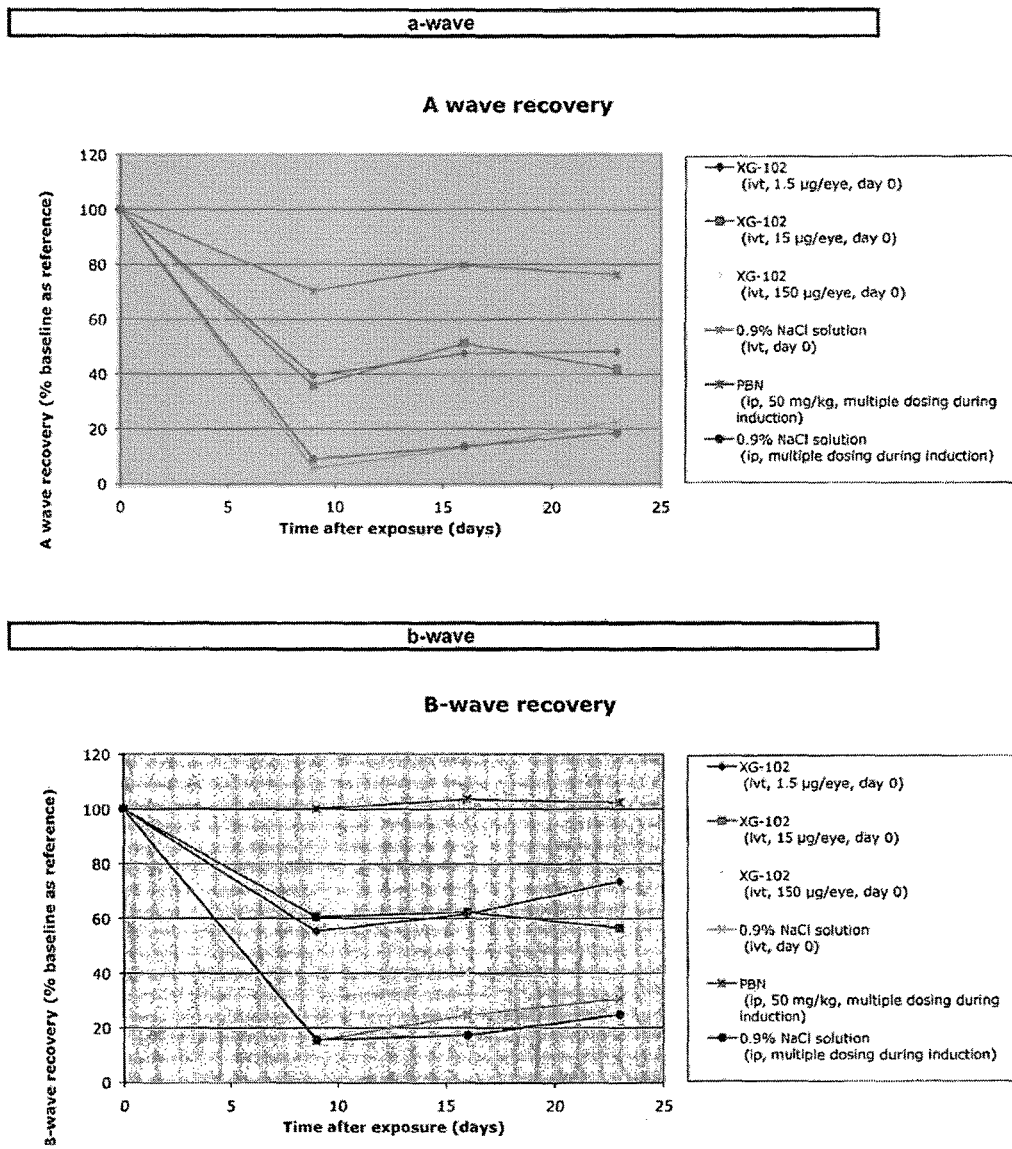
FIG. 77 shows for Example 34 the electroretinography (ERG) measurements in right eyes of albino rats.

To investigate the protective effect on photoreceptors, test, vehicle and reference items were evaluated in light-induced photodegeneration model. The functional status of retina was evaluated by electroretinography. Electroretinography waves' amplitudes were normalized to baseline values and expressed as a percent of the baseline. FIG. 77 illustrates the time course of recovery for the different groups.

Phenyl-N-tert-Butylnitrone, a synthetic anti-oxidant that has been shown to protect albino rat from light-induced photoreceptor death was used as reference in the assay. Three doses of XG-102 were tested: 1.5 µg/eye (0.3 mg/ml, Low dose), 15 µg/eye (3 mg/ml, Mid dose) and 150 µg/eye (30 mg/ml, High dose). The mean values of the a and b-waves for amplitude (in %; mean±SD) are summarized in the following tables:

| A-wave | Time after the beginning of exposure | | |
|---|---|---|---|
| | Day 9 Mean ± SD | Day 16 Mean ± SD | Day 23 Mean ± SD |
| Vehicle (IVT) | 5.7 ± 4.9 | 13.2 ± 9.7 | 22.5 ± 9.6 |
| XG-102 (ivt, 1.5 µg/eye) | 39.5§ ± 19.0 | 47.5§ ± 16.5 | 48.3§ ± 15.2 |
| XG-102 (ivt, 15 µg/eye) | 35.7§ ± 22.0 | 51.1§ ± 18.9 | 41.8 ± 23.6 |
| XG-102 (ivt, 150 µg/eye) | 23.6 ± 25.3 | 24.1 ± 28.1 | 23.7 ± 27.2 |
| Vehicle (ip) | 9.0 ± 19.2 | 13.6 ± 24.0 | 18.6 ± 22.0 |
| PBN (ip, 50 mg/kg) | 70.4§ ± 16.2 | 79.6§ ± 9.4 | 76.2§ ± 13.1 |

§p < 0.05 by Mann and Whitney test, x vs. vehicle.

| B-wave | Time after the beginning of exposure | | |
|---|---|---|---|
| | Day 9 Mean ± SD | Day 16 Mean ± SD | Day 23 Mean ± SD |
| Vehicle (IVT) | 15.3 ± 11.4 | 24.8 ± 15.9 | 30.6 ± 13.8 |
| XG-102 (ivt, 1.5 µg/eye) | 55.3§ ± 23.8 | 61.7§ ± 19.7 | 73.5§ ± 22.0 |
| XG-102 (ivt, 15 µg/eye) | 60.6§ ± 32.8 | 62.3§ ± 18.5 | 56.5 ± 29.8 |
| XG-102 (ivt, 150 µg/eye) | 31.9 ± 42.6 | 38.9 ± 51.5 | 37.1 ± 54.4 |
| Vehicle (ip) | 15.6 ± 29.3 | 17.3 ± 30.6 | 24.9 ± 33.9 |
| PBN (ip, 50 mg/kg) | 100§ ± 18.6 | 103.6§ ± 12.1 | 102.4§ ± 11.0 |

§p < 0.05 by Mann and Whitney test, x vs. vehicle.

As also shown in FIG. 77, the mean a-wave amplitude in the induced groups that was injected with vehicle by intraperitoneal or intravitreal injection showed reduction at Days 9, 16 and 23 compared with control values on baseline. The a-wave was reduced to less than 50% of control values on Day 9 (p<0.01), Days 16 (p<0.01) and 23 (p<0.05). The b-wave was significantly reduced to less than 50% of control values on Day 9 (p<0.01) and Day 16 (p<0.01). On Day 23, the reduction was not statistically significant. In the group treated with PBN and exposed to the damaging light, the retinal function was preserved to a large extent. The recovery of the a-wave was significantly improved compared with vehicle at Day 9 (p<0.01), at Day 16 (p<0.01) and Day 23 (p<0.01) and was 70.4%, 79.6% and 76.2%, respectively. Similarly, the recovery of the b-wave was significantly greater (p<0.01) than the vehicle, 100%, 103.6% and 102.4% at days 9, 16 and 23, respectively.

Rats treated with different doses of intravitreous XG-102 up to 15 µg/eye and exposed to the damaging light, showed a preservation of the retinal function to a large extend compared with vehicle at Days 9, 16 and 23. The recovery of the a-wave was 47.5% (p<0.01) and 51.1% (p<0.01) at Day 16 and 48.3% (p<0.01) and 41.8% (p<0.05) at Day 23 for the low and mid dose, respectively. Similarly, the recovery of the b-wave was greater than the vehicle and was 55.3% and 60.6% at Day 9, 61.7% and 62.3% at Day 16, 73.5% and 56.5% at Day 23, for the low and mid dose respectively. On the other hand, high-dose (150 µg/eye group) XG-102 showed no effect in preventing light damage. The recovery of the a-wave was 23.6%, 24.1% and 23.7% versus 5.7%, 13.2% and 22.5% for the vehicle group at Days 9, 16 and 23, respectively. Similarly, the recovery of the b-wave was 31.9%, 38.9% and 37.1% versus 15%, 24.8% and 30.6% for the vehicle group at Days 9, 16 and 23, respectively.

ONL Thickness

To assess the ability of treatment to preserve photoreceptor structure, the thickness of the ONL was evaluated 21 days after cessation of exposure (Day 23). The mean values are summarized in the following table:

| Treatment | ONL thickness (µm) | ONL thickness Loss (% comparison with control non-induced eye) |
|---|---|---|
| Non-induced eyes (internal data) | 40.6 ± 4.6 | — |
| Vehicle (IVT) | 13.94 ± 3.35 | 66% |
| XG-102 (ivt, 1.5 µg/eye) | 24.89 ± 4.01§ | 39% |
| XG-102 (ivt, 15 µg/eye) | 24.42 ± 5.99§ | 40% |
| XG-102 (ivt, 150 µg/eye) | 18.95 ± 9.17 | 53% |
| Vehicle (ip) | 12.56 ± 8.15 | 69% |
| PBN (ip, 50 mg/kg) | 34.05 ± 4.00§ | 16% |

§ $p < 0.05$ by Mann and Whitney test, x vs. vehicle (ivt, ip).

A decrease in ONL thickness was observed in the eyes of vehicle-treated rats. A 66% to 69% loss of mean ONL thickness was observed in vehicle-treated eyes after exposure compared with untreated eyes. Administration of PBN showed a significant protection compared with vehicle groups (ivt and ip, $p < 0.001$). When the rats were treated with PBN, the ONL was preserved. Only a small decrease (16%) was observed compared with untreated eyes in normal condition (40.6±4.6 µm, internal data). The decrease in ONL thickness was inhibited in the XG-102-treated rats with the low and mid doses ($p < 0.01$ compared with vehicle). No protection was observed with high dose XG-102. A 40% loss of the mean ONL thickness was observed in low and mid doses XG-102-treated eyes.

Thus, under these experimental conditions, it can be stated that:

In vehicle treated groups (2 routes of administration: ivt, ip) a bright light exposure induced a decrease of retinal function and a loss of photoreceptor. 23 days after exposure, the recovery of the a-wave was 18.6% (ip) and 22.5% (ivt); 69% (ip) and 66% (ivt) loss of mean ONL thickness was observed.

Systemic administration (i.p.) of PBN protects significantly the retina from light damage. The PBN-treated group maintained 76.2% of a-wave and only a small loss (16%) of mean ONL thickness was observed.

Intravitreal injection of 1.5 and 15 µg/eye XG-102 protects significantly the retina from light damage. The XG-102 treated group maintained 48.3% and 41.8% of a-wave and a 40% loss of mean ONL thickness was observed.

Taken together, according to the statistical analyses, intravitreal injection of XG-102 (1.5 and 15 µg/eye) was efficient to protect retinal function. Under these experimental conditions, the results indicate that XG-102 by IVT at doses 1.5 µg and 15 µg/eye protects the structure and function of the retina from acute light-induced damage.

The invention claimed is:

1. A method of treating cystitis in a subject in need thereof, the method comprising administering to the subject a pharmaceutical composition that specifically inhibits the activity of c-Jun amino terminal kinase 2 (JNK2), the composition comprising a chimeric peptide comprising a first domain having the amino acid sequence of SEQ ID NO: 6 and a second domain having the amino acid sequence of SEQ ID NO: 2.

2. The method of claim 1, wherein the chimeric peptide inhibits the activation of at least one JNK targeted transcription factor when the chimeric peptide is present in a JNK expressing cell.

3. The method according to claim 2, wherein the JNK targeted transcription factor is selected from the group consisting of c-Jun, ATF2, and Elk1.

4. The method according to claim 1, wherein the chimeric peptide alters a JNK effect when the peptide is presented in a JNK expressing cell.

5. The method of claim 1, wherein the chimeric peptide consists of the amino acid sequence of SEQ ID NO: 11.

6. The method of claim 1, wherein the pharmaceutical composition is administered by an administration route selected from the group consisting of intravenous route, intramuscular route, subcutaneous route, intradermal route, transdermal route, oral route, rectal route, topical routes, nasal route, intranasal route, epidermal route and patch delivery.

7. The method of claim 1, wherein the chimeric peptide comprises the amino acid sequence of SEQ ID NO: 11.

8. The method of claim 1, wherein the cystitis is interstitial cystitis.

\* \* \* \* \*

SEQUENCE LISTING

```
<160> NUMBER OF SEQ ID NOS: 105

<210> SEQ ID NO 1
<211> LENGTH: 19
<212> TYPE: PRT
<213> ORGANISM: Artificial
<220> FEATURE:
<223> OTHER INFORMATION: Description of sequence: Peptide L-IB1(s) (see
      Table 1)

<400> SEQUENCE: 1

Arg Pro Lys Arg Pro Thr Thr Leu Asn Leu Phe Pro Gln Val Pro Arg
1               5                   10                  15

Ser Gln Asp

<210> SEQ ID NO 2
<211> LENGTH: 19
<212> TYPE: PRT
<213> ORGANISM: Artificial
<220> FEATURE:
<223> OTHER INFORMATION: Description of sequence: Peptide D-IB1(s) (see
      Table 1)
<220> FEATURE:
<221> NAME/KEY: MUTAGEN
<222> LOCATION: (1)..(19)
<223> OTHER INFORMATION: all amino acids are D-amino acids

<400> SEQUENCE: 2

Asp Gln Ser Arg Pro Val Gln Pro Phe Leu Asn Leu Thr Thr Pro Arg
1               5                   10                  15

Lys Pro Arg
```

```
<210> SEQ ID NO 3
<211> LENGTH: 19
<212> TYPE: PRT
<213> ORGANISM: Artificial
<220> FEATURE:
<223> OTHER INFORMATION: Description of sequence: Peptide L-IB (generic)
      (s) (see Table 1)
<220> FEATURE:
<221> NAME/KEY: misc_feature
<223> OTHER INFORMATION: Description of sequence: Description of
      sequence: general formula: NH2-Xnb-Xna-RPTTLXLXXXXXXXQD-Xnb-COOH
      (see Table 1)
<220> FEATURE:
<221> NAME/KEY: VARIANT
<222> LOCATION: (1)..(1)
<223> OTHER INFORMATION: Xaa can be any naturally occurring amino acid
      (see Table 1 in the description)
<220> FEATURE:
<221> NAME/KEY: VARIANT
<222> LOCATION: (2)..(2)
<223> OTHER INFORMATION: <223>  Xaa can be any naturally occurring amino
      acid residue except serine and threonine (see Table 1 in the
      description)
<220> FEATURE:
<221> NAME/KEY: VARIANT
<222> LOCATION: (8)..(8)
<223> OTHER INFORMATION: Xaa can be any naturally occurring amino acid;
<220> FEATURE:
<221> NAME/KEY: VARIANT
<222> LOCATION: (10)..(16)
<223> OTHER INFORMATION: Xaa can be any naturally occurring amino acid
<220> FEATURE:
<221> NAME/KEY: VARIANT
<222> LOCATION: (19)..(19)
<223> OTHER INFORMATION: Xaa can be any naturally occurring amino acid
      (see Table 1 in the description)

<400> SEQUENCE: 3

Xaa Xaa Arg Pro Thr Thr Leu Xaa Leu Xaa Xaa Xaa Xaa Xaa Xaa Xaa
1               5                   10                  15

Gln Asp Xaa

<210> SEQ ID NO 4
<211> LENGTH: 19
<212> TYPE: PRT
<213> ORGANISM: Artificial
<220> FEATURE:
<223> OTHER INFORMATION: Description of sequence: Peptide D-IB (generic)
      (s) (see Table 1)
<220> FEATURE:
<221> NAME/KEY: misc_feature
<223> OTHER INFORMATION: Description of sequence: general formula:
      NH2-Xnb-DQXXXXXXXLXLTTPR-Xna-Xnb-COOH,
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa can be any naturally occurring amino acid
      (see Table 1 in the description)
<220> FEATURE:
<221> NAME/KEY: VARIANT
<222> LOCATION: (4)..(10)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: Xaa can be any naturally occurring amino acid
<220> FEATURE:
<221> NAME/KEY: VARIANT
<222> LOCATION: (18)..(18)
<223> OTHER INFORMATION: Xaa can be any naturally occurring amino acid
      residue except serine and threonine (see Table 1 in the
```

```
           description)
<220> FEATURE:
<221> NAME/KEY: VARIANT
<222> LOCATION: (19)..(19)
<223> OTHER INFORMATION: Xaa can be any naturally occurring amino acid
      (see Table 1 in the description)

<400> SEQUENCE: 4

Xaa Asp Gln Xaa Xaa Xaa Xaa Xaa Xaa Xaa Leu Xaa Leu Thr Thr Pro
1               5                   10                  15

Arg Xaa Xaa

<210> SEQ ID NO 5
<211> LENGTH: 10
<212> TYPE: PRT
<213> ORGANISM: Artificial
<220> FEATURE:
<223> OTHER INFORMATION: Description of sequence:  Peptide L-TAT (see
      Table 1)

<400> SEQUENCE: 5

Gly Arg Lys Lys Arg Arg Gln Arg Arg Arg
1               5                   10

<210> SEQ ID NO 6
<211> LENGTH: 10
<212> TYPE: PRT
<213> ORGANISM: Artificial
<220> FEATURE:
<223> OTHER INFORMATION: Description of sequence: Peptide D-TAT (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 6

Arg Arg Arg Gln Arg Arg Lys Lys Arg Gly
1               5                   10

<210> SEQ ID NO 7
<211> LENGTH: 11
<212> TYPE: PRT
<213> ORGANISM: Artificial
<220> FEATURE:
<223> OTHER INFORMATION: Description of sequence: Peptide L-generic-TAT
      (s) (see Table 1)
<220> FEATURE:
<221> NAME/KEY: misc_feature
<223> OTHER INFORMATION: General formula: NH2-Xnb-RKKRRQRRR-Xnb-COOH
      (see Table 1)
<220> FEATURE:
<221> NAME/KEY: VARIANT
<222> LOCATION: (1)..(1)
<223> OTHER INFORMATION: Xaa can be any naturally occurring amino acid
      (see Table 1 in the description)
<220> FEATURE:
<221> NAME/KEY: VARIANT
<222> LOCATION: (11)..(11)
<223> OTHER INFORMATION: Xaa can be any naturally occurring amino acid
      (see Table 1 in the description)

<400> SEQUENCE: 7

Xaa Arg Lys Lys Arg Arg Gln Arg Arg Arg Xaa
1               5                   10

<210> SEQ ID NO 8
<211> LENGTH: 11
<212> TYPE: PRT
<213> ORGANISM: Artificial
```

```
<220> FEATURE:
<223> OTHER INFORMATION: Description of sequence: Peptide D-generic-TAT
      (s) (see Table 1)
<220> FEATURE:
<221> NAME/KEY: misc_feature
<223> OTHER INFORMATION: General formula: NH2-Xnb-RRRQRRKKR-Xnb-COOH
<220> FEATURE:
<221> NAME/KEY: MUTAGEN
<222> LOCATION: (1)..(10)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa can be any naturally occurring amino acid
      (see Table 1 in the description)
<220> FEATURE:
<221> NAME/KEY: VARIANT
<222> LOCATION: (11)..(11)
<223> OTHER INFORMATION: Xaa can be any naturally occurring amino acid
      (see Table 1 in the description)

<400> SEQUENCE: 8

Xaa Arg Arg Arg Gln Arg Arg Lys Lys Arg Xaa
1               5                   10

<210> SEQ ID NO 9
<211> LENGTH: 31
<212> TYPE: PRT
<213> ORGANISM: Artificial
<220> FEATURE:
<223> OTHER INFORMATION: Description of sequence: L-TAT-IB1 (s) (see
      Table 1)

<400> SEQUENCE: 9

Gly Arg Lys Lys Arg Arg Gln Arg Arg Arg Pro Pro Arg Pro Lys Arg
1               5                   10                  15

Pro Thr Thr Leu Asn Leu Phe Pro Gln Val Pro Arg Ser Gln Asp
            20                  25                  30

<210> SEQ ID NO 10
<211> LENGTH: 29
<212> TYPE: PRT
<213> ORGANISM: Artificial
<220> FEATURE:
<223> OTHER INFORMATION: Description of sequence: Peptide L-TAT
      (generic) (s) (see Table 1)
<220> FEATURE:
<221> NAME/KEY: misc_feature
<223> OTHER INFORMATION: Description of sequence: General formula:
      NH2-Xnb-RKKRRQRRR-Xnb-Xna-RPTTLXLXXXXXXXQD-Xnb-COOH
<220> FEATURE:
<221> NAME/KEY: VARIANT
<222> LOCATION: (1)..(1)
<223> OTHER INFORMATION: Xaa can be any naturally occurring amino acid
      (see Table 1 in the description)
<220> FEATURE:
<221> NAME/KEY: VARIANT
<222> LOCATION: (11)..(11)
<223> OTHER INFORMATION: Xaa can be any naturally occurring amino acid
      (see Table 1 in the description)
<220> FEATURE:
<221> NAME/KEY: VARIANT
<222> LOCATION: (12)..(12)
<223> OTHER INFORMATION: Xaa can be any naturally occurring amino acid
      residue except serine and threonine (see Table 1 in the
      description)
<220> FEATURE:
<221> NAME/KEY: VARIANT
<222> LOCATION: (18)..(18)
<223> OTHER INFORMATION: Xaa can be any naturally occurring amino acid
<220> FEATURE:
<221> NAME/KEY: VARIANT
<222> LOCATION: (20)..(26)
<223> OTHER INFORMATION: Xaa can be any naturally occurring amino acid
```

```
<220> FEATURE:
<221> NAME/KEY: VARIANT
<222> LOCATION: (29)..(29)
<223> OTHER INFORMATION: Xaa can be any naturally occurring amino acid
      (see Table 1 in the description)

<400> SEQUENCE: 10

Xaa Arg Lys Lys Arg Arg Gln Arg Arg Xaa Xaa Arg Pro Thr Thr
1               5                   10                  15

Leu Xaa Leu Xaa Xaa Xaa Xaa Xaa Xaa Xaa Gln Asp Xaa
            20                  25

<210> SEQ ID NO 11
<211> LENGTH: 31
<212> TYPE: PRT
<213> ORGANISM: Artificial
<220> FEATURE:
<223> OTHER INFORMATION: Description of sequence: Peptid D-TAT-IB1 (s)
      (see Table 1)
<220> FEATURE:
<221> NAME/KEY: MUTAGEN
<222> LOCATION: (1)..(31)
<223> OTHER INFORMATION: all amino acids are D-amino acids

<400> SEQUENCE: 11

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg Gly
            20                  25                  30

<210> SEQ ID NO 12
<211> LENGTH: 29
<212> TYPE: PRT
<213> ORGANISM: Artificial
<220> FEATURE:
<223> OTHER INFORMATION: Description of sequence: Peptid: D-TAT
      (generic) (s) (see Table 1)
<220> FEATURE:
<221> NAME/KEY: misc_feature
<223> OTHER INFORMATION: General formula:
      NH2-Xnb-DQXXXXXXXLXLTTPR-Xna-Xnb-RRRQRRKKR-Xnb-COOH,
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa can be any naturally occurring amino acid
      (see Table 1 in the description)
<220> FEATURE:
<221> NAME/KEY: VARIANT
<222> LOCATION: (4)..(10)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: Xaa can be any naturally occurring amino acid
<220> FEATURE:
<221> NAME/KEY: VARIANT
<222> LOCATION: (18)..(18)
<223> OTHER INFORMATION: Xaa can be any naturally occurring amino acid
      residue except serine and threonine (see Table 1 in the
      description)
<220> FEATURE:
<221> NAME/KEY: VARIANT
<222> LOCATION: (19)..(19)
<223> OTHER INFORMATION: Xaa can be any naturally occurring amino acid
      (see Table 1 in the description)
<220> FEATURE:
<221> NAME/KEY: VARIANT
<222> LOCATION: (29)..(29)
<223> OTHER INFORMATION: Xaa can be any naturally occurring amino acid
```

-continued (see Table 1 in the description)

<400> SEQUENCE: 12

Xaa Asp Gln Xaa Xaa Xaa Xaa Xaa Xaa Xaa Leu Xaa Leu Thr Thr Pro
1               5                   10                  15

Arg Xaa Xaa Arg Arg Arg Gln Arg Arg Lys Lys Arg Xaa
            20                  25

<210> SEQ ID NO 13
<211> LENGTH: 29
<212> TYPE: PRT
<213> ORGANISM: Artificial
<220> FEATURE:
<223> OTHER INFORMATION: Description of sequence: peptide IB1-long (see
      Table 1)

<400> SEQUENCE: 13

Pro Gly Thr Gly Cys Gly Asp Thr Tyr Arg Pro Lys Arg Pro Thr Thr
1               5                   10                  15

Leu Asn Leu Phe Pro Gln Val Pro Arg Ser Gln Asp Thr
            20                  25

<210> SEQ ID NO 14
<211> LENGTH: 27
<212> TYPE: PRT
<213> ORGANISM: Artificial
<220> FEATURE:
<223> OTHER INFORMATION: Description of sequence: Peptide IB2-long (see
      Table 1)

<400> SEQUENCE: 14

Ile Pro Ser Pro Ser Val Glu Glu Pro His Lys His Arg Pro Thr Thr
1               5                   10                  15

Leu Arg Leu Thr Thr Leu Gly Ala Gln Asp Ser
            20                  25

<210> SEQ ID NO 15
<211> LENGTH: 29
<212> TYPE: PRT
<213> ORGANISM: Artificial
<220> FEATURE:
<223> OTHER INFORMATION: Description of sequence: Peptide derived from
      c-Jun (see Table 1)

<400> SEQUENCE: 15

Gly Ala Tyr Gly Tyr Ser Asn Pro Lys Ile Leu Lys Gln Ser Met Thr
1               5                   10                  15

Leu Asn Leu Ala Asp Pro Val Gly Asn Leu Lys Pro His
            20                  25

<210> SEQ ID NO 16
<211> LENGTH: 29
<212> TYPE: PRT
<213> ORGANISM: Artificial
<220> FEATURE:
<223> OTHER INFORMATION: Description of sequence: Peptide derived from
      ATF2 (see Table 1)

<400> SEQUENCE: 16

Thr Asn Glu Asp His Leu Ala Val His Lys His Lys His Glu Met Thr
1               5                   10                  15

Leu Lys Phe Gly Pro Ala Arg Asn Asp Ser Val Ile Val
            20                  25

-continued

```
<210> SEQ ID NO 17
<211> LENGTH: 23
<212> TYPE: PRT
<213> ORGANISM: Artificial
<220> FEATURE:
<223> OTHER INFORMATION: Description of sequence: Peptide L-IB1 (see
      Table 1)

<400> SEQUENCE: 17

Asp Thr Tyr Arg Pro Lys Arg Pro Thr Thr Leu Asn Leu Phe Pro Gln
1               5                   10                  15

Val Pro Arg Ser Gln Asp Thr
            20

<210> SEQ ID NO 18
<211> LENGTH: 23
<212> TYPE: PRT
<213> ORGANISM: Artificial
<220> FEATURE:
<223> OTHER INFORMATION: Description of sequence: Peptide D-IB1 (see
      Table 1)
<220> FEATURE:
<221> NAME/KEY: MUTAGEN
<222> LOCATION: (1)..(23)
<223> OTHER INFORMATION: all amino acids are D-amino acids

<400> SEQUENCE: 18

Thr Asp Gln Ser Arg Pro Val Gln Pro Phe Leu Asn Leu Thr Thr Pro
1               5                   10                  15

Arg Lys Pro Arg Tyr Thr Asp
            20

<210> SEQ ID NO 19
<211> LENGTH: 19
<212> TYPE: PRT
<213> ORGANISM: Artificial
<220> FEATURE:
<223> OTHER INFORMATION: Description of sequence: Peptide L-IB (generic)
      (see Table 1)
<220> FEATURE:
<221> NAME/KEY: VARIANT
<222> LOCATION: (1)..(1)
<223> OTHER INFORMATION: Xaa is selected from any amino acid residue
<220> FEATURE:
<221> NAME/KEY: VARIANT
<222> LOCATION: (7)..(7)
<223> OTHER INFORMATION: Xaa is selected from any amino acid residue
<220> FEATURE:
<221> NAME/KEY: VARIANT
<222> LOCATION: (9)..(15)
<223> OTHER INFORMATION: Xaa is selected from any amino acid residue
<220> FEATURE:
<221> NAME/KEY: VARIANT
<222> LOCATION: (18)..(18)
<223> OTHER INFORMATION: Xaa is selected from serine or threonine
<220> FEATURE:
<221> NAME/KEY: VARIANT
<222> LOCATION: (19)..(19)
<223> OTHER INFORMATION: Xaa is selected from any amino acid residue

<400> SEQUENCE: 19

Xaa Arg Pro Thr Thr Leu Xaa Leu Xaa Xaa Xaa Xaa Xaa Xaa Xaa Gln
1               5                   10                  15

Asp Xaa Xaa

<210> SEQ ID NO 20
<211> LENGTH: 19
<212> TYPE: PRT
<213> ORGANISM: Artificial
<220> FEATURE:
```

```
<223> OTHER INFORMATION: Description of sequence: Peptide D-IB (generic)
      (see Table 1)
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is selected from any amino acid residue
<220> FEATURE:
<221> NAME/KEY: VARIANT
<222> LOCATION: (2)..(2)
<223> OTHER INFORMATION: Xaa is selected from serine or threonine
<220> FEATURE:
<221> NAME/KEY: VARIANT
<222> LOCATION: (5)..(11)
<223> OTHER INFORMATION: Xaa is selected from any amino acid residue
<220> FEATURE:
<221> NAME/KEY: VARIANT
<222> LOCATION: (13)..(13)
<223> OTHER INFORMATION: Xaa is selected from any amino acid residue
<220> FEATURE:
<221> NAME/KEY: VARIANT
<222> LOCATION: (19)..(19)
<223> OTHER INFORMATION: Xaa is selected from any amino acid residue

<400> SEQUENCE: 20

Xaa Xaa Asp Gln Xaa Xaa Xaa Xaa Xaa Xaa Xaa Leu Xaa Leu Thr Thr
1               5                   10                  15

Pro Arg Xaa

<210> SEQ ID NO 21
<211> LENGTH: 17
<212> TYPE: PRT
<213> ORGANISM: Artificial
<220> FEATURE:
<223> OTHER INFORMATION: Description of sequence: Peptide L-generic-TAT
      (see Table 1)
<220> FEATURE:
<221> NAME/KEY: VARIANT
<222> LOCATION: (1)..(17)
<223> OTHER INFORMATION: Xaa is selected from any amino acid residue

<400> SEQUENCE: 21

Xaa Xaa Xaa Xaa Arg Lys Lys Arg Arg Gln Arg Arg Xaa Xaa Xaa
1               5                   10                  15

Xaa

<210> SEQ ID NO 22
<211> LENGTH: 17
<212> TYPE: PRT
<213> ORGANISM: Artificial
<220> FEATURE:
<223> OTHER INFORMATION: Description of sequence: Peptide D-generic-TAT
      (see Table 1)
<220> FEATURE:
<221> NAME/KEY: MUTAGEN
<222> LOCATION: (1)..(17)
<223> OTHER INFORMATION: all amino acids are D-amino acids
<220> FEATURE:
<221> NAME/KEY: VARIANT
<222> LOCATION: (1)..(17)
<223> OTHER INFORMATION: Xaa is selected from any amino acid residue

<400> SEQUENCE: 22

Xaa Xaa Xaa Xaa Arg Arg Arg Gln Arg Arg Lys Lys Arg Xaa Xaa Xaa
1               5                   10                  15

Xaa
```

-continued

```
<210> SEQ ID NO 23
<211> LENGTH: 35
<212> TYPE: PRT
<213> ORGANISM: Artificial
<220> FEATURE:
<223> OTHER INFORMATION: Description of sequence: Peptide L-TAT-IB1 (see
      Table 1)

<400> SEQUENCE: 23

Gly Arg Lys Lys Arg Arg Gln Arg Arg Pro Pro Asp Thr Tyr Arg
1               5                   10                  15

Pro Lys Arg Pro Thr Thr Leu Asn Leu Phe Pro Gln Val Pro Arg Ser
                20                  25                  30

Gln Asp Thr
        35

<210> SEQ ID NO 24
<211> LENGTH: 42
<212> TYPE: PRT
<213> ORGANISM: Artificial
<220> FEATURE:
<223> OTHER INFORMATION: Description of sequence: Peptide L-TAT IB
      (generic) (see Table 1)
<220> FEATURE:
<221> NAME/KEY: VARIANT
<222> LOCATION: (1)..(40)
<223> OTHER INFORMATION: Xaa is selected from any amino acid residue
<220> FEATURE:
<221> NAME/KEY: VARIANT
<222> LOCATION: (41)..(41)
<223> OTHER INFORMATION: Xaa is selected from serine or threonine
<220> FEATURE:
<221> NAME/KEY: VARIANT
<222> LOCATION: (42)..(42)
<223> OTHER INFORMATION: Xaa is selected from any amino acid residue

<400> SEQUENCE: 24

Xaa Xaa Xaa Xaa Xaa Xaa Xaa Arg Lys Lys Arg Arg Gln Arg Arg
1               5                   10                  15

Xaa Xaa Xaa Xaa Xaa Xaa Xaa Xaa Arg Pro Thr Thr Leu Xaa Leu Xaa
                20                  25                  30

Xaa Xaa Xaa Xaa Xaa Xaa Gln Asp Xaa Xaa
        35                  40

<210> SEQ ID NO 25
<211> LENGTH: 35
<212> TYPE: PRT
<213> ORGANISM: Artificial
<220> FEATURE:
<223> OTHER INFORMATION: Description of sequence: Peptide D-TAT-IB1 (see
      Table 1)
<220> FEATURE:
<221> NAME/KEY: MUTAGEN
<222> LOCATION: (1)..(35)
<223> OTHER INFORMATION: all amino acids are D-amino acids

<400> SEQUENCE: 25

Thr Asp Gln Ser Arg Pro Val Gln Pro Phe Leu Asn Leu Thr Thr Pro
1               5                   10                  15

Arg Lys Pro Arg Tyr Thr Asp Pro Pro Arg Arg Gln Arg Arg Lys
                20                  25                  30

Lys Arg Gly
        35

<210> SEQ ID NO 26
<211> LENGTH: 42
<212> TYPE: PRT
```

```
<213> ORGANISM: Artificial
<220> FEATURE:
<223> OTHER INFORMATION: Description of sequence: Peptide D-TAT IB
      (generic) (see Table 1)
<220> FEATURE:
<221> NAME/KEY: MUTAGEN
<222> LOCATION: (1)..(42)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is selected from any amino acid residue
<220> FEATURE:
<221> NAME/KEY: VARIANT
<222> LOCATION: (2)..(2)
<223> OTHER INFORMATION: Xaa is selected from serine or threonine
<220> FEATURE:
<221> NAME/KEY: VARIANT
<222> LOCATION: (3)..(42)
<223> OTHER INFORMATION: Xaa is selected from any amino acid residue

<400> SEQUENCE: 26

Xaa Xaa Asp Gln Xaa Xaa Xaa Xaa Xaa Xaa Xaa Leu Xaa Leu Thr Thr
1               5                   10                  15

Pro Arg Xaa Xaa Xaa Xaa Xaa Xaa Xaa Xaa Arg Arg Arg Gln Arg Arg
            20                  25                  30

Lys Lys Arg Xaa Xaa Xaa Xaa Xaa Xaa Xaa
        35                  40

<210> SEQ ID NO 27
<211> LENGTH: 30
<212> TYPE: PRT
<213> ORGANISM: Artificial
<220> FEATURE:
<223> OTHER INFORMATION: Description of sequence: chimeric peptide
      sequence L-TAT-IB1(s1) (see Table 1)

<400> SEQUENCE: 27

Arg Lys Lys Arg Arg Gln Arg Arg Arg Pro Pro Arg Pro Lys Arg Pro
1               5                   10                  15

Thr Thr Leu Asn Leu Phe Pro Gln Val Pro Arg Ser Gln Asp
            20                  25                  30

<210> SEQ ID NO 28
<211> LENGTH: 30
<212> TYPE: PRT
<213> ORGANISM: Artificial
<220> FEATURE:
<223> OTHER INFORMATION: Description of sequence: chimeric peptide
      sequence L-TAT-IB1(s2) (see Table 1)
<220> FEATURE:
<221> NAME/KEY: VARIANT
<222> LOCATION: (11)..(11)
<223> OTHER INFORMATION: Xaa is selected from glycine or proline
<220> FEATURE:
<221> NAME/KEY: REPEAT
<222> LOCATION: (11)..(11)
<223> OTHER INFORMATION: Xaa is Xnc as defined in the general formula,
      wherein n is 0-5, 5-10, 10-15, 15-20, 20-30 or more for Xnc

<400> SEQUENCE: 28

Gly Arg Lys Lys Arg Arg Gln Arg Arg Arg Xaa Arg Pro Lys Arg Pro
1               5                   10                  15

Thr Thr Leu Asn Leu Phe Pro Gln Val Pro Arg Ser Gln Asp
            20                  25                  30

<210> SEQ ID NO 29
<211> LENGTH: 29
<212> TYPE: PRT
```

```
<213> ORGANISM: Artificial
<220> FEATURE:
<223> OTHER INFORMATION: Description of sequence: chimeric peptide
      sequence L-TAT-IB1(s3) (see Table 1)
<220> FEATURE:
<221> NAME/KEY: VARIANT
<222> LOCATION: (10)..(10)
<223> OTHER INFORMATION: Xaa is selected from glycine or proline
<220> FEATURE:
<221> NAME/KEY: REPEAT
<222> LOCATION: (10)..(10)
<223> OTHER INFORMATION: Xaa is Xnc as defined in the general formula,
      wherein n is 0-5, 5-10, 10-15, 15-20, 20-30 or more for Xnc

<400> SEQUENCE: 29

Arg Lys Lys Arg Arg Gln Arg Arg Xaa Arg Pro Lys Arg Pro Thr
1               5                   10                  15

Thr Leu Asn Leu Phe Pro Gln Val Pro Arg Ser Gln Asp
            20                  25

<210> SEQ ID NO 30
<211> LENGTH: 30
<212> TYPE: PRT
<213> ORGANISM: Artificial
<220> FEATURE:
<223> OTHER INFORMATION: Description of sequence: chimeric peptide
      sequence D-TAT-IB1(s1) (see Table 1)
<220> FEATURE:
<221> NAME/KEY: MUTAGEN
<222> LOCATION: (1)..(30)
<223> OTHER INFORMATION: all amino acids are D-amino acids

<400> SEQUENCE: 30

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg
            20                  25                  30

<210> SEQ ID NO 31
<211> LENGTH: 30
<212> TYPE: PRT
<213> ORGANISM: Artificial
<220> FEATURE:
<223> OTHER INFORMATION: Description of sequence: chimeric peptide
      sequence D-TAT-IB1(s2) (see Table 1)
<220> FEATURE:
<221> NAME/KEY: MUTAGEN
<222> LOCATION: (1)..(30)
<223> OTHER INFORMATION: all amino acids are D-amino acids
<220> FEATURE:
<221> NAME/KEY: VARIANT
<222> LOCATION: (20)..(20)
<223> OTHER INFORMATION: Xaa is selected from glycine or proline
<220> FEATURE:
<221> NAME/KEY: REPEAT
<222> LOCATION: (20)..(20)
<223> OTHER INFORMATION: Xaa is Xnc as defined in the general formula,
      wherein n is 0-5, 5-10, 10-15, 15-20, 20-30 or more for Xnc

<400> SEQUENCE: 31

Asp Gln Ser Arg Pro Val Gln Pro Phe Leu Asn Leu Thr Thr Pro Arg
1               5                   10                  15

Lys Pro Arg Xaa Arg Arg Arg Gln Arg Arg Lys Lys Arg Gly
            20                  25                  30

<210> SEQ ID NO 32
<211> LENGTH: 29
<212> TYPE: PRT
<213> ORGANISM: Artificial
<220> FEATURE:
```

```
<223> OTHER INFORMATION: Description of sequence: chimeric peptide
      sequence D-TAT-IB1(s3) (see Table 1)
<220> FEATURE:
<221> NAME/KEY: MUTAGEN
<222> LOCATION: (1)..(29)
<223> OTHER INFORMATION: all amino acids are D-amino acids
<220> FEATURE:
<221> NAME/KEY: VARIANT
<222> LOCATION: (20)..(20)
<223> OTHER INFORMATION: Xaa is selected from glycine or proline
<220> FEATURE:
<221> NAME/KEY: REPEAT
<222> LOCATION: (20)..(20)
<223> OTHER INFORMATION: Xaa is Xnc as defined in the general formula,
      wherein n is 0-5, 5-10, 10-15, 15-20, 20-30 or more for Xnc

<400> SEQUENCE: 32

Asp Gln Ser Arg Pro Val Gln Pro Phe Leu Asn Leu Thr Thr Pro Arg
1               5                   10                  15

Lys Pro Arg Xaa Arg Arg Arg Gln Arg Arg Lys Lys Arg
            20                  25

<210> SEQ ID NO 33
<211> LENGTH: 13
<212> TYPE: PRT
<213> ORGANISM: Artificial
<220> FEATURE:
<223> OTHER INFORMATION: Description of sequence: L-IB1(s1) (see Table
      1)

<400> SEQUENCE: 33

Thr Leu Asn Leu Phe Pro Gln Val Pro Arg Ser Gln Asp
1               5                   10

<210> SEQ ID NO 34
<211> LENGTH: 13
<212> TYPE: PRT
<213> ORGANISM: Artificial
<220> FEATURE:
<223> OTHER INFORMATION: Description of sequence: L-IB1(s2) (see Table
      1)

<400> SEQUENCE: 34

Thr Thr Leu Asn Leu Phe Pro Gln Val Pro Arg Ser Gln
1               5                   10

<210> SEQ ID NO 35
<211> LENGTH: 13
<212> TYPE: PRT
<213> ORGANISM: Artificial
<220> FEATURE:
<223> OTHER INFORMATION: Description of sequence: L-IB1(s3) (see Table
      1)

<400> SEQUENCE: 35

Pro Thr Thr Leu Asn Leu Phe Pro Gln Val Pro Arg Ser
1               5                   10

<210> SEQ ID NO 36
<211> LENGTH: 13
<212> TYPE: PRT
<213> ORGANISM: Artificial
<220> FEATURE:
<223> OTHER INFORMATION: Description of sequence: L-IB1(s4) (see Table
      1)

<400> SEQUENCE: 36

Arg Pro Thr Thr Leu Asn Leu Phe Pro Gln Val Pro Arg
1               5                   10
```

```
<210> SEQ ID NO 37
<211> LENGTH: 13
<212> TYPE: PRT
<213> ORGANISM: Artificial
<220> FEATURE:
<223> OTHER INFORMATION: Description of sequence: L-IB1(s5) (see Table
      1)

<400> SEQUENCE: 37

Lys Arg Pro Thr Thr Leu Asn Leu Phe Pro Gln Val Pro
1               5                   10

<210> SEQ ID NO 38
<211> LENGTH: 13
<212> TYPE: PRT
<213> ORGANISM: Artificial
<220> FEATURE:
<223> OTHER INFORMATION: Description of sequence: L-IB1(s6) (see Table
      1)

<400> SEQUENCE: 38

Pro Lys Arg Pro Thr Thr Leu Asn Leu Phe Pro Gln Val
1               5                   10

<210> SEQ ID NO 39
<211> LENGTH: 13
<212> TYPE: PRT
<213> ORGANISM: Artificial
<220> FEATURE:
<223> OTHER INFORMATION: Description of sequence: L-IB1(s7) (see Table
      1)

<400> SEQUENCE: 39

Arg Pro Lys Arg Pro Thr Thr Leu Asn Leu Phe Pro Gln
1               5                   10

<210> SEQ ID NO 40
<211> LENGTH: 12
<212> TYPE: PRT
<213> ORGANISM: Artificial
<220> FEATURE:
<223> OTHER INFORMATION: Description of sequence: L-IB1(s8) (see Table
      1)

<400> SEQUENCE: 40

Leu Asn Leu Phe Pro Gln Val Pro Arg Ser Gln Asp
1               5                   10

<210> SEQ ID NO 41
<211> LENGTH: 12
<212> TYPE: PRT
<213> ORGANISM: Artificial
<220> FEATURE:
<223> OTHER INFORMATION: Description of sequence: L-IB1(s9) (see Table
      1)

<400> SEQUENCE: 41

Thr Leu Asn Leu Phe Pro Gln Val Pro Arg Ser Gln
1               5                   10

<210> SEQ ID NO 42
<211> LENGTH: 12
<212> TYPE: PRT
<213> ORGANISM: Artificial
<220> FEATURE:
<223> OTHER INFORMATION: Description of sequence: L-IB1(s10) (see Table
      1)
```

```
<400> SEQUENCE: 42

Thr Thr Leu Asn Leu Phe Pro Gln Val Pro Arg Ser
1               5                   10

<210> SEQ ID NO 43
<211> LENGTH: 12
<212> TYPE: PRT
<213> ORGANISM: Artificial
<220> FEATURE:
<223> OTHER INFORMATION: Description of sequence: L-IB1(s11) (see Table
      1)

<400> SEQUENCE: 43

Pro Thr Thr Leu Asn Leu Phe Pro Gln Val Pro Arg
1               5                   10

<210> SEQ ID NO 44
<211> LENGTH: 12
<212> TYPE: PRT
<213> ORGANISM: Artificial
<220> FEATURE:
<223> OTHER INFORMATION: Description of sequence: L-IB1(s12) (see Table
      1)

<400> SEQUENCE: 44

Arg Pro Thr Thr Leu Asn Leu Phe Pro Gln Val Pro
1               5                   10

<210> SEQ ID NO 45
<211> LENGTH: 12
<212> TYPE: PRT
<213> ORGANISM: Artificial
<220> FEATURE:
<223> OTHER INFORMATION: Description of sequence: L-IB1(s13) (see Table
      1)

<400> SEQUENCE: 45

Lys Arg Pro Thr Thr Leu Asn Leu Phe Pro Gln Val
1               5                   10

<210> SEQ ID NO 46
<211> LENGTH: 12
<212> TYPE: PRT
<213> ORGANISM: Artificial
<220> FEATURE:
<223> OTHER INFORMATION: Description of sequence: L-IB1(s14) (see Table
      1)

<400> SEQUENCE: 46

Pro Lys Arg Pro Thr Thr Leu Asn Leu Phe Pro Gln
1               5                   10

<210> SEQ ID NO 47
<211> LENGTH: 12
<212> TYPE: PRT
<213> ORGANISM: Artificial
<220> FEATURE:
<223> OTHER INFORMATION: Description of sequence: L-IB1(s15) (see Table
      1)

<400> SEQUENCE: 47

Arg Pro Lys Arg Pro Thr Thr Leu Asn Leu Phe Pro
1               5                   10

<210> SEQ ID NO 48
<211> LENGTH: 11
```

```
<212> TYPE: PRT
<213> ORGANISM: Artificial
<220> FEATURE:
<223> OTHER INFORMATION: Description of sequence: L-IB1(s16) (see Table
      1)

<400> SEQUENCE: 48

Asn Leu Phe Pro Gln Val Pro Arg Ser Gln Asp
1               5                   10

<210> SEQ ID NO 49
<211> LENGTH: 11
<212> TYPE: PRT
<213> ORGANISM: Artificial
<220> FEATURE:
<223> OTHER INFORMATION: Description of sequence: L-IB1(s17) (see Table
      1)

<400> SEQUENCE: 49

Leu Asn Leu Phe Pro Gln Val Pro Arg Ser Gln
1               5                   10

<210> SEQ ID NO 50
<211> LENGTH: 11
<212> TYPE: PRT
<213> ORGANISM: Artificial
<220> FEATURE:
<223> OTHER INFORMATION: Description of sequence: L-IB1(s18) (see Table
      1)

<400> SEQUENCE: 50

Thr Leu Asn Leu Phe Pro Gln Val Pro Arg Ser
1               5                   10

<210> SEQ ID NO 51
<211> LENGTH: 11
<212> TYPE: PRT
<213> ORGANISM: Artificial
<220> FEATURE:
<223> OTHER INFORMATION: Description of sequence: L-IB1(s19) (see Table
      1)

<400> SEQUENCE: 51

Thr Thr Leu Asn Leu Phe Pro Gln Val Pro Arg
1               5                   10

<210> SEQ ID NO 52
<211> LENGTH: 11
<212> TYPE: PRT
<213> ORGANISM: Artificial
<220> FEATURE:
<223> OTHER INFORMATION: Description of sequence: L-IB1(s20) (see Table
      1)

<400> SEQUENCE: 52

Pro Thr Thr Leu Asn Leu Phe Pro Gln Val Pro
1               5                   10

<210> SEQ ID NO 53
<211> LENGTH: 11
<212> TYPE: PRT
<213> ORGANISM: Artificial
<220> FEATURE:
<223> OTHER INFORMATION: Description of sequence: L-IB1(s21) (see Table
      1)

<400> SEQUENCE: 53

Arg Pro Thr Thr Leu Asn Leu Phe Pro Gln Val
```

```
1               5                   10

<210> SEQ ID NO 54
<211> LENGTH: 11
<212> TYPE: PRT
<213> ORGANISM: Artificial
<220> FEATURE:
<223> OTHER INFORMATION: Description of sequence: L-IB1(s22) (see Table
      1)

<400> SEQUENCE: 54

Lys Arg Pro Thr Thr Leu Asn Leu Phe Pro Gln
1               5                   10

<210> SEQ ID NO 55
<211> LENGTH: 11
<212> TYPE: PRT
<213> ORGANISM: Artificial
<220> FEATURE:
<223> OTHER INFORMATION: Description of sequence: L-IB1(s23) (see Table
      1)

<400> SEQUENCE: 55

Pro Lys Arg Pro Thr Thr Leu Asn Leu Phe Pro
1               5                   10

<210> SEQ ID NO 56
<211> LENGTH: 11
<212> TYPE: PRT
<213> ORGANISM: Artificial
<220> FEATURE:
<223> OTHER INFORMATION: Description of sequence: L-IB1(s24) (see Table
      1)

<400> SEQUENCE: 56

Arg Pro Lys Arg Pro Thr Thr Leu Asn Leu Phe
1               5                   10

<210> SEQ ID NO 57
<211> LENGTH: 10
<212> TYPE: PRT
<213> ORGANISM: Artificial
<220> FEATURE:
<223> OTHER INFORMATION: Description of sequence: L-IB1(s25) (see Table
      1)

<400> SEQUENCE: 57

Leu Phe Pro Gln Val Pro Arg Ser Gln Asp
1               5                   10

<210> SEQ ID NO 58
<211> LENGTH: 10
<212> TYPE: PRT
<213> ORGANISM: Artificial
<220> FEATURE:
<223> OTHER INFORMATION: Description of sequence: L-IB1(s26) (see Table
      1)

<400> SEQUENCE: 58

Asn Leu Phe Pro Gln Val Pro Arg Ser Gln
1               5                   10

<210> SEQ ID NO 59
<211> LENGTH: 10
<212> TYPE: PRT
<213> ORGANISM: Artificial
<220> FEATURE:
<223> OTHER INFORMATION: Description of sequence: L-IB1(s27) (see Table
```

1)

<400> SEQUENCE: 59

Leu Asn Leu Phe Pro Gln Val Pro Arg Ser
1               5                   10

<210> SEQ ID NO 60
<211> LENGTH: 10
<212> TYPE: PRT
<213> ORGANISM: Artificial
<220> FEATURE:
<223> OTHER INFORMATION: Description of sequence: L-IB1(s28) (see Table
      1)

<400> SEQUENCE: 60

Thr Leu Asn Leu Phe Pro Gln Val Pro Arg
1               5                   10

<210> SEQ ID NO 61
<211> LENGTH: 10
<212> TYPE: PRT
<213> ORGANISM: Artificial
<220> FEATURE:
<223> OTHER INFORMATION: Description of sequence: L-IB1(s29) (see Table
      1)

<400> SEQUENCE: 61

Thr Thr Leu Asn Leu Phe Pro Gln Val Pro
1               5                   10

<210> SEQ ID NO 62
<211> LENGTH: 10
<212> TYPE: PRT
<213> ORGANISM: Artificial
<220> FEATURE:
<223> OTHER INFORMATION: Description of sequence: L-IB1(s30) (see Table
      1)

<400> SEQUENCE: 62

Pro Thr Thr Leu Asn Leu Phe Pro Gln Val
1               5                   10

<210> SEQ ID NO 63
<211> LENGTH: 10
<212> TYPE: PRT
<213> ORGANISM: Artificial
<220> FEATURE:
<223> OTHER INFORMATION: Description of sequence: L-IB1(s31) (see Table
      1)

<400> SEQUENCE: 63

Arg Pro Thr Thr Leu Asn Leu Phe Pro Gln
1               5                   10

<210> SEQ ID NO 64
<211> LENGTH: 10
<212> TYPE: PRT
<213> ORGANISM: Artificial
<220> FEATURE:
<223> OTHER INFORMATION: Description of sequence: L-IB1(s32) (see Table
      1)

<400> SEQUENCE: 64

Lys Arg Pro Thr Thr Leu Asn Leu Phe Pro
1               5                   10

<210> SEQ ID NO 65

-continued

```
<211> LENGTH: 10
<212> TYPE: PRT
<213> ORGANISM: Artificial
<220> FEATURE:
<223> OTHER INFORMATION: Description of sequence: L-IB1(s33) (see Table
      1)

<400> SEQUENCE: 65

Pro Lys Arg Pro Thr Thr Leu Asn Leu Phe
1               5                   10

<210> SEQ ID NO 66
<211> LENGTH: 10
<212> TYPE: PRT
<213> ORGANISM: Artificial
<220> FEATURE:
<223> OTHER INFORMATION: Description of sequence: L-IB1(s34) (see Table
      1)

<400> SEQUENCE: 66

Arg Pro Lys Arg Pro Thr Thr Leu Asn Leu
1               5                   10

<210> SEQ ID NO 67
<211> LENGTH: 13
<212> TYPE: PRT
<213> ORGANISM: Artificial
<220> FEATURE:
<223> OTHER INFORMATION: Description of sequence: D-IB1(s1) (see Table
      1)
<220> FEATURE:
<221> NAME/KEY: MUTAGEN
<222> LOCATION: (1)..(13)
<223> OTHER INFORMATION: all amino acids are D-amino acids

<400> SEQUENCE: 67

Gln Pro Phe Leu Asn Leu Thr Thr Pro Arg Lys Pro Arg
1               5                   10

<210> SEQ ID NO 68
<211> LENGTH: 13
<212> TYPE: PRT
<213> ORGANISM: Artificial
<220> FEATURE:
<223> OTHER INFORMATION: Description of sequence: D-IB1(s2) (see Table
      1)
<220> FEATURE:
<221> NAME/KEY: MUTAGEN
<222> LOCATION: (1)..(13)
<223> OTHER INFORMATION: all amino acids are D-amino acids

<400> SEQUENCE: 68

Val Gln Pro Phe Leu Asn Leu Thr Thr Pro Arg Lys Pro
1               5                   10

<210> SEQ ID NO 69
<211> LENGTH: 13
<212> TYPE: PRT
<213> ORGANISM: Artificial
<220> FEATURE:
<223> OTHER INFORMATION: Description of sequence: D-IB1(s3) (see Table
      1)
<220> FEATURE:
<221> NAME/KEY: MUTAGEN
<222> LOCATION: (1)..(13)
<223> OTHER INFORMATION: all amino acids are D-amino acids

<400> SEQUENCE: 69

Pro Val Gln Pro Phe Leu Asn Leu Thr Thr Pro Arg Lys
1               5                   10
```

<210> SEQ ID NO 70
<211> LENGTH: 13
<212> TYPE: PRT
<213> ORGANISM: Artificial
<220> FEATURE:
<223> OTHER INFORMATION: Description of sequence: D-IB1(s4) (see Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 70

Arg Pro Val Gln Pro Phe Leu Asn Leu Thr Thr Pro Arg
1               5                   10

<210> SEQ ID NO 71
<211> LENGTH: 13
<212> TYPE: PRT
<213> ORGANISM: Artificial
<220> FEATURE:
<223> OTHER INFORMATION: Description of sequence: D-IB1(s5) (see Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 71

Ser Arg Pro Val Gln Pro Phe Leu Asn Leu Thr Thr Pro
1               5                   10

<210> SEQ ID NO 72
<211> LENGTH: 13
<212> TYPE: PRT
<213> ORGANISM: Artificial
<220> FEATURE:
<223> OTHER INFORMATION: Description of sequence: D-IB1(s6) (see Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 72

Gln Ser Arg Pro Val Gln Pro Phe Leu Asn Leu Thr Thr
1               5                   10

<210> SEQ ID NO 73
<211> LENGTH: 13
<212> TYPE: PRT
<213> ORGANISM: Artificial
<220> FEATURE:
<223> OTHER INFORMATION: Description of sequence: D-IB1(s7) (see Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 73

Asp Gln Ser Arg Pro Val Gln Pro Phe Leu Asn Leu Thr
1               5                   10

<210> SEQ ID NO 74
<211> LENGTH: 12
<212> TYPE: PRT
<213> ORGANISM: Artificial
<220> FEATURE:

-continued

```
<223> OTHER INFORMATION: Description of sequence: D-IB1(s8) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 74

Pro Phe Leu Asn Leu Thr Thr Pro Arg Lys Pro Arg
1               5                   10

<210> SEQ ID NO 75
<211> LENGTH: 12
<212> TYPE: PRT
<213> ORGANISM: Artificial
<220> FEATURE:
<223> OTHER INFORMATION: Description of sequence: D-IB1(s9) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 75

Gln Pro Phe Leu Asn Leu Thr Thr Pro Arg Lys Pro
1               5                   10

<210> SEQ ID NO 76
<211> LENGTH: 12
<212> TYPE: PRT
<213> ORGANISM: Artificial
<220> FEATURE:
<223> OTHER INFORMATION: Description of sequence: D-IB1(s10) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 76

Val Gln Pro Phe Leu Asn Leu Thr Thr Pro Arg Lys
1               5                   10

<210> SEQ ID NO 77
<211> LENGTH: 12
<212> TYPE: PRT
<213> ORGANISM: Artificial
<220> FEATURE:
<223> OTHER INFORMATION: Description of sequence: D-IB1(s11) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 77

Pro Val Gln Pro Phe Leu Asn Leu Thr Thr Pro Arg
1               5                   10

<210> SEQ ID NO 78
<211> LENGTH: 12
<212> TYPE: PRT
<213> ORGANISM: Artificial
<220> FEATURE:
<223> OTHER INFORMATION: Description of sequence: D-IB1(s12) (see Table
      1)
<220> FEATURE:
<221> NAME/KEY: MUTAGEN
<222> LOCATION: (1)..(12)
<223> OTHER INFORMATION: all amino acids are D-amino acids
```

<400> SEQUENCE: 78

Arg Pro Val Gln Pro Phe Leu Asn Leu Thr Thr Pro
1               5                   10

<210> SEQ ID NO 79
<211> LENGTH: 12
<212> TYPE: PRT
<213> ORGANISM: Artificial
<220> FEATURE:
<223> OTHER INFORMATION: Description of sequence: D-IB1(s13) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 79

Ser Arg Pro Val Gln Pro Phe Leu Asn Leu Thr Thr
1               5                   10

<210> SEQ ID NO 80
<211> LENGTH: 12
<212> TYPE: PRT
<213> ORGANISM: Artificial
<220> FEATURE:
<223> OTHER INFORMATION: Description of sequence: D-IB1(s14) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 80

Gln Ser Arg Pro Val Gln Pro Phe Leu Asn Leu Thr
1               5                   10

<210> SEQ ID NO 81
<211> LENGTH: 12
<212> TYPE: PRT
<213> ORGANISM: Artificial
<220> FEATURE:
<223> OTHER INFORMATION: Description of sequence: D-IB1(s15) (see Table
      1)
<220> FEATURE:
<221> NAME/KEY: MUTAGEN
<222> LOCATION: (1)..(12)
<223> OTHER INFORMATION: all amino acids are D-amino acids

<400> SEQUENCE: 81

Asp Gln Ser Arg Pro Val Gln Pro Phe Leu Asn Leu
1               5                   10

<210> SEQ ID NO 82
<211> LENGTH: 11
<212> TYPE: PRT
<213> ORGANISM: Artificial
<220> FEATURE:
<223> OTHER INFORMATION: Description of sequence: D-IB1(s16) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 82

Phe Leu Asn Leu Thr Thr Pro Arg Lys Pro Arg
1               5                   10

<210> SEQ ID NO 83

```
<211> LENGTH: 11
<212> TYPE: PRT
<213> ORGANISM: Artificial
<220> FEATURE:
<223> OTHER INFORMATION: Description of sequence: D-IB1(s17) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 83

Pro Phe Leu Asn Leu Thr Thr Pro Arg Lys Pro
1               5                   10

<210> SEQ ID NO 84
<211> LENGTH: 11
<212> TYPE: PRT
<213> ORGANISM: Artificial
<220> FEATURE:
<223> OTHER INFORMATION: Description of sequence: D-IB1(s18) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 84

Gln Pro Phe Leu Asn Leu Thr Thr Pro Arg Lys
1               5                   10

<210> SEQ ID NO 85
<211> LENGTH: 11
<212> TYPE: PRT
<213> ORGANISM: Artificial
<220> FEATURE:
<223> OTHER INFORMATION: Description of sequence: D-IB1(s19) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 85

Val Gln Pro Phe Leu Asn Leu Thr Thr Pro Arg
1               5                   10

<210> SEQ ID NO 86
<211> LENGTH: 11
<212> TYPE: PRT
<213> ORGANISM: Artificial
<220> FEATURE:
<223> OTHER INFORMATION: Description of sequence: D-IB1(s20) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 86

Pro Val Gln Pro Phe Leu Asn Leu Thr Thr Pro
1               5                   10

<210> SEQ ID NO 87
<211> LENGTH: 11
<212> TYPE: PRT
<213> ORGANISM: Artificial
<220> FEATURE:
<223> OTHER INFORMATION: Description of sequence: D-IB1(s21) (see Table
      1)
<220> FEATURE:
```

```
<221> NAME/KEY: MUTAGEN
<222> LOCATION: (1)..(11)
<223> OTHER INFORMATION: all amino acids are D-amino acids

<400> SEQUENCE: 87

Arg Pro Val Gln Pro Phe Leu Asn Leu Thr Thr
1               5                   10

<210> SEQ ID NO 88
<211> LENGTH: 11
<212> TYPE: PRT
<213> ORGANISM: Artificial
<220> FEATURE:
<223> OTHER INFORMATION: Description of sequence: D-IB1(s22) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 88

Ser Arg Pro Val Gln Pro Phe Leu Asn Leu Thr
1               5                   10

<210> SEQ ID NO 89
<211> LENGTH: 11
<212> TYPE: PRT
<213> ORGANISM: Artificial
<220> FEATURE:
<223> OTHER INFORMATION: Description of sequence: D-IB1(s23) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 89

Gln Ser Arg Pro Val Gln Pro Phe Leu Asn Leu
1               5                   10

<210> SEQ ID NO 90
<211> LENGTH: 11
<212> TYPE: PRT
<213> ORGANISM: Artificial
<220> FEATURE:
<223> OTHER INFORMATION: Description of sequence: D-IB1(s24) (see Table
      1)
<220> FEATURE:
<221> NAME/KEY: MUTAGEN
<222> LOCATION: (1)..(11)
<223> OTHER INFORMATION: all amino acids are D-amino acids

<400> SEQUENCE: 90

Asp Gln Ser Arg Pro Val Gln Pro Phe Leu Asn
1               5                   10

<210> SEQ ID NO 91
<211> LENGTH: 10
<212> TYPE: PRT
<213> ORGANISM: Artificial
<220> FEATURE:
<223> OTHER INFORMATION: Description of sequence: D-IB1(s25) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 91

Asp Gln Ser Arg Pro Val Gln Pro Phe Leu
```

```
1               5                  10

<210> SEQ ID NO 92
<211> LENGTH: 10
<212> TYPE: PRT
<213> ORGANISM: Artificial
<220> FEATURE:
<223> OTHER INFORMATION: Description of sequence: D-IB1(s26) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 92

Gln Ser Arg Pro Val Gln Pro Phe Leu Asn
1               5                  10

<210> SEQ ID NO 93
<211> LENGTH: 10
<212> TYPE: PRT
<213> ORGANISM: Artificial
<220> FEATURE:
<223> OTHER INFORMATION: Description of sequence: D-IB1(s27) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 93

Ser Arg Pro Val Gln Pro Phe Leu Asn Leu
1               5                  10

<210> SEQ ID NO 94
<211> LENGTH: 10
<212> TYPE: PRT
<213> ORGANISM: Artificial
<220> FEATURE:
<223> OTHER INFORMATION: Description of sequence: D-IB1(s28) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 94

Arg Pro Val Gln Pro Phe Leu Asn Leu Thr
1               5                  10

<210> SEQ ID NO 95
<211> LENGTH: 10
<212> TYPE: PRT
<213> ORGANISM: Artificial
<220> FEATURE:
<223> OTHER INFORMATION: Description of sequence: D-IB1(s29) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 95

Pro Val Gln Pro Phe Leu Asn Leu Thr Thr
1               5                  10

<210> SEQ ID NO 96
<211> LENGTH: 10
<212> TYPE: PRT
<213> ORGANISM: Artificial
```

```
<220> FEATURE:
<223> OTHER INFORMATION: Description of sequence: D-IB1(s30) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 96

Val Gln Pro Phe Leu Asn Leu Thr Thr Pro
1               5                   10

<210> SEQ ID NO 97
<211> LENGTH: 10
<212> TYPE: PRT
<213> ORGANISM: Artificial
<220> FEATURE:
<223> OTHER INFORMATION: Description of sequence: D-IB1(s31) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 97

Gln Pro Phe Leu Asn Leu Thr Thr Pro Arg
1               5                   10

<210> SEQ ID NO 98
<211> LENGTH: 10
<212> TYPE: PRT
<213> ORGANISM: Artificial
<220> FEATURE:
<223> OTHER INFORMATION: Description of sequence: D-IB1(s32) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 98

Pro Phe Leu Asn Leu Thr Thr Pro Arg Lys
1               5                   10

<210> SEQ ID NO 99
<211> LENGTH: 10
<212> TYPE: PRT
<213> ORGANISM: Artificial
<220> FEATURE:
<223> OTHER INFORMATION: Description of sequence: D-IB1(s33) (see Table
      1)
<220> FEATURE:
<221> NAME/KEY: MUTAGEN
<222> LOCATION: (1)..(10)
<223> OTHER INFORMATION: all amino acids are D-amino acids

<400> SEQUENCE: 99

Phe Leu Asn Leu Thr Thr Pro Arg Lys Pro
1               5                   10

<210> SEQ ID NO 100
<211> LENGTH: 10
<212> TYPE: PRT
<213> ORGANISM: Artificial
<220> FEATURE:
<223> OTHER INFORMATION: Description of sequence: D-IB1(s34) (see Table
      1)
<220> FEATURE:
<221> NAME/KEY: MUTAGEN
<222> LOCATION: (1)..(10)
<223> OTHER INFORMATION: all amino acids are D-amino acids
```

<400> SEQUENCE: 100

Leu Asn Leu Thr Thr Pro Arg Lys Pro Arg
1               5                   10

<210> SEQ ID NO 101
<211> LENGTH: 21
<212> TYPE: DNA
<213> ORGANISM: Artificial
<220> FEATURE:
<223> OTHER INFORMATION: Description of sequence: ap-1 doubled labeled
      probe (see p. 66)

<400> SEQUENCE: 101
cgcttgatga gtcagccgga a                                              21

<210> SEQ ID NO 102
<211> LENGTH: 2953
<212> TYPE: DNA
<213> ORGANISM: Artificial
<220> FEATURE:
<223> OTHER INFORMATION: description of sequence: rat IB1 cDNA sequence
      and its predicted amino acid sequence (see Figure 1)
<220> FEATURE:
<221> NAME/KEY: CDS
<222> LOCATION: (108)..(2252)

<400> SEQUENCE: 102 ccgcccagc tcagtccgaa ccccgcggcg gcggcggcct cctccacacg cctccacctc       60
cgccgccgcc gccgccgccg ccgcctcccg cgccgctctc gcccgg atg gcc agg       116
                                                    Met Ala Arg
                                                      1 ctg agc ccg gga atg gcg gag cga gag agc ggc ctg agc ggg ggt gcc      164
Leu Ser Pro Gly Met Ala Glu Arg Glu Ser Gly Leu Ser Gly Gly Ala
    5                  10                  15 gcg tcc cca ccg gcc gct tcc cca ttc ctg gga ctg cac atc gcg tcg      212
Ala Ser Pro Pro Ala Ala Ser Pro Phe Leu Gly Leu His Ile Ala Ser
 20                  25                  30                  35 cct ccc aat ttc agg ctc acc cat gat atc agc ctg gag gag ttt gag      260
Pro Pro Asn Phe Arg Leu Thr His Asp Ile Ser Leu Glu Glu Phe Glu
                 40                  45                  50 gat gaa gac ctt tcg gag atc act gat gag tgt ggc atc agc ctg cag      308
Asp Glu Asp Leu Ser Glu Ile Thr Asp Glu Cys Gly Ile Ser Leu Gln
             55                  60                  65 tgc aaa gac acc ttg tct ctc cgg ccc ccg cgc gcc ggg cta ctg tct      356
Cys Lys Asp Thr Leu Ser Leu Arg Pro Pro Arg Ala Gly Leu Leu Ser
         70                  75                  80 gcg ggt agc agc ggt agc gcg ggg agc cgg ctg cag gcg gag atg ctg      404
Ala Gly Ser Ser Gly Ser Ala Gly Ser Arg Leu Gln Ala Glu Met Leu
     85                  90                  95 cag atg gac ctg atc gac gcg gca agt gac act ccg ggc gcc gag gac      452
Gln Met Asp Leu Ile Asp Ala Ala Ser Asp Thr Pro Gly Ala Glu Asp
100                 105                 110                 115 gac gaa gag gac gac gac gag ctc gct gcc caa cgg cca gga gtg ggg      500
Asp Glu Glu Asp Asp Asp Glu Leu Ala Ala Gln Arg Pro Gly Val Gly
                 120                 125                 130 cct tcc aaa gcc gag tct ggc cag gag ccg gcg tct cgc agc cag ggt      548
Pro Ser Lys Ala Glu Ser Gly Gln Glu Pro Ala Ser Arg Ser Gln Gly
             135                 140                 145 cag ggc cag ggc ccc ggc aca ggc tgc gga gac acc tac cgg ccc aag      596
Gln Gly Gln Gly Pro Gly Thr Gly Cys Gly Asp Thr Tyr Arg Pro Lys
         150                 155                 160

```
                                                            -continued agg cct acc acg ctc aac ctt ttc ccg cag gtg ccg cgg tct cag gac      644
Arg Pro Thr Thr Leu Asn Leu Phe Pro Gln Val Pro Arg Ser Gln Asp
    165                 170                 175 acg ctg aat aat aac tct tta ggc aaa aag cac agt tgg cag gac cgt      692
Thr Leu Asn Asn Asn Ser Leu Gly Lys Lys His Ser Trp Gln Asp Arg
180                 185                 190                 195 gtg tct cga tca tcc tcc cct ctg aag aca ggg gag cag acg cct cca      740
Val Ser Arg Ser Ser Ser Pro Leu Lys Thr Gly Glu Gln Thr Pro Pro
                200                 205                 210 cat gaa cat atc tgc ctg agt gat gag ctg ccg ccc cag ggc agt cct      788
His Glu His Ile Cys Leu Ser Asp Glu Leu Pro Pro Gln Gly Ser Pro
            215                 220                 225 gtt ccc acc cag gat cgt ggc act tcc acc gac agc cct tgt cgc cgt      836
Val Pro Thr Gln Asp Arg Gly Thr Ser Thr Asp Ser Pro Cys Arg Arg
        230                 235                 240 act gca gcc acc cag atg gca cct cca agt ggt ccc cct gcc act gca      884
Thr Ala Ala Thr Gln Met Ala Pro Pro Ser Gly Pro Pro Ala Thr Ala
    245                 250                 255 cct ggt ggc cgg ggc cac tcc cat cga gat cgg tcc ata tca gca gat      932
Pro Gly Gly Arg Gly His Ser His Arg Asp Arg Ser Ile Ser Ala Asp
260                 265                 270                 275 gtg cgg ctc gag gcg act gag gag atc tac ctg acc cca gtg cag agg      980
Val Arg Leu Glu Ala Thr Glu Glu Ile Tyr Leu Thr Pro Val Gln Arg
                280                 285                 290 ccc cca gac cct gca gaa ccc acc tcc acc ttc ttg cca ccc act gag     1028
Pro Pro Asp Pro Ala Glu Pro Thr Ser Thr Phe Leu Pro Pro Thr Glu
            295                 300                 305 agc cgg atg tct gtc agc tcg gat cct gac cct gcc gct tac tct gta     1076
Ser Arg Met Ser Val Ser Ser Asp Pro Asp Pro Ala Ala Tyr Ser Val
        310                 315                 320 act gca ggg cga ccg cac cct tcc atc agt gaa gag gat gag ggc ttc     1124
Thr Ala Gly Arg Pro His Pro Ser Ile Ser Glu Glu Asp Glu Gly Phe
    325                 330                 335 gac tgt ctg tca tcc cca gag caa gct gag cca cca ggt gga ggg tgg     1172
Asp Cys Leu Ser Ser Pro Glu Gln Ala Glu Pro Pro Gly Gly Gly Trp
340                 345                 350                 355 cgg gga agc ctc ggg gag cca cca ccg cct cca cgg gcc tca ctg agc     1220
Arg Gly Ser Leu Gly Glu Pro Pro Pro Pro Pro Arg Ala Ser Leu Ser
                360                 365                 370 tcg gac acc agc gca ctg tcc tac gac tct gtc aag tac aca ctg gtg     1268
Ser Asp Thr Ser Ala Leu Ser Tyr Asp Ser Val Lys Tyr Thr Leu Val
            375                 380                 385 gtg gat gag cat gcc cag ctt gag ttg gtg agc ctg cgg cca tgt ttt     1316
Val Asp Glu His Ala Gln Leu Glu Leu Val Ser Leu Arg Pro Cys Phe
        390                 395                 400 gga gat tac agt gac gaa agc gac tct gcc act gtc tat gac aac tgt     1364
Gly Asp Tyr Ser Asp Glu Ser Asp Ser Ala Thr Val Tyr Asp Asn Cys
    405                 410                 415 gcc tct gcc tcc tcg ccc tac gag tca gcc att ggt gag gaa tat gag     1412
Ala Ser Ala Ser Ser Pro Tyr Glu Ser Ala Ile Gly Glu Glu Tyr Glu
420                 425                 430                 435 gag gcc cct caa ccc cgg cct ccc acc tgc ctg tca gag gac tcc aca     1460
Glu Ala Pro Gln Pro Arg Pro Pro Thr Cys Leu Ser Glu Asp Ser Thr
                440                 445                 450 ccg gat gag cct gac gtc cac ttc tct aag aag ttt ctg aat gtc ttc     1508
Pro Asp Glu Pro Asp Val His Phe Ser Lys Lys Phe Leu Asn Val Phe
            455                 460                 465 atg agt ggc cgc tct cgt tcc tcc agt gcc gag tcc ttt ggg ctg ttc     1556
Met Ser Gly Arg Ser Arg Ser Ser Ser Ala Glu Ser Phe Gly Leu Phe
        470                 475                 480
```

```
tcc tgt gtc atc aat ggg gag gag cat gag caa acc cat cgg gct ata    1604
Ser Cys Val Ile Asn Gly Glu Glu His Glu Gln Thr His Arg Ala Ile
    485                 490                 495 ttc agg ttt gtg cct cgg cat gaa gat gaa ctt gag ctg gaa gtg gac    1652
Phe Arg Phe Val Pro Arg His Glu Asp Glu Leu Glu Leu Glu Val Asp
500                 505                 510                 515 gac cct ctg ctg gtg gag ctg cag gca gaa gac tat tgg tat gag gcc    1700
Asp Pro Leu Leu Val Glu Leu Gln Ala Glu Asp Tyr Trp Tyr Glu Ala
                520                 525                 530 tat aac atg cgc act gga gcc cgt ggt gtc ttt cct gcc tac tat gcc    1748
Tyr Asn Met Arg Thr Gly Ala Arg Gly Val Phe Pro Ala Tyr Tyr Ala
            535                 540                 545 att gag gtc acc aag gag cct gag cac atg gca gcc ctt gcc aaa aac    1796
Ile Glu Val Thr Lys Glu Pro Glu His Met Ala Ala Leu Ala Lys Asn
        550                 555                 560 agc gac tgg att gac cag ttc cgg gtg aag ttc ctg ggc tct gtc cag    1844
Ser Asp Trp Ile Asp Gln Phe Arg Val Lys Phe Leu Gly Ser Val Gln
565                 570                 575 gtt cct tat cac aag ggc aat gat gtc ctc tgt gct gct atg caa aag    1892
Val Pro Tyr His Lys Gly Asn Asp Val Leu Cys Ala Ala Met Gln Lys
580                 585                 590                 595 atc gcc acc acc cgc cgg ctc acc gtg cac ttt aac ccg ccc tcc agc    1940
Ile Ala Thr Thr Arg Arg Leu Thr Val His Phe Asn Pro Pro Ser Ser
                600                 605                 610 tgt gtc ctt gaa atc agc gtt agg ggt gtc aag ata ggt gtc aaa gct    1988
Cys Val Leu Glu Ile Ser Val Arg Gly Val Lys Ile Gly Val Lys Ala
            615                 620                 625 gat gaa gct cag gag gcc aag gga aat aaa tgt agc cac ttt ttc cag    2036
Asp Glu Ala Gln Glu Ala Lys Gly Asn Lys Cys Ser His Phe Phe Gln
        630                 635                 640 cta aaa aac atc tct ttc tgt ggg tac cat cca aag aac aac aag tac    2084
Leu Lys Asn Ile Ser Phe Cys Gly Tyr His Pro Lys Asn Asn Lys Tyr
645                 650                 655 ttt ggg ttt atc act aag cac cct gct gac cac cgg ttt gcc tgc cat    2132
Phe Gly Phe Ile Thr Lys His Pro Ala Asp His Arg Phe Ala Cys His
660                 665                 670                 675 gtc ttt gtg tct gaa gat tcc acc aaa gcc ctg gca gag tct gtg ggg    2180
Val Phe Val Ser Glu Asp Ser Thr Lys Ala Leu Ala Glu Ser Val Gly
                680                 685                 690 cgt gca ttt cag cag ttc tac aag caa ttt gtg gaa tat acc tgt cct    2228
Arg Ala Phe Gln Gln Phe Tyr Lys Gln Phe Val Glu Tyr Thr Cys Pro
            695                 700                 705 aca gaa gat atc tac ttg gag tag cagcaacccc cctctctgca gcccctcagc   2282
Thr Glu Asp Ile Tyr Leu Glu
        710 cccaggccag tactaggaca gctgactgct gacaggatgt tgtactgcca cgagagaatg   2342 ggggagtgag ggctgttggg gtcgggggggc agggggtttgg ggagaggcag atgcagttta   2402 ttgtaatata tggggttaga ttaatctatg gaggacagta caggctctct cggggctggg   2462 gaagggcagg gctgggggtgg gggtcaggca tctggccaca aagggggtccc ctagggacag   2522 aggcgctgca ccatcctggg cttgtttcat actagaggcc ctggctttct ggctcttggg   2582 tcctgccttg acaaagccca gccacctgga agtgtcacct tcccttgtcc acctcaccca   2642 gtgccctgag ctcatgctga gcccaagcac ctccgaagga ctttccagta aggaaatggc   2702 aacatgtgac agtgagaccc tgttctcatc tgtggggctc cggcagctcc gacccccagc   2762 ctggccagca cgctgaccct ggcaagcttg tgtgttcaaa gaaggagagg gccacagcaa   2822
```

```
gccctgcctg ccagggaagg ttccctctca gctggcccca gccaactggt cactgtcttg   2882
tcacctggct actactatta aagtgccatt tcttgtctga aaaaaaaaaa aaaaaaaaa    2942 aaaaactcga g                                                         2953
```

<210> SEQ ID NO 103
<211> LENGTH: 714
<212> TYPE: PRT
<213> ORGANISM: Artificial
<220> FEATURE:
<223> OTHER INFORMATION: description of sequence: Protein encoded by
      Exon-Intron Boundary of the rIB1 Gene - Splice donor

<400> SEQUENCE: 103

```
Met Ala Arg Leu Ser Pro Gly Met Ala Glu Arg Glu Ser Gly Leu Ser
1               5                   10                  15

Gly Gly Ala Ala Ser Pro Ala Ala Ser Pro Phe Leu Gly Leu His
            20                  25                  30

Ile Ala Ser Pro Pro Asn Phe Arg Leu Thr His Asp Ile Ser Leu Glu
        35                  40                  45

Glu Phe Glu Asp Glu Asp Leu Ser Glu Ile Thr Asp Glu Cys Gly Ile
    50                  55                  60

Ser Leu Gln Cys Lys Asp Thr Leu Ser Leu Arg Pro Pro Arg Ala Gly
65                  70                  75                  80

Leu Leu Ser Ala Gly Ser Ser Gly Ser Ala Gly Ser Arg Leu Gln Ala
                85                  90                  95

Glu Met Leu Gln Met Asp Leu Ile Asp Ala Ala Ser Asp Thr Pro Gly
            100                 105                 110

Ala Glu Asp Asp Glu Glu Asp Asp Glu Leu Ala Ala Gln Arg Pro
        115                 120                 125

Gly Val Gly Pro Ser Lys Ala Glu Ser Gly Gln Glu Pro Ala Ser Arg
    130                 135                 140

Ser Gln Gly Gln Gly Gln Gly Pro Gly Thr Gly Cys Gly Asp Thr Tyr
145                 150                 155                 160

Arg Pro Lys Arg Pro Thr Thr Leu Asn Leu Phe Pro Gln Val Pro Arg
                165                 170                 175

Ser Gln Asp Thr Leu Asn Asn Asn Ser Leu Gly Lys Lys His Ser Trp
            180                 185                 190

Gln Asp Arg Val Ser Arg Ser Ser Pro Leu Lys Thr Gly Glu Gln
        195                 200                 205

Thr Pro Pro His Glu His Ile Cys Leu Ser Asp Glu Leu Pro Pro Gln
    210                 215                 220

Gly Ser Pro Val Pro Thr Gln Asp Arg Gly Thr Ser Thr Asp Ser Pro
225                 230                 235                 240

Cys Arg Arg Thr Ala Ala Thr Gln Met Ala Pro Pro Ser Gly Pro Pro
                245                 250                 255

Ala Thr Ala Pro Gly Gly Arg Gly His Ser His Arg Asp Arg Ser Ile
            260                 265                 270

Ser Ala Asp Val Arg Leu Glu Ala Thr Glu Glu Ile Tyr Leu Thr Pro
        275                 280                 285

Val Gln Arg Pro Pro Asp Pro Ala Glu Pro Thr Ser Thr Phe Leu Pro
    290                 295                 300

Pro Thr Glu Ser Arg Met Ser Val Ser Ser Asp Pro Asp Pro Ala Ala
305                 310                 315                 320

Tyr Ser Val Thr Ala Gly Arg Pro His Pro Ser Ile Ser Glu Glu Asp
                325                 330                 335
```

Glu Gly Phe Asp Cys Leu Ser Ser Pro Glu Gln Ala Glu Pro Pro Gly
            340                 345                 350

Gly Gly Trp Arg Gly Ser Leu Gly Glu Pro Pro Pro Pro Arg Ala
        355                 360                 365

Ser Leu Ser Ser Asp Thr Ser Ala Leu Ser Tyr Asp Ser Val Lys Tyr
370                 375                 380

Thr Leu Val Val Asp Glu His Ala Gln Leu Glu Leu Val Ser Leu Arg
385                 390                 395                 400

Pro Cys Phe Gly Asp Tyr Ser Asp Glu Ser Asp Ser Ala Thr Val Tyr
                405                 410                 415

Asp Asn Cys Ala Ser Ala Ser Ser Pro Tyr Glu Ser Ala Ile Gly Glu
            420                 425                 430

Glu Tyr Glu Glu Ala Pro Gln Pro Arg Pro Pro Thr Cys Leu Ser Glu
        435                 440                 445

Asp Ser Thr Pro Asp Glu Pro Asp Val His Phe Ser Lys Lys Phe Leu
    450                 455                 460

Asn Val Phe Met Ser Gly Arg Ser Arg Ser Ser Ser Ala Glu Ser Phe
465                 470                 475                 480

Gly Leu Phe Ser Cys Val Ile Asn Gly Glu Glu His Glu Gln Thr His
                485                 490                 495

Arg Ala Ile Phe Arg Phe Val Pro Arg His Glu Asp Glu Leu Glu Leu
            500                 505                 510

Glu Val Asp Asp Pro Leu Leu Val Glu Leu Gln Ala Glu Asp Tyr Trp
        515                 520                 525

Tyr Glu Ala Tyr Asn Met Arg Thr Gly Ala Arg Gly Val Phe Pro Ala
    530                 535                 540

Tyr Tyr Ala Ile Glu Val Thr Lys Glu Pro Glu His Met Ala Ala Leu
545                 550                 555                 560

Ala Lys Asn Ser Asp Trp Ile Asp Gln Phe Arg Val Lys Phe Leu Gly
                565                 570                 575

Ser Val Gln Val Pro Tyr His Lys Gly Asn Asp Val Leu Cys Ala Ala
            580                 585                 590

Met Gln Lys Ile Ala Thr Thr Arg Arg Leu Thr Val His Phe Asn Pro
        595                 600                 605

Pro Ser Ser Cys Val Leu Glu Ile Ser Val Arg Gly Val Lys Ile Gly
    610                 615                 620

Val Lys Ala Asp Glu Ala Gln Glu Ala Lys Gly Asn Lys Cys Ser His
625                 630                 635                 640

Phe Phe Gln Leu Lys Asn Ile Ser Phe Cys Gly Tyr His Pro Lys Asn
                645                 650                 655

Asn Lys Tyr Phe Gly Phe Ile Thr Lys His Pro Ala Asp His Arg Phe
            660                 665                 670

Ala Cys His Val Phe Val Ser Glu Asp Ser Thr Lys Ala Leu Ala Glu
        675                 680                 685

Ser Val Gly Arg Ala Phe Gln Gln Phe Tyr Lys Gln Phe Val Glu Tyr
    690                 695                 700

Thr Cys Pro Thr Glu Asp Ile Tyr Leu Glu
705                 710

<210> SEQ ID NO 104
<211> LENGTH: 711
<212> TYPE: PRT
<213> ORGANISM: Homo sapiens
<220> FEATURE:

<223> OTHER INFORMATION: description of sequence: human IB1 protein sequence

<400> SEQUENCE: 104

| | | | | | | | | | | | | | | | |
|---|---|---|---|---|---|---|---|---|---|---|---|---|---|---|---|
| Met | Ala | Glu | Arg | Glu | Ser | Gly | Leu | Gly | Gly | Ala | Ala | Ser | Pro | | |
| 1 | | | | 5 | | | | | 10 | | | | | 15 | |
| Pro | Ala | Ala | Ser | Pro | Phe | Leu | Gly | Leu | His | Ile | Ala | Ser | Pro | Pro | Asn |
| | | | 20 | | | | | 25 | | | | | 30 | | |
| Phe | Arg | Leu | Thr | His | Asp | Ile | Ser | Leu | Glu | Glu | Phe | Glu | Asp | Glu | Asp |
| | | | 35 | | | | | 40 | | | | | 45 | | |
| Leu | Ser | Glu | Ile | Thr | Asp | Glu | Cys | Gly | Ile | Ser | Leu | Gln | Cys | Lys | Asp |
| | 50 | | | | | 55 | | | | | 60 | | | | |
| Thr | Leu | Ser | Leu | Arg | Pro | Pro | Arg | Ala | Gly | Leu | Leu | Ser | Ala | Gly | Gly |
| 65 | | | | | 70 | | | | | 75 | | | | | 80 |
| Gly | Gly | Ala | Gly | Ser | Arg | Leu | Gln | Ala | Glu | Met | Leu | Gln | Met | Asp | Leu |
| | | | | 85 | | | | | 90 | | | | | 95 | |
| Ile | Asp | Ala | Thr | Gly | Asp | Thr | Pro | Gly | Ala | Glu | Asp | Asp | Glu | Glu | Asp |
| | | | | 100 | | | | | 105 | | | | | 110 | |
| Asp | Asp | Glu | Glu | Arg | Ala | Ala | Arg | Arg | Pro | Gly | Ala | Gly | Pro | Pro | Lys |
| | | | 115 | | | | | 120 | | | | | 125 | | |
| Ala | Glu | Ser | Gly | Gln | Glu | Pro | Ala | Ser | Arg | Gly | Gln | Gly | Gln | Ser | Gln |
| | 130 | | | | | 135 | | | | | 140 | | | | |
| Gly | Gln | Ser | Gln | Gly | Pro | Gly | Ser | Gly | Asp | Thr | Tyr | Arg | Pro | Lys | Arg |
| 145 | | | | | 150 | | | | | 155 | | | | | 160 |
| Pro | Thr | Thr | Leu | Asn | Leu | Phe | Pro | Gln | Val | Pro | Arg | Ser | Gln | Asp | Thr |
| | | | | 165 | | | | | 170 | | | | | 175 | |
| Leu | Asn | Asn | Asn | Ser | Leu | Gly | Lys | Lys | His | Ser | Trp | Gln | Asp | Arg | Val |
| | | | | 180 | | | | | 185 | | | | | 190 | |
| Ser | Arg | Ser | Ser | Ser | Pro | Leu | Lys | Thr | Gly | Glu | Gln | Thr | Pro | Pro | His |
| | | | 195 | | | | | 200 | | | | | 205 | | |
| Glu | His | Ile | Cys | Leu | Ser | Asp | Glu | Leu | Pro | Pro | Gln | Ser | Gly | Pro | Ala |
| | | 210 | | | | | 215 | | | | | 220 | | | |
| Pro | Thr | Thr | Asp | Arg | Gly | Thr | Ser | Thr | Asp | Ser | Pro | Cys | Arg | Arg | Ser |
| 225 | | | | | 230 | | | | | 235 | | | | | 240 |
| Thr | Ala | Thr | Gln | Met | Ala | Pro | Pro | Gly | Gly | Pro | Ala | Ala | Pro | Pro | |
| | | | | 245 | | | | | 250 | | | | | 255 | |
| Gly | Gly | Arg | Gly | His | Ser | His | Arg | Asp | Arg | Ile | His | Tyr | Gln | Ala | Asp |
| | | | 260 | | | | | 265 | | | | | 270 | | |
| Val | Arg | Leu | Glu | Ala | Thr | Glu | Glu | Ile | Tyr | Leu | Thr | Pro | Val | Gln | Arg |
| | | | 275 | | | | | 280 | | | | | 285 | | |
| Pro | Pro | Asp | Ala | Ala | Glu | Pro | Thr | Ser | Ala | Phe | Leu | Pro | Pro | Thr | Glu |
| | | 290 | | | | | 295 | | | | | 300 | | | |
| Ser | Arg | Met | Ser | Val | Ser | Ser | Asp | Pro | Asp | Pro | Ala | Ala | Tyr | Pro | Ser |
| 305 | | | | | 310 | | | | | 315 | | | | | 320 |
| Thr | Ala | Gly | Arg | Pro | His | Pro | Ser | Ile | Ser | Glu | Glu | Glu | Glu | Gly | Phe |
| | | | | 325 | | | | | 330 | | | | | 335 | |
| Asp | Cys | Leu | Ser | Ser | Pro | Glu | Arg | Ala | Glu | Pro | Pro | Gly | Gly | Gly | Trp |
| | | | | 340 | | | | | 345 | | | | | 350 | |
| Arg | Gly | Ser | Leu | Gly | Glu | Pro | Pro | Pro | Pro | Arg | Ala | Ser | Leu | Ser | |
| | | | 355 | | | | | 360 | | | | | 365 | | |
| Ser | Asp | Thr | Ser | Ala | Leu | Ser | Tyr | Asp | Ser | Val | Lys | Tyr | Thr | Leu | Val |
| | 370 | | | | | 375 | | | | | 380 | | | | |
| Val | Asp | Glu | His | Ala | Gln | Leu | Glu | Leu | Val | Ser | Leu | Arg | Pro | Cys | Phe |
| 385 | | | | | 390 | | | | | 395 | | | | | 400 |

Gly Asp Tyr Ser Asp Glu Ser Asp Ser Ala Thr Val Tyr Asp Asn Cys
            405                 410                 415

Ala Ser Val Ser Ser Pro Tyr Glu Ser Ala Ile Gly Glu Glu Tyr Glu
        420                 425                 430

Glu Ala Pro Arg Pro Gln Pro Pro Ala Cys Leu Ser Glu Asp Ser Thr
    435                 440                 445

Pro Asp Glu Pro Asp Val His Phe Ser Lys Lys Phe Leu Asn Val Phe
450                 455                 460

Met Ser Gly Arg Ser Arg Ser Ser Ser Ala Glu Ser Phe Gly Leu Phe
465                 470                 475                 480

Ser Cys Ile Ile Asn Gly Glu Glu Gln Glu Gln Thr His Arg Ala Ile
                485                 490                 495

Phe Arg Phe Val Pro Arg His Glu Asp Glu Leu Glu Leu Glu Val Asp
            500                 505                 510

Asp Pro Leu Leu Val Glu Leu Gln Ala Glu Asp Tyr Trp Tyr Glu Ala
        515                 520                 525

Tyr Asn Met Arg Thr Gly Ala Arg Gly Val Phe Pro Ala Tyr Tyr Ala
    530                 535                 540

Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
                565                 570                 575

Val Pro Tyr His Lys Gly Asn Asp Val Leu Cys Ala Ala Met Gln Lys
            580                 585                 590

Ile Ala Thr Thr Arg Arg Leu Thr Val His Phe Asn Pro Pro Ser Ser
        595                 600                 605

Cys Val Leu Glu Ile Ser Val Arg Gly Val Lys Ile Gly Val Lys Ala
    610                 615                 620

Asp Asp Ser Gln Glu Ala Lys Gly Asn Lys Cys Ser His Phe Phe Gln
625                 630                 635                 640

Leu Lys Asn Ile Ser Phe Cys Gly Tyr His Pro Lys Asn Asn Lys Tyr
                645                 650                 655

Phe Gly Phe Ile Thr Lys His Pro Ala Asp His Arg Phe Ala Cys His
            660                 665                 670

Val Phe Val Ser Glu Asp Ser Thr Lys Ala Leu Ala Glu Ser Val Gly
        675                 680                 685

Arg Ala Phe Gln Gln Phe Tyr Lys Gln Phe Val Glu Tyr Thr Cys Pro
    690                 695                 700

Thr Glu Asp Ile Tyr Leu Glu
705                 710

<210> SEQ ID NO 105
<211> LENGTH: 2136
<212> TYPE: DNA
<213> ORGANISM: Homo sapiens
<220> FEATURE:
<223> OTHER INFORMATION: description of sequence: nucleic acid sequence
      encoding human IB1 protein

<400> SEQUENCE: 105
atggcggagc gagaaagcgg cggcctggga ggggggccg cgtccccgcc cgccgcctcc      60
ccgttcctgg ggctgcacat cgcttcgcct cccaatttca ggctcaccca tgacatcagc     120
ctggaggagt ttgaggatga agacctctcg gagatcactg atgagtgtgg catcagctta     180
cagtgcaaag acaccctgtc cttacggccc ccgcgcgccg ggctgctctc tgcgggcggc     240

```
ggcggcgcgg ggagccggtt gcaggccgag atgctgcaga tggacctgat cgacgcgacg    300
ggggacactc ccggggccga ggacgacgag gaggacgacg acgaggagcg cgcggcccgg    360
cggccgggag cggggccgcc caaggccgag tccggccagg agccggcgtc ccgcggccag    420
ggccagagcc aaggccagag ccagggcccg ggcagcgggg acacgtaccg gcccaagcgg    480
cccaccacgc tcaacctctt tccgcaggtg ccgcggtctc aggacacact gaataataat    540
tctctgggca aaaagcacag ttggcaggat cgggtgtctc gatcatcctc acccctgaag    600 acagggagc agacaccacc gcatgaacac atctgcctga gcgatgagct gccccccag     660 agcggccccg cccccaccac agatcgaggc acctccaccg acagcccttg ccgccgcagc    720
acagccaccc agatggcacc tccgggtggt cccctgctg ccccgcctgg gggtcggggc     780
cactcgcatc gagaccgaat ccactaccag gccgatgtgc gactagaggc cactgaggag    840
atctacctga ccccagtgca gaggccccca gacgctgcag agcccacctc cgccttcctg    900
ccgcccactg agagccggat gtcagtcagc tccgatccag accctgccgc ctacccctcc    960
acggcagggc ggccgcaccc ctccatcagt gaagaggaag agggcttcga ctgcctgtcg   1020
tccccagagc gggctgagcc cccaggcgga gggtggcggg ggagcctggg ggagccgccg   1080
ccacctccac gggcctctct gagctcggac accagcgccc tgtcctatga ctctgtcaag   1140
tacacgctgg tggtagatga gcatgcacag ctggagctgg tgagcctgcg gccgtgcttc   1200
ggagactaca gtgacgagag tgactctgcc accgtctatg acaactgtgc ctccgtctcc   1260
tcgccctatg agtcggccat cggagaggaa tatgaggagg ccccgcggcc ccagcccccct   1320 gcctgcctct ccgaggactc cacgcctgat gaacccgacg tccatttctc caagaaattc   1380
ctgaacgtct tcatgagtgg ccgctcccgc tcctccagtg ctgagtcctt cgggctgttc   1440
tcctgcatca tcaacgggga ggagcaggag cagacccacc gggccatatt caggtttgtg   1500
cctcgacacg aagacgaact tgagctgaa gtggatgacc ctctgctagt ggagctccag   1560
gctgaagact actggtacga ggcctacaac atgcgcactg gtgcccgggg tgtctttcct   1620
gcctattacg ccatcgaggt caccaaggag cccgagcaca tggcagccct ggccaaaaac   1680
agtgactggg tggaccagtt ccgggtgaag ttcctgggct cagtccaggt tccctatcac   1740
aagggcaatg acgtcctctg tgctgctatg caaaagattg ccaccacccg ccggctcacc   1800
gtgcacttta acccgccctc cagctgtgtc ctggagatca gcgtgcgggg tgtgaagata   1860
ggcgtcaagg ccgatgactc ccaggaggcc aaggggaata aatgtagcca ctttttccag   1920
ttaaaaaaca tctctttctg cggatatcat ccaaagaaca acaagtactt tgggttcatc   1980
accaagcacc ccgccgacca ccggtttgcc tgccacgtct ttgtgtctga agactccacc   2040
aaagccctgg cagagtccgt ggggagagca ttccagcagt tctacaagca gtttgtggag   2100
tacacctgcc ccacagaaga tatctacctg gagtag                               2136
```